(12) United States Patent
Zhang et al.

(10) Patent No.: US 12,012,403 B2
(45) Date of Patent: Jun. 18, 2024

(54) ARYL SULFONYL COMPOUNDS AS CCR6 INHIBITORS

(71) Applicant: CHEMOCENTRYX, INC., San Carlos, CA (US)

(72) Inventors: Penglie Zhang, Foster City, CA (US); Daniel R. Marshall, San Mateo, CA (US); Howard S. Roth, Sunnyvale, CA (US); Aubrie Harland, Redwood City, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

(21) Appl. No.: 17/820,281

(22) Filed: Aug. 17, 2022

(65) Prior Publication Data
US 2023/0125684 A1    Apr. 27, 2023

Related U.S. Application Data

(60) Provisional application No. 63/234,274, filed on Aug. 18, 2021.

(51) Int. Cl.
| | |
|---|---|
| C07D 471/04 | (2006.01) |
| C07D 401/14 | (2006.01) |
| C07D 405/14 | (2006.01) |
| C07D 413/14 | (2006.01) |
| C07D 417/14 | (2006.01) |
| C07D 471/10 | (2006.01) |
| C07D 487/04 | (2006.01) |
| C07D 491/107 | (2006.01) |
| C07D 491/20 | (2006.01) |
| C07D 513/04 | (2006.01) |

(52) U.S. Cl.
CPC ......... *C07D 471/04* (2013.01); *C07D 401/14* (2013.01); *C07D 405/14* (2013.01); *C07D 413/14* (2013.01); *C07D 417/14* (2013.01); *C07D 471/10* (2013.01); *C07D 487/04* (2013.01); *C07D 491/107* (2013.01); *C07D 491/20* (2013.01); *C07D 513/04* (2013.01)

(58) Field of Classification Search
None
See application file for complete search history.

(56) References Cited

U.S. PATENT DOCUMENTS

| | | |
|---|---|---|
| 8,153,793 B2 | 4/2012 | Kugimiya et al. |
| 9,163,017 B2 | 10/2015 | Degoey et al. |
| 2008/0255222 A1 | 10/2008 | Halazy et al. |
| 2015/0175547 A1 | 6/2015 | Dairaghi et al. |
| 2016/0206613 A1 | 7/2016 | Groppe |
| 2016/0289212 A1 | 10/2016 | Qiu et al. |
| 2020/0297710 A1 | 9/2020 | Axten et al. |
| 2023/0133406 A1 | 5/2023 | Zhang et al. |

FOREIGN PATENT DOCUMENTS

| | | |
|---|---|---|
| CN | 113135896 A | 7/2021 |
| JP | 2005119987 A | 5/2005 |
| WO | 02/074761 A1 | 9/2002 |
| WO | 03/042174 A1 | 5/2003 |
| WO | 03/075929 A1 | 9/2003 |
| WO | 03/076395 A1 | 9/2003 |
| WO | 03/076400 A1 | 9/2003 |
| WO | 03/076401 A1 | 9/2003 |
| WO | 03/076421 A1 | 9/2003 |
| WO | 03/076430 A1 | 9/2003 |
| WO | 03/076438 A1 | 9/2003 |
| WO | 2004/033632 A2 | 4/2004 |
| WO | 2004/033632 A3 | 4/2004 |
| WO | 2005/014579 A1 | 2/2005 |
| WO | 2005/014593 A1 | 2/2005 |
| WO | 2006/034341 A2 | 3/2006 |
| WO | 2006/034341 A3 | 3/2006 |
| WO | 2007/037187 A1 | 4/2007 |
| WO | 2007/047431 A2 | 4/2007 |
| WO | 2007/047431 A3 | 4/2007 |
| WO | 2007/092435 A2 | 8/2007 |
| WO | 2007/092435 A3 | 8/2007 |
| WO | 2008/077057 A2 | 6/2008 |
| WO | 2008/077057 A3 | 6/2008 |
| WO | 2009/158587 A1 | 12/2009 |
| WO | 2010/065782 A1 | 6/2010 |
| WO | 2010/075376 A2 | 7/2010 |
| WO | 2010/075376 A3 | 7/2010 |

(Continued)

OTHER PUBLICATIONS

Database Registry Chemical Abstracts Service, Columbus, Ohio, Accession No. RN 2197659-25-7, Entered STN: Mar. 23, 2018.*
International Search Report dated Feb. 23, 2023 corresponding to PCT/US2022/075047 filed Aug. 17, 2022; 11 pages.
International Search Report dated Mar. 2023 corresponding to PCT/US2022/075045 filed Aug. 17, 2022; 11 pages.
Pubchem, Substance Record for SID 160846779, Modify Date: Sep. 9, 2020 [retrieved on Dec. 1, 2022]; Retrieved from the Internet: <URL: https://pubchem.ncbi.nlm.nih.giv/substance/ 160846779>; 1 page.
Pubchem, Substance Record for SID 350049627, Modify Date: Dec. 20, 2017 [retrieved on Dec. 12, 2022]; p. 2, figure, this is a purchasable chemical; 1 page.

(Continued)

*Primary Examiner* — Samantha L Shterengarts
(74) *Attorney, Agent, or Firm* — Robert Bernstein

(57) ABSTRACT

Compounds of formula (I) are provided which are useful in the treatment of diseases or conditions modulated at least in part by CCR6:

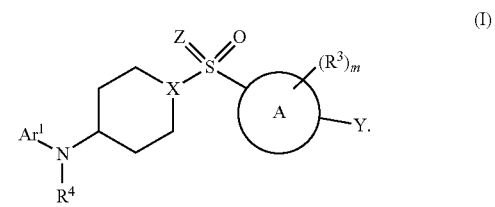

(I)

21 Claims, No Drawings

(56) References Cited

FOREIGN PATENT DOCUMENTS

| WO | 2011078370 A1 | 6/2011 |
| --- | --- | --- |
| WO | 2011/088192 A1 | 7/2011 |
| WO | 2012/012282 A1 | 1/2012 |
| WO | 2012/015760 A1 | 2/2012 |
| WO | 2013/157021 A1 | 10/2013 |
| WO | 2014/127350 A1 | 8/2014 |
| WO | 2015/058163 A2 | 4/2015 |
| WO | 2015/058163 A3 | 4/2015 |
| WO | 2015/078374 A1 | 6/2015 |
| WO | 2015/123465 A1 | 8/2015 |
| WO | 2016/205633 A1 | 12/2016 |
| WO | 2016/210296 A1 | 12/2016 |
| WO | 2017/070320 A1 | 4/2017 |
| WO | 2017/172802 A1 | 10/2017 |
| WO | 2017/212425 A1 | 12/2017 |
| WO | 2018/098361 A1 | 5/2018 |
| WO | 2018/106818 A1 | 6/2018 |
| WO | 2019/204442 A1 | 10/2019 |
| WO | 2019/204505 A2 | 10/2019 |
| WO | 2019/204505 A3 | 10/2019 |
| WO | 2020/006497 A1 | 1/2020 |
| WO | 2020/014599 A1 | 1/2020 |
| WO | 2021/102361 A1 | 5/2021 |
| WO | 2022/173849 A1 | 8/2022 |

OTHER PUBLICATIONS

Martina, Maria Grazia et al., "Discovery of small-moelcules targeting the CCL20/CCR6 axis as first-in-class inhibitors for inflammatory bowel diseases," *European Journal of Medicinal Chemistry* (Aug. 29, 2022) 243:114703; 11 pages.

Tawaraishi, Taisuke et al., "Identification of a novel series of potent and selective CCR6 inhibitors as biological probes," *Bioorganic & Medicinal Chemistry Letters* (Jul. 30, 2018) 28:3067-3072.

* cited by examiner

ARYL SULFONYL COMPOUNDS AS CCR6 INHIBITORS

CROSS-REFERENCES TO RELATED APPLICATIONS

This application claims the benefit of priority under 35 U.S.C § 119(e) to U.S. Provisional Application Ser. No. 63/234,274 filed Aug. 18, 2021, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr Opin. Immunol.* 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ([Ca2+]), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are two main classes of chemokines, CXC (alpha) and CC (beta), depending on whether the first two cysteines are separated by a single amino acid (C-X-C) or are adjacent (C—C). The alpha-chemokines, such as interleukin-8 (IL-8), neutrophil-activating protein-2 (NAP-2) and melanoma growth stimulatory activity protein (MGSA) are chemotactic primarily for neutrophils, whereas beta-chemokines, such as RANTES, MIP-la, MIP-lb, monocyte chemotactic protein-1 (MCP-1), MCP-2, MCP-3 and eotaxin are chemotactic for macrophages, T-cells, eosinophils and basophils (Deng, et al., *Nature*, 381:661-666 (1996)). The chemokines bind specific cell-surface receptors belonging to the family of G-protein-coupled seven-transmembrane-domain proteins (reviewed in Horuk, *Trends Pharm. Sci.*, 15:159-165 (1994)) which are termed "chemokine receptors."

On binding their cognate ligands, chemokine receptors transduce an intracellular signal though the associated trimeric G protein, resulting in a rapid increase in intracellular calcium concentration. There are at least eleven human chemokine receptors that bind or respond to beta-chemokines and at least seven human chemokine receptors that bind to the alpha chemokines. Additionally CX3CR1 (fractalkine receptor) can bind to the fractalkine chemokine, which is distinguished by a series of three amino acids between the first two cysteines. Chemokine receptors, have been implicated as being important mediators of inflammatory and immunoregulatory disorders and diseases, including asthma and allergic diseases, as well as autoimmune pathologies such as rheumatoid arthritis and atherosclerosis.

CCR6 is known to be expressed primarily in B cells, IL17 secreting T cells, regulatory T cells and dendritic cells and shows strong binding to its cognate ligand CCL20 (MIP-3α). It is expressed on approximately 30-60% of adult peripheral blood effector/memory CD4+ T cells. CCR6 is involved in leukocyte homing to inflamed tissue, particularly the skin and lungs and is co-expressed on almost all T cells that have a skin homing phenotype, the CLA+ T cells. Thus CCR6 may be an important player in skin pathologies in which leukocytes participate.

CCR6 expression has been linked to psoriasis in the following manner. In humans, a large majority of skin-homing CD4 T cells in the peripheral blood express CCR6 with a greater degree of CCL20-mediated chemotaxis occurring in T cells isolated from psoriatic patients (Homey, et. al., *JI*, 2000). IL17 secreting cells are central agents in several inflammatory diseases. T cells, such as γδ T cells and TH17 T cells produce IL17 after activation. The pathogenic effects of IL17 have been associated with human diseases such as rheumatoid arthritis (Patel D D et. al., *Ann Rheum Dis* 2013), multiple sclerosis (Zepp J, Wu L, and X Li *Trends Immunol* 2011), and psoriasis (Martin D A et. al., *J Invest Dermatol* 2012). Evidence strongly linking IL17 with psoriasis include gene wide association studies that show strong association between psoriasis and genes upstream (IL-23) or downstream (NFκb) of IL17 signaling pathways as well as efficacy in targeting IL17 in a clinical setting (Martin D A et. al., *J Invest Dermat.* 2012; Papp et. al., *NEJM*, 2012; Papp et. al., *NEJM*, 2012). In addition to enhanced CCL20-mediated chemotaxis, CCR6+ T cells isolated from psoriatic patients preferentially secrete IL-17A, IL22, and TNFα when compared to healthy controls (Kagami, et. al., *J Invest. Dermatol.*, 2010). Lastly, ccl20 mRNA was up-regulated in lesional psoriatic skin samples (Homey, et. al., *JI*, 2000; Dieu-Nosjean, et. al., *JEM*, 2000). In mice, CCR6 knock-out mice were protected from IL-23 driven psoriasis. Thus, a multitude of evidence in both mice and men suggest a protective role for CCR6 blockade in psoriasis and psoriasis-like models.

Recent work on the search for CCR6 inhibitor compounds is described in Tawaraishi, et al., *Bioorg. Med. Chem. Lett.* 28:3067-3072 (2018).

In view of the clinical importance of CCR6, the identification of compounds that modulate CCR6 function represent an attractive avenue into the development of new therapeutic agents. Such compounds and methods for their use are provided herein.

BRIEF SUMMARY OF THE INVENTION

Described herein are compounds having formula (I):

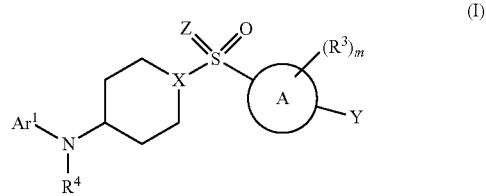

wherein $Ar^1$, X, Y, Z, Ring A, the subscript m, $R^3$ and $R^4$ have the meanings provided in the Detailed Description below. The compounds have utility in the treatment of diseases or conditions modulated at least in part by CCR6.

Pharmaceutical compositions of the compounds of formula (I) are also provided.

Further provided in the present disclosure preparative methods for the synthesis of compounds of formula (I), as well as selected intermediates useful in the preparation.

BRIEF DESCRIPTION OF THE DRAWINGS

NOT APPLICABLE.

DETAILED DESCRIPTION OF THE INVENTION

Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycyclic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "⌇", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —$NR^aR^b$ is meant to include piperidinyl, pyrrolidinyl, morpholinyl, azetidinyl and the like.

The term "hydroxyalkyl" refers to an alkyl group where one, two, or three of the hydrogen atoms is substituted with a hydroxy (—OH) group. In some embodiments, the hydroxyalkyl has one to two hydroxy groups. In some embodiments, the hydroxyalkyl has one hydroxy group. As for the alkyl portion, hydroxyalkyl groups can have any suitable number of carbon atoms, such as $C_1$-6, and can be straight or branched. Hydroxyalkyl groups include, for example, hydroxymethyl, 1-hydroxyethyl, 2-hydroxyethyl, 2-hydroxypropan-2-yl, etc.

The term "di-($C_{1-4}$ alkyl)amino-$C_{1-4}$ alkyl" refers to an amino group bearing two $C_{1-4}$ alkyl groups that can be the same or different (e.g., methyl, ethyl, propyl, isopropyl, n-butyl, sec-butyl, isobutyl and tert-butyl) and which is attached to the remainder of the molecule through a $C_{1-4}$ alkyl group (a one to four carbon alkylene linking group). Examples of di-($C_{1-4}$ alkyl)amino-$C_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

As used herein, the term "heteroatom" is meant to include oxygen (O), nitrogen (N), sulfur (S) and silicon (Si).

More specifically, the phrase "5- or 6-membered heterocyclic ring having 1 or 2 heteroatoms as ring vertices selected from N, O and S" refers to a single ring have 5 or 6 ring vertices, wherein 1 or 2 of the ring vertices are heteroatoms (N, O, or S). Examples of such rings include morpholine, pyrrolidine, tetrahydrofuran, thiomorpholine, piperidine, piperazine, and the like. The ring may have 0 or 1 double bond between ring vertices.

The phrase "bicyclic 9- or 10-membered fused aromatic or heteroaromatic ring having 0 to 4 heteroatoms as ring vertices selected from N, O, S, and S(O)$_2$" refers to a ring system in which two adjacent ring vertices of a first ring are also adjacent ring vertices of a second ring (i.e., a fused ring system), and wherein at least one of the two rings is aromatic. In some embodiments, both rings have aromatic character (e.g., naphthalene, quinolone, quinazoline, benzimidazole, benzothiophene, benzopyrazole). In some embodiments, only one ring is aromatic (e.g., indane, 1,2,3,4-tetrahydronaphthalene, 5,6,7,8-tetrahydroquinoline, 1,2,3,4-tetrahydroisoquinoline).

The phrase "monocyclic 5- or 6-membered aromatic or heteroaromatic ring having 0 to 3 heteroatoms as ring vertices selected from N, O and S" refers to a single ring which is aromatic (phenyl) or heteroaromatic (e.g., pyridine, thiophene, furan, pyrimidine, pyrazine).

A "3- to 6-membered spirocyclic ring" refers to a group having two points of attachment to a carbon atom that is a ring vertex or part of an alkylene group. For example, the group:

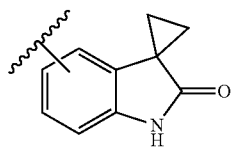

is a bicyclic 9- or 10-membered fused aromatic or heteroaromatic ring having 1 heteroatom as a ring vertex, and which is substituted with a 3-membered spirocyclic ring and oxo.

The terms "spiroheterocyclic ring" "spiroheterocyclyl" or "spiroheterocycloalkyl" refer to a saturated or partially unsaturated bicyclic ring having 6 to 12 ring atoms, where the two rings are connected via a single carbon atom (also called the spiroatom). Spiroheterocyclyl groups have from one to five heteroatoms selected from N, O, and S as ring vertices, and the nitrogen atom(s) are optionally quaternized. Partially unsaturated spiroheterocycloalkyl groups have a double bond in one of the rings. Representative examples include, but are not limited to, 2,6-diazaspiro[3.3]heptane, 2,6-diazaspiro[3.4]octane, 2-azaspiro[3.4]octane, 2-azaspiro [3.5]-nonane, 2,7-diazaspiro[4.4]nonane, and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The term "and acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include, hydroxamic acids, sulfonic acids, sulfinic acids, sulfonamides, acyl-sulfonamides, phosphonic acids, phosphinic acids, phosphoric acids, tetrazole, and oxo-oxadiazoles.

Compounds of the invention having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more 6 bonds. Rotamers are conformers that differ by rotation about only a single a bond.

General

The present invention derives from the discovery that compounds of formula I act as potent antagonists of the CCR6 receptor. The compounds have in vivo anti-inflammatory activity and have superior pharmacokinetic properties. Accordingly, the compounds provided herein are useful in pharmaceutical compositions, methods for the treatment of CCR6-mediated diseases, and as controls in assays for the identification of competitive CCR6 antagonists.

Compounds

In one aspect, provided herein are compounds of Formula I:

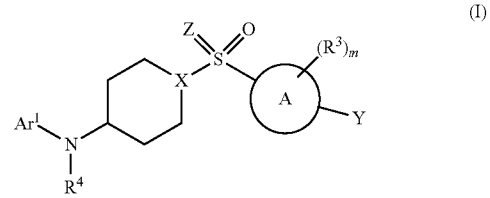

or a pharmaceutically acceptable salt, hydrate, solvate, N-oxide, optically enriched form, or rotamer thereof, wherein X is N or C H;

Z is O or N(R$^f$)—, wherein R$^f$ is selected from the group consisting of hydrogen, C$_{1-4}$ alkyl, C$_{1-4}$ haloalkyl, C$_{1-4}$ hydroxyalkyl, and C$_{3-6}$ cycloalkyl;

Ring A is a benzene or pyridine ring;

Ar$^1$ is a monocyclic 5- or 6-membered aromatic or heteroaromatic ring having 0 to 3 heteroatoms as ring vertices selected from N, O, and S, substituted with from 0 to 5 R$^1$ substituents independently selected from the group consisting of halogen, CN, C$_{1-8}$ alkyl, C$_{3-8}$ cycloalkyl, C$_{2-8}$ alkenyl, C$_{2-8}$ alkynyl, C$_{1-8}$ haloalkyl, C$_{1-8}$ hydroxyalkyl, —OR$^a$, and —NR$^a$R$^b$;

each R$^a$ and R$^b$ is independently selected from the group consisting of hydrogen, hydroxyl, C$_{1-4}$ alkyl, C$_{1-4}$ haloalkyl, C$_{1-4}$ hydroxyalkyl, and C$_{3-6}$ cycloalkyl;

Y is selected from the group consisting of:
  i) bicyclic 9- or 10-membered fused aromatic or heteroaromatic ring having 0 to 4 heteroatoms as ring vertices selected from N, O, S and S(O)$_2$, and which is substituted with 0 to 5 R$^2$;
  ii) 4- to 7-membered monocyclic heterocyclic ring having 1 or 2 heteroatoms as ring vertices selected from N, O, S and S(O)$_2$, and which is substituted with 0 to 5 R$^2$;
  iii) 6- to 12-membered fused or bridged heterocyclic ring having 1 to 4 heteroatoms as ring vertices selected from N, O, S and S(O)$_2$, and which is substituted with 0 to 6 R$^2$; and
  iv) 7- to 12-membered spiroheterocyclic ring having 0 to 4 heteroatoms as ring vertices selected from N, O and S, and which is substituted with 0 to 6 R$^2$;

each R$^2$ is independently selected from the group consisting of halogen, CN, C$_{1-8}$ alkyl, C$_{3-8}$ cycloalkyl, C$_{2-8}$ alkenyl, C$_{2-8}$ alkynyl, C$_{1-8}$ haloalkyl, C$_{1-8}$ hydroxyalkyl, —OR$^c$, —SR$^c$, —OSi(R$^c$)$_3$, —COR$^c$, —CO$_2$R$^c$, —NR$^c$R$^d$, —NR$^c$R$^d$, —CONR$^c$R$^d$, —(CO)$_2$NR$^c$R$^d$, —NR$^c$CO$_2$R$^d$, —NR$^c$COR$^d$, —NR$^c$CONR$^c$R$^d$, —NR$^c$SO$_2$R$^d$, —SO$_2$R$^d$, —CO—C$_{1-4}$ hydroxyalkyl, —SO$_2$NR$^c$R$^d$, —X$^2$—NR$^c$R$^d$, —X$^2$—CONR$^c$R$^d$, —X$^2$—NR$^c$CONR$^c$R$^d$, —X$^2$—NR$^c$CO$_2$R$^d$, —X$^2$—NR$^c$COR$^d$, —X$^2$—NR$^c$SO$_2$R$^d$, —CO—X$^2$—NR$^c$COR$^d$, oxo, 4- to 7-membered heterocyclic ring having 1 or 2 heteroatoms as ring vertices selected from N, O, S and S(O)$_2$, 5- or 6-membered heteroaryl, and —X$^2$-5- or 6-membered heteroaryl; and wherein the 5- or 6-membered heteroaryl ring and the 4- to 7-membered heterocyclic ring of R$^2$ have from 1 to 3 heteroatoms selected from N, O, and S, and are each unsubstituted or substituted with one or two members independently selected from the group consisting of halogen, hydroxyl, amino, C$_{1-4}$ alkyl, C$_{1-4}$ alkoxy, C$_{1-4}$ haloalkyl, —COR$^c$, —CO$_2$R$^c$, and —CONR$^c$R$^d$; and wherein two R$^2$ groups attached to the same carbon atom are optionally combined to form a 3- to 6-membered spirocyclic ring or a 3- to 6-membered spiroheterocyclic ring having 1 to 3 heteroatoms as ring vertices selected from N, O and S, and which is unsubstituted or substituted with 1 or 2 members independently selected from C$_{1-4}$ alkyl, —COR$^c$, —CO$_2$R$^c$, and —CONR$^c$R$^d$;

each R$^c$ and R$^d$ is independently selected from the group consisting of hydrogen, hydroxyl, C$_{1-6}$ alkyl, C$_{1-6}$ haloalkyl, C$_{1-6}$ hydroxyalkyl, and C$_{3-6}$ cycloalkyl; or R$^c$ and R$^d$, when attached to the same nitrogen atom are joined to form a 4- to 7-membered heterocyclic ring having from 0 to 2 additional heteroatoms as ring vertices selected from O, S, S(O), S(O)$_2$, NH and N(C$_{1-4}$ alkyl);

each R$^e$ is selected from the group consisting of phenyl;

X$^2$ is C$_{1-4}$ alkylene or cyclopropyl;

the subscript m is 0, 1 or 2;

each R$^3$ is a member independently selected from the group consisting of halogen, CN, C$_{1-4}$ alkyl, C$_{1-4}$ alkoxy, C$_{3-8}$ cycloalkyl, C$_{1-4}$ haloalkyl, C$_{1-4}$ haloalkoxy, and C$_{2-4}$ hydroxyalkyl; and R$^4$ is a member selected from the group consisting of H, C$_{1-4}$ alkyl, C$_{3-8}$ cycloalkyl, and C$_{1-4}$ haloalkyl.

In one group of embodiments, compounds of Formula (I) are provided wherein Y is a bicyclic 9- or 10-membered fused aromatic or heteroaromatic ring having 0 to 4 heteroatoms as ring vertices selected from N, O and S, and which is substituted with 0 to 5 R$^2$. In some embodiments, Y is substituted with 0, 1, 2, 3 or 4 R$^2$ substituents. In related embodiments, compounds of Formula (I) are provided wherein Y is a bicyclic 9- or 10-membered fused aromatic or heteroaromatic ring selected from the group consisting of

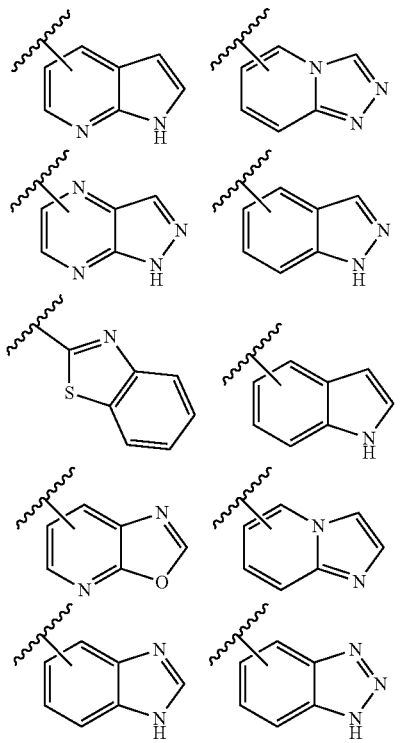

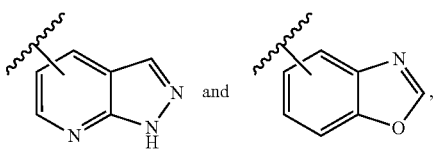

each of which is substituted with 0 to 5 R$^2$. In some embodiments, Y is substituted with 0, 1, 2, 3 or 4 R$^2$ substituents. In other related embodiments, compounds of Formula (I) are provided wherein Y is a bicyclic 9- or 10-membered fused aromatic or heteroaromatic ring selected from the group consisting of

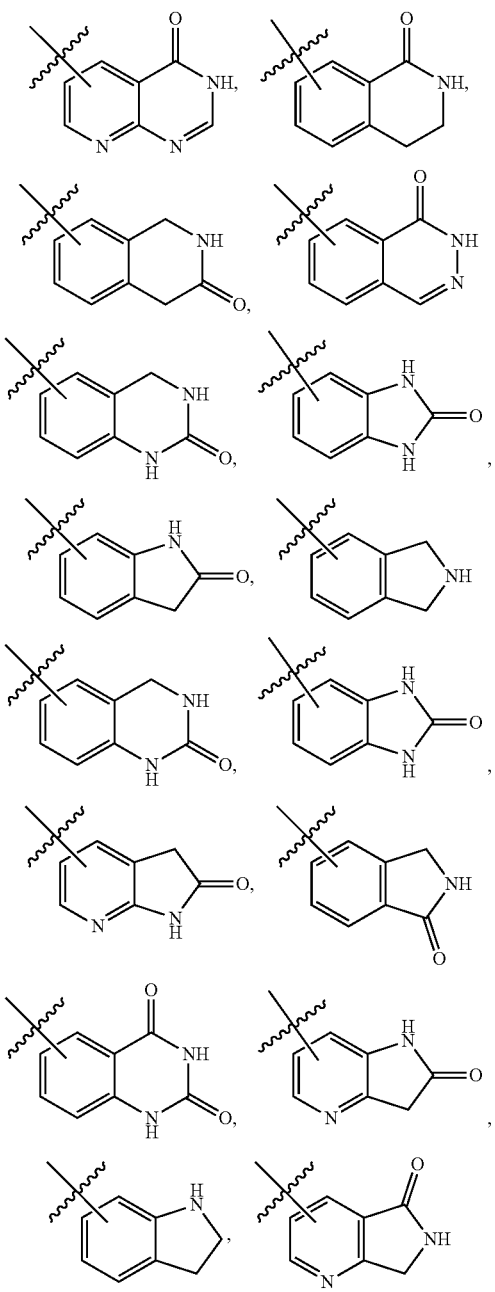

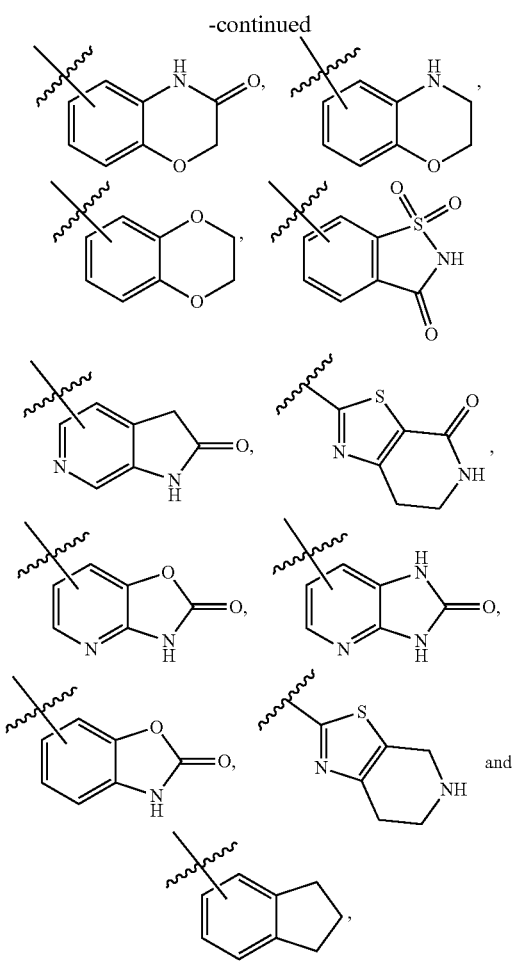

each of which is substituted with 0 to 3 $R^2$. In some embodiments, Y is substituted with 0, 1, 2, or 3 $R^2$ substituents. In still other related embodiments, compounds of Formula (I) are provided wherein Y is a bicyclic 9- or 10-membered fused aromatic or heteroaromatic ring selected from the group consisting of

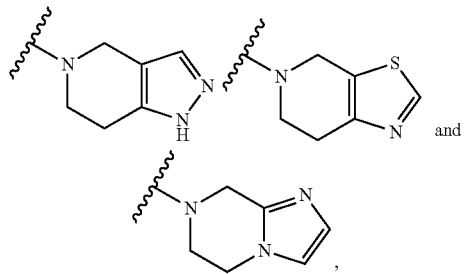

each of which is substituted with 0 to 5 $R^2$. In some embodiments, Y is substituted with 0, 1, 2, 3 or 4 $R^2$ substituents.

In another group of embodiments, compounds of Formula (I) are provided wherein Y is a 4- to 7-membered monocyclic heterocyclic ring having 1 or 2 heteroatoms as ring vertices selected from N, O and S, and which is substituted with 0 to 5 $R^2$. In some embodiments, Y is substituted with 0, 1, 2, 3 or 4 $R^2$ substituents. In some related embodiments, Y is a 4- to 7-membered monocyclic heterocyclic ring selected from the group consisting of azetidine, pyrrolidine, piperidine, piperazine, morpholine, thiomorpholine, dihydropyran, tetrahydropyridine and diazepine, and which is substituted with 0 to 5 $R^2$, and in some embodiments, each Y ring is substituted with 0, 1, 2, 3 or 4 $R^2$ substituents. In other related embodiments, Y is a 4- to 7-membered monocyclic heterocyclic ring selected from the group consisting of

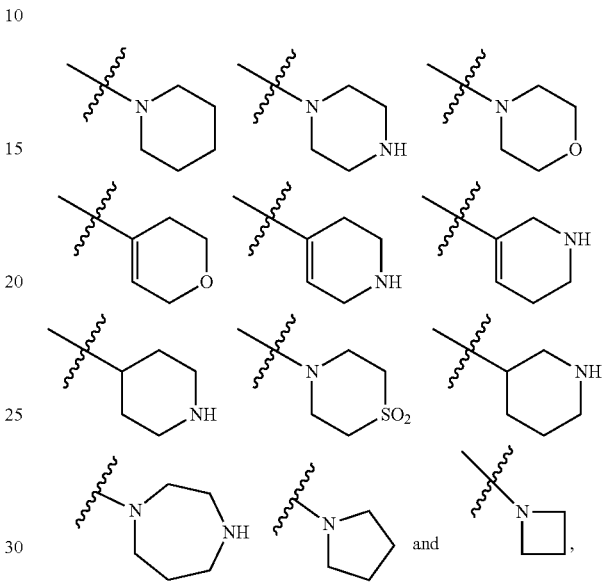

each of which is substituted with 0 to 5 $R^2$. In some embodiments, each Y is substituted with 0, 1, 2, 3 or 4 $R^2$ substituents.

In yet another group of embodiments, compounds of Formula (I) are provided wherein Y is a 6- to 12-membered fused or bridged heterocyclic ring having 1 to 4 heteroatoms as ring vertices selected from N, O and S, and which is substituted with 0 to 6 $R^2$. In some embodiments, Y is substituted with 0, 1, 2, 3, 4 or 5 $R^2$ substituents. In some related embodiments, Y is a 6- to 12-membered fused or bridged heterocyclic ring selected from the group consisting of

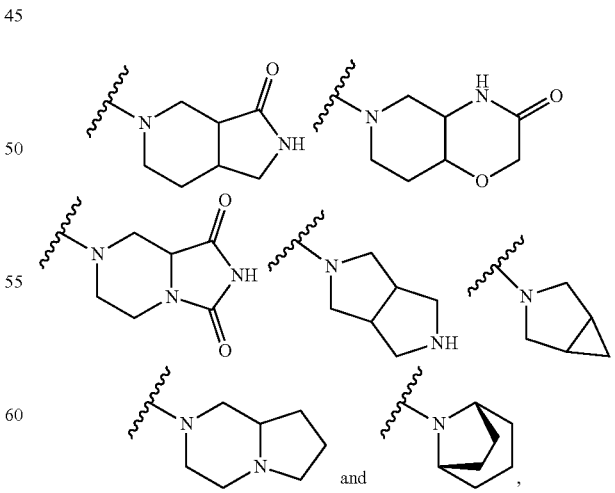

each of which is substituted with 0 to 4 $R^2$. In some embodiments, each Y is substituted with 0, 1, 2, or 3 $R^2$ substituents.

In still another group of embodiments, compounds of Formula (I) are provided wherein Y is a 7- to 12-membered spiroheterocyclic ring having 1 to 4 heteroatoms as ring vertices selected from N, O and S, and which is substituted with 0 to 6 R². In some embodiments, Y is substituted with 0, 1, 2, 3, 4 or 5 R² substituents. In some related embodiments, Y is a 7- to 12-membered spiroheterocyclic ring selected from the group consisting of

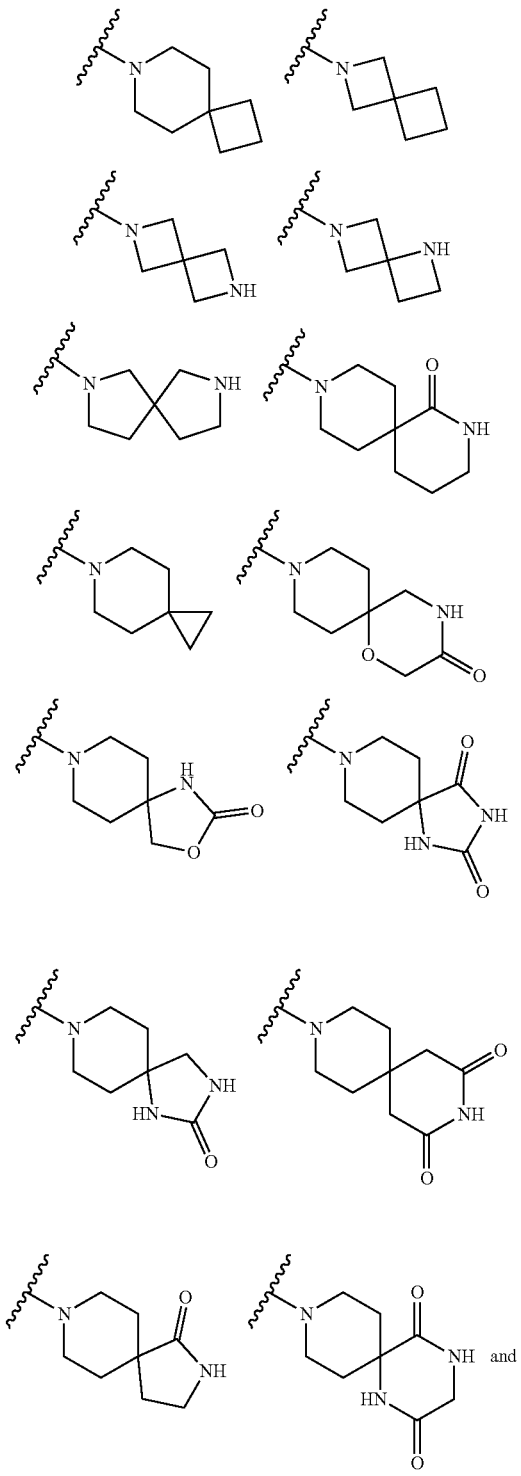

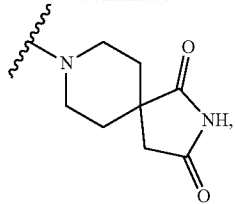

each of which is substituted with 0 to 4 R². In some embodiments, each Y is substituted with 0, 1, 2, or 3 R² substituents.

In some embodiments, compounds of Formula (I), or any embodiments noted above, are provided wherein Ar¹ is phenyl, substituted with from 1 to 3 R¹ substituents.

In other embodiments, compounds of Formula (I) or any embodiments noted above for the 'Y' groups, are provided wherein Ar¹ is pyridyl, substituted with from 1 to 3 R¹ substituents.

In some embodiments, compounds of Formula (I), or any embodiments noted above, are provided wherein R³ is H, Z is O, and X is N. In other embodiments, compounds of Formula (I) are provided (as well as any embodiments noted above for Y and Ar¹ or combinations), wherein R³ is H, Z is O, and X is CH.

In some embodiments, compounds of Formula (I), or any embodiments noted above, are provided having Formula (Ia):

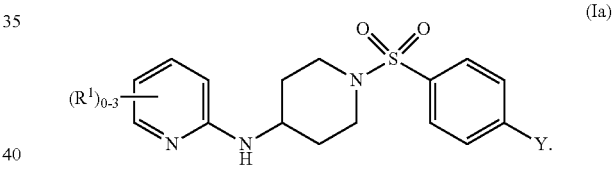

(Ia)

In some selected embodiments, compounds of Formula (Ia) are provided wherein each R¹ is independently selected from the group consisting of CH₃, CF₃ and CN. In one group of embodiments, compounds of Formula (Ia) are provided wherein Y is a bicyclic 9- or 10-membered fused aromatic or heteroaromatic ring having 0 to 4 heteroatoms as ring vertices selected from N, O, S and S(O)₂, and which is substituted with 0 to 5 R². In another group of embodiments, compounds of Formula (Ia) are provided wherein Y is a 6- to 12-membered fused or bridged heterocyclic ring having 1 to 4 heteroatoms as ring vertices selected from N, O, S and S(O)₂, and which is substituted with 0 to 6 R². In yet another group of embodiments, compounds of Formula (Ia) are provided wherein Y is a 7- to 12-membered spiroheterocyclic ring having 0 to 4 heteroatoms as ring vertices selected from N, O and S, and which is substituted with 0 to 5 R². In still another group of embodiments, compounds of Formula (Ia) are provided wherein Y is a 4- to 7-membered monocyclic heterocyclic ring having 1 or 2 heteroatoms as ring vertices selected from N, O, S and S(O)₂, and which is substituted with 0 to 5 R².

In other embodiments, compounds of Formula (I), or any embodiments noted above, are provided having Formula (Ia1):

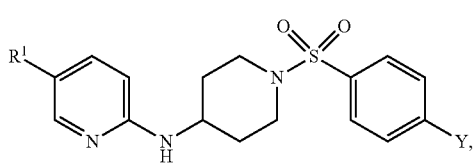
(Ia1)
wherein R¹ is —CN or —CF₃.
In some embodiments, compounds of Formula (Ia1) are provided wherein Y is selected from the group consisting of:
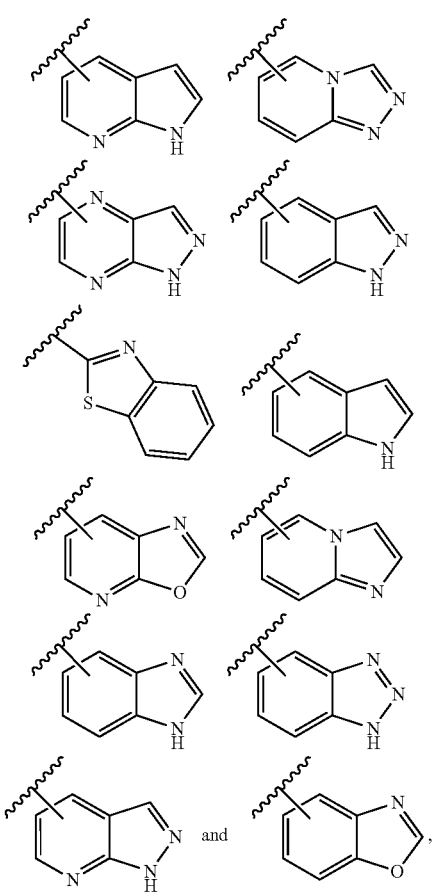
each of which is substituted with 0 to 5 R².
In some embodiments, compounds of Formula (Ia1) are provided wherein Y is selected from the group consisting of:
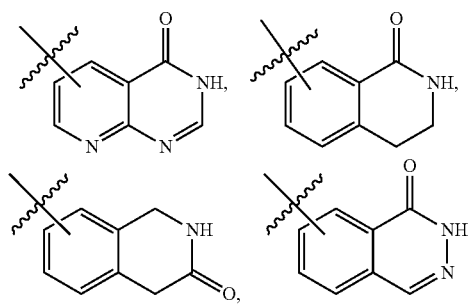
-continued
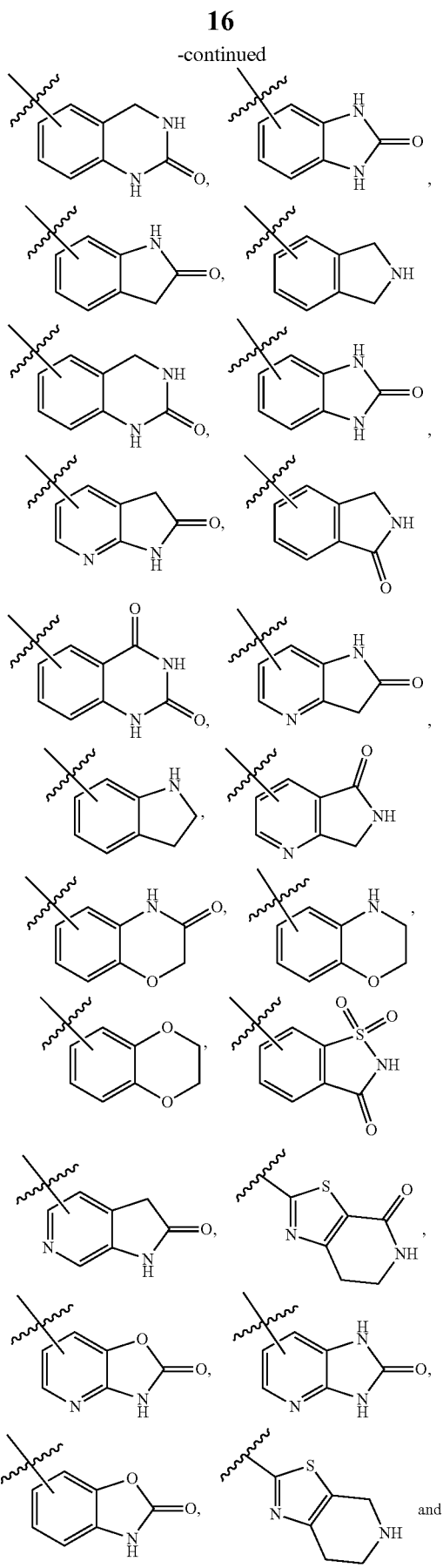
and

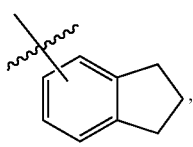

each of which is substituted with 0 to 3 $R^2$.

In some embodiments, compounds of Formula (Ia1) are provided wherein Y is selected from the group consisting of:

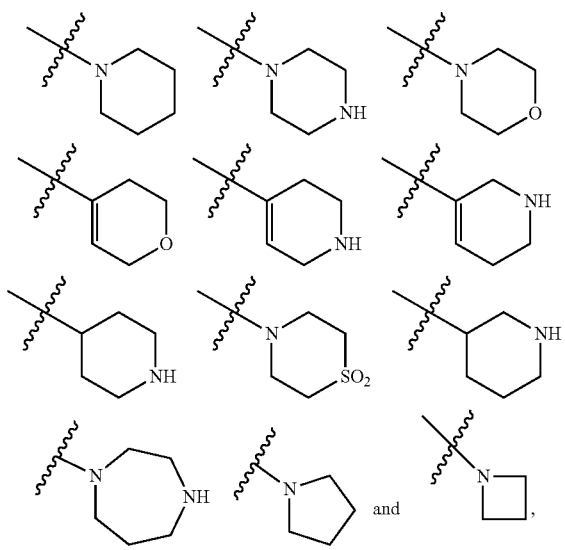

each of which is substituted with 0 to 5 $R^2$.

In some embodiments, compounds of Formula (Ia1) are provided wherein Y is selected from the group consisting of:

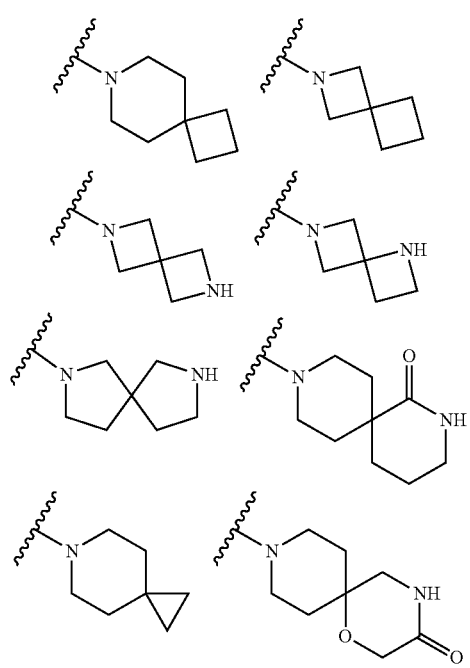

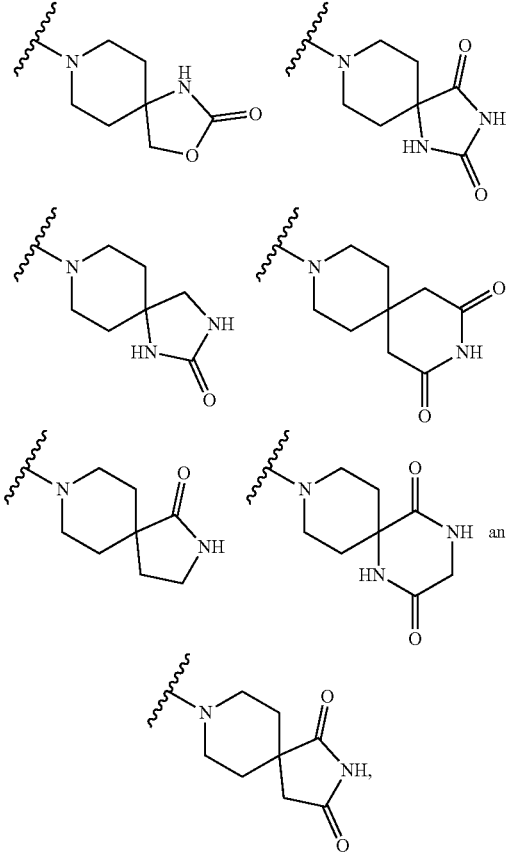

each of which is substituted with 0 to 4 $R^2$.

In some embodiments, including the embodiments noted above, the subscript m is 0 ($R^3$ is absent). In other embodiments, including the embodiments noted above, the subscript m is 1. In still other embodiments, including the embodiments noted above, the subscript m is 2.

In still other selected embodiments, the compounds of Formula (I) are selected from the compounds provided in Table 1.

For all of the embodiments noted above, each compound is also provided as additional embodiments as a pharmaceutically acceptable salt, hydrate, solvate, N-oxide or rotamer thereof, in addition to a free base or otherwise neutral form.

Preparation of Compounds

The schemes in the Examples below provide certain synthetic routes that can be followed to access certain compounds of the present invention. Other routes or modification of the routes presented below would be readily apparent to a skilled artisan and are within the scope of the present invention.

General Synthetic Methods

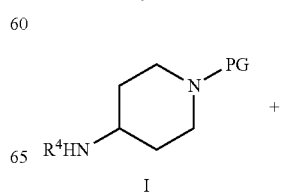

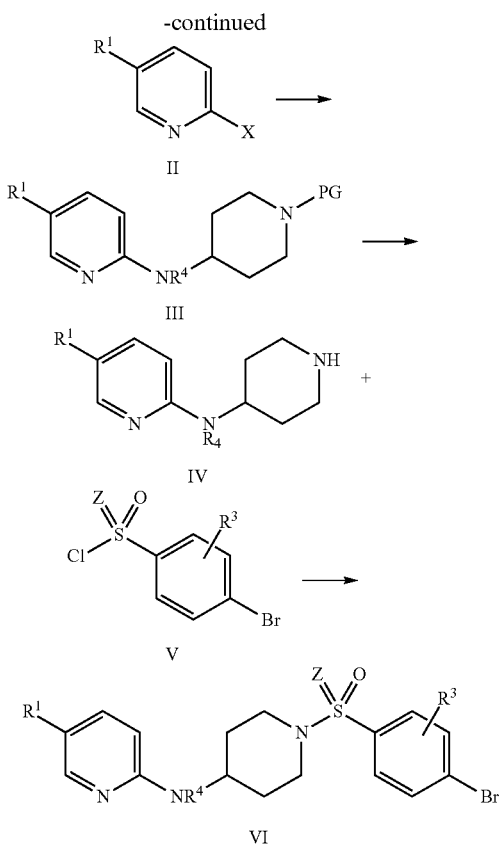

Suitably 1-N-protected 4-amino-piperidines I can be reacted with 2-halo-5-substituted pyridines II (X=F or Cl) and base in an S$_N$Ar displacement reaction to form 4-aminopyridyl piperidines III. The protecting group can be removed under appropriate conditions to give 1-NH piperidines IV as a free-base or protonated species with counterion. This amine can be further treated with base and 4-bromosulfonyl chlorides V bearing, substitutions if required, in a sulfonamidation reaction to give 4-aminopyridyl-1-N-sulfonamides VI.

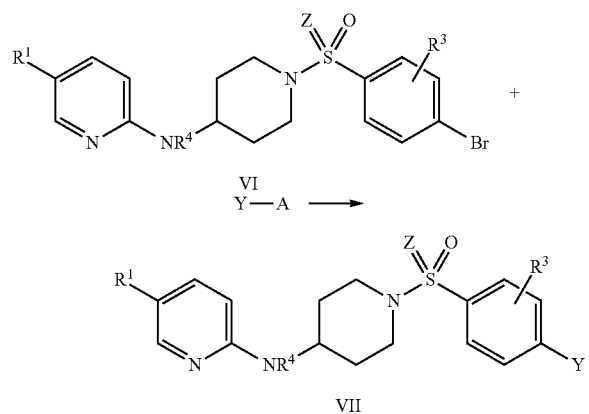

4-Aminopyridyl-1-N-piperidinyl-sulfonamides VI can be further elaborated in a direct Suzuki cross-coupling reaction (A=Boron species; Aryl/Hetaryl boronic acids or esters) or a Miyura Bromide/Boronic ester exchange on bromide VI, followed by Suzuki coupling with Aryl/Hetaryl bromides (A=Br) to give final compounds VII.

Pharmaceutical Compositions

In addition the compounds provided above, the compositions for modulating CCR6, activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug.

Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

Methods of Treating Diseases Modulated by CCR6

In one aspect, the present invention provides methods of treating or preventing a CCR6-mediated condition or disease by administering to a subject having such a condition or disease, a therapeutically effective amount of any compound of the invention. Preferred compounds for use in the present methods are those compounds provided above as preferred embodiments, as well as compounds specifically exemplified in the Examples below, and provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR6-mediated condition or disease" and related phrases and terms refer to a condition or disease characterized by inappropriate, e.g., less than or greater than normal, CCR6 functional activity. Inappropriate CCR6 functional activity might arise as the result of CCR6 expression in cells which normally do not express CCR6, increased CCR6 expression (leading to, e.g., inflammatory and immunoregulatory disorders and diseases) or decreased CCR6 expression. Inappropriate CCR6 functional activity might also arise as the result of CCL20 secretion by cells which normally do not secrete CCL20, increased CCL20 expression (leading to, e.g., inflammatory and immunoregulatory disorders and diseases) or decreased CCL20 expression. A CCR6-mediated condition or disease may be completely or partially mediated by inappropriate CCR6 functional activity. However, a CCR6-mediated condition or disease is one in which modulation of CCR6 results in some effect on the underlying condition or disease (e.g., a CCR6 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated or prevented with the present compounds and compositions. In one group of embodiments, diseases or conditions, including chronic diseases, of humans or other species can be treated with inhibitors of CCR6 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, Vitiligo (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic) as well as for instance Hashimoto's thyroiditis and Grave's disease, multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

Preferably, the present methods are directed to the treatment of diseases or conditions selected from allergic diseases, psoriasis, skin conditions such as atopic dermatitis and asthma and scleroderma.

In another group of embodiments, modulation of CCR6 dependent regulatory T cell trafficking may be modulated to treat diseases or conditions including cancers, infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

Those of skill in the art will understand that agents that modulate CCR6 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiaition.

The compounds of the present invention are accordingly useful in the prevention and treatment of a wide variety of inflammatory and immunoregulatory disorders and diseases.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®), Tofacitinib (Xeljanz®) and other FK-506 type immunosuppressants, and rycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106, 203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi®), rituximab (Rituxan®), tocilizumab (Actemra®), (1) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (0-la (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide (u) other compounds such as 5-aminosalicylic acid and prodrugs thereof, hydroxychloroquine; D-penicillamine; antimetabolites such as azathioprine, 6-mercaptopurine and methotrexate; DNA synthesis inhibitors such as hydroxyurea and microtubule disrupters such as colchicine and proteasome inhibitors such as bortezomib (Velcade®). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

The following examples are offered to illustrate, but not to limit the claimed invention.

Reagents and solvents used below can be obtained from commercial sources such as Aldrich Chemical Co. (Milwaukee, Wisconsin, USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes.

Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention:
HPLC, High Pressure Liquid Chromatography; DMF, Dimethyl formamide; TFA, Trifluoroacetic Acid; THF, Tetrahydrofuran; EtOAc, Ethyl acetate; $BOC_2O$, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; $Pd_2(dba)_3$, Tris(dibenzylideneacetone)dipalladium (0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Procedure for N-(1-((4-bromophenyl)sulfonyl)piperidin-4-yl)-5-(trifluoromethyl)pyridin-2-amine (Intermediate 1)

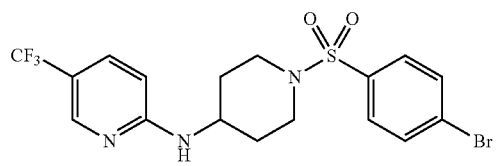 [SMILES: O=S(=O)(c1ccc(Br)cc1)N1CCC(Nc2ccc(C(F)(F)F)cn2)CC1]

Step a: To a round-bottom flask were added 1-Boc-4-aminopiperidine (10.01 g, 50.0 mmol, 1.0 equiv), $K_2CO_3$ (20.73 g, 150.0 mmol, 3.0 equiv), DMF (100 mL), and 2-fluoro-5-(trifluoromethyl)-pyridine (12.1 mL, 100.0 mmol, 2.0 equiv). The reaction mixture was stirred at 100° C. overnight. The reaction mixture was cooled to rt, diluted with $H_2O$ (200 mL) and brine (100 mL), and extracted with EtOAc (3×200 mL). The combined organic layers were washed with brine (2×100 mL), dried over $MgSO_4$, filtered, and concentrated. Purification by silica gel column chromatography (0-100% MTBE/hexanes) yielded tert-butyl 4-((5-(trifluoromethyl)pyridin-2-yl)amino)piperidine-1-carboxylate as a pale yellow solid.

Step b: To a round-bottom flask were added tert-butyl 4-((5-(trifluoromethyl)pyridin-2-yl)amino)piperidine-1-carboxylate (11.37 g, 32.9 mmol, 1.0 equiv), dioxane (100 mL), and 4 M HCl/dioxane (100 mL). The reaction mixture was stirred at rt overnight. The reaction mixture was concentrated and dried under vacuum to yield N-(piperidin-4-yl)-5-(trifluoromethyl)pyridin-2-amine hydrochloride as an off-white solid.

Step c: To a round-bottom flask were added N-(piperidin-4-yl)-5-(trifluoromethyl)pyridin-2-amine hydrochloride (4.23 g, 15.0 mmol, 1.0 equiv), THF (75 mL), $iPr_2NEt$ (10.5 mL, 60.0 mmol, 4.0 equiv), and 4-bromobenzensulfonyl chloride (5.75 g, 22.5 mmol, 1.5 equiv). The reaction mixture was stirred at rt for 1 h. The resulting solid was filtered, and the filtrate was concentrated. Purification by silica gel column chromatography (0-100% EtOAc/hexanes) yielded N-(1-((4-bromophenyl)sulfonyl)piperidin-4-yl)-5-(trifluoromethyl)pyridin-2-amine as a pale yellow solid.

General Procedure for N-(1-((4-(4,4,5,5-tetramethyl-1,3,2-dioxaborolan-2-yl)phenyl)sulfonyl)piperidin-4-yl)-5-(trifluoromethyl)pyridin-2-amine (Intermediate 2)

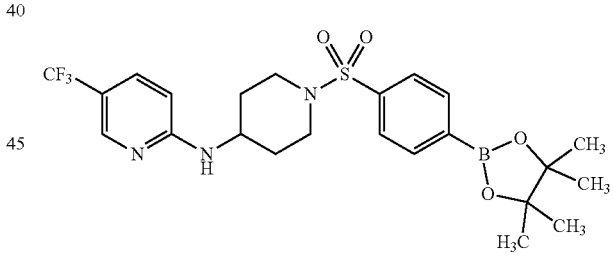

To a 50-mL rbf equipped with stir bar are added the bromide (1.0 equiv), bis(pinacolato)diboron (2.0 equiv), KOAc (2.0 equiv), and $Pd(dppf)Cl_2.DCM$ (0.1 equiv). The reaction vessel is placed under vacuum for 2 min. Next, anhydrous dioxane (~15-20 mL, from a fresh bottle) is added to the reaction vessel via syringe and $N_2$ gas is bubbled through the reaction mixture for 2 min. The reaction is heated to 100° C. for 16 h and monitored by LC-MS.

Once product conversion is complete, the crude reaction contents are adhered to Celite® and a normal phase column is run using EtOAc:hex (product elutes at 50% EtOAc). Fractions containing product are combined and concentrated under reduced pressure to yield an off-white solid. N-(1-((4-(4,4,5,5-tetramethyl-1,3,2-dioxaborolan-2-yl)phenyl)sulfonyl)piperidin-4-yl)-5-(trifluoro-methyl)pyridin-2-amine

Example 1: 1-(2-(dimethylamino)ethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile

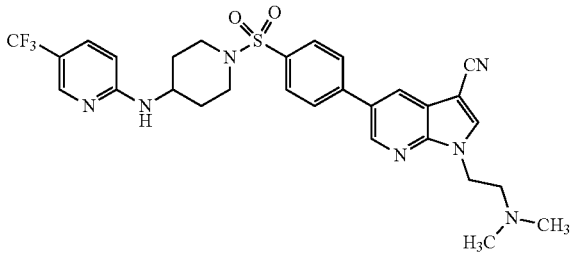 [SMILES: CN(C)CCn1cc(C#N)c2cc(-c3ccc(S(=O)(=O)N4CCC(Nc5ccc(C(F)(F)F)cn5)CC4)cc3)cnc21]

To a solution of 1-(2-aminoethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile (40 mg; 0.06 mmol) in 1 mL of $CH_3CN$ is added AcOH (100 uL; 1.6 mmol) and Formalin (50 uL). The mixture stirs for 1 h. To this is added $NaBH(CN)_3$ (10 mg, 0.15 mmol). The mixture stirs at RT for 60 h. LC-MS indicates the desired product. The reaction is cooled diluted with 50 mL of EtOAc, filtered through a syringe filter and concentrated. The material is purified by reverse phase preparative HPLC to give 1-(2-(dimethylamino)ethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile. MS: (ES) m/z calculated for $C_{29}H_{30}F_3N_7O_2S$ $[M+H]^+$ 598.2, found 598.0. $^1$H NMR (400 MHz, DMSO-$d_6$) δ 8.87 (d, J=2.1 Hz, 1H), 8.63 (s, 1H), 8.59 (d, J=2.1 Hz, 1H), 8.23-8.16 (m, 1H), 8.11 (d, J=8.2 Hz, 1H), 7.86 (d, J=8.2 Hz, 2H), 7.59 (dd, J=8.9, 2.5 Hz, 1H), 7.34 (d, J=7.3 Hz, 1H), 6.53 (d, J=9.0 Hz, 1H), 4.75 (t, J=6.1 Hz, 2H), (m, 5H), 2.87 (d, J=4.4 Hz, 6H), 2.60-2.36 (m, 2H), 2.01-1.92 (m, 2H), 1.50 (q, J=11.3, 10.7 Hz, 2H).

Example 2: 1'-(2-Aminoethyl)-5'-(4-((4-((5-(trifluoromethyl)pyridin-2-yl)amino)piperidin-1-yl)sulfonyl)phenyl)spiro[cyclopropane-1,3'-pyrrolo[2,3-b]pyridin]-2'(1'H)-one

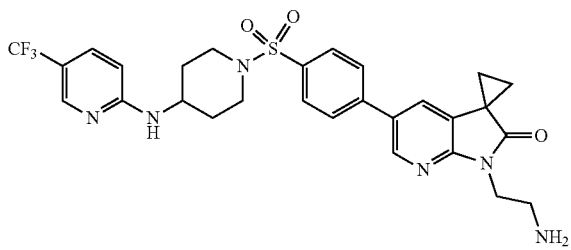 [SMILES: NCCN1C(=O)C2(CC2)c2cc(-c3ccc(S(=O)(=O)N4CCC(Nc5ccc(C(F)(F)F)cn5)CC4)cc3)cnc21]

Step a: To a solution of tert-butyl (2-(2'-oxo-5'-(4-((4-((5-(trifluoromethyl)pyridin-2-yl)amino)piperidin-1-yl)sulfonyl)phenyl)spiro[cyclopropane-1,3'-pyrrolo[2,3-b]pyridin]-1'(2'H)-yl)ethyl)carbamate (88.0 mg; 0.13 mmol) in 1 mL of $CH_2Cl_2$ was added 1 mL of TFA. The mixture stirred for 16 h. LC-MS indicated the desired product. The mixture was concentrated to give 1'-(2-aminoethyl)-5'-(4-((4-((5-(trifluoromethyl)pyridin-2-yl)amino)piperidin-1-yl)sulfonyl)phenyl)spiro[cyclopropane-1,3'-pyrrolo[2,3-b]pyridin]-2'(1'H)-one. MS: (ES) m/z calculated for $C_{28}H_{29}F_3N_6O_3S$ $[M+H]^+$ 587.2, found 587.0 $^1$H NMR (400 MHz, DMSO-$d_6$) δ 8.53 (d, J=2.1 Hz, 1H), 8.20 (d, J=2.5 Hz, 1H), 7.95 (d, J=8.2 Hz, 2H), 7.86 (d, J=2.1 Hz, 1H), 7.81 (d, J=8.5 Hz, 2H), 7.58 (dd, J=9.0, 2.6 Hz, 1H), 7.29 (d, J=7.3 Hz, 1H), 6.52 (d, J=8.9 Hz, 1H), 3.81 (td, J=24.3, 21.7, 11.9 Hz, 2H), 3.55 (d, J=12.1 Hz, 2H), 2.82 (t, J=6.9 Hz, 1H), 2.60-2.43 (m, 2H), 1.98-1.90 (m, 2H), 1.82 (q, J=4.0 Hz, 2H), 1.71-1.56 (m, 2H), 1.56-1.41 (m, 2H).

Step b: 2-(2-((tert-butyldimethylsilyl)oxy)ethyl)-5-(4-((4-((5-(trifluoromethyl)pyridin-2-yl)amino)piperidin-1-yl)sulfonyl)phenyl)isoindolin-1-one (38.9 mg; 0.06 mmol) in 1 mL of THF was added 0.1 mL of 1 M TBAF in THF. The mixture stirred for 1 h. LC-MS indicates the desired product. The reaction was diluted with 10 mL of EtOAc, washed with 3×5 mL of $H_2O$ and 10 mL of brine. The organic phase was dried with $MgSO_4$, filtered and concentrated. The crude residue was purified by $SiO_2$ prep plate chromatography to give 2-(2-hydroxyethyl)-5-[4-[[4-[[5-(trifluoromethyl)-2-pyridyl]amino]-1-piperidyl]sulfonyl]phenyl]isoindolin-1-one. (ES) m/z calculated for $C_{27}H_{27}F_3N_4O_4S$ $[M+H]^+$ 561.2, found 560.9. $^1$H NMR (400 MHz, DMSO-$d_6$) δ 8.20 (d, J=2.4 Hz, 1H), 7.99 (dd, J=9.2, 2.4 Hz, 3H), 7.85 (dd, J=8.4, 2.0 Hz, 3H), 7.78 (d, J=7.9 Hz, 1H), 7.58 (dd, J=9.1, 2.6 Hz, 1H), 7.29 (d, J=7.4 Hz, 1H), 6.52 (d, J=8.8 Hz, 1H), 4.93-4.79 (m, 1H), 4.62 (s, 2H), 3.76 (bs, 1H), 3.67-3.52 (m, 6H), 2.63-2.40 (m, 2H), 1.95 (d, J=12.7 Hz, 2H), 1.58-1.43 (m, 2H).

Example 3: 1-(2-(3-Cyano-5-(4-((4-((5-(trifluoromethyl)pyridin-2-yl)amino)piperidin-1-yl)sulfonyl)phenyl)-1H-pyrrolo[2,3-b]pyridin-1-yl)ethyl)urea

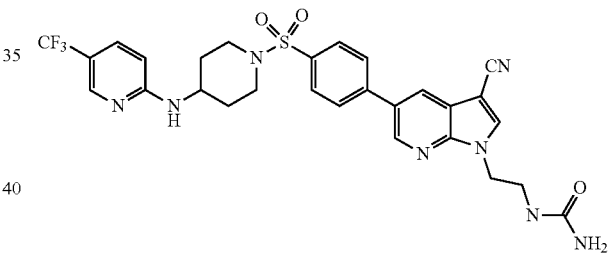

To a solution of 1-(2-aminoethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile (50 mg; 0.08 mmol) in 2 mL of $CH_3CN$ was added DIPEA (68 uL, 0.38 mmol) and TMS isocyanate (23.5 uL, 0.17 mmol). The mixture was stirred at RT for 2 h. LC-MS indicates the desired product. The reaction is concentrated, diluted with 15 mL of EtOAc, washed with 10 mL of sat $NH_4Cl$ and sat. brine. The organic phase is dried with $MgSO_4$, filtered and concentrated. The residue purified by $SiO_2$ chromatography to give 1-(2-(3-Cyano-5-(4-((4-((5-(trifluoromethyl)pyridin-2-yl)amino)piperidin-1-yl)sulfonyl)phenyl)-1H-pyrrolo[2,3-b]pyridin-1-yl)ethyl)urea (27.3 mg; 0.04 mmol, 57.3% yield). MS: (ES) m/z calculated for $C_{28}H_{27}F_3N_8O_3S$ $[M+H]^+$ 613.2, found 612.9. $^1$H NMR (400 MHz, DMSO-$d_6$) δ 8.83 (d, J=2.1 Hz, 1H), 8.53-8.43 (m, 2H), 8.20 (d, J=2.5 Hz, 1H), 8.10 (d, J=8.4 Hz, 2H), 7.84 (d, J=8.3 Hz, 2H), 7.58 (dd, J=8.9, 2.6 Hz, 1H), 7.30 (d, J=7.4 Hz, 1H), 6.53 (d, J=8.9 Hz, 1H), 6.06 (t, J=6.0 Hz, 1H), 4.37 (t, J=5.8 Hz, 2H), 3.74 (d, J=12.9 Hz, 1H), 3.58 (t, J=12.0 Hz, 2H), 3.46 (q, J=5.9 Hz, 2H), 2.63-2.40 (m, 2H), 2.00-1.90 (m, 2H), 1.49 (q, J=13.1, 11.9 Hz, 2H).

Example 4: tert-Butyl (2-(2'-oxo-5'-(4-((4-((5-(trifluoromethyl)pyridin-2-yl)amino)piperidin-1-yl)sulfonyl)phenyl)spiro[cyclopropane-1,3'-pyrrolo[2,3-b]pyridin]-1'(2'H)-yl)ethyl)carbamate

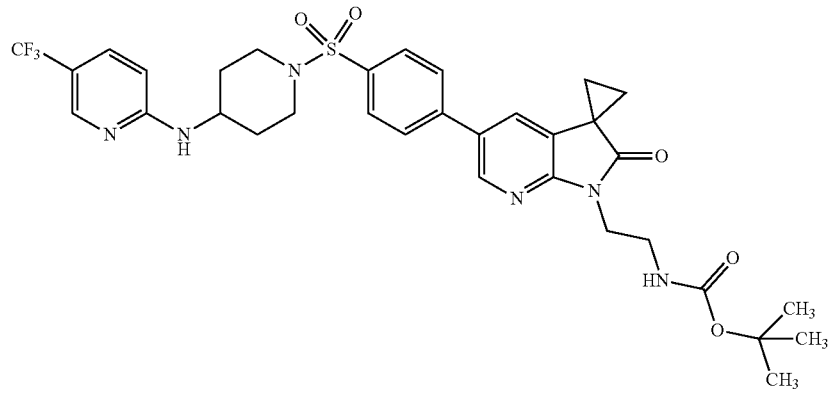 [SMILES: CC(C)(C)OC(=O)NCCN1C(=O)C2(CC2)c2cc(-c3ccc(S(=O)(=O)N4CCC(Nc5ccc(C(F)(F)F)cn5)CC4)cc3)cnc21]

To N-[1-[4-(4,4,5,5-tetramethyl-1,3,2-dioxaborolan-2-yl)phenyl]sulfonyl-4-piperidyl]-5-(trifluoromethyl)pyridin-2-amine (150.0 mg, 0.30 mmol) in 4.8 mL dioxane were added $K_2CO_3$ (75.0 mg, 0.54 mmol), tert-butyl N-[2-(5'-bromo-2'-oxo-spiro[cyclopropane-1,3'-pyrrolo[2,3-b]pyridine]-1'-yl)ethyl]carbamate (150.0 mg, 0.39 mmol), Pd(dppf)Cl$_2$.DCM (27.0 mg, 0.03 mmol) and 1.2 mL of water. The mixture was sparged with nitrogen for 10 minutes. The vial was sealed, the mixture stirred at 100° C. for 2 h, and cooled when the reaction had proceeded to completion. The mixture was purified via $SiO_2$ gel chromatography, to give tert-butyl (2-(2'-oxo-5'-(4-((4-((5-(trifluoromethyl)pyridin-2-yl)amino)piperidin-1-yl)sulfonyl)phenyl)spiro[cyclopropane-1,3'-pyrrolo[2,3-b]pyridin]-1'(2'H)-yl)ethyl)carbamate. MS: (ES) m/z calculated for $C_{33}H_{37}F_3N_6O_5SSi$ [M+H]$^+$ 687.3, found 687.0. $^1$H NMR (400 MHz, DMSO-d$_6$) δ 8.52 (d, J=2.1 Hz, 1H), 8.20 (d, J=2.7 Hz, 1H), 7.94 (d, J=8.2 Hz, 2H), 7.90-7.77 (m, 3H), 7.58 (dd, J=9.0, 2.5 Hz, 1H), 7.29 (d, J=7.3 Hz, 1H), 6.94 (t, J=6.0 Hz, 1H), 6.52 (d, J=9.0 Hz, 1H), 3.84 (q, J=8.5, 7.2 Hz, 2H), 3.75 (s, 1H), 3.61-3.50 (m, 2H), 2.60-2.40 (m, 3H), 1.95 (d, J=13.3 Hz, 2H), 1.80 (q, J=3.8 Hz, 2H), 1.61 (q, J=4.5, 3.9 Hz, 2H), 1.48 (q, J=12.3, 11.3 Hz, 2H), 1.29 (s, 9H).

Example 5: 2-Oxo-5-(4-((4-((5-(trifluoromethyl)pyridin-2-yl)amino)piperidin-1-yl)sulfonyl)phenyl)indoline-7-carboxamide

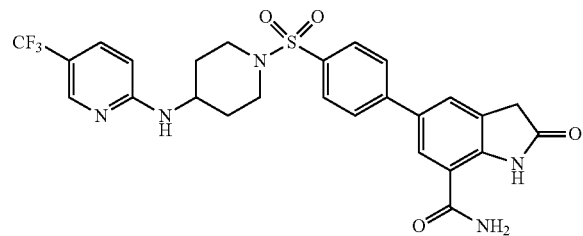 [SMILES: NC(=O)c1cc(-c2ccc(S(=O)(=O)N3CCC(Nc4ccc(C(F)(F)F)cn4)CC3)cc2)cc2c1NC(=O)C2]

To methyl 2-oxo-5-(4-((4-((5-(trifluoromethyl)pyridin-2-yl)amino)piperidin-1-yl)sulfonyl)phenyl)indoline-7-carboxylate in a septum-cap vial were added (NH$_4$)$_2$CO$_3$ (21 mg, 0.22 mmol), HATU (25 mg, 0.067 mmol) and 1 mL DMF, followed by DIPEA (39 µL, 0.22 mmol). The reaction stirred at RT for 1 hour. Once complete, the reaction was quenched with dI H$_2$O, and purified via reverse-phase HPLC to give 2-oxo-5-(4-((4-((5-(trifluoromethyl)pyridin-2-yl)amino)piperidin-1-yl)sulfonyl)phenyl)indoline-7-carboxamide. MS: (ES) m/z calculated for $C_{26}H_{24}F_3N_5O_4S$ [M+H]$^+$ 560.2, found 560. $^1$H NMR (400 MHz, DMSO-d$_6$) δ 9.99 (s, 1H), 8.31 (s, 1H), 8.23 (s, 1H), 8.12 (s, 1H), 8.02-7.97 (m, 2H), 7.85-7.79 (m, 3H), 7.65-7.59 (m, 2H), 7.42 (bs, 1H), 6.58 (d, J=9.0 Hz, 1H), 3.81-3.69 (m, 1H), 3.65-3.54 (m, 4H), 2.62-2.51 (m, 2H), 2.02-1.92 (m, 2H), 1.57-1.42 (m, 2H).

Example 6: 1'-Methyl-5-(4-((4-((5-(trifluoromethyl)pyridin-2-yl)amino)piperidin-1-yl)sulfonyl)phenyl)spiro[indoline-3,4'-piperidin]-2-one

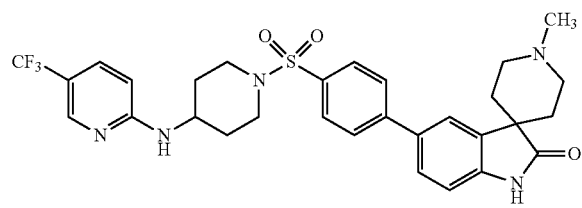 [SMILES: CN1CCC2(CC1)C(=O)Nc1ccc(-c3ccc(S(=O)(=O)N4CCC(Nc5ccc(C(F)(F)F)cn5)CC4)cc3)cc12]

To 2-oxo-5-(4-((4-((5-(trifluoromethyl)pyridin-2-yl)amino)piperidin-1-yl)sulfonyl)phenyl)spiro[indoline-3,4'-piperidin]-1'-ium chloride and 13 µL 37% formaldehyde in MeOH (1 mL) in a septum-cap vial were added NaBH(CN)$_3$ (7 mg, 0.11 mmol) and 20 µL acetic acid. The reaction stirred at RT for one hour. Once complete, the reaction mixture was purified via reverse-phase HPLC to give 1'-methyl-5-(4-((4-((5-(trifluoromethyl)pyridin-2-yl)amino)piperidin-1-yl)sulfonyl)phenyl)spiro[indoline-3,4'-piperidin]-2-one. MS: (ES) m/z calculated for $C_{30}H_{32}F_3N_5O_3S$ [M+H]$^+$ 600.2, found 600. $^1$H NMR (400 MHz, DMSO-d$_6$) δ 10.59 (s, 1H), 8.24-8.20 (m, 1H), 7.93-7.88 (m, 2H), 7.84-7.75 (m, 3H), 7.65-7.56 (m, 2H), 7.31 (d, J=7.3 Hz, 1H), 6.99 (d, J=8.1 Hz, 1H), 6.54 (d, J=8.9 Hz, 1H), 3.81-3.71 (m, 1H), 3.62-3.53 (m, 2H), 2.88 (bs, 1H), 2.69 (bs, 1H), 2.60-2.52 (m, 2H), 2.46-2.30 (m, 3H), 2.01-1.77 (m, 6H), 1.56-1.44 (m, 2H).

Example 7: 5-(4-((4-((5-(Trifluoromethyl)pyridin-2-yl)amino)piperidin-1-yl)sulfonyl)phenyl)-1H-pyrazolo[3,4-b]pyrazin-3-amine

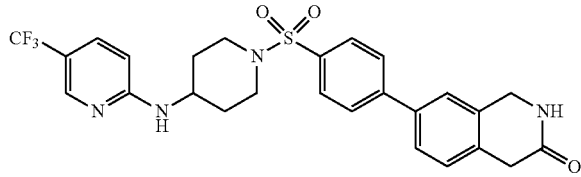 [SMILES: O=C1Cc2ccc(-c3ccc(S(=O)(=O)N4CCC(Nc5ccc(C(F)(F)F)cn5)CC4)cc3)cc2CN1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 7-bromo-1,4-dihydroisoquinolin-3(2H)-one (22 mg, 0.10 mmol), and Pd(dppf)$Cl_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via $SiO_2$ gel chromatography and reverse-phase HPLC to give 5-(4-((4-((5-(trifluoromethyl)pyridin-2-yl)amino)piperidin-1-yl)sulfonyl)phenyl)-1H-pyrazolo[3,4-b]pyrazin-3-amine. MS: (ES) m/z calculated for $C_{26}H_{25}F_3N_4O_3S$ [M+H]$^+$ 531.2, found 531. $^1$H NMR (400 MHz, DMSO-$d_6$) δ 8.22 (s, 1H), 8.08 (s, 1H), 7.97-7.92 (m, 2H), 7.84-7.80 (m, 2H), 7.71 (s, 1H), 7.67-7.63 (m, 1H), 7.60 (dd, J=9.0, 2.6 Hz, 1H), 7.36 (d, J=8.0 Hz, 1H), 7.31 (d, J=7.3 Hz, 1H), 6.54 (d, J=8.9 Hz, 1H), 4.43 (s, 2H), 3.82-3.72 (m, 1H), 3.61-3.53 (m, 2H), 3.51 (s, 2H), 2.64-2.53 (m, 2H), 2.01-1.91 (m, 2H), 1.57-1.43 (m, 2H).

Example 8: 2-Oxo-5-(4-((4-((5-(trifluoromethyl)pyridin-2-yl)amino)piperidin-1-yl)sulfonyl)phenyl)indoline-7-carboxylic acid

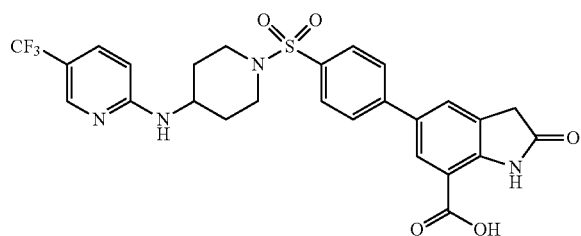 [SMILES: O=C1Cc2cc(-c3ccc(S(=O)(=O)N4CCC(Nc5ccc(C(F)(F)F)cn5)CC4)cc3)cc(C(=O)O)c2N1]

Methyl 2-oxo-5-(4-((4-((5-(trifluoromethyl)pyridin-2-yl)amino)piperidin-1-yl)sulfonyl)phenyl)indoline-7-carboxylate (76 mg, 0.13 mmol), $K_2CO_3$ (20 mg, 0.15 mmol), and 1 mL of 4:1 dioxane:$H_2O$ were added to a septum-cap vial. The reaction was heated to 50° C. and stirred for 75 min. Once complete, the reaction cooled to RT and solid precipitated and was separated via filtration. The solid was resuspended in dI $H_2O$, acidified using a few drops of glacial acetic acid, and extracted with EtOAc to give 2-oxo-5-(4-((4-((5-(trifluoromethyl)pyridin-2-yl)amino)piperidin-1-yl)sulfonyl)phenyl)indoline-7-carboxylic acid. MS: (ES) m/z calculated for $C_{26}H_{23}F_3N_4O_5S$ [M–H]$^-$ 531.6, found 531. $^1$H NMR (400 MHz, DMSO-$d_6$) δ 10.12 (s, 1H), 8.23-8.21 (m, 1H), 8.04-8.01 (m, 1H), 7.94-7.90 (m, 2H), 7.87-7.84 (m, 1H), 7.83-7.79 (m, 2H), 7.59 (dd, J=9.0, 2.5 Hz, 1H), 7.35 (d, J=7.3 Hz, 1H), 6.55 (d, J=8.9 Hz, 1H), 3.83-3.72 (m, 1H), 3.65 (s, 2H), 3.60-3.51 (m, 2H), 2.62-2.53 (m, 2H), 2.00-1.91 (m, 2H), 1.56-1.43 (m, 2H), —COOH not obs.

Example 9: 3,3-Dimethyl-5-(4-((4-((5-(trifluoromethyl)pyridin-2-yl)amino)piperidin-1-yl)sulfonyl)phenyl)isoindolin-1-one

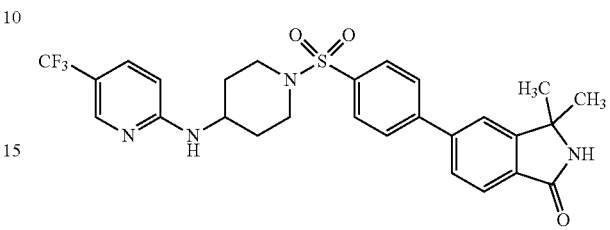

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5-bromo-3,3-dimethylisoindolin-1-one (23 mg, 0.10 mmol), and Pd(dppf)$Cl_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via reverse-phase HPLC to give 3,3-dimethyl-5-(4-((4-((5-(trifluoromethyl)pyridin-2-yl)amino)piperidin-1-yl)sulfonyl)phenyl)isoindolin-1-one. MS: (ES) m/z calculated for $C_{27}H_{27}F_3N_4O_3S$ [M+H]$^+$ 545.2, found 545. $^1$H NMR (400 MHz, DMSO-$d_6$) δ 8.73 (s, 1H), 8.20 (s, 1H), 8.06-7.98 (m, 3H), 7.87-7.79 (m, 3H), 7.70 (d, J=7.9 Hz, 1H), 7.58 (dd, J=8.9, 2.4 Hz, 1H), 7.29 (d, J=7.2 Hz, 1H), 6.52 (d, J=8.9 Hz, 1H), 3.81-3.68 (m, 1H), 3.60-3.51 (m, 2H), 2.59-2.53 (m, 2H), 1.99-1.90 (m, 2H), 1.55-1.42 (m, 8H).

Example 10: 3-(4-((4-((5-(Trifluoromethyl)pyridin-2-yl)amino)piperidin-1-yl)sulfonyl)phenyl)-6,7-dihydro-5H-pyrrolo[3,4-b]pyridin-5-one

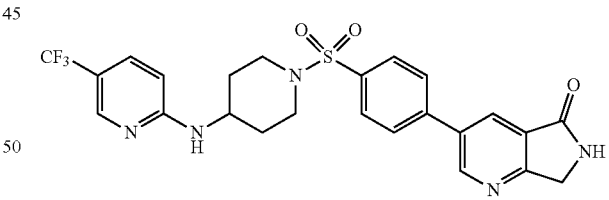

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 3-bromo-6,7-dihydro-5H-pyrrolo[3,4-b]pyridin-5-one (21 mg, 0.10 mmol), and Pd(dppf)$Cl_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via reverse-phase HPLC to give 3-(4-((4-((5-(trifluoromethyl)pyridin-2-yl)amino)piperidin-1-yl)sulfonyl)phenyl)-6,7-dihydro-5H-pyrrolo[3,4-b]pyridin-5-one. MS: (ES) m/z calculated for $C_{24}H_{22}F_3N_5O_3S$ [M+H]$^+$ 518.2, found 518. $^1$H NMR (400 MHz, DMSO-$d_6$) δ 9.18 (d, J=2.2 Hz, 1H), 8.94 (s, 1H), 8.42 (d, J=2.2 Hz, 1H), 8.22 (s, 1H), 8.13 (d, J=8.1 Hz, 2H), 7.87 (d, J=8.1 Hz, 2H), 7.60 (dd, J=8.7, 2.0 Hz, 1H), 7.32 (d, J=7.3 Hz, 1H), 6.54 (d, J=8.9 Hz, 1H), 4.52 (s, 2H), 3.84-3.72 (m, 1H), 3.63-3.53 (m, 2H), 2.64-2.55 (m, 2H), 2.02-1.92 (m, 2H), 1.57-1.43 (m, 2H).

Example 11: 6-(4-((4-((5-(Trifluoromethyl)pyridin-2-yl)amino)piperidin-1-yl)sulfonyl)phenyl)-3,4-dihydroquinazolin-2(1H)-one

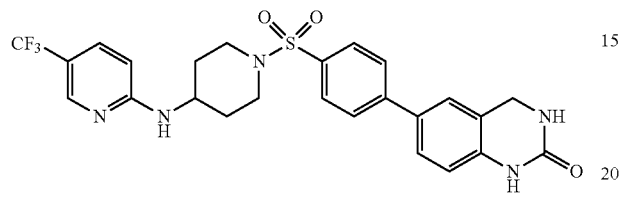

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 6-bromo-1,4-dihydroisoquinolin-3(2H)-one (22 mg, 0.10 mmol), and Pd(dppf)$Cl_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via reverse-phase HPLC to give 6-(4-((4-((5-(trifluoromethyl)pyridin-2-yl)amino)piperidin-1-yl)sulfonyl)phenyl)-3,4-dihydroquinazolin-2(1H)-one. MS: (ES) m/z calculated for $C_{25}H_{24}F_3N_5O_3S$ [M+H]$^+$ 532.2, found 532. $^1$H NMR (400 MHz, DMSO-$d_6$) δ 9.23 (d, J=2.0 Hz, 1H), 8.22 (s, 1H), 7.87 (d, J=8.5 Hz, 2H), 7.74 (d, J=8.4 Hz, 2H), 7.63-7.51 (m, 4H), 7.31 (d, J=7.3 Hz, 1H), 6.94-6.86 (m, 2H), 6.54 (d, J=8.9 Hz, 1H), 4.40 (s, 2H), 3.82-3.70 (m, 1H), 3.60-3.49 (m, 3H), 2.61-2.50 (m, 2H), 2.01-1.90 (m, 2H), 1.57-1.42 (m, 2H).

Example 12: N-(2-(3-Cyano-5-(4-((4-((5-(trifluoromethyl)pyridin-2-yl)amino)piperidin-1-yl)sulfonyl)phenyl-1H-pyrrolo[2,3-b]pyridin-1-yl)ethyl) acetamide

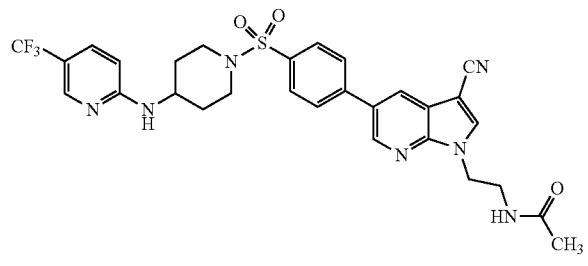 [SMILES: CC(=O)NCCn1cc(C#N)c2cc(-c3ccc(S(=O)(=O)N4CCC(Nc5ccc(C(F)(F)F)cn5)CC4)cc3)cnc21]

To a solution of 1-(2-aminoethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile (50 mg; 0.08 mmol) in 1 mL of DMF, is added AcOH (10 mg; 0.1 mmol), DIPEA (101 uL; 0.58 mmol) and HATU (50 mg; 0.13 mmol). The mixture was stirred for 2 h. LC-MS indicated the desired product. The reaction was diluted with 15 mL of EtOAc, washed with 10 mL of sat NH$_4$Cl and sat. brine. The organic phase was dried with MgSO4, filtered and concentrated. The residue purified by prep plate SiO$_2$ chromatography to give N-(2-(3-cyano-5-(4-((4-((5-(trifluoromethyl) pyridin-2-yl)amino)piperidin-1-yl)sulfonyl)phenyl)-1H-pyrrolo[2,3-b]pyridin-1-yl)ethyl)acetamide. MS: (ES) m/z calculated for $C_{28}H_{28}F_3N_7O_3S$ [M+H]$^+$ 612.2, found 611.9. $^1$H NMR (400 MHz, DMSO-$d_6$) δ 8.84 (d, J=2.1 Hz, 1H), 8.55 (s, 1H), 8.51 (d, J=2.1 Hz, 1H), 8.23-8.17 (m, 1H), 8.10 (d, J=8.3 Hz, 2H), 7.95 (q, J=7.2, 6.6 Hz, 1H), 7.84 (d, J=8.1 Hz, 2H), 7.58 (dd, J=9.0, 2.5 Hz, 1H), 7.31 (t, J=6.2 Hz, 1H), 6.53 (d, J=8.9 Hz, 1H), 4.37 (dt, J=18.0, 5.5 Hz, 2H), 3.80-3.72 (m, 1H), 3.63-3.41 (m, 4H), 2.62-2.43 (m, 2H), 2.00-1.91 (m, 2H), 1.72 (s, 3H), 1.57-1.42 (m, 2H).

Example 13: 6-(4-((4-((5-(Trifluoromethyl)pyridin-2-yl)amino)piperidin-1-yl)sulfonyl)phenyl)-1,4-dihydroisoquinolin-3(2H)-one

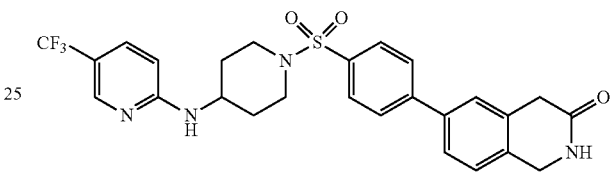

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 6-bromo-1,4-dihydroisoquinolin-3(2H)-one (22 mg, 0.10 mmol), and Pd(dppf)$Cl_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography to give 6-(4-((4-((5-(trifluoromethyl)pyridin-2-yl)amino)piperidin-1-yl)sulfonyl)phenyl)-1,4-dihydroisoquinolin-3(2H)-one. MS: (ES) m/z calculated for $C_{26}H_{25}F_3N_4O_3S$ [M+H]$^+$ 531.2, found 531. $^1$H NMR (400 MHz, DMSO-$d_6$) δ 8.22 (s, 1H), 8.07 (bs, 1H), 7.94 (d, J=8.4 Hz, 2H), 7.82 (d, J=8.4 Hz, 2H), 7.65-7.57 (m, 3H), 7.42 (d, J=8.4 Hz, 1H), 7.32 (d, J=7.3 Hz, 1H), 6.54 (d, J=8.9 Hz, 1H), 4.40 (s, 2H), 3.83-3.72 (m, 1H), 3.62-3.51 (m, 4H), 2.62-2.52 (m, 2H), 2.00-1.92 (m, 2H), 1.56-1.44 (m, 2H).

Example 14: 1-(2-aminoethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile

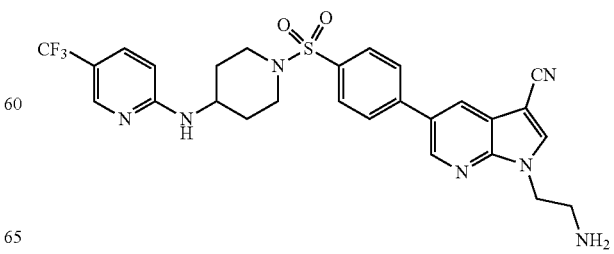

To a solution of tert-butyl N-[2-[3-cyano-5-[4-[[5-(trifluoromethyl)-2-pyridyl]amino]-1-piperidyl]sulfonyl]phenyl]pyrrolo[2,3-b]pyridin-1-yl]ethyl]carbamate (155 mg; 0.23 mmol) in 2 mL of CH$_2$Cl$_2$ was added 2 mL of 4.0M HCl. The mixture stirred for 16 h. LC-MS indicated the desired product. The mixture was concentrated to give 1-(2-aminoethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile. MS: (ES) m/z calculated for C$_{27}$H$_{26}$F$_3$N$_7$O$_2$S [M+H]$^+$ 570.2, found 569.9.

Example 15: tert-Butyl (2-(3-cyano-5-(4-((4-((5-(trifluoromethyl)pyridin-2-yl)amino)piperidin-1-yl)sulfonyl)phenyl)-1H-pyrrolo[2,3-b]pyridin-1-yl)ethyl)carbamate

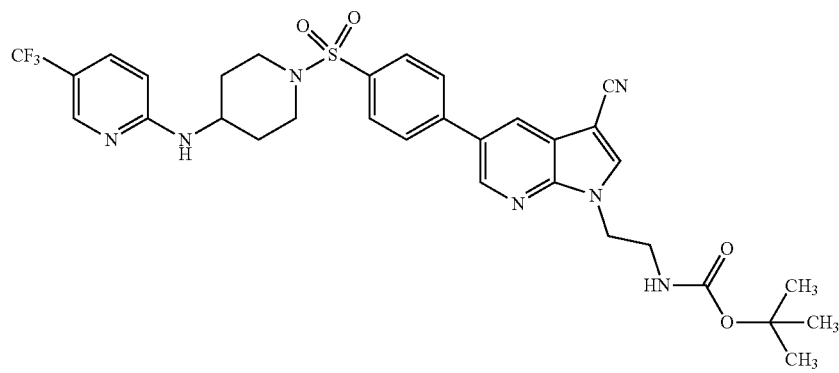 [SMILES: CC(C)(C)OC(=O)NCCn1cc(C#N)c2cc(-c3ccc(S(=O)(=O)N4CCC(Nc5ccc(C(F)(F)F)cn5)CC4)cc3)cnc21]

To N-[1-[4-(4,4,5,5-tetramethyl-1,3,2-dioxaborolan-2-yl)phenyl]sulfonyl-4-piperidyl]-5-(trifluoromethyl)pyridin-2-amine (150.0 mg, 0.29 mmol) in 7.2 mL dioxane were added K$_2$CO$_3$ (75.0 mg, 0.53 mmol), tert-butyl N-[2-(5-bromo-3-cyano-pyrrolo[2,3-b]pyridin-1-yl)ethyl]carbamate (150.0 mg, 0.41 mmol), Pd(dppf)Cl$_2$.DCM (27.0 mg, 0.03 mmol) and 1.8 mL of water. The mixture was sparged with nitrogen for 10 minutes. The vial was sealed, the mixture stirred at 100° C. for 2 h, and cooled when the reaction had proceeded to completion. The mixture was purified via SiO$_2$ gel chromatography, to give tert-butyl (2-(3-cyano-5-(4-((4-((5-(trifluoromethyl)pyridin-2-yl)amino)piperidin-1-yl)sulfonyl)phenyl)-1H-pyrrolo[2,3-b]pyridin-1-yl)ethyl)carbamate. MS: (ES) m/z calculated for C$_{32}$H$_{34}$F$_3$N$_7$O$_4$S [M+H]$^+$ 670.2, found 670.0.

Example 16: 2-Amino-6-(4-((4-((5-(trifluoromethyl)pyridin-2-yl)amino)piperidin-1-yl)sulfonyl)phenyl)quinazolin-4(1H)-one

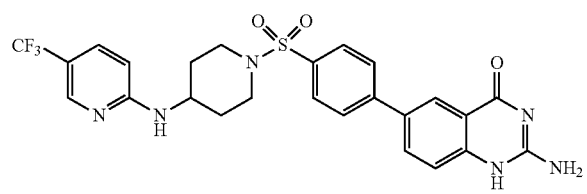 [SMILES: Nc1nc(=O)c2cc(-c3ccc(S(=O)(=O)N4CCC(Nc5ccc(C(F)(F)F)cn5)CC4)cc3)ccc2[nH]1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 2-amino-6-bromoquinazolin-4(1H)-one (23 mg, 0.10 mmol), and Pd(dppf)Cl$_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via reverse-phase HPLC to give 2-amino-6-(4-((4-((5-(trifluoromethyl)pyridin-2-yl)amino)piperidin-1-yl)sulfonyl)phenyl)quinazolin-4(1H)-one. MS: (ES) m/z calculated for C$_{25}$H$_{23}$F$_3$N$_6$O$_3$S [M+H]$^+$ 545.2, found 545. $^1$H NMR (400 MHz, DMSO-d$_6$) δ 8.24-8.20 (m, 2H), 8.02-7.95 (m, 3H), 7.82 (d, J=8.5 Hz, 2H), 7.59 (dd, J=9.0, 2.7 Hz, 1H), 7.35-7.28 (m, 2H), 6.61 (bs, 2H), 6.54 (d, J=8.9 Hz, 1H), 3.84-3.70 (m, 1H), 3.61-3.51 (m, 2H), 2.65-2.52 (m, 2H), 2.01-1.92 (m, 2H), 1.57-1.43 (m, 2H).

Example 17: 6-(4-((4-((5-(Trifluoromethyl)pyridin-2-yl)amino)piperidin-1-yl)sulfonyl)phenyl)-[1,2,4]triazolo[4,3-a]pyridin-3-amine

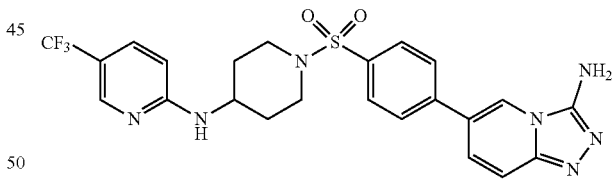

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromo-[1,2,4]triazolo[4,3-a]pyridin-3-amine (21 mg, 0.10 mmol), and Pd(dppf)Cl$_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via reverse-phase HPLC to give 6-(4-((4-((5-(trifluoromethyl)pyridin-2-yl)amino)piperidin-1-yl)sulfonyl)phenyl)-[1,2,4]triazolo[4,3-a]pyridin-3-amine. MS: (ES) m/z calculated for C$_{23}$H$_{22}$F$_3$N$_7$O$_2$S [M+H]$^+$ 518.2, found 518. $^1$H NMR (400 MHz, DMSO-d$_6$) δ 8.64 (s, 1H), 8.22 (s, 1H), 7.98 (d, J=8.4

Hz, 2H), 7.89 (d, J=8.5 Hz, 2H), 7.63-7.57 (m, 3H), 7.31 (d, J=7.2 Hz, 1H), 6.74 (bs, 2H), 6.54 (d, J=8.9 Hz, 1H), 3.82-3.71 (m, 1H), 3.62-3.52 (m, 2H), 2.64-2.53 (m, 2H), 2.01-1.92 (m, 2H), 1.57-1.44 (m, 2H).

Example 18: 5-(4-((4-((5-(Trifluoromethyl)pyridin-2-yl)amino)piperidin-1-yl)sulfonyl)phenyl)-1H-pyrazolo[3,4-b]pyrazin-3-amine

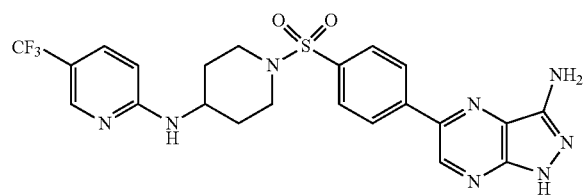 [SMILES: Nc1n[nH]c2ncc(-c3ccc(S(=O)(=O)N4CCC(Nc5ccc(C(F)(F)F)cn5)CC4)cc3)nc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-1H-pyrazolo[3,4-b]pyrazin-3-amine (21 mg, 0.10 mmol), and Pd(dppf)Cl$_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via reverse-phase HPLC to give 5-(4-((4-((5-(trifluoromethyl)pyridin-2-yl)amino)piperidin-1-yl)sulfonyl)phenyl)-1H-pyrazolo[3,4-b]pyrazin-3-amine. MS: (ES) m/z calculated for C$_{22}$H$_{21}$F$_3$N$_8$O$_2$S [M+H]$^+$ 519.2, found 519. $^1$H NMR (400 MHz, DMSO-d$_6$) δ 12.57 (s, 1H), 9.15 (s, 1H), 8.41 (d, J=8.5 Hz, 2H), 8.22 (d, J=2.4 Hz, 1H), 7.89 (d, J=8.6 Hz, 2H), 7.59 (dd, J=9.1, 2.7 Hz, 1H), 7.30 (d, J=7.3 Hz, 1H), 6.54 (d, J=8.9 Hz, 1H), 5.88 (s, 2H), 3.83-3.72 (m, 1H), 3.62-3.53 (m, 2H), 2.69-2.57 (m, 2H), 1.96 (d, J=12.1 Hz, 2H), 1.56-1.43 (m, 2H).

Example 19: 5-(2-methyl-4-((4-((5-(trifluoromethyl)pyridin-2-yl)amino)piperidin-1-yl)sulfonyl)phenyl)indolin-2-one

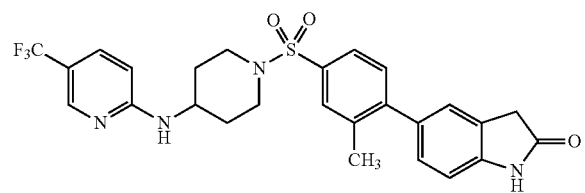 [SMILES: Cc1cc(S(=O)(=O)N2CCC(Nc3ccc(C(F)(F)F)cn3)CC2)ccc1-c1ccc2c(c1)CC(=O)N2]

Step a: A mixture of N-(piperidin-4-yl)-5-(trifluoromethyl)pyridin-2-amine hydrochloride (282 mg, 1.0 mmol), 4-bromo-3-methylbenzenesulfonyl chloride (404 mg, 1.5 mmol), and K$_2$CO$_3$ (553 mg, 4.0 mmol) in 2-methyltetrahydrofuran (10 mL) and water (2 mL) was stirred at room temperature for 1.5 hours. The aqueous layer was removed, and the organic layer was concentrated and purified by SiO$_2$ gel chromatography (0-100% EtOAc/hexanes) to give N-(1-((4-bromo-3-methylphenyl)sulfonyl)piperidin-4-yl)-5-(trifluoromethyl)pyridin-2-amine.

Step b: To N-(1-((4-bromo-3-methylphenyl)sulfonyl)piperidin-4-yl)-5-(trifluoromethyl)pyridin-2-amine (48 mg, 0.10 mmol) in a septum-cap vial were added K$_2$CO$_3$ (30 mg, 0.22 mmol), 5-(4,4,5,5-tetramethyl-1,3,2-dioxaborolan-2-yl)indolin-2-one (31 mg, 0.12 mmol), dioxane (1.5 mL) and water (0.5 mmol). The mixture was sparged with nitrogen for 20 minutes. Pd(dppf)Cl$_2$.DCM (8 mg, 0.010 mmol) was added, and the mixture was sparged with nitrogen for an additional 5 minutes. The vial was sealed, the mixture stirred at 100° C. for 17 hours, and cooled when the reaction had proceeded to completion. The reaction mixture was diluted with EtOAc (10 mL), filtered through Celite®, and concentrated. The mixture was purified via SiO$_2$ gel followed by preparative reverse-phase HPLC to give 5-(2-methyl-4-((4-((5-(trifluoromethyl)pyridin-2-yl)amino)piperidin-1-yl)sulfonyl)phenyl)indolin-2-one. MS: (ES) m/z calculated for C$_{26}$H$_{26}$F$_3$N$_4$O$_3$S [M+H]$^+$ 531.17, found 531.3. $^1$H NMR (400 MHz, DMSO-d$_6$) δ 10.52 (s, 1H), 8.26-8.20 (m, 1H), 7.70-7.54 (m, 3H), 7.46-7.39 (m, 1H), 7.36-7.29 (m, 1H), 7.28-7.24 (m, 1H), 7.24-7.18 (m, 1H), 6.95-6.87 (m, 1H), 6.60-6.51 (m, 1H), 3.84-3.70 (m, 1H), 3.63-3.48 (m, 4H), 2.62-2.50 (m, 2H), 2.36 (s, 3H), 2.03-1.90 (m, 2H), 1.59-1.44 (m, 2H).

Example 20: 2,2-Dimethyl-7-(4-((4-((5-(trifluoromethyl)pyridin-2-yl)amino)piperidin-1-yl)sulfonyl)phenyl)-2H-benzo[b][1,4]oxazin-3(4H)-one

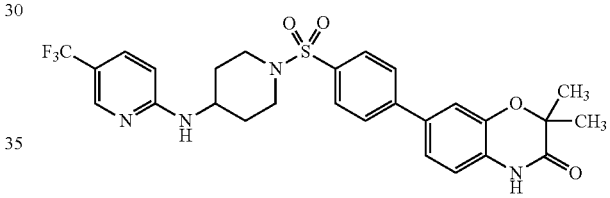

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added K$_2$CO$_3$ (41 mg, 0.30 mmol), 7-bromo-2,2-dimethyl-2H-benzo[b][1,4]oxazin-3(4H)-one (31 mg, 0.12 mmol), dioxane (1.5 mL) and water (0.5 mmol). The mixture was sparged with nitrogen for 20 minutes. Pd(dppf)Cl$_2$.DCM (8 mg, 0.010 mmol) was added, and the mixture was sparged with nitrogen for an additional 5 minutes. The vial was sealed, the mixture stirred at 100° C. for 17 hours, and cooled when the reaction had proceeded to completion. The reaction mixture was diluted with EtOAc (10 mL), filtered through Celite®, and concentrated. The mixture was purified via SiO$_2$ gel chromatography followed by preparative reverse-phase HPLC to give 2,2-dimethyl-7-(4-((4-((5-(trifluoromethyl)pyridin-2-yl)amino)piperidin-1-yl)sulfonyl)phenyl)-2H-benzo[b][1,4]oxazin-3(4H)-one. MS: (ES) m/z calculated for C$_{27}$H$_{28}$F$_3$N$_4$O$_4$S [M+H]$^+$ 561.18, found 561.3. $^1$H NMR (400 MHz, DMSO-d$_6$) δ 10.82 (s, 1H), 8.22 (s, 1H), 7.92 (d, J=8.6 Hz, 2H), 7.77 (d, J=8.5 Hz, 2H), 7.59 (dd, J=9.0, 2.5 Hz, 1H), 7.43-7.37 (m, 2H), 7.31 (d, J=7.3 Hz, 1H), 7.01 (d, J=8.0 Hz, 1H), 6.54 (d, J=8.9 Hz, 1H), 3.82-3.70 (m, 1H), 3.60-3.51 (m, 2H), 2.62-2.53 (m, 2H), 2.00-1.91 (m, 2H), 1.55-1.46 (m, 2H), 1.44 (s, 6H).

Example 21: 1'-(2-Hydroxyethyl)-5'-(4-((4-((5-(trifluoromethyl)pyridin-2-yl)amino)piperidin-1-yl)sulfonyl)phenyl)-2,3,5,6-tetrahydrospiro[pyran-4,3'-pyrrolo[2,3-b]pyridin]-2'(1'H)-one

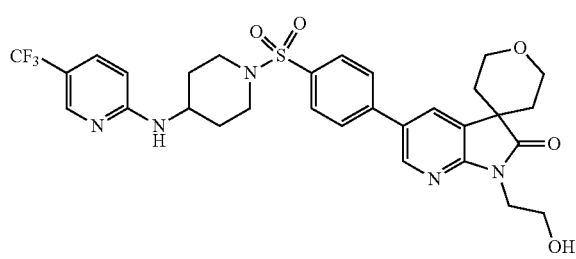 [SMILES: O=C1N(CCO)c2ncc(-c3ccc(S(=O)(=O)N4CCC(Nc5ccc(C(F)(F)F)cn5)CC4)cc3)cc2C12CCOCC2]

Step a: To N-[1-[4-(4,4,5,5-tetramethyl-1,3,2-dioxaborolan-2-yl)phenyl]sulfonyl-4-piperidyl]-5-(trifluoromethyl)pyridin-2-amine (40.0 mg, 0.08 mmol) in 2.25 mL dioxane were added K$_2$CO$_3$ (25.0 mg, 0.18 mmol), 5-bromo-1-[2-[tert-butyl(dimethyl)silyl]oxyethyl]spiro[pyrrolo[2,3-b]pyridine-3,4'-tetrahydropyran]-2-one (40.0 mg, 0.10 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 1'-(2-(((tert-butyldimethylsilyl)oxy)ethyl)-5'-(4-((4-((5-(trifluoromethyl)pyridin-2-yl)amino)piperidin-1-yl)sulfonyl)phenyl)-2,3,5,6-tetrahydrospiro[pyran-4,3'-pyrrolo[2,3-b]pyridin]-2'(1'H)-one. MS: (ES) m/z calculated for C$_{33}$H$_{42}$F$_3$N$_4$O$_4$SSi [M+H]$^+$ 746.3, found 746.0.

Step b: 2-(2-(((tert-butyldimethylsilyl)oxy)ethyl)-5-(4-((4-((5-(trifluoromethyl)pyridin-2-yl)amino)piperidin-1-yl)sulfonyl)phenyl)isoindolin-1-one (57.0 mg; 0.08 mmol) in 1 mL of THF was added 0.1 mL of 1 M TBAF in THF. The mixture stirred for 1 h. LC-MS indicates the desired product. The reaction was diluted with 10 mL of EtOAc, washed with 3×5 mL of H$_2$O and 10 mL of brine. The organic phase was dried with MgSO$_4$, filtered and concentrated. The crude residue was purified by SiO$_2$ prep plate chromatography to give 1'-(2-hydroxyethyl)-5'-(4-((4-((5-(trifluoromethyl)pyridin-2-yl)amino)piperidin-1-yl)sulfonyl)phenyl)-2,3,5,6-tetrahydrospiro[pyran-4,3'-pyrrolo[2,3-b]pyridin]-2'(1'H)-one. (ES) m/z calculated for C$_{30}$H$_{32}$F$_3$N$_5$O$_5$S [M+H]$^+$ 632.2, found 632.2. $^1$H NMR (400 MHz, DMSO-d$_6$) 8.58 (d, J=2.0 Hz, 1H), 8.32 (d, J=2.1 Hz, 1H), 8.20 (s, 1H), 8.00 (d, J=8.5 Hz, 2H), 7.81 (d, J=8.5 Hz, 2H), 7.58 (dd, J=8.9, 2.5 Hz, 1H), 7.30 (d, J=7.3 Hz, 1H), 6.53 (d, J=8.9 Hz, 1H), 4.89-4.77 (m, 1H), 4.03 (ddd, J=11.8, 7.4, 4.1 Hz, 3H), 3.88 (dt, J=11.4, 5.0 Hz, 2H), 3.78 (m, 3H), 3.65 (t, J=6.2 Hz, 2H), 3.57 (d, J=11.9 Hz, 2H), 2.60-2.40 (m, 2H), 2.00-1.91 (m, 2H), 1.89-1.73 (m, 3H), 1.49 (q, J=12.6, 11.1 Hz, 2H).

Example 22: 2-(2-Hydroxyethyl)-5-(4-((4-((5-(trifluoromethyl)pyridin-2-yl)amino)piperidin-1-yl)sulfonyl)phenyl)isoindolin-1-one

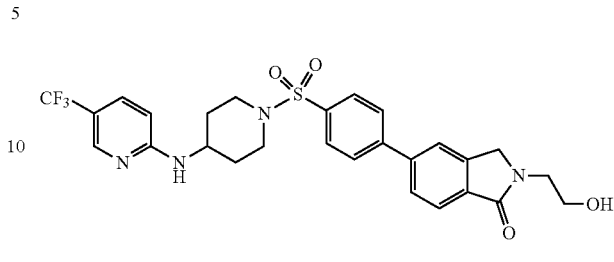

Step a: To N-[1-[4-(4,4,5,5-tetramethyl-1,3,2-dioxaborolan-2-yl)phenyl]sulfonyl-4-piperidyl]-5-(trifluoromethyl)pyridin-2-amine (40.0 mg, 0.07 mmol) in 2.25 mL dioxane were added K$_2$CO$_3$ (25.0 mg, 0.18 mmol), 1-[2-[tert-butyl(dimethyl)silyl]oxyethyl]-5-[4-[[4-[[5-(trifluoromethyl)-2-pyridyl]amino]-1-piperidyl]sulfonyl]phenyl]pyrrolo[2,3-b]pyridine-3-carbonitrile (40.0 mg, 0.11 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 2-(2-(((tert-butyldimethylsilyl)oxy)ethyl)-5-(4-((4-((5-(trifluoromethyl)pyridin-2-yl)amino)piperidin-1-yl)sulfonyl)phenyl)isoindolin-1-one. MS: (ES) m/z calculated for C$_{33}$H$_{41}$F$_3$N$_4$O$_4$SSi [M+H]$^+$ 675.3, found 675.0.

Example 23: 6-(4-((4-((5-(Trifluoromethyl)pyridin-2-yl)amino)piperidin-1-yl)sulfonyl)phenyl)-1,3-dihydro-2H-pyrrolo[3,2-b]pyridin-2-one

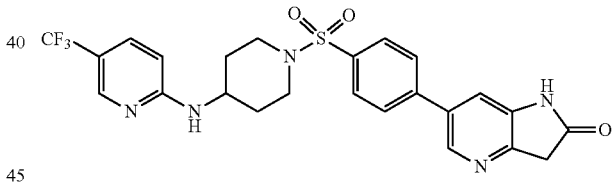

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromo-1,3-dihydro-2H-pyrrolo[3,2-b]pyridin-2-one (21 mg, 0.10 mmol), and Pd(dppf)Cl$_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via SiO$_2$ gel chromatography and reverse-phase HPLC to give 6-(4-((4-((5-(trifluoromethyl)pyridin-2-yl)amino)piperidin-1-yl)sulfonyl)phenyl)-1,3-dihydro-2H-pyrrolo[3,2-b]pyridin-2-one. MS: (ES) m/z calculated for C$_{24}$H$_{22}$F$_3$N$_5$O$_3$S [M+H]$^+$ 518.2, found 518. $^1$H NMR (400 MHz, DMSO-d$_6$) δ 10.76 (s, 1H), 8.46 (d, J=2.0 Hz, 1H), 8.22 (s, 1H), 7.97 (d, J=8.4 Hz, 2H), 7.84 (d, J=8.4 Hz, 2H), 7.60 (dd, J=8.9, 2.5 Hz, 1H), 7.40 (d, J=2.0 Hz, 1H), 7.32 (d, J=7.3 Hz, 1H), 6.54 (d, J=9.0 Hz, 1H), 3.84-3.72 (m, 1H), 3.62-3.51 (m, 2H), 2.64-2.54 (m, 2H), 2.01-1.93 (m, 2H), 1.57-1.43 (m, 2H), one methylene under residual solvent peak.

Example 24: N-(1-((4-(4-methyl-1H-pyrrolo[2,3-b]pyridin-5-yl)phenyl)sulfonyl)piperidin-4-yl)-5-(trifluoromethyl)pyridin-2-amine

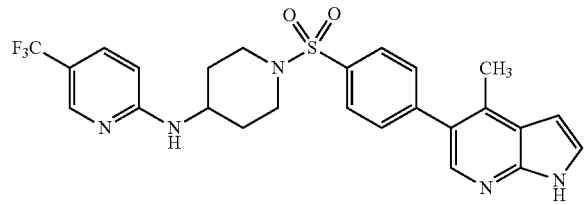 [SMILES: Cc1c(-c2ccc(S(=O)(=O)N3CCC(Nc4ccc(C(F)(F)F)cn4)CC3)cc2)cnc2[nH]ccc12]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added K$_2$CO$_3$ (41 mg, 0.30 mmol), 5-bromo-4-methyl-1H-pyrrolo[2,3-b]pyridine (25 mg, 0.12 mmol), dioxane (1.5 mL) and water (0.5 mmol). The mixture was sparged with nitrogen for 20 minutes. Pd(dppf)Cl$_2$.DCM (8 mg, 0.010 mmol) was added, and the mixture was sparged with nitrogen for an additional 5 minutes. The vial was sealed, the mixture stirred at 100° C. for 16 hours, and cooled when the reaction had proceeded to completion. The reaction mixture was diluted with EtOAc (10 mL), filtered through Celite®, and concentrated. The mixture was purified via SiO$_2$ gel chromatography followed by preparative reverse-phase HPLC to give N-(1-((4-(4-methyl-1H-pyrrolo[2,3-b]pyridin-5-yl)phenyl)sulfonyl)piperidin-4-yl)-5-(trifluoromethyl)pyridin-2-amine. MS: (ES) m/z calculated for C$_{25}$H$_{25}$F$_3$N$_5$O$_2$S [M+H]$^+$ 516.17, found 516.3. $^1$H NMR (400 MHz, DMSO-d$_6$) δ 11.74 (s, 1H), 8.24 (s, 1H), 8.12 (s, 1H), 7.83 (d, J=7.6 Hz, 2H), 7.71 (d, J=7.8 Hz, 2H), 7.64-7.57 (m, 1H), 7.54-7.48 (m, 1H), 7.37-7.30 (m, 1H), 6.64-6.53 (m, 2H), 3.87-3.71 (m, 1H), 3.67-3.56 (m, 2H), 2.65-2.52 (m, 2H), 2.50 (s, 3H), 2.04-1.94 (m, 2H), 1.60-1.45 (m, 2H).

Example 25: N-(1-((4-(6-methyl-1H-pyrrolo[2,3-b]pyridin-5-yl)phenyl)sulfonyl)piperidin-4-yl)-5-(trifluoromethyl)pyridin-2-amine

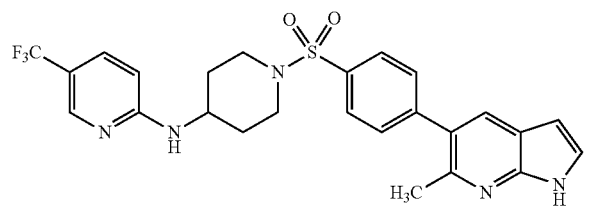 [SMILES: Cc1nc2[nH]ccc2cc1-c1ccc(S(=O)(=O)N2CCC(Nc3ccc(C(F)(F)F)cn3)CC2)cc1]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added K$_2$CO$_3$ (41 mg, 0.30 mmol), 5-bromo-6-methyl-1H-pyrrolo[2,3-b]pyridine (25 mg, 0.12 mmol), dioxane (1.5 mL) and water (0.5 mmol). The mixture was sparged with nitrogen for 20 minutes. Pd(dppf)Cl$_2$.DCM (8 mg, 0.010 mmol) was added, and the mixture was sparged with nitrogen for an additional 5 minutes. The vial was sealed, the mixture stirred at 100° C. for 16 hours, and cooled when the reaction had proceeded to completion. The reaction mixture was diluted with EtOAc (10 mL), filtered through Celite®, and concentrated. The mixture was purified via SiO$_2$ gel chromatography followed by preparative reverse-phase HPLC to give N-(1-((4-(6-methyl-1H-pyrrolo[2,3-b]pyridin-5-yl)phenyl)sulfonyl)piperidin-4-yl)-5-(trifluoromethyl)pyridin-2-amine. MS: (ES) m/z calculated for C$_{25}$H$_{25}$F$_3$N$_5$O$_2$S [M+H]$^+$ 516.17, found 516.3. $^1$H NMR (400 MHz, DMSO-d$_6$) δ 11.62 (s, 1H), 8.24 (s, 1H), 7.87-7.78 (m, 3H), 7.70 (d, J=7.4 Hz, 2H), 7.62 (d, J=8.9 Hz, 1H), 7.45 (s, 1H), 7.34 (s, 1H), 6.61-6.51 (m, 1H), 6.45 (s, 1H), 3.86-3.72 (m, 1H), 3.67-3.55 (m, 2H), 2.64-2.50 (m, 2H), 2.50 (s, 3H), 2.06-1.92 (m, 2H), 1.60-1.44 (m, 2H).

Example 26: 2-Oxo-5-(4-((4-((5-(trifluoromethyl)pyridin-2-yl)amino)piperidin-1-yl)sulfonyl)phenyl)spiro[indoline-3,4'-piperidine]-1'-carboxamide

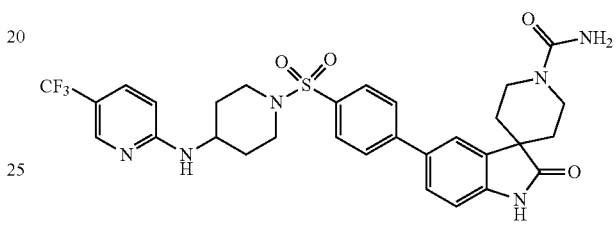

To 2-oxo-5-(4-((4-((5-(trifluoromethyl)pyridin-2-yl)amino)piperidin-1-yl)sulfonyl)phenyl)spiro[indoline-3,4'-piperidin]-1'-ium chloride in a septum-cap vial were added THF (3 mL) and DIPEA (56 μL, 0.32 mmol) followed by (Trimethylsilyl)isocyanate (12 μL, 0.090 mmol). The mixture stirred at RT until the reaction had proceeded to completion. The mixture was purified via reverse-phase HPLC to give 2-oxo-5-(4-((4-((5-(trifluoromethyl)pyridin-2-yl)amino)piperidin-1-yl)sulfonyl)phenyl)spiro[indoline-3,4'-piperidine]-1'-carboxamide. MS: (ES) m/z calculated for C$_{30}$H$_{31}$F$_3$N$_6$O$_4$S [M+H]$^+$ 629.2, found 629.

Example 27: 1'-Acetyl-5-(4-((4-((5-(trifluoromethyl)pyridin-2-yl)amino)piperidin-1-yl)sulfonyl)phenyl)spiro[indoline-3,4'-piperidin]-2-one

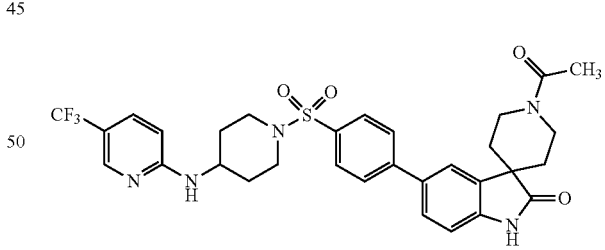

To 2-oxo-5-(4-((4-((5-(trifluoromethyl)pyridin-2-yl)amino)piperidin-1-yl)sulfonyl)phenyl)spiro[indoline-3,4'-piperidin]-1'-ium chloride in a septum-cap vial were added DMF (1 mL) and DIPEA (56 μL, 0.32 mmol) followed by acetic acid (9 μL, 0.090 mmol) and then HATU (37 mg, 0.096 mmol). The mixture stirred at RT until the reaction had proceeded to completion. The mixture was purified via reverse-phase HPLC to give 1'-acetyl-5-(4-((4-((5-(trifluoromethyl)pyridin-2-yl)amino)piperidin-1-yl)sulfonyl)phenyl) spiro[indoline-3,4'-piperidin]-2-one. MS: (ES) m/z calculated for C$_{31}$H$_{32}$F$_3$N$_5$O$_4$S [M+H]$^+$ 628.2, found 628. $^1$H NMR (400 MHz, DMSO-d$_6$) δ 10.61 (s, 1H), 8.20 (s, 1H), 7.98-7.82 (m, 3H), 7.80-7.69 (m, 2H), 7.65-7.54 (m, 2H), 7.32-7.24 (m, 1H), 6.97 (d, J=8.2 Hz, 1H), 6.52 (d, J=9.1 Hz, 1H), 4.05-3.92 (m, 1H), 3.89-3.49 (m, 6H), 2.59-2.49 (m, 2H), 2.06 (s, 3H), 1.98-1.85 (m, 3H), 1.84-1.61 (m, 3H), 1.56-1.39 (m, 2H).

Example 28: Methyl 2-oxo-5-(4-((4-((5-(trifluoromethyl)pyridin-2-yl)amino)piperidin-1-yl)sulfonyl)phenyl) indoline-7-carboxylate

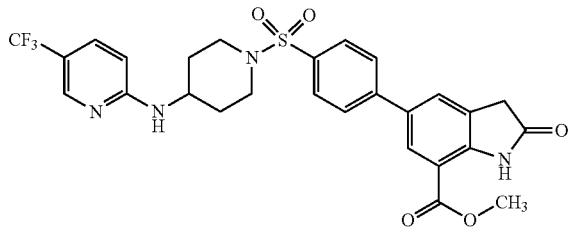 [SMILES: COC(=O)c1cc(-c2ccc(S(=O)(=O)N3CCC(Nc4ccc(C(F)(F)F)cn4)CC3)cc2)cc2c1NC(=O)C2]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), methyl 5-bromo-2-oxoindoline-7-carboxylate (26 mg, 0.1 mmol), and Pd(dppf)Cl$_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via $SiO_2$ gel chromatography and reverse-phase HPLC to give methyl 2-oxo-5-(4-((4-((5-(trifluoromethyl)pyridin-2-yl)amino)piperidin-1-yl)sulfonyl)phenyl) indoline-7-carboxylate. MS: (ES) m/z calculated for $C_{27}H_{25}F_3N_4O_5S$ [M+H]$^+$ 575.2, found 575. $^1$H NMR (400 MHz, DMSO-d$_6$) δ 10.46 (s, 1H), 8.20 (s, 1H), 8.02 (s, 1H), 7.97-7.75 (m, 5H), 7.63-7.54 (m, 1H), 7.34 (d, J=8.7 Hz, 1H), 6.53 (d, J=9.4 Hz, 1H), 3.88 (s, 3H), 3.79-3.69 (m, 1H), 3.70-3.60 (m, 2H), 3.60-3.48 (m, 2H), 2.62-2.52 (m, 2H), 2.00-1.87 (m, 2H), 1.57-1.39 (m, 2H).

Example 29: 2-Oxo-5-(4-((4-((5-(trifluoromethyl)pyridin-2-yl)amino)piperidin-1-yl)sulfonyl)phenyl) spiro[indoline-3,4'-piperidin]-1'-ium chloride

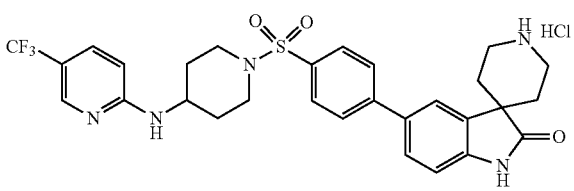 [SMILES: O=C1Nc2ccc(-c3ccc(S(=O)(=O)N4CCC(Nc5ccc(C(F)(F)F)cn5)CC4)cc3)cc2C12CCNCC2 ; Cl]

To tert-butyl-2-oxo-5-(4-((4-((5-(trifluoromethyl)pyridin-2-yl)amino)piperidin-1-yl)sulfonyl)phenyl) spiro[indoline-3,4'-piperidine]-1'-carboxylate in a septum-cap vial were added 2 mL dioxane and contents were stirred to dissolve. Once dissolved 0.5 mL 4M HCl in dioxane added and reaction stirred for 24 h at RT. Once complete, solvent was removed under reduced pressure and the residue was resuspended in $CH_3CN$ and lyophilized to give 2-oxo-5-(4-((4-((5-(trifluoromethyl)pyridin-2-yl)amino)piperidin-1-yl)sulfonyl)phenyl)spiro[indoline-3,4'-piperidin]-1'-ium chloride. MS: (ES) m/z calculated for $C_{29}H_{30}F_3N_5O_3S$ [M+H]$^+$ 586.2, found 586. $^1$H NMR (400 MHz, DMSO-d$_6$) δ 10.70 (s, 1H), 8.22 (d, J=3.8 Hz, 1H), 8.05-7.55 (m, 7H), 7.32 (s, 1H), 7.06-6.97 (m, 1H), 6.54 (d, J=9.0 Hz, 1H), 3.82-3.69 (m, 1H), 3.64-3.52 (m, 2H), 3.43-3.38 (m, 2H, under residual $H_2O$ peak), 3.26-3.14 (m, 2H), 2.62-2.52 (m, 2H), 2.05-1.81 (m, 6H), 1.59-1.42 (m, 2H).

Example 30: 1-(2-Hydroxyethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile

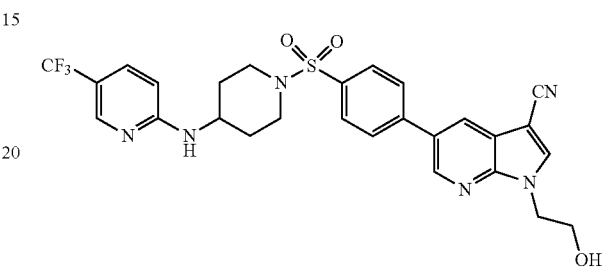

Step a: To N-[1-[4-(4,4,5,5-tetramethyl-1,3,2-dioxaborolan-2-yl)phenyl]sulfonyl-4-piperidyl]-5-(trifluoromethyl)pyridin-2-amine (40.0 mg, 0.07 mmol) in 2.25 mL dioxane were added $K_2CO_3$ (25.0 mg, 0.18 mmol), 1-[2-[tert-butyl(dimethyl)silyl]oxyethyl]-5-[4-[[5-(trifluoromethyl)-2-pyridyl]amino]-1-piperidyl]sulfonyl]phenyl]pyrrolo[2,3-b]pyridine-3-carbonitrile (40.0 mg, 0.11 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via $SiO_2$ gel chromatography, to give 1-(2-((tert-butyldimethylsilyl)oxy)ethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile. MS: (ES) m/z calculated for $C_{33}H_{39}F_3N_6O_3SSi$ [M+H]$^+$ 685.3, found 685.0.

Step b: To a solution of 1-(2-((tert-butyldimethylsilyl)oxy)ethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile (42.5 mg; 0.06 mmol) in 1 mL of THF is added 0.1 mL of 1 M TBAF in THF. The mixture stirred for 1 h. LC-MS indicates the desired product. The reaction was diluted with 10 mL of EtOAc, washed with 3×5 mL of $H_2O$ and 10 mL of brine. The organic phase was dried with $MgSO_4$, filtered and concentrated. The material was purified by reverse phase preparative HPLC to give 1-(2-Hydroxyethyl)-5-(4-((4-((5-(trifluoromethyl)pyridin-2-yl)amino)piperidin-1-yl)sulfonyl)phenyl)-1H-pyrrolo[2,3-b]pyridine-3-carbonitrile. (ES) m/z calculated for $C_{27}H_{25}F_3N_6O_3S$ [M+H]$^+$ 571.2, found 570.9. $^1$H NMR (400 MHz, DMSO-d$_6$) δ 8.86 (d, J=1.7 Hz, 1H), 8.81 (d, J=1.8 Hz, 1H), 8.36 (s, 1H), 8.21 (d, J=2.3 Hz, 1H), 8.13 (d, J=8.5 Hz, 2H), 7.88 (d, J=8.5 Hz, 2H), 7.58 (dd, J=9.0, 2.6 Hz, 1H), 7.30 (d, J=7.3 Hz, 1H), 6.53 (d, J=8.9 Hz, 1H), 5.11 (t, J=5.5 Hz, 1H), 4.88 (t, J=5.2 Hz, 2H), 3.96 (q, J=5.3 Hz, 2H), 3.76 (bs, 1H), 3.58 (d, J=11.8 Hz, 2H), 2.64-2.51 (m, 2H), 1.96 (d, J=12.6 Hz, 2H), 1.50 (d, J=11.4 Hz, 2H).

Example 31: N-(1-((4-(4-fluoro-1H-pyrrolo[2,3-b]pyridin-5-yl)phenyl)sulfonyl)piperidin-4-yl)-5-(trifluoromethyl)pyridin-2-amine

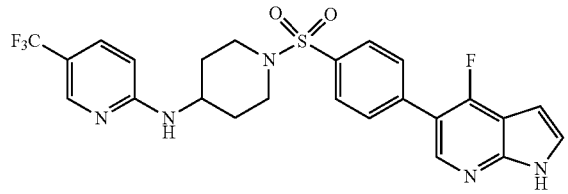 [SMILES: O=S(=O)(c1ccc(-c2cnc3[nH]ccc3c2F)cc1)N1CCC(Nc2ccc(C(F)(F)F)cn2)CC1]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added $K_2CO_3$ (41 mg, 0.30 mmol), 5-bromo-4-fluoro-1H-pyrrolo[2,3-b]pyridine (26 mg, 0.12 mmol), dioxane (1.5 mL) and water (0.5 mmol). The mixture was sparged with nitrogen for 20 minutes. Pd(dppf)$Cl_2$.DCM (8 mg, 0.010 mmol) was added, and the mixture was sparged with nitrogen for an additional 5 minutes. The vial was sealed, the mixture stirred at 100° C. for 2 hours, and cooled when the reaction had proceeded to completion. The reaction mixture was concentrated and purified via $SiO_2$ gel chromatography followed by preparative reverse-phase HPLC to give N-(1-((4-(4-fluoro-1H-pyrrolo[2,3-b]pyridin-5-yl)phenyl)sulfonyl)piperidin-4-yl)-5-(trifluoromethyl)pyridin-2-amine. MS: (ES) m/z calculated for $C_{24}H_{22}F_4N_5O_2S$ [M+H]$^+$ 520.14, found 520.3. $^1$H NMR (400 MHz, DMSO-d$_6$) δ 12.20 (s, 1H), 8.42 (d, J=10.3 Hz, 1H), 8.23 (s, 1H), 7.91 (d, J=8.7 Hz, 2H), 7.87 (d, J=8.7 Hz, 2H), 7.62-7.58 (m, 2H), 7.33 (d, J=7.3 Hz, 1H), 6.64 (d, J=3.4 Hz, 1H), 6.55 (d, J=8.9 Hz, 1H), 3.86-3.74 (m, 1H), 3.63-3.55 (m, 2H), 2.65-2.57 (m, 2H), 2.02-1.94 (m, 2H), 1.58-1.46 (m, 2H).

Example 32: 2,2-dimethyl-6-(4-((4-((5-(trifluoromethyl)pyridin-2-yl)amino)piperidin-1-yl)sulfonyl)phenyl)-2H-benzo[b][1,4]oxazin-3(4H)-one

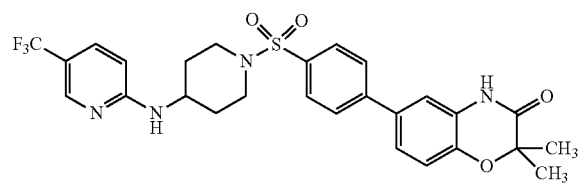 [SMILES: CC1(C)Oc2ccc(-c3ccc(S(=O)(=O)N4CCC(Nc5ccc(C(F)(F)F)cn5)CC4)cc3)cc2NC1=O]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added $K_2CO_3$ (41 mg, 0.30 mmol), 6-bromo-2,2-dimethyl-2H-benzo[b][1,4]oxazin-3(4H)-one (31 mg, 0.12 mmol), dioxane (1.5 mL) and water (0.5 mmol). The mixture was sparged with nitrogen for 20 minutes. Pd(dppf)$Cl_2$.DCM (8 mg, 0.010 mmol) was added, and the mixture was sparged with nitrogen for an additional 5 minutes. The vial was sealed, the mixture stirred at 100° C. for 2 hours, and cooled when the reaction had proceeded to completion. The reaction mixture was concentrated and purified via $SiO_2$ gel chromatography followed by preparative reverse-phase HPLC to give 2,2-dimethyl-6-(4-((4-((5-(trifluoromethyl)pyridin-2-yl)amino)piperidin-1-yl)sulfonyl)phenyl)-2H-benzo[b][1,4]oxazin-3(4H)-one. MS: (ES) m/z calculated for $C_{27}H_{28}F_3N_4O_4S$ [M+H]$^+$ 561.18, found 561.3. $^1$H NMR (400 MHz, DMSO-d$_6$) δ 10.81 (s, 1H), 8.22 (s, 1H), 7.82 (s, 4H), 7.60 (dd, J=9.0, 2.6 Hz, 1H), 7.34 (dd, J=8.3, 2.2 Hz, 1H), 7.31 (d, J=7.4 Hz, 1H), 7.21 (d, J=2.2 Hz, 1H), 7.08 (d, J=8.3 Hz, 1H), 6.54 (d, J=8.7 Hz, 1H), 3.84-3.70 (m, 1H), 3.60-3.50 (m, 2H), 2.62-2.54 (m, 2H), 2.01-1.90 (m, 2H), 1.57-1.47 (m, 2H), 1.44 (s, 6H).

Example 33: N-(1-((4-(2,3-Dihydrobenzo[b][1,4]dioxin-6-yl)phenyl)sulfonyl)piperidin-4-yl)-5-(trifluoromethyl)pyridin-2-amine

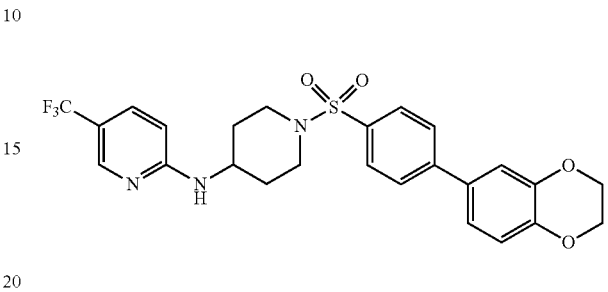

To N-(1-((4-bromophenyl)sulfonyl)piperidin-4-yl)-5-(trifluoromethyl)pyridin-2-amine (46 mg, 0.10 equiv) were added $K_2CO_3$ (41 mg, 0.30 mmol), benzodioxane-6-boronic acid (22 mg, 0.12 mmol), dioxane (1.5 mL), and water (0.5 mL), and Pd(dppf)$Cl_2$.DCM (33 mg, 0.040 mmol) in a septum-cap vial. The mixture was sparged with nitrogen for 20 minutes. Pd(dppf)$Cl_2$.DCM (8 mg, 0.010 mmol) was added, and the mixture was sparged with nitrogen for an additional 5 minutes. The vial was sealed, the mixture stirred at 100° C. for 2 hours, and cooled when the reaction had proceeded to completion. The reaction mixture was diluted with EtOAc (10 mL), filtered through Celite®, and concentrated. The mixture was purified via $SiO_2$ gel chromatography, followed by preparative reverse-phase HPLC to give N-(1-((4-(2,3-dihydrobenzo[b][1,4]dioxin-6-yl)phenyl)sulfonyl)piperidin-4-yl)-5-(trifluoromethyl)pyridin-2-amine. MS: (ES) m/z calculated for $C_{25}H_{25}F_3N_3O_4S$ [M+H]$^+$ 520.15, found 520.3. $^1$H NMR (400 MHz, DMSO-d$_6$) δ 8.22 (s, 1H), 7.88 (d, J=8.7 Hz, 2H), 7.76 (d, J=8.6 Hz, 2H), 7.59 (dd, J=8.8, 2.4 Hz, 1H), 7.31 (d, J=7.4 Hz, 1H), 7.29 (d, J=2.3 Hz, 1H), 7.25 (dd, J=8.4, 2.3 Hz, 1H), 6.99 (d, J=8.4 Hz, 1H), 6.54 (d, J=9.0 Hz, 1H), 4.30 (s, 4H), 3.82-3.70 (m, 1H), 3.59-3.50 (m, 2H), 2.61-2.52 (m, 2H), 2.02-1.91 (m, 2H), 1.56-1.43 (m, 2H).

Example 34: 2-(2-Hydroxyethyl)-6-(4-((4-((5-(trifluoromethyl)pyridin-2-yl)amino)piperidin-1-yl)sulfonyl)phenyl)isoindolin-1-one

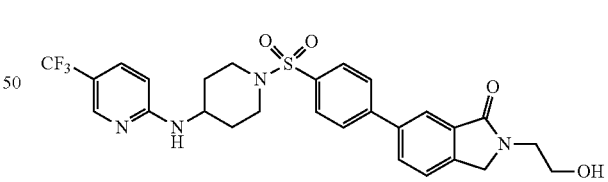

2-(2-((tert-butyldimethylsilyl)oxy)ethyl)-6-(4-((4-((5-(trifluoromethyl)pyridin-2-yl)amino)piperidin-1-yl)sulfonyl)phenyl)isoindolin-1-one (35.0 mg; 0.05 mmol) in 1 mL of THF is added 0.1 mL of 1 M TBAF in THF. The mixture stirred for 1 h. LC-MS indicates the desired product. The reaction was diluted with 10 mL of EtOAc, washed with 3×5 mL of $H_2O$ and 10 mL of brine. The organic phase is dried with $MgSO_4$, filtered and concentrated. The material was purified by reverse phase preparative HPLC to give 2-(2-hydroxyethyl)-6-(4-((4-((5-(trifluoromethyl)pyridin-2-yl)amino)piperidin-1-yl)sulfonyl)phenyl)isoindolin-1-one. MS: (ES) m/z calculated for $C_{27}H_{27}F_3N_4O_4S$ [M+H]$^+$ 5610.2, found 560.9.

Example 35: N-(1-((4-(2',3',5',6'-tetrahydrospiro[indoline-3,4'-pyran]-5-yl)phenyl)sulfonyl)piperidin-4-yl)-5-(trifluoromethyl)pyridin-2-amine

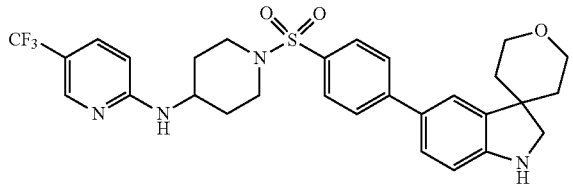 [SMILES: O=S(=O)(c1ccc(-c2ccc3c(c2)C2(CCOCC2)CN3)cc1)N1CCC(Nc2ccc(C(F)(F)F)cn2)CC1]

To N-[1-[4-(4,4,5,5-tetramethyl-1,3,2-dioxaborolan-2-yl)phenyl]sulfonyl-4-piperidyl]-5-(trifluoromethyl)pyridin-2-amine (50.0 mg, 0.10 mmol) in 2.25 mL dioxane were added K$_2$CO$_3$ (25.0 mg, 0.18 mmol), 5-bromospiro[indoline-3,4'-tetrahydropyran] (40.0 mg, 0.15 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give N-(1-((4-(2',3',5',6'-tetrahydrospiro[indoline-3,4'-pyran]-5-yl)phenyl)sulfonyl)piperidin-4-yl)-5-(trifluoromethyl)pyridin-2-amine. MS: (ES) m/z calculated for C$_{29}$H$_{31}$F$_3$N$_4$O$_3$S [M+H]$^+$ 573.2, found 573.0

Example 36: N-(1-((4-(3,4-dihydro-2H-benzo[b][1,4]oxazin-6-yl)phenyl)sulfonyl)piperidin-4-yl)-5-(trifluoromethyl)pyridin-2-amine

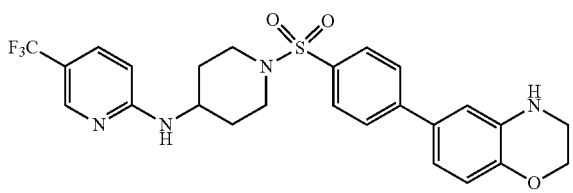 [SMILES: O=S(=O)(c1ccc(-c2ccc3c(c2)NCCO3)cc1)N1CCC(Nc2ccc(C(F)(F)F)cn2)CC1]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added K$_2$CO$_3$ (41 mg, 0.30 mmol), 6-bromo-3,4-dihydro-2H-benzo[b][1,4]oxazine (26 mg, 0.12 mmol), dioxane (1.5 mL) and water (0.5 mmol). The mixture was sparged with nitrogen for 20 minutes. Pd(dppf)Cl$_2$.DCM (8 mg, 0.010 mmol) was added, and the mixture was sparged with nitrogen for an additional 5 minutes. The vial was sealed, the mixture stirred at 100° C. for 2 hours, and cooled when the reaction had proceeded to completion. The reaction mixture was diluted with EtOAc (10 mL), filtered through Celite®, and concentrated. The mixture was purified via SiO$_2$ gel chromatography (0-100% EtOAc/hexanes), followed by preparative reverse-phase HPLC (H$_2$O/MeCN+0.1% TFA), to give N-(1-((4-(3,4-dihydro-2H-benzo[b][1,4]oxazin-6-yl)phenyl)sulfonyl)piperidin-4-yl)-5-(trifluoromethyl)pyridin-2-amine. MS: (ES) m/z calculated for C$_{25}$H$_{26}$F$_3$N$_4$O$_3$S [M+H]$^+$ 519.17, found 519.3. $^1$H NMR (400 MHz, DMSO-d) δ 8.22 (s, 1H), 7.77 (s, 4H), 7.60 (d, J=9.0 Hz, 1H), 7.30 (d, J=6.2 Hz, 1H), 6.93 (s, 1H), 6.87 (d, J=8.3 Hz, 1H), 6.76 (d, J=8.4 Hz, 1H), 6.54 (d, J=9.0 Hz, 1H), 5.96 (s, 1H), 4.17 (s, 2H), 3.83-3.69 (m, 1H), 3.60-3.48 (m, 2H), 3.34-3.29 (m, 2H), 2.63-2.50 (m, 2H), 2.01-1.90 (m, 2H), 1.57-1.43 (m, 2H).

Example 37: 5-(4-((4-((5-(Trifluoromethyl)pyridin-2-yl)amino)piperidin-1-yl)sulfonyl)phenyl)-2',3',5',6'-tetrahydrospiro[indoline-3,4'-pyran]-2-one

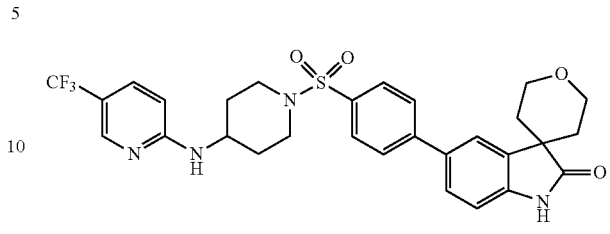

To N-[1-[4-(4,4,5,5-tetramethyl-1,3,2-dioxaborolan-2-yl)phenyl]sulfonyl-4-piperidyl]-5-(trifluoromethyl)pyridin-2-amine (50.0 mg, 0.10 mmol) in 2.25 mL dioxane were added K$_2$CO$_3$ (25.0 mg, 0.18 mmol), 5-bromospiro[indoline-3,4'-tetrahydropyran]-2-one (40.0 mg, 0.15 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 5-(4-((4-((5-(trifluoromethyl)pyridin-2-yl)amino)piperidin-1-yl)sulfonyl)phenyl)-2',3',5',6'-tetrahydrospiro[indoline-3,4'-pyran]-2-one. MS: (ES) m/z calculated for C$_{29}$H$_{29}$F$_3$N$_4$O$_4$S [M+H]$^+$ 587.2, found 586.9. $^1$H NMR (400 MHz, DMSO-d$_6$) δ 10.58 (s, 1H), 8.20 (d, J=2.5 Hz, 1H), 7.93 (d, J=8.5 Hz, 2H), 7.87 (d, J=1.9 Hz, 1H), 7.76 (d, J=8.5 Hz, 2H), 7.60 (ddd, J=14.5, 8.5, 2.2 Hz, 2H), 7.30 (d, J=7.3 Hz, 1H), 6.97 (d, J=8.1 Hz, 1H), 6.52 (d, J=8.9 Hz, 1H), 4.06 (ddd, J=11.8, 8.4, 3.5 Hz, 2H), 3.90-3.72 (m, 3H), 3.59-3.51 (m, 2H), 2.59-2.37 (m, 2H), 2.00-1.80 (m, 4H), 1.73 (dt, J=13.6, 4.4 Hz, 2H), 1.56-1.41 (m, 2H).

Example 38: 5'-(4-((4-((5-(Trifluoromethyl)pyridin-2-yl)amino)piperidin-1-yl)sulfonyl)phenyl)spiro[cyclopropane-1,3'-indolin]-2'-one

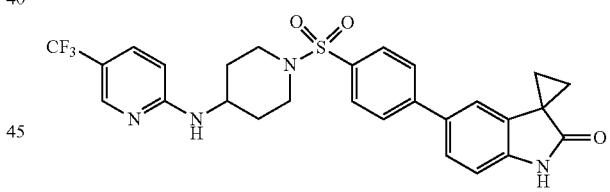

To N-[1-[4-(4,4,5,5-tetramethyl-1,3,2-dioxaborolan-2-yl)phenyl]sulfonyl-4-piperidyl]-5-(trifluoromethyl)pyridin-2-amine (50.0 mg, 0.10 mmol) in 2.25 mL dioxane were added K$_2$CO$_3$ (25.0 mg, 0.18 mmol), 5'-bromospiro[cyclopropane-1,3'-indoline]-2'-one (35.0 mg, 0.15 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 5'-(4-((4-((5-(trifluoromethyl)pyridin-2-yl)amino)piperidin-1-yl)sulfonyl)phenyl)spiro[cyclopropane-1,3'-indolin]-2'-one. MS: (ES) m/z calculated for C$_{27}$H$_{25}$F$_3$N$_4$O$_3$S [M+H]$^+$ 543.2, found 443.0. $^1$H NMR (400 MHz, DMSO-d$_6$) δ 10.72 (s, 1H), 8.20 (d, J=2.5 Hz, 1H), 7.88 (d, J=8.5 Hz, 2H), 7.76 (d, J=8.5 Hz, 2H), 7.57 (ddd, J=7.8, 5.2, 2.2 Hz, 2H), 7.42 (d, J=1.9 Hz, 1H), 7.29 (d, J=7.3 Hz, 1H), 7.01 (d, J=8.1 Hz, 1H), 6.52 (d, J=8.9 Hz, 1H), 3.73 (d, J=11.6 Hz, 1H), 3.54 (dd, J=10.4, 6.0 Hz, 2H), 2.56-2.43 (m, 2H), 1.94 (d, J=13.1 Hz, 2H), 1.69 (q, J=3.8 Hz, 2H), 1.57-1.41 (m, 4H).

Example 39: 2-(2-((tert-Butyldimethylsilyl)oxy)ethyl)-6-(4-((4-((5-(trifluoromethyl)pyridin-2-yl)amino)piperidin-1-yl)sulfonyl)phenyl)isoindolin-1-one

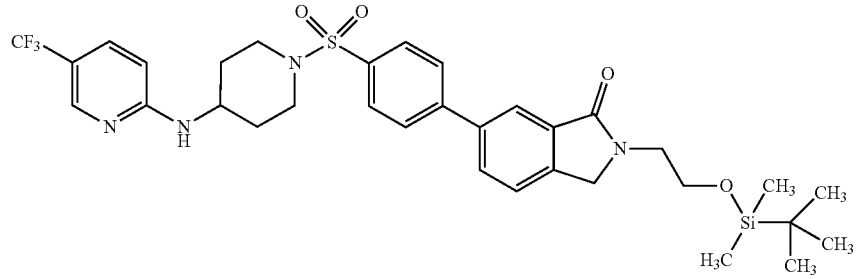 [SMILES: CC(C)(C)[Si](C)(C)OCCN1Cc2ccc(-c3ccc(S(=O)(=O)N4CCC(Nc5ccc(C(F)(F)F)cn5)CC4)cc3)cc2C1=O]

To N-[1-[4-(4,4,5,5-tetramethyl-1,3,2-dioxaborolan-2-yl)phenyl]sulfonyl-4-piperidyl]-5-(trifluoromethyl)pyridin-2-amine (50.0 mg, 0.10 mmol) in 2.25 mL dioxane were added K$_2$CO$_3$ (25.0 mg, 0.18 mmol), 6-bromo-2-[2-[tert-butyl(dimethyl)silyl]oxyethyl]isoindolin-1-one (46.0 mg, 0.12 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 2-(2-((tert-butyldimethylsilyl)oxy)ethyl)-6-(4-((4-((5-(trifluoromethyl)pyridin-2-yl)amino)piperidin-1-yl)sulfonyl)phenyl)isoindolin-1-one. MS: (ES) m/z calculated for C$_{33}$H$_{41}$F$_3$N$_4$O$_4$SSi [M+H]$^+$ 675.3, found 675.0. $^1$H NMR (400 MHz, DMSO-d$_6$) 8.20 (s, 1H), 8.07-7.95 (m, 4H), 7.82 (d, J=7.8 Hz, 2H), 7.75 (d, J=7.9 Hz, 1H), 7.58 (dd, J=8.8, 2.5 Hz, 1H), 7.30 (d, J=7.3 Hz, 1H), 6.52 (d, J=9.0 Hz, 1H), 4.61 (s, 2H), 3.67-3.52 (m, 4H), 3.38 (s, 1H), 3.28 (s, 2H), 2.63-2.43 (m, 2H), 1.99-1.91 (m, 2H), 1.49 (q, J=10.5, 9.2 Hz, 2H), 0.82 (s, 9H), 0.0 (s, 6H).

Example 40: 2-(3-Cyano-5-(4-((4-((5-(trifluoromethyl)pyridin-2-yl)amino)piperidin-1-yl)sulfonyl)phenyl)-1H-pyrrolo[2,3-b]pyridin-1-yl)acetamide

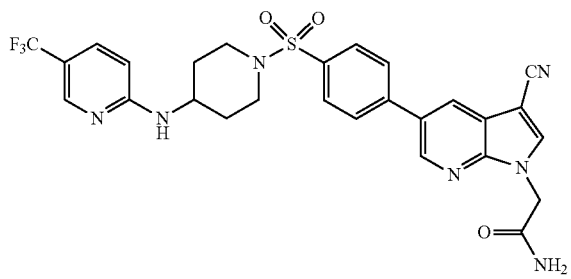 [SMILES: N#Cc1cn(CC(N)=O)c2ncc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added K$_2$CO$_3$ (41 mg, 0.30 mmol), 2-(5-bromo-3-cyano-1H-pyrrolo[2,3-b]pyridin-1-yl)acetamide (42 mg, 0.15 mmol), dioxane (1.5 mL) and water (0.5 mL). The mixture was sparged with nitrogen for 20 minutes. Pd(dppf)Cl$_2$.DCM (8 mg, 0.010 mmol) was added, and the mixture was sparged with nitrogen for an additional 5 minutes. The vial was sealed, the mixture stirred at 100° C. for 2 hours, and cooled when the reaction had proceeded to completion. The reaction mixture was concentrated and purified via preparative reverse-phase HPLC (H$_2$O/MeCN+0.1% TFA) to give 2-(3-cyano-5-(4-((4-((5-(trifluoromethyl)pyridin-2-yl)amino)piperidin-1-yl)sulfonyl)phenyl)-1H-pyrrolo[2,3-b]pyridin-1-yl)acetamide. MS: (ES) m/z calculated for C$_{27}$H$_{25}$F$_3$N$_7$O$_3$S [M+H]$^+$ 584.17, found 584.4. $^1$H NMR (400 MHz, DMSO-d$_6$) δ 8.82 (d, J=2.1 Hz, 1H), 8.54-8.52 (m, 2H), 8.24-8.20 (m, 1H), 8.12 (d, J=8.5 Hz, 2H), 7.86 (d, J=8.5 Hz, 2H), 7.82 (s, 1H), 7.60 (dd, J=9.0, 2.5 Hz, 1H), 7.39 (s, 1H), 7.32 (d, J=7.3 Hz, 1H), 6.54 (d, J=8.9 Hz, 1H), 5.04 (s, 2H), 3.84-3.72 (m, 1H), 3.63-3.52 (m, 2H), 2.65-2.54 (m, 2H), 2.02-1.93 (m, 2H), 1.58-1.45 (m, 2H).

Example 41: 2-(1-Oxo-6-(4-((4-((5-(trifluoromethyl)pyridin-2-yl)amino)piperidin-1-yl)sulfonyl)phenyl)isoindolin-2-yl)acetamide

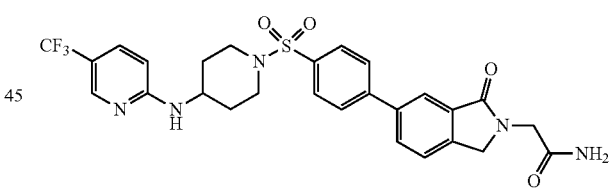

To N-[1-[4-(4,4,5,5-tetramethyl-1,3,2-dioxaborolan-2-yl)phenyl]sulfonyl-4-piperidyl]-5-(trifluoromethyl)pyridin-2-amine (50.0 mg, 0.10 mmol) in 2.25 mL dioxane were added K$_2$CO$_3$ (25.0 mg, 0.18 mmol), 2-(6-bromo-1-oxo-isoindolin-2-yl)acetamide (35.0 mg, 0.13 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 2-(1-Oxo-6-(4-((4-((5-(trifluoromethyl)pyridin-2-yl)amino)piperidin-1-yl)sulfonyl)phenyl)isoindolin-2-yl)acetamide. MS: (ES) m/z calculated for C$_{27}$H$_{26}$F$_3$N$_5$O$_4$S [M+H]$^+$ 574.2, found 573.9. $^1$H NMR (400 MHz, DMSO-d$_6$) δ 8.20 (d, J=2.4 Hz, 1H), 8.10-7.97 (m, 4H), 7.86-7.79 (d, J=8.0 Hz, 2H), 7.75 (d, J=7.9 Hz, 1H), 7.62-7.54 (m, 2H), 7.30 (d, J=7.2 Hz, 1H), 7.22-7.16 (m, 1H), 6.52 (d, J=8.9 Hz, 1H), 4.57 (s, 2H), 4.15 (s, 2H), 3.76 (dd, J=15.0, 8.1 Hz, 1H), 3.56 (d, J=12.3 Hz, 2H), 2.64-2.50 (m, 2H), 1.99-1.90 (m, 2H), 1.49 (q, J=9.7, 9.3 Hz, 2H).

Example 42: 1-Cyclopropyl-6-(4-((4-((5-(trifluoromethyl)pyridin-2-yl)amino)piperidin-1-yl)sulfonyl)phenyl)-1,3-dihydro-2H-benzo[d]imidazol-2-one

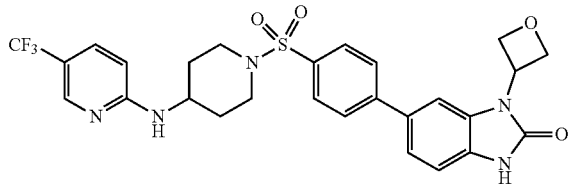 [SMILES: O=c1[nH]c2ccc(-c3ccc(S(=O)(=O)N4CCC(Nc5ccc(C(F)(F)F)cn5)CC4)cc3)cc2n1C1COC1]

To N-[1-[4-(4,4,5,5-tetramethyl-1,3,2-dioxaborolan-2-yl)phenyl]sulfonyl-4-piperidyl]-5-(trifluoromethyl)pyridin-2-amine (50.0 mg, 0.10 mmol) in 2.25 mL dioxane were added $K_2CO_3$ (25.0 mg, 0.18 mmol), 5-bromo-3-(oxetan-3-yl)-1H-benzimidazol-2-one (35.0 mg, 0.13 mmol), Pd(dppf)Cl$_2$.DCM (9.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via $SiO_2$ gel chromatography, to give 1-cyclopropyl-6-(4-((4-((5-(trifluoromethyl)pyridin-2-yl)amino)piperidin-1-yl)sulfonyl)phenyl)-1,3-dihydro-2H-benzo[d]imidazol-2-one. MS: (ES) m/z calculated for $C_{27}H_{26}F_3N_5O_2S$ [M+H]$^+$ 574.2, found 573.9. $^1$H NMR (400 MHz, DMSO-d$_6$) □ 11.18 (s, 1H), 8.20 (d, J=2.5 Hz, 1H), 7.91 (d, J=8.4 Hz, 2H), 7.80 (d, J=8.5 Hz, 2H), 7.76 (d, J=1.8 Hz, 1H), 7.58 (dd, J=8.9, 2.6 Hz, 1H), 7.43 (dd, J=8.2, 1.7 Hz, 1H), 7.30 (d, J=7.4 Hz, 1H), 7.14 (d, J=8.1 Hz, 1H), 6.52 (d, J=8.9 Hz, 1H), 5.53 (p, J=6.9 Hz, 1H), 5.14 (t, J=6.5 Hz, 2H), 4.95 (q, J=7.6 Hz, 2H), 3.75 (s, 1H), 3.54 (d, J=11.0 Hz, 2H), 3.38-3.27 (m, 1H), 2.62-2.50 (m, 1H), 1.95 (d, J=13.7 Hz, 2H), 1.49 (q, J=11.0, 10.1 Hz, 2H).

Example 43: (N-(1-((4-(6-fluoro-1H-pyrrolo[2,3-b]pyridin-5-yl)phenyl)sulfonyl)piperidin-4-yl)-5-(trifluoromethyl)pyridin-2-amine

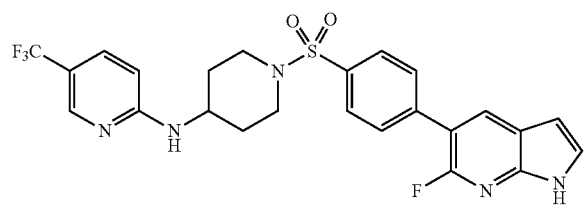 [SMILES: O=S(=O)(c1ccc(-c2cc3cc[nH]c3nc2F)cc1)N1CCC(Nc2ccc(C(F)(F)F)cn2)CC1]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine (51 mg, 0.10 mmol) in a septum-cap vial were added $K_2CO_3$ (41 mg, 0.30 mmol), 5-bromo-6-fluoro-1H-pyrrolo[2,3-b]pyridine (26 mg, 0.12 mmol), dioxane (1.5 mL) and water (0.5 mmol). The mixture was sparged with nitrogen for 20 minutes.
Pd(dppf)Cl$_2$.DCM (8 mg, 0.010 mmol) was added, and the mixture was sparged with nitrogen for an additional 5 minutes. The vial was sealed, the mixture stirred at 100° C. for 1 hour, and cooled when the reaction had proceeded to completion. The reaction mixture was diluted with EtOAc (10 mL), filtered through Celite®, and concentrated. The mixture was purified via $SiO_2$ gel chromatography (0-100% EtOAc/hexanes), followed by preparative reverse-phase HPLC (H$_2$O/MeCN+0.1% TFA) to give (N-(1-((4-(6-fluoro-1H-pyrrolo[2,3-b]pyridin-5-yl)phenyl)sulfonyl)piperidin-4-yl)-5-(trifluoromethyl)pyridin-2-amine. MS: (ES) m/z calculated for $C_{24}H_{22}F_4N_5O_2S$ [M+H]$^+$ 520.14, found 520.3 $^1$H NMR (400 MHz, DMSO-d$_6$) δ 11.96 (s, 1H), 8.33 (d, J=10.0 Hz, 1H), 8.23 (s, 1H), 7.89 (d, J=8.7 Hz, 2H), 7.85 (d, J=8.2 Hz, 2H), 7.60 (d, J=8.8 Hz, 1H), 7.53 (s, 1H), 7.33 (d, J=7.4 Hz, 1H), 6.62-6.50 (m, 2H), 3.86-3.72 (m, 1H), 3.67-3.49 (m, 2H), 2.65-2.55 (m, 2H), 2.04-1.92 (m, 2H), 1.59-1.46 (m, 2H).

Example 44: 5-(4-((4-((5-(Trifluoromethyl)pyridin-2-yl)amino)piperidin-1-yl)sulfonyl) phenyl)-1,3-dihydro-2H-pyrrolo[2,3-c]pyridin-2-one

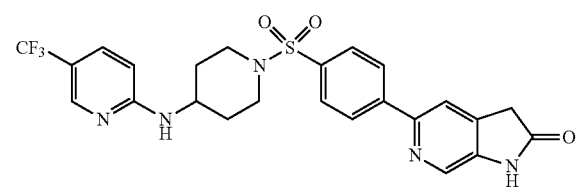 [SMILES: O=C1Cc2cc(-c3ccc(S(=O)(=O)N4CCC(Nc5ccc(C(F)(F)F)cn5)CC4)cc3)ncc2N1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5-bromo-1,3-dihydro-2H-pyrrolo[2,3-c]pyridin-2-one (21 mg, 0.10 mmol), and Pd(dppf)Cl$_2$.DCM (8.0 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via $SiO_2$ gel chromatography and reverse-phase HPLC to give 5-(4-((4-((5-(trifluoromethyl)pyridin-2-yl)amino)piperidin-1-yl)sulfonyl) phenyl)-1,3-dihydro-2H-pyrrolo[2,3-c]pyridin-2-one. MS: (ES) m/z calculated for $C_{24}H_{22}F_3N_5O_3S$ [M+H]$^+$ 518.2, found 518. $^1$H NMR (400 MHz, DMSO-d$_6$) δ 10.75 (s, 1H), 8.26 (dd, J=18.6, 8.3 Hz, 3H), 8.13-7.94 (m, 3H), 7.82 (d, J=7.8 Hz, 1H), 7.61 (d, J=9.7 Hz, 1H), 7.38 (bs, 1H), 6.56 (d, J=9.1 Hz, 1H), 3.82-3.51 (m, 5H), 2.64-2.54 (m, 2H), 2.03-1.89 (m, 2H), 1.50 (d, J=13.0 Hz, 2H).

Example 45: tert-Butyl-2-oxo-5-(4-((4-((5-(trifluoromethyl)pyridin-2-yl)amino)piperidin-1-yl)sulfonyl)phenyl)spiro[indoline-3,4'-piperidine]-1'-carboxylate

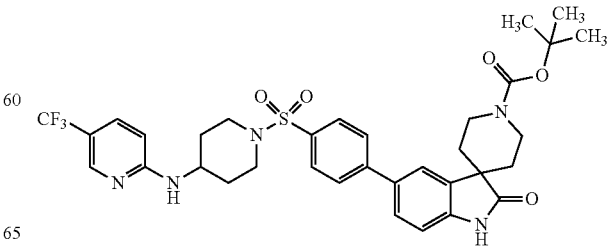

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (160 mg, 1.2 mmol), tert-butyl 5-bromo-2-oxospiro[indoline-3,4'-piperidine]-1'-carboxylate (150 mg, 0.40 mmol), and Pd(dppf)Cl$_2$.DCM (32 mg, 0.040 mmol). To this were added 3.2 mL dioxane and 0.8 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel to give tert-butyl-2-oxo-5-(4-((4-((5-(trifluoromethyl)pyridin-2-yl)amino)piperidin-1-yl)sulfonyl)phenyl)spiro[indoline-3,4'-piperidine]-1'-carboxylate. MS: (ES) m/z calculated for C$_{34}$H$_{38}$F$_3$N$_5$O$_5$S [M+H]$^+$ 686.3, found 686. $^1$H NMR (400 MHz, DMSO-d$_6$) δ 10.61 (s, 1H), 8.20 (s, 1H), 7.93 (d, J=8.1 Hz, 2H), 7.85 (s, 1H), 7.75 (d, J=8.1 Hz, 2H), 7.65-7.53 (m, 2H), 7.29 (d, J=7.3 Hz, 1H), 6.97 (d, J=8.0 Hz, 1H), 6.52 (d, J=9.0 Hz, 1H), 3.79-3.62 (m, 5H), 3.60-3.50 (m, 2H), 2.61-2.49 (m, 2H), 2.00-1.90 (m, 2H), 1.84-1.65 (m, 4H), 1.43 (s, 11H).

Example 46: 7-Methoxy-5-(4-((4-((5-(trifluoromethyl)pyridin-2-yl)amino)piperidin-1-yl)sulfonyl)phenyl)indolin-2-one

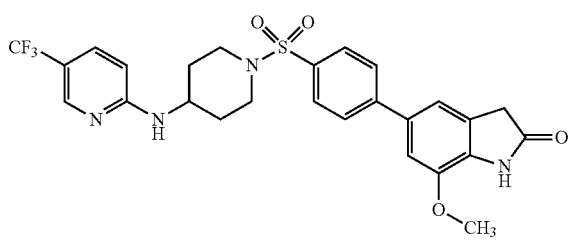 [SMILES: COc1cc(-c2ccc(S(=O)(=O)N3CCC(Nc4ccc(C(F)(F)F)cn4)CC3)cc2)cc2c1NC(=O)C2]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-7-methoxyindolin-2-one (24 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography and reverse-phase HPLC to give 7-methoxy-5-(4-((4-((5-(trifluoromethyl)pyridin-2-yl)amino)piperidin-1-yl)sulfonyl)phenyl)indolin-2-one. MS: (ES) m/z calculated for C$_{26}$H$_{25}$F$_3$N$_4$O$_4$S [M+H]$^+$ 547.2, found 547. $^1$H NMR (400 MHz, DMSO-d$_6$) δ 10.60 (s, 1H), 8.23 (s, 1H), 7.92 (d, J=8.2 Hz, 2H), 7.78 (d, J=8.1 Hz, 2H), 7.62 (d, J=7.8 Hz, 1H), 7.39 (s, 1H), 7.27 (s, 1H), 6.57 (d, J=9.0 Hz, 1H), 3.92 (s, 3H), 3.82-3.69 (m, 1H), 3.62-3.51 (m, 4H), 2.61-2.51 (m, 2H), 2.01-1.91 (m, 2H), 1.57-1.44 (m, 2H).

Example 47: 1-Methyl-5-(4-((4-((5-(trifluoromethyl)pyridin-2-yl)amino)piperidin-1-yl)sulfonyl)phenyl)-1H-indazol-3-amine

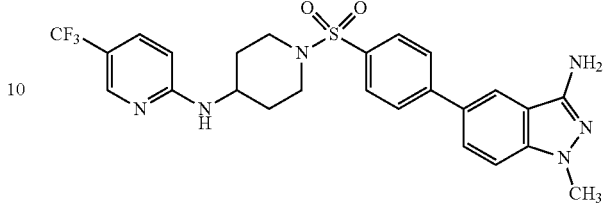

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-N-methyl-1H-pyrazolo[3,4-b]pyridin-3-amine (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via reverse-phase HPLC to give 1-methyl-5-(4-((4-((5-(trifluoromethyl)pyridin-2-yl)amino)piperidin-1-yl)sulfonyl)phenyl)-1H-indazol-3-amine. MS: (ES) m/z calculated for C$_{25}$H$_{25}$F$_3$N$_6$O$_2$S [M+H]$^+$ 531.2, found 531. $^1$H NMR (400 MHz, DMSO-d$_6$) δ 8.22 (s, 1H), 8.17 (d, J=1.3 Hz, 1H), 7.93 (d, J=8.4 Hz, 2H), 7.82 (d, J=8.5 Hz, 2H), 7.71 (dd, J=8.9, 1.8 Hz, 1H), 7.59 (dd, J=8.9, 2.6 Hz, 1H), 7.46 (d, J=8.8 Hz, 1H), 7.31 (d, J=7.2 Hz, 1H), 6.54 (d, J=8.9 Hz, 1H), 5.60 (s, 2H), 3.77 (s, 3H), 3.61-3.52 (m, 2H), 2.63-2.54 (m, 2H), 2.01-1.91 (m, 2H), 1.58-1.45 (m, 2H).

Example 48: 7-(4-((4-((5-(Trifluoromethyl)pyridin-2-yl)amino)piperidin-1-yl)sulfonyl)phenyl)-3,4-dihydroquinolin-2(1H)-one

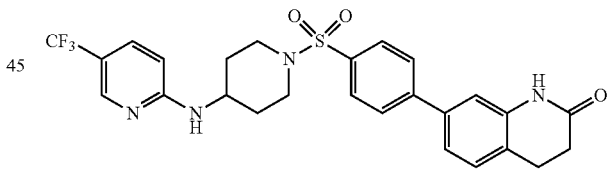

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 7-bromo-3,4-dihydroquinolin-2(1H)-one (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography and reverse-phase HPLC to give 7-(4-((4-((5-(trifluoromethyl)pyridin-2-yl)amino)piperidin-1-yl)sulfonyl)phenyl)-3,4-dihydroquinolin-2(1H)-one. MS: (ES) m/z calculated for C$_{26}$H$_{25}$F$_3$N$_4$O$_3$S [M+H]$^+$ 531.2, found 531. $^1$H NMR (400 MHz, DMSO-d$_6$) δ 10.24 (app s, 1H), 8.22 (app s, 1H), 7.91-7.75 (m, 4H), 7.65-7.54 (m, 1H), 7.39-7.25 (m, 3H), 7.21-7.13 (m, 1H), 6.60-6.48 (m, 1H), 3.85-3.71 (m, 1H), 3.62-3.47 (m, 2H), 3.33-3.23 (m, 2H, under residual H$_2$O peak), 2.99-2.85 (m, 2H), 2.65-2.55 (m, 2H), 2.02-1.88 (m, 2H), 1.58-1.40 (m, 2H).

Example 49: 2-(4-((4-((5-(trifluoromethyl)pyridin-2-yl)amino)piperidin-1-yl)sulfonyl)phenyl)-6,7-dihydrothiazolo [5,4-c]pyridin-4(5H)-one

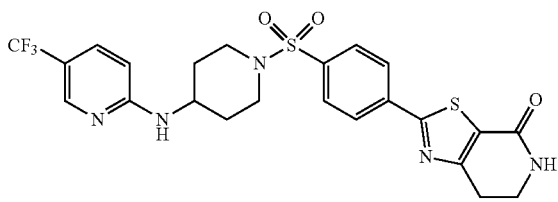 [SMILES: O=C1NCCc2nc(-c3ccc(S(=O)(=O)N4CCC(Nc5ccc(C(F)(F)F)cn5)CC4)cc3)sc21]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 2-bromo-6,7-dihydrothiazolo[5,4-c]pyridin-4(5H)-one (23 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography and reverse-phase HPLC to give 2-(4-((4-((5-(trifluoromethyl)pyridin-2-yl)amino)piperidin-1-yl)sulfonyl)phenyl)-6,7-dihydrothiazolo [5,4-c]pyridin-4(5H)-one. MS: (ES) m/z calculated for C$_{23}$H$_{22}$F$_3$N$_5$O$_3$S$_2$ [M+H]$^+$ 538.1, found 538. $^1$H NMR (400 MHz, DMSO-d$_6$) δ 8.25 (d, J=8.5 Hz, 1H), 8.22 (s, 1H), 8.04 (bs, 1H), 7.89 (d, J=8.5 Hz, 2H), 7.59 (dd, J=9.0, 2.6 Hz, 1H), 7.29 (d, J=7.4 Hz, 1H), 6.53 (d, J=8.9 Hz, 1H), 3.84-3.73 (m, 1H), 3.61-3.50 (m, 4H), 3.12-3.03 (m, 2H), 2.69-2.58 (m, 2H), 1.99-1.91 (m, 2H), 1.55-1.41 (m, 2H).

Example 50: N-Methyl-5-(4-((4-((5-(trifluoromethyl)pyridin-2-yl)amino)piperidin-1-yl)sulfonyl) phenyl)-1H-pyrazolo[3,4-b]pyridin-3-amine

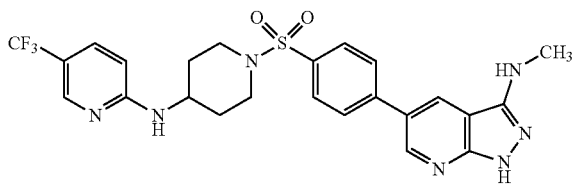 [SMILES: CNc1n[nH]c2ncc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-N-methyl-1H-pyrazolo[3,4-b]pyridin-3-amine (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via reverse-phase HPLC to give N-Methyl-5-(4-((4-((5-(trifluoromethyl)pyridin-2-yl)amino)piperidin-1-yl)sulfonyl)phenyl)-1H-pyrazolo[3,4-b]pyridin-3-amine. MS: (ES) m/z calculated for C$_{24}$H$_{24}$F$_3$N$_7$O$_2$S [M+H]$^+$ 532.2, found 532. $^1$H NMR (400 MHz, DMSO-d$_6$) δ 12.21 (s, 1H), 8.78 (d, J=2.2 Hz, 1H), 8.51 (d, J=2.2 Hz, 1H), 8.22 (s, 1H), 7.96 (d, J=8.2 Hz, 2H), 7.85 (d, J=8.2 Hz, 2H), 7.60 (dd, J=9.0, 2.5 Hz, 1H), 7.31 (d, J=7.3 Hz, 1H), 6.54 (d, J=8.8 Hz, 1H), 6.34 (d, J=5.3 Hz, 1H), 3.84-3.72 (s, 1H), 3.63-3.52 (m, 2H), 2.89 (d, J=5.0 Hz, 3H), 2.64-2.56 (m, 2H), 2.03-1.92 (m, 2H), 1.59-1.44 (m, 2H).

Example 51: 5-(4-((4-((4-(Trifluoromethyl)phenyl)amino)piperidin-1-yl)sulfonyl)phenyl)indolin-2-one

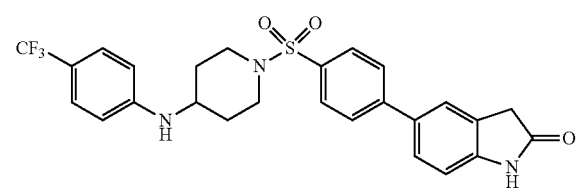 [SMILES: O=C1Cc2cc(-c3ccc(S(=O)(=O)N4CCC(Nc5ccc(C(F)(F)F)cc5)CC4)cc3)ccc2N1]

To 1-((4-bromophenyl)sulfonyl)-N-(4-(trifluoromethyl)phenyl)piperidin-4-amine in a septum-cap vial were added K$_2$CO$_3$ (41 mg, 0.29 mmol), 5-(4,4,5,5-tetramethyl-1,3,2-dioxaborolan-2-yl)indolin-2-one (28 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography to give 5-(4-((4-((4-(trifluoromethyl)phenyl)amino)piperidin-1-yl)sulfonyl)phenyl)indolin-2-one. MS: (ES) m/z calculated for C$_{26}$H$_{24}$F$_3$N$_3$O$_3$S [M+H]$^+$ 516.2, found 516. $^1$H NMR (400 MHz, DMSO-d$_6$) δ 10.57 (s, 1H), 7.89 (d, J=8.3 Hz, 2H), 7.78 (d, J=8.4 Hz, 2H), 7.66-7.57 (m, 2H), 7.33-7.27 (m, 2H), 6.95 (d, J=8.0 Hz, 1H), 6.64 (d, J=8.5 Hz, 2H), 6.28 (d, J=7.9 Hz, 1H), 3.65-3.53 (m, 4H), 3.32-3.29 (m, 1H, under residual solvent peak), 2.59-2.50 (m, 2H), 2.02-1.92 (m, 2H), 1.51-1.37 (m, 2H).

Example 52: 5'-(4-((4-((5-(Trifluoromethyl)pyridin-2-yl)amino)piperidin-1-yl)sulfonyl) phenyl)spiro[cyclopropane-1,3'-pyrrolo[2,3-b]pyridin]-2'(1'H)-one

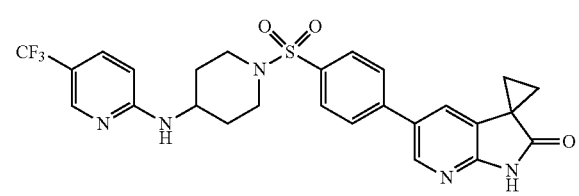 [SMILES: O=C1Nc2ncc(-c3ccc(S(=O)(=O)N4CCC(Nc5ccc(C(F)(F)F)cn5)CC4)cc3)cc2C12CC2]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5'-bromospiro[cyclopropane-1,3'-indolin]-2'-one (25 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via SiO$_2$ gel chromatography and reverse-phase HPLC to give 5'-(4-((4-((5-(trifluoromethyl)pyridin-2-yl)amino)piperidin-1-yl)sulfonyl) phenyl)spiro[cyclopropane-1,3'-pyrrolo[2,3-b]pyridin]-2'(1'H)-one. MS: (ES) m/z calculated for C$_{26}$H$_{24}$F$_3$N$_5$O$_3$S [M+H]$^+$ 544.2, found 544. $^1$H NMR (400 MHz, DMSO-d$_6$) δ 11.38 (s, 1H), 8.49 (d, J=2.1 Hz, 1H), 8.22 (d, J=2.4 Hz, 1H), 7.96 (d, J=8.5 Hz, 2H), 7.86-7.79 (m, 3H), 7.61 (dd, J=8.7, 2.2 Hz, 1H), 7.37 (s, 1H), 6.55 (d, J=8.9 Hz, 1H), 3.79-3.65 (m, 1H, under residual H$_2$O peak), 3.61-3.53 (m, 2H), 2.58-2.43 (m, 2H, under DMSO solvent peak), 2.02-1.91 (m, 2H), 1.79 (q, J=3.9 Hz, 2H), 1.59 (q, J=3.7 Hz, 2H), 1.57-1.43 (m, 2H).

Example 53: 1-Cyclopropyl-6-(4-((4-((5-(trifluoromethyl)pyridin-2-yl)amino)piperidin-1-yl)sulfonyl) phenyl)-1,3-dihydro-2H-benzo[d]imidazol-2-one

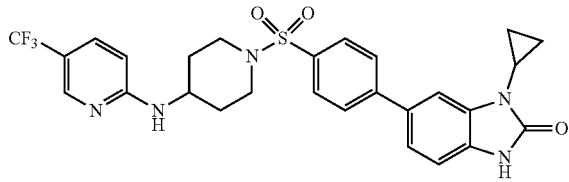 [SMILES: O=c1[nH]c2ccc(-c3ccc(S(=O)(=O)N4CCC(Nc5ccc(C(F)(F)F)cn5)CC4)cc3)cc2n1C1CC1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromo-1-cyclopropyl-1,3-dihydro-2H-benzo[d]imidazol-2-one (25 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 2 hours, and cooled when the reaction had proceeded to completion. The mixture was purified via SiO$_2$ gel chromatography and reverse-phase HPLC to give 1-cyclopropyl-6-(4-((4-((5-(trifluoromethyl)pyridin-2-yl)amino)piperidin-1-yl)sulfonyl) phenyl)-1,3-dihydro-2H-benzo[d]imidazol-2-one. MS: (ES) m/z calculated for C$_{27}$H$_{26}$F$_3$N$_5$O$_3$S [M+H]$^+$ 558.2, found 558. $^1$H NMR (400 MHz, DMSO-d$_6$) δ 10.93 (s, 1H), 8.23 (app s, 1H), 7.92 (d, J=8.5 Hz, 2H), 7.81 (d, J=8.5 Hz, 2H), 7.61 (dd, J=9.1, 2.5 Hz, 1H), 7.46 (s, 1H), 7.42-7.26 (m, 2H), 7.08 (d, J=8.1 Hz, 1H), 6.56 (d, J=9.0 Hz, 1H), 3.83-3.70 (m, 1H), 3.61-3.51 (m, 2H), 2.95-2.85 (m, 1H), 2.62-2.52 (m, 2H), 2.02-1.92 (m, 2H), 1.59-1.43 (m, 2H), 1.10-1.00 (m, 2H), 0.95-0.88 (m, 2H).

Example 54: 1-(5-(4-((4-((5-(Trifluoromethyl)pyridin-2-yl)amino)piperidin-1-yl)sulfonyl)phenyl)isoindolin-2-yl)ethan-1-one

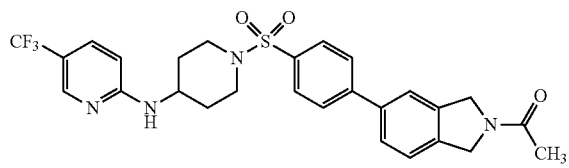 [SMILES: CC(=O)N1Cc2ccc(-c3ccc(S(=O)(=O)N4CCC(Nc5ccc(C(F)(F)F)cn5)CC4)cc3)cc2C1]

To N-(1-((4-(isoindolin-5-yl)phenyl)sulfonyl)piperidin-4-yl)-5-(trifluoromethyl)pyridin-2-amine in a septum-cap vial were added DMF (2 mL) and DIPEA (26 μL, 0.15 mmol) followed by acetic acid (3 μL, 0.050 mmol) and then HATU (28 mg, 0.075 mmol). The mixture stirred at RT until the reaction had proceeded to completion. The mixture was purified via reverse-phase HPLC to give 1-(5-(4-((4-((5-(trifluoromethyl)pyridin-2-yl)amino)piperidin-1-yl)sulfonyl)phenyl)isoindolin-2-yl)ethan-1-one. MS: (ES) m/z calculated for C$_{27}$H$_{27}$F$_3$N$_4$O$_3$S [M+H]$^+$ 545.2, found 545. $^1$H NMR (400 MHz, DMSO-d$_6$) δ 8.23 (app s, 1H), 7.97-7.92 (m, 2H), 7.86-7.81 (m, 2H), 7.77-7.68 (m, 2H), 7.63 (dd, J=9.1, 2.6 Hz, 1H), 7.50 (t, J=7.2 Hz, 1H), 7.46-7.39 (m, 1H), 6.58 (d, J=8.8 Hz, 1H), 4.90 (d, J=5.6 Hz, 2H), 4.68 (d, J=8.0 Hz, 2H), 3.81-3.71 (m, 1H), 3.62-3.51 (m, 2H), 2.61-2.53 (m, 2H), 2.09 (d, J=2.1 Hz, 3H), 2.01-1.91 (m, 2H), 1.58-1.44 (m, 2H).

Example 55: 5-(4-((4-((5-(Trifluoromethyl)pyridin-2-yl)amino)piperidin-1-yl)sulfonyl)phenyl)isoindoline-2-carboxamide

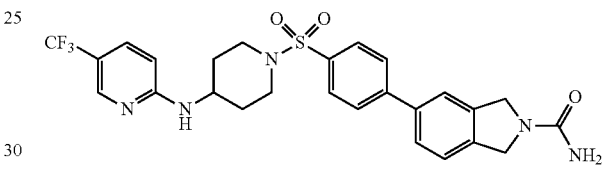

To N-(1-((4-(isoindolin-5-yl)phenyl)sulfonyl)piperidin-4-yl)-5-(trifluoromethyl)pyridin-2-amine in a septum-cap vial were added DCM (3 mL) and DIPEA (26 μL, 0.15 mmol) followed by (Trimethylsilyl)isocyanate (13 μL, 0.10 mmol). The mixture stirred at RT until the reaction had proceeded to completion. The mixture was purified via reverse-phase HPLC to give 5-(4-((4-((5-(trifluoromethyl)pyridin-2-yl)amino)piperidin-1-yl)sulfonyl)phenyl)isoindoline-2-carboxamide. MS: (ES) m/z calculated for C$_{26}$H$_{26}$F$_3$N$_5$O$_3$S [M+H]$^+$ 546.2, found 546. $^1$H NMR (400 MHz, DMSO-d$_6$) δ 8.22 (s, 1H), 7.98-7.92 (m, 2H), 7.82 (dd, J=8.6, 2.2 Hz, 2H), 7.73-7.65 (m, 2H), 7.61 (dd, J=8.9, 2.5 Hz, 1H), 7.47 (d, J=7.7 Hz, 1H), 7.35 (bs, 1H), 6.55 (d, J=8.9 Hz, 1H), 6.01 (bs, 2H), 4.70-4.56 (m, 4H), 3.57-3.44 (m, 3H, under residual H$_2$O peak), 2.63-2.53 (m, 2H), 2.02-1.91 (m, 2H), 1.58-1.45 (m, 2H).

Example 56: 5-(4-((4-((4-(Trifluoromethyl)phenyl)amino)piperidin-1-yl)sulfonyl)phenyl)-1H-indazole-3-carbonitrile

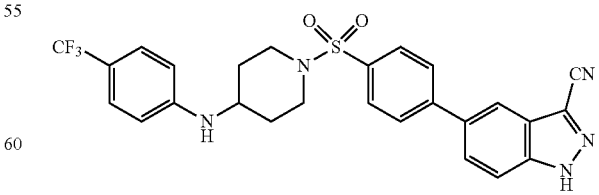

To 1-((4-(4,4,5,5-tetramethyl-1,3,2-dioxaborolan-2-yl)phenyl)sulfonyl)-N-(4-(trifluoromethyl)phenyl) piperidin-4-amine in a septum-cap vial were added K$_2$CO$_3$ (41 mg, 0.29 mmol), 5-bromo-1H-indazole-3-carbonitrile (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 3 hours, and cooled when the reaction had proceeded to completion. The mixture was purified via reverse-phase HPLC to give 5-(4-((4-((4-(trifluoromethyl) phenyl)amino)piperidin-1-yl)sulfonyl)phenyl)-1H-indazole-3-carbonitrile. MS: (ES) m/z calculated for C$_{26}$H$_{22}$F$_3$N$_5$O$_2$S [M+H]$^+$ 526.2, found 526. $^1$H NMR (400 MHz, DMSO-d$_6$) δ 8.29-8.21 (m, 1H), 8.14-8.03 (m, 2H), 7.98-7.78 (m, 4H), 7.34-7.23 (m, 2H), 6.68-6.58 (m, 2H), 3.67-3.54 (m, 2H), 3.40-3.27 (m, 1H), 2.60-2.51 (m, 2H), 2.02-1.88 (m, 2H), 1.51-1.35 (m, 2H).

Example 57: 5-(4-((4-((4-(Trifluoromethyl)phenyl) amino)piperidin-1-yl)sulfonyl)phenyl)-1H-pyrrolo[2,3-b]pyridine-3-carbonitrile

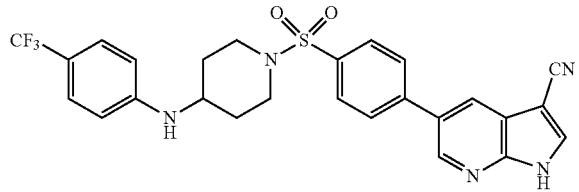 [SMILES: N#Cc1c[nH]c2ncc(-c3ccc(S(=O)(=O)N4CCC(Nc5ccc(C(F)(F)F)cc5)CC4)cc3)cc12]

To 1-((4-(4,4,5,5-tetramethyl-1,3,2-dioxaborolan-2-yl) phenyl)sulfonyl)-N-(4-(trifluoromethyl)phenyl) piperidin-4-amine in a septum-cap vial were added K$_2$CO$_3$ (41 mg, 0.29 mmol), 5-bromo-1H-pyrrolo[2,3-b]pyridine-3-carbonitrile (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hours, and cooled when the reaction had proceeded to completion. The mixture was purified via reverse-phase HPLC to give 5-(4-((4-((4-(trifluoromethyl) phenyl)amino) piperidin-1-yl)sulfonyl)phenyl)-1H-pyrrolo[2,3-b]pyridine-3-carbonitrile. MS: (ES) m/z calculated for C$_{26}$H$_{22}$F$_3$N$_5$O$_2$S [M+H]$^+$ 526.2, found 526. $^1$H NMR (400 MHz, DMSO-d$_6$) δ 13.03 (bs, 1H), 8.83 (s, 1H), 8.60-8.45 (m, 2H), 8.20-8.07 (m, 2H), 7.92-7.80 (m, 2H), 7.38-7.25 (m, 2H), 6.71-6.59 (m, 2H), 3.69-3.55 (m, 2H), 3.42-3.28 (m, 1H), 2.63-2.53 (m, 2H), 2.03-1.90 (m, 2H), 1.53-1.36 (m, 2H).

Example 58: 7-(4-((4-((5-(Trifluoromethyl)pyridin-2-yl)amino)piperidin-1-yl)sulfonyl)phenyl)quinazoline-2,4(1H,3H)-dione

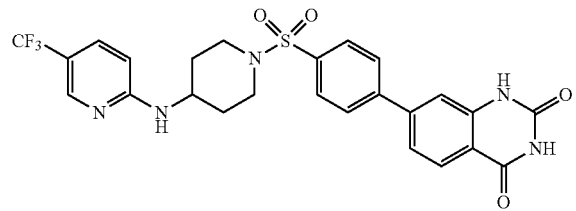 [SMILES: O=c1[nH]c(=O)c2ccc(-c3ccc(S(=O)(=O)N4CCC(Nc5ccc(C(F)(F)F)cn5)CC4)cc3)cc2[nH]1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 7-bromoquinazoline-2,4(1H,3H)-dione (24 mg, 0.10 mmol), and Pd(dppf)Cl$_2$.DCM (8 mg, 0.010 mmol). To this were added 1.6 mL of dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via reverse-phase HPLC to give 7-(4-((4-((5-(trifluoromethyl)pyridin-2-yl) amino)piperidin-1-yl)sulfonyl)phenyl)quinazoline-2,4(1H,3H)-dione. MS: (ES) m/z calculated for C$_{25}$H$_{22}$F$_3$N$_5$O$_4$S [M+H]$^+$ 546.1, found 546. $^1$H NMR (400 MHz, DMSO-d$_6$) δ 11.39 (s, 1H), 11.30 (s, 1H), 8.23 (s, 1H), 8.05-7.85 (m, 5H), 7.66-7.50 (m, 2H), 7.48-7.40 (m, 1H), 7.34 (app bs, 1H), 6.60-6.50 (m, 1H), 3.57-3.44 (m, 3H, under residual H$_2$O), 2.68-2.55 (m, 2H), 2.02-1.90 (m, 2H), 1.58-1.43 (m, 2H).

Example 59: N-(1-((4-(isoindolin-5-yl)phenyl)sulfonyl)piperidin-4-yl)-5-(trifluoromethyl)pyridin-2-amine

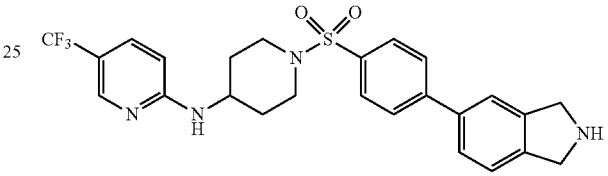

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (82 mg, 0.58 mmol), 5-bromoisoindoline (39 mg, 0.20 mmol), and Pd(dppf)Cl$_2$.DCM (16 mg, 0.020 mmol).

To this were added 1.6 mL dioxane and 0.4 mL of water. The mixture was sparged with nitrogen for 20 minutes. The vial was sealed, the mixture stirred at 100° C. for 1.3 hours, and cooled when the reaction had proceeded to completion. The mixture was purified via reverse-phase HPLC to give N-(1-((4-(isoindolin-5-yl)phenyl)sulfonyl)piperidin-4-yl)-5-(trifluoromethyl)pyridin-2-amine. MS: (ES) m/z calculated for C$_{25}$H$_{25}$F$_3$N$_4$O$_2$S [M+H]$^+$ 503.2, found 503. $^1$H NMR (400 MHz, DMSO-d$_6$) δ 9.57-9.37 (m, 2H), 8.27-8.18 (m, 1H), 8.03-7.73 (m, 6H), 7.67-7.51 (m, 2H), 7.38-7.30 (m, 1H), 6.60-6.51 (m, 1H), 4.66-4.49 (m, 4H), 3.84-3.69 (m, 1H), 3.65-3.51 (m, 2H), 2.66-2.51 (m, 2H), 2.06-1.88 (m, 2H), 1.61-1.42 (m, 2H).

Example 60: 6-(4-((4-((5-(Trifluoromethyl)pyridin-2-yl)amino)piperidin-1-yl)sulfonyl)phenyl)phthalazin-1(2H)-one

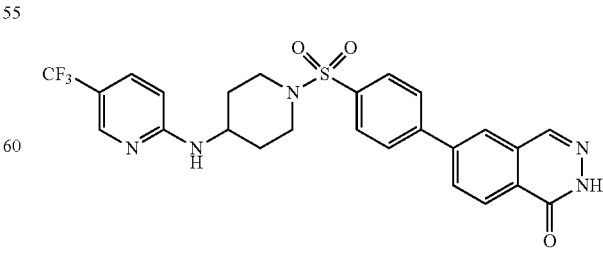

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromophthalazin-1(2H)-one (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via reverse-phase HPLC to give 6-(4-((4-((5-(trifluoromethyl)pyridin-2-yl)amino)piperidin-1-yl)sulfonyl)phenyl)phthalazin-1(2H)-one. MS: (ES) m/z calculated for C$_{25}$H$_{22}$F$_3$N$_5$O$_3$S [M+H]$^+$530.2, found 530. $^1$H NMR (400 MHz, DMSO-d$_6$) δ 12.75 (s, 1H), 8.50-8.42 (m, 1H), 8.40-8.30 (m, 2H), 8.29-8.19 (m, 2H), 8.16-8.06 (m, 2H), 7.98-7.86 (m, 2H), 7.66-7.56 (m, 1H), 7.39-7.29 (m, 1H), 6.60-6.50 (m, 1H), 3.86-3.72 (m, 1H), 3.66-3.55 (m, 2H), 2.70-2.56 (m, 2H), 2.03-1.90 (m, 2H), 1.58-1.42 (m, 2H).

Example 61: 2-(4-((4-((5-(Trifluoromethyl)pyridin-2-yl)amino)piperidin-1-yl)sulfonyl)phenyl)benzo[d]thiazole-6-carbonitrile

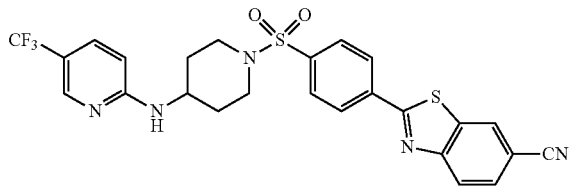 [SMILES: N#Cc1ccc2nc(-c3ccc(S(=O)(=O)N4CCC(Nc5ccc(C(F)(F)F)cn5)CC4)cc3)sc2c1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 2-bromobenzo[d]thiazole-6-carbonitrile (23 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via reverse-phase HPLC to give 2-(4-((4-((5-(trifluoromethyl)pyridin-2-yl)amino)piperidin-1-yl)sulfonyl)phenyl)benzo[d]thiazole-6-carbonitrile. MS: (ES) m/z calculated for C$_{25}$H$_{20}$F$_3$N$_5$O$_2$S$_2$ [M+H]$^+$ 544.1, found 544. $^1$H NMR (400 MHz, DMSO-d$_6$) δ 8.87 (s, 1H), 8.46-8.37 (m, 2H), 8.35-8.27 (m, 1H), 8.22 (s, 1H), 8.06-7.93 (m, 3H), 7.65-7.57 (m, 1H), 7.43-7.33 (m, 1H), 6.60-6.51 (m, 1H), 3.84-3.72 (m, 1H), 3.64-3.54 (m, 2H), 2.72-2.60 (m, 2H), 2.03-1.91 (m, 2H), 1.57-1.42 (m, 2H).

Example 62: 4-(4-((4-((5-(Trifluoromethyl)pyridin-2-yl)amino)piperidin-1-yl)sulfonyl)phenyl)-1H-indole-7-carboxamide

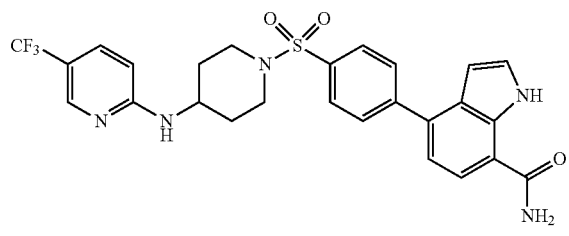 [SMILES: NC(=O)c1ccc(-c2ccc(S(=O)(=O)N3CCC(Nc4ccc(C(F)(F)F)cn4)CC3)cc2)c2cc[nH]c12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 4-bromo-1H-indole-7-carboxamide (23 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via reverse-phase HPLC to give 4-(4-((4-((5-(trifluoromethyl)pyridin-2-yl)amino)piperidin-1-yl)sulfonyl)phenyl)-1H-indole-7-carboxamide. MS: (ES) m/z calculated for C$_{26}$H$_{24}$F$_3$N$_5$O$_3$S [M+H]$^+$ 544.2, found 544. $^1$H NMR (400 MHz, DMSO-d$_6$) δ 11.39 (s, 1H), 8.30-8.12 (m, 2H), 8.03-7.79 (m, 5H), 7.68-7.59 (m, 1H), 7.54-7.39 (m, 3H), 7.30-7.21 (m, 1H), 6.69-6.54 (m, 2H), 3.88-3.72 (m, 1H), 3.67-3.53 (m, 2H), 2.68-2.55 (m, 2H), 2.04-1.91 (m, 2H), 1.63-1.44 (m, 2H).

Example 63: 6-(4-((4-((5-(Trifluoromethyl)pyridin-2-yl)amino)piperidin-1-yl)sulfonyl)phenyl)benzo[d]isothiazol-3(2H)-one 1,1-dioxide

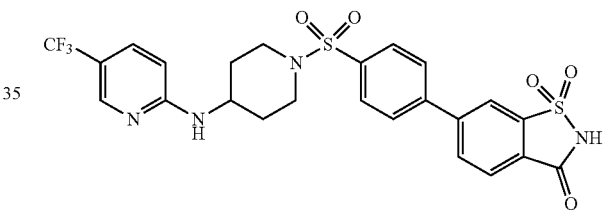

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromobenzo[d]isothiazol-3(2H)-one 1,1-dioxide (26 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via reverse-phase HPLC to give 6-(4-((4-((5-(trifluoromethyl)pyridin-2-yl)amino)piperidin-1-yl)sulfonyl)phenyl)benzo[d]isothiazol-3(2H)-one 1,1-dioxide. MS: (ES) m/z calculated for C$_{24}$H$_{21}$F$_3$N$_4$O$_5$S$_2$ [M+H]$^+$ 567.1, found 567. $^1$H NMR (400 MHz, DMSO-d$_6$) δ 8.51 (s, 1H), 8.29-8.20 (m, 2H), 8.16-8.09 (m, 2H), 8.08-7.99 (m, 1H), 7.92-7.83 (m, 2H), 7.61 (d, J=8.9 Hz, 1H), 7.42-7.32 (m, 1H), 6.56 (d, J=8.5 Hz, 1H), 3.85-3.71 (m, 1H, under residual H$_2$O peak), 3.64-3.51 (m, 2H), 2.71-2.54 (m, 2H), 2.03-1.90 (m, 2H), 1.58-1.42 (m, 2H).

Example 64: 5-(4-((4-((5-(Trifluoromethyl)pyridin-2-yl)amino)piperidin-1-yl)sulfonyl)phenyl)benzo[d]isothiazol-3(2H)-one 1,1-dioxide

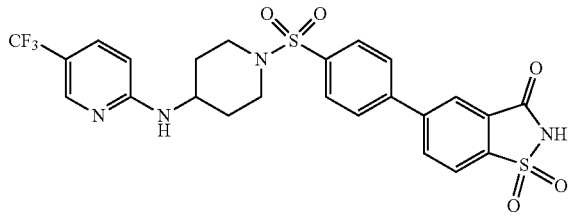 [SMILES: O=C1NS(=O)(=O)c2ccc(-c3ccc(S(=O)(=O)N4CCC(Nc5ccc(C(F)(F)F)cn5)CC4)cc3)cc21]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5-bromobenzo[d]isothiazol-3(2H)-one 1,1-dioxide (26 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.3 hours, and cooled when the reaction had proceeded to completion. The mixture was purified via reverse-phase HPLC to give 5-(4-((4-((5-(trifluoromethyl)pyridin-2-yl)amino)piperidin-1-yl)sulfonyl)phenyl)benzo[d]isothiazol-3(2H)-one 1,1-dioxide. MS: (ES) m/z calculated for $C_{24}H_{21}F_3N_4O_5S_2$ [M+H]$^+$ 567.1, found 567. $^1$H NMR (400 MHz, DMSO-d$_6$) δ 8.36-8.18 (m, 4H), 8.16-8.04 (m, 2H), 7.94-7.82 (m, 2H), 7.68-7.58 (m, 1H), 7.44 (bs, 1H), 6.58 (d, J=8.8 Hz, 1H), 3.85-3.71 (m, 1H), 3.65-3.51 (m, 2H), 2.67-2.54 (m, 2H), 2.03-1.89 (m, 2H), 1.59-1.43 (m, 2H).

Example 65: 5'-(4-((4-((5-(Trifluoromethyl)pyridin-2-yl)amino)piperidin-1-yl)sulfonyl)phenyl)-2,3,5,6-tetrahydro-spiro[pyran-4,3'-pyrrolo[2,3-b]pyridin]-2'(1'H)-one

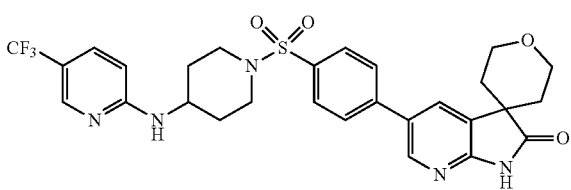

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5'-bromo-2,3,5,6-tetrahydrospiro[pyran-4,3'-pyrrolo[2,3-b]pyridin]-2'(1'H)-one (28 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.3 hours, and cooled when the reaction had proceeded to completion. The mixture was purified via reverse-phase HPLC to give 5'-(4-((4-((5-(trifluoromethyl)pyridin-2-yl)amino)piperidin-1-yl)sulfonyl)phenyl)-2,3,5,6-tetrahydro-spiro[pyran-4,3'-pyrrolo[2,3-b]pyridin]-2'(1'H)-one. MS: (ES) m/z calculated for $C_{28}H_{28}F_3N_5O_4S$ [M+H]$^+$ 588.2, found 588. $^1$H NMR (400 MHz, DMSO-d$_6$) δ 11.26 (s, 1H), 8.53 (s, 1H), 8.30 (s, 1H), 8.26 (s, 1H), 8.07-7.96 (m, 2H), 7.87-7.75 (m, 2H), 7.67-7.58 (m, 1H), 7.40 (bs, 1H), 6.57 (d, J=8.9 Hz, 1H), 4.08-3.97 (m, 2H), 3.95-3.83 (m, 2H), 3.82-3.69 (m, 1H), 3.65-3.52 (m, 2H), 2.62-2.52 (m, 2H), 2.03-1.91 (m, 2H), 1.84 (s, 4H), 1.59-1.42 (m, 2H).

Example 66: 6-(4-((4-((5-(Trifluoromethyl)pyridin-2-yl)amino)piperidin-1-yl)sulfonyl)phenyl)oxazolo[4,5-b]pyridin-2(3H)-one

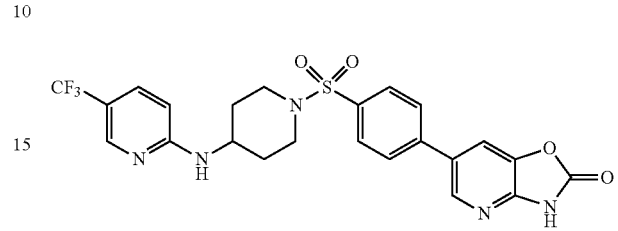

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 6-bromooxazolo[4,5-b]pyridin-2(3H)-one (21 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.3 hours, and cooled when the reaction had proceeded to completion. The mixture was purified via reverse-phase HPLC to give 6-(4-((4-((5-(trifluoromethyl)pyridin-2-yl)amino)piperidin-1-yl)sulfonyl)phenyl)oxazolo[4,5-b]pyridin-2(3H)-one. MS: (ES) m/z calculated for $C_{23}H_{20}F_3N_5O_4S$ [M+H]$^+$ 520.1, found 520. $^1$H NMR (400 MHz, DMSO-d$_6$) δ 12.64 (s, 1H), 8.49 (s, 1H), 8.23 (s, 1H), 8.13 (s, 1H), 8.05-7.95 (m, 2H), 7.88-7.77 (m, 2H), 7.67-7.57 (m, 1H), 7.46-7.31 (m, 1H), 6.56 (d, J=9.1 Hz, 1H), 3.84-3.70 (m, 1H), 3.65-3.49 (m, 2H), 2.64-2.54 (m, 2H), 2.03-1.88 (m, 2H), 1.59-1.42 (m, 2H).

Example 67: 7-(4-((4-((5-(Trifluoromethyl)pyridin-2-yl)amino)piperidin-1-yl)sulfonyl)phenyl)-3,4-dihydroisoquinolin-1(2H)-one

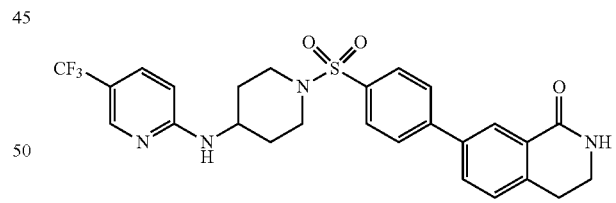

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (49 mg, 0.35 mmol), 7-bromo-3,4-dihydroisoquinolin-1(2H)-one (25 mg, 0.12 mmol), and Pd(dppf)Cl$_2$.DCM (10 mg, 0.012 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography and reverse-phase HPLC to give 7-(4-((4-((5-(trifluoromethyl)pyridin-2-yl)amino)piperidin-1-yl)sulfonyl)phenyl)-3,4-dihydroisoquinolin-1(2H)-one. MS: (ES) m/z calculated for $C_{26}H_{25}F_3N_4O_3S$ [M+H]$^+$ 531.2, found 531. $^1$H NMR (400 MHz, DMSO-d$_6$) δ 8.29-8.15 (m, 2H), 8.08 (s, 1H), 8.01-7.93 (m, 2H), 7.93-7.80 (m, 3H), 7.63 (d, J=8.8 Hz, 1H), 7.52-7.38 (m, 2H), 6.58 (d, J=8.9 Hz, 1H), 3.85-3.70 (m, 1H), 3.63-3.51 (m, 2H), 3.47-3.36 (m, 2H), 3.03-2.91 (m, 2H), 2.64-2.53 (m, 2H), 2.02-1.88 (m, 2H), 1.58-1.42 (m, 2H).

Example 68: 6-(4-((4-((5-(Trifluoromethyl)pyridin-2-yl)amino)piperidin-1-yl)sulfonyl)phenyl)-1,3-dihydro-2H-imidazo[4,5-b]pyridin-2-one

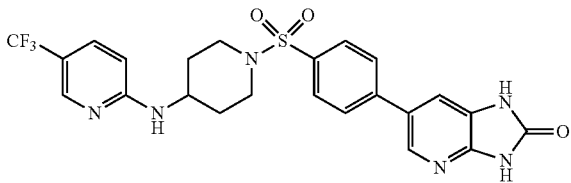 [SMILES: O=c1[nH]c2cc(-c3ccc(S(=O)(=O)N4CCC(Nc5ccc(C(F)(F)F)cn5)CC4)cc3)cnc2[nH]1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (49 mg, 0.35 mmol), 6-bromo-1,3-dihydro-2H-imidazo[4,5-b]pyridin-2-one (25 mg, 0.12 mmol), and Pd(dppf)Cl$_2$.DCM (10 mg, 0.012 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography and reverse-phase HPLC to give 6-(4-((4-((5-(trifluoromethyl)pyridin-2-yl)amino)piperidin-1-yl)sulfonyl)phenyl)-1,3-dihydro-2H-imidazo[4,5-b]pyridin-2-one. MS: (ES) m/z calculated for C$_{23}$H$_{21}$F$_3$N$_6$O$_3$S [M+H]$^+$ 519.1, found 519. $^1$H NMR (400 MHz, DMSO-d$_6$) δ 11.54 (s, 1H), 11.08 (s, 1H), 8.26 (d, J=22.5 Hz, 2H), 7.99-7.92 (m, 2H), 7.85-7.77 (m, 2H), 7.65-7.58 (m, 1H), 7.55 (s, 1H), 7.42-7.31 (m, 1H), 6.56 (d, J=8.4 Hz, 1H), 3.86-3.71 (m, 1H, under residual H$_2$O peak), 3.62-3.52 (m, 2H), 2.63-2.53 (m, 2H), 2.02-1.91 (m, 2H), 1.58-1.43 (m, 2H).

Example 69: 5-(4-((4-((5-(Trifluoromethyl)pyridin-2-yl)amino)piperidin-1-yl)sulfonyl)cyclohexa-1,3-dien-1-yl)-1H-pyrazolo[3,4-b]pyridin-3-amine

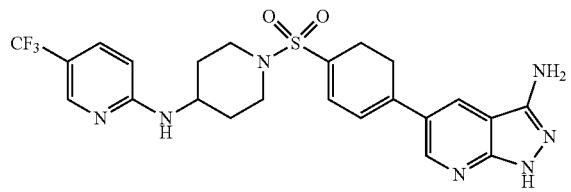 [SMILES: Nc1n[nH]c2ncc(C3=CC=C(S(=O)(=O)N4CCC(Nc5ccc(C(F)(F)F)cn5)CC4)CC3)cc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (82 mg, 0.58 mmol), 5-bromo-1H-pyrazolo[3,4-b]pyridin-3-amine (42 mg, 0.20 mmol), and Pd(dppf)Cl$_2$.DCM (16 mg, 0.020 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography and reverse-phase HPLC to give 5-(4-((4-((5-(trifluoromethyl)pyridin-2-yl)amino)piperidin-1-yl)sulfonyl)cyclohexa-1,3-dien-1-yl)-1H-pyrazolo[3,4-b]pyridin-3-amine. MS: (ES) m/z calculated for C$_{23}$H$_{24}$F$_3$N$_7$O$_2$S [M+H]$^+$ 520.2, found 520. $^1$H NMR (400 MHz, DMSO-d$_6$) δ 12.16 (s, 1H), 8.78 (s, 1H), 8.55 (s, 1H), 8.22 (s, 1H), 7.97 (d, J=7.8 Hz, 2H), 7.86 (d, J=8.2 Hz, 2H), 7.60 (d, J=8.9 Hz, 1H), 7.31 (d, J=6.0 Hz, 1H), 6.54 (d, J=7.8 Hz, 1H), 5.73 (bs, 2H), 3.86-3.71 (m, 1H), 3.62-3.51 (m, 2H), 2.65-2.54 (m, 2H), 2.03-1.92 (m, 2H), 1.59-1.44 (m, 2H).

Example 70: N,N-dimethyl-5-(4-((4-((5-(trifluoromethyl)pyridin-2-yl)amino)piperidin-yl)sulfonyl)cyclohexa-1,3-dien-1-yl)-1H-indazol-3-amine

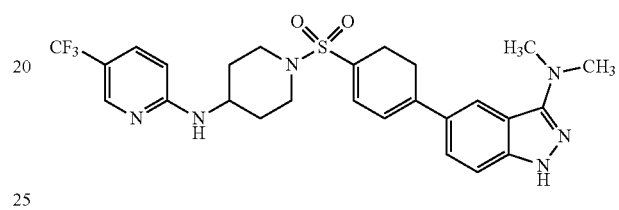

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (82 mg, 0.58 mmol), 5-bromo-N,N-dimethyl-1H-indazol-3-amine (47 mg, 0.20 mmol), and Pd(dppf)Cl$_2$.DCM (16 mg, 0.020 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography and reverse-phase HPLC to give N,N-dimethyl-5-(4-((4-((5-(trifluoromethyl)pyridin-2-yl)amino)piperidin-1-yl)sulfonyl) cyclohexa-1,3-dien-1-yl)-1H-indazol-3-amine. MS: (ES) m/z calculated for C$_{26}$H$_{29}$F$_3$N$_6$O$_2$S [M+H]$^+$ 547.2, found 547. $^1$H NMR (400 MHz, DMSO-d$_6$) δ 12.04 (s, 1H), 8.22 (s, 1H), 8.13 (s, 1H), 8.03-7.94 (m, 2H), 7.84-7.74 (m, 2H), 7.72-7.65 (m, 1H), 7.63-7.55 (m, 1H), 7.50-7.42 (m, 1H), 7.31 (d, J=7.0 Hz, 1H), 6.59-6.51 (m, 1H), 3.84-3.71 (m, 1H), 3.63-3.50 (m, 2H), 3.04 (s, 6H), 2.64-2.51 (m, 2H), 2.03-1.90 (m, 2H), 1.58-1.43 (m, 2H).

Example 71: 5-(4-((4-((5-(Trifluoromethyl)pyridin-2-yl)amino)piperidin-1-yl)sulfonyl)phenyl)-1,3-dihydro-2H-pyrrolo[2,3-b]pyridin-2-one

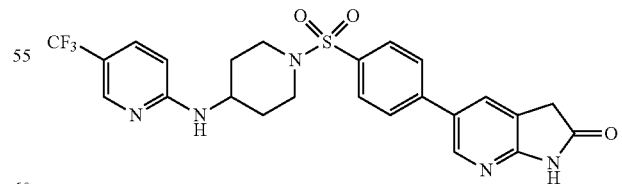

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (82 mg, 0.58 mmol), 5-bromo-1,3-dihydro-2H-pyrrolo[2,3-b]pyridin-2-one (34 mg, 0.20 mmol), and Pd(dppf)Cl$_2$.DCM (16 mg, 0.020 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography and reverse-phase HPLC to give 5-(4-((4-((5-(trifluoromethyl)pyridin-2-yl)amino)piperidin-1-yl)sulfonyl)phenyl)-1,3-dihydro-2H-pyrrolo[2,3-b]pyridin-2-one. MS: (ES) m/z calculated for C$_{24}$H$_{22}$F$_3$N$_5$O$_3$S [M+H]$^+$ 518.2, found 518. $^1$H NMR (400 MHz, DMSO-d$_6$) δ 11.20 (s, 1H), 8.49 (d, J=2.1 Hz, 1H), 8.23 (s, 1H), 7.98 (s, 1H), 7.94 (d, J=8.4 Hz, 2H), 7.81 (d, J=8.5 Hz, 2H), 7.63 (dd, J=9.3, 2.6 Hz, 1H), 7.48-7.35 (m, 1H), 6.58 (d, J=9.0 Hz, 1H), 3.82-3.68 (m, 1H), 3.65 (s, 2H), 3.62-3.52 (m, 2H), 2.62-2.52 (m, 2H), 2.02-1.91 (m, 2H), 1.58-1.42 (m, 2H).

Example 72: 7-(4-((4-((5-(Trifluoromethyl)pyridin-2-yl)amino)piperidin-1-yl)sulfonyl)phenyl)-2H-benzo[b][1,4]oxazin-3(4H)-one

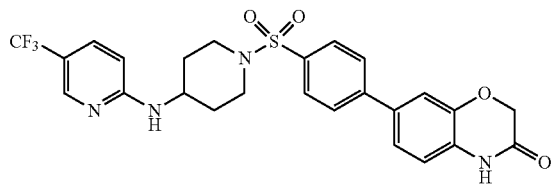 [SMILES: O=C1COc2cc(-c3ccc(S(=O)(=O)N4CCC(Nc5ccc(C(F)(F)F)cn5)CC4)cc3)ccc2N1]

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 7-(4,4,5,5-tetramethyl-1,3,2-dioxaborolan-2-yl)-2H-benzo[b][1,4]oxazin-3(4H)-one (30 mg, 0.11 mmol), and Pd(dppf)Cl$_2$.DCM (9 mg, 0.011 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography to give 7-(4-((4-((5-(trifluoromethyl)pyridin-2-yl)amino)piperidin-1-yl)sulfonyl)phenyl)-2H-benzo[b][1,4]oxazin-3(4H)-one. MS: (ES) m/z calculated for C$_{25}$H$_{23}$F$_3$N$_4$O$_4$S [M+H]$^+$ 533.2, found 533. $^1$H NMR (400 MHz, DMSO-d$_6$) δ 10.89 (s, 1H), 8.22 (s, 1H), 7.91 (d, J=8.1 Hz, 2H), 7.78 (d, J=7.9 Hz, 2H), 7.60 (d, J=8.7 Hz, 1H), 7.39 (app s, 1H), 7.30 (d, J=7.4 Hz, 1H), 7.02 (d, J=8.9 Hz, 1H), 6.54 (d, J=9.1 Hz, 1H), 4.65 (s, 2H), 3.83-3.69 (m, 1H), 3.62-3.47 (m, 2H), 2.64-2.54 (m, 2H), 2.03-1.89 (m, 2H), 1.58-1.41 (m, 2H).

Example 73: 6-(4-((4-((5-(Trifluoromethyl)pyridin-2-yl)amino)piperidin-1-yl)sulfonyl)phenyl)-3,4-dihydroisoquinolin-1(2H)-one

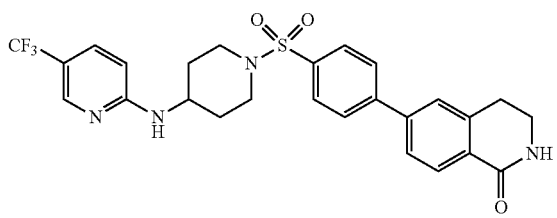 [SMILES: O=C1NCCc2cc(-c3ccc(S(=O)(=O)N4CCC(Nc5ccc(C(F)(F)F)cn5)CC4)cc3)ccc21]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromo-3,4-dihydroisoquinolin-1(2H)-one (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1.5 hours, and cooled when the reaction had proceeded to completion. The mixture was purified via SiO$_2$ gel chromatography to give 6-(4-((4-((5-(trifluoromethyl)pyridin-2-yl)amino)piperidin-1-yl)sulfonyl)phenyl)-3,4-dihydroisoquinolin-1(2H)-one. MS: (ES) m/z calculated for C$_{26}$H$_{25}$F$_3$N$_4$O$_3$S [M+H]$^+$ 531.2, found 531. $^1$H NMR (400 MHz, DMSO-d$_6$) δ 8.22 (s, 1H), 8.05-7.94 (m, 4H), 7.85 (d, J=8.2 Hz, 2H), 7.78-7.69 (m, 2H), 7.60 (d, J=9.3 Hz, 1H), 7.30 (d, J=7.3 Hz, 1H), 6.58-6.51 (m, 1H), 3.85-3.72 (m, 1H), 3.62-3.53 (m, 2H), 3.47-3.39 (m, 2H), 3.05-2.95 (m, 2H), 2.64-2.55 (m, 2H), 2.02-1.91 (m, 2H), 1.57-1.44 (m, 2H).

Example 74: N-(1-((4-(3-methoxy-1H-indazol-5-yl)phenyl)sulfonyl)piperidin-4-yl)-5-(trifluoromethyl)pyridin-2-amine

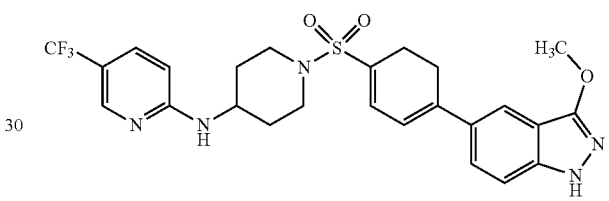

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-3-methoxy-1H-indazole (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography to give N-(1-((4-(3-methoxy-1H-indazol-5-yl)phenyl)sulfonyl)piperidin-4-yl)-5-(trifluoromethyl)pyridin-2-amine. MS: (ES) m/z calculated for C$_{25}$H$_{24}$F$_3$N$_5$O$_3$S [M+H]$^+$ 532.2, found 532. $^1$H NMR (400 MHz, DMSO-d$_6$) δ 12.11 (s, 1H), 8.22 (s, 1H), 8.03-7.93 (m, 3H), 7.83-7.73 (m, 3H), 7.60 (d, J=9.2 Hz, 1H), 7.50 (d, J=8.6 Hz, 1H), 7.31 (d, J=7.2 Hz, 1H), 6.54 (d, J=9.1 Hz, 1H), 4.04 (s, 3H), 3.84-3.72 (m, 1H), 3.62-3.50 (m, 2H), 2.64-2.53 (m, 2H), 2.06-1.89 (m, 2H), 1.59-1.43 (m, 2H).

Example 75: 6-(4-((4-((5-(Trifluoromethyl)pyridin-2-yl)amino)piperidin-1-yl)sulfonyl)phenyl)-3,4-dihydroquinolin-2(1H)-one

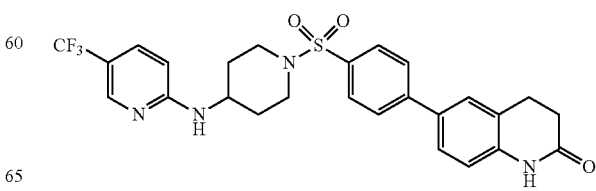

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 6-(4,4,5,5-tetramethyl-1,3,2-dioxaborolan-2-yl)-3,4-dihydroquinolin-2(1H)-one (29 mg, 0.11 mmol), and Pd(dppf)Cl$_2$.DCM (9 mg, 0.011 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography to give 6-(4-((4-((5-(trifluoromethyl)pyridin-2-yl)amino)piperidin-1-yl)sulfonyl)phenyl)-3,4-dihydroquinolin-2(1H)-one. MS: (ES) m/z calculated for C$_{26}$H$_{25}$F$_3$N$_4$O$_3$S [M+H]$^+$ 531.2, found 531. $^1$H NMR (400 MHz, DMSO-d$_6$) δ 10.26 (s, 1H), 8.22 (s, 1H), 7.89 (d, J=7.8 Hz, 2H), 7.78 (d, J=8.2 Hz, 2H), 7.66-7.53 (m, 3H), 7.35-7.25 (m, 1H), 6.98 (d, J=8.5 Hz, 1H), 6.54 (d, J=9.1 Hz, 1H), 3.82-3.70 (m, 1H), 3.60-3.50 (m, 2H), 2.97 (t, J=7.6 Hz, 2H), 2.63-2.54 (m, 2H), 2.00-1.90 (m, 2H), 1.58-1.42 (m, 2H), one methylene presumably under solvent peak.

Example 76: 6-(4-((4-((5-(Trifluoromethyl)pyridin-2-yl)amino)piperidin-1-yl)sulfonyl)phenyl)-1H-indole-2-carbonitrile

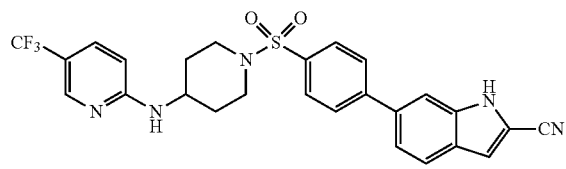 [SMILES: N#Cc1cc2ccc(-c3ccc(S(=O)(=O)N4CCC(Nc5ccc(C(F)(F)F)cn5)CC4)cc3)cc2[nH]1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromo-1H-indole-2-carbonitrile (22 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography to give 6-(4-((4-((5-(trifluoromethyl)pyridin-2-yl)amino)piperidin-1-yl)sulfonyl)phenyl)-1H-indole-2-carbonitrile. MS: (ES) m/z calculated for C$_{26}$H$_{22}$F$_3$N$_5$O$_2$S [M+H]$^+$ 526.2, found 526. $^1$H NMR (400 MHz, DMSO-d$_6$) δ 12.60 (s, 1H), 8.22 (s, 1H), 8.00 (d, J=8.2 Hz, 2H), 7.88-7.77 (m, 4H), 7.63-7.53 (m, 2H), 7.44 (s, 1H), 7.31 (d, J=7.3 Hz, 1H), 6.54 (d, J=9.2 Hz, 1H), 3.84-3.71 (m, 1H), 3.63-3.51 (m, 2H), 2.65-2.54 (m, 2H), 2.02-1.91 (m, 2H), 1.58-1.44 (m, 2H).

Example 77: 5-(4-((4-((5-(Trifluoromethyl)pyridin-2-yl)amino)piperidin-1-yl)sulfonyl)phenyl)-1H-indole-3-carboxamide

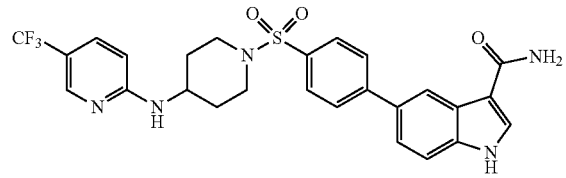 [SMILES: NC(=O)c1c[nH]c2ccc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-1H-indole-3-carboxamide (23 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 12 hours, and cooled when the reaction had proceeded to completion. The mixture was purified via SiO$_2$ gel chromatography and reverse-phase HPLC to give 5-(4-((4-((5-(trifluoromethyl)pyridin-2-yl)amino)piperidin-1-yl)sulfonyl)phenyl)-1H-indole-3-carboxamide. MS: (ES) m/z calculated for C$_{26}$H$_{24}$F$_3$N$_5$O$_3$S [M+H]$^+$ 544.2, found 544. $^1$H NMR (400 MHz, DMSO-d$_6$) δ 11.70 (s, 1H), 8.51 (s, 1H), 8.23 (s, 1H), 8.10 (s, 1H), 7.93 (d, J=7.9 Hz, 2H), 7.83 (d, J=8.3 Hz, 2H), 7.65-7.50 (m, 4H), 7.46-7.36 (m, 1H), 6.63-6.52 (m, 1H), 3.84-3.71 (m, 1H), 3.62-3.49 (m, 2H), 2.66-2.56 (m, 2H), 2.03-1.90 (m, 2H), 1.59-1.46 (m, 2H).

Example 78: 6-(4-((4-((5-(Trifluoromethyl)pyridin-2-yl)amino)piperidin-1-yl)sulfonyl)phenyl)oxazolo[5,4-b]pyridin-2-amine

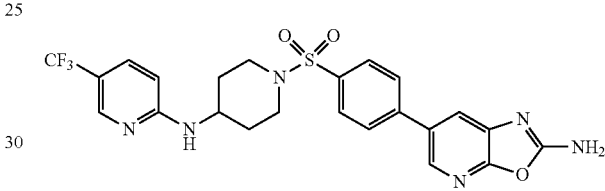

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (82 mg, 0.58 mmol), 6-bromooxazolo[4,5-b]pyridin-2-amine (42 mg, 0.20 mmol), and Pd(dppf)Cl$_2$.DCM (16 mg, 0.020 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO$_2$ gel chromatography to give 6-(4-((4-((5-(trifluoromethyl)pyridin-2-yl)amino)piperidin-1-yl)sulfonyl)phenyl)oxazolo[5,4-b]pyridin-2-amine. MS: (ES) m/z calculated for C$_{23}$H$_{21}$F$_3$N$_6$O$_3$S [M+H]$^+$ 519.1, found 519. $^1$H NMR (400 MHz, DMSO-d$_6$) δ 8.23 (app s, 2H), 8.00 (d, J=8.1 Hz, 2H), 7.94-7.88 (m, 3H), 7.82 (d, J=8.0 Hz, 2H), 7.60 (d, J=9.2 Hz, 1H), 7.31 (d, J=7.1 Hz, 1H), 6.54 (d, J=9.1 Hz, 1H), 3.84-3.71 (m, 1H), 3.63-3.52 (m, 2H), 2.65-2.54 (m, 2H), 2.07-1.88 (m, 2H), 1.59-1.43 (m, 2H).

Example 79: 5-(4-((4-((5-(Trifluoromethyl)pyridin-2-yl)amino)piperidin-1-yl)sulfonyl)phenyl)benzo-[d]oxazol-2(3H)-one

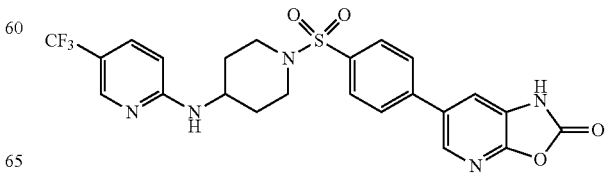

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K₂CO₃ (82 mg, 0.58 mmol), 5-bromobenzo[d]oxazol-2(3H)-one (42 mg, 0.20 mmol), and Pd(dppf)Cl₂.DCM (16 mg, 0.020 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO₂ gel chromatography to give 5-(4-((4-((5-(trifluoromethyl)pyridin-2-yl)amino)piperidin-1-yl)sulfonyl)phenyl)benzo-[d]oxazol-2(3H)-one. MS: (ES) m/z calculated for C₂₄H₂₁F₃N₄O₄S [M+H]⁺ 519.1, found 519. ¹H NMR (400 MHz, DMSO-d₆) δ 11.87 (s, 1H), 8.22 (s, 1H), 7.93 (d, J=7.9 Hz, 2H), 7.81 (d, J=7.3 Hz, 2H), 7.60 (d, J=9.0 Hz, 1H), 7.52-7.38 (m, 3H), 7.31 (d, J=7.6 Hz, 1H), 6.54 (d, J=8.9 Hz, 1H), 3.85-3.69 (m, 1H), 3.63-3.49 (m, 2H), 2.64-2.54 (m, 2H), 2.03-1.90 (m, 2H), 1.58-1.43 (m, 2H).

Example 80: N-(1-((4-(1H-pyrrolo[2,3-b]pyridin-4-yl)phenyl)sulfonyl)piperidin-4-yl)-5-(trifluoromethyl)pyridin-2-amine

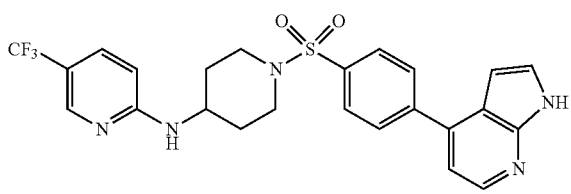 [SMILES: O=S(=O)(c1ccc(-c2ccnc3[nH]ccc23)cc1)N1CCC(Nc2ccc(C(F)(F)F)cn2)CC1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K₂CO₃ (41 mg, 0.29 mmol), 4-bromo-1H-pyrrolo[2,3-b]pyridine (19 mg, 0.10 mmol), and Pd(dppf)Cl₂.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO₂ gel chromatography to give N-(1-((4-(1H-pyrrolo[2,3-b]pyridin-4-yl)phenyl)sulfonyl)piperidin-4-yl)-5-(trifluoromethyl)pyridin-2-amine. MS: (ES) m/z calculated for C₂₄H₂₂F₃N₅O₂S [M+H]⁺ 502.2, found 502. ¹H NMR (400 MHz, DMSO-d₆) δ 11.93 (s, 1H), 8.35 (d, J=4.9 Hz, 1H), 8.23 (s, 1H), 8.05 (d, J=8.1 Hz, 2H), 7.92 (d, J=7.9 Hz, 2H), 7.66-7.56 (m, 2H), 7.36-7.25 (m, 2H), 6.68 (s, 1H), 6.55 (d, J=9.1 Hz, 1H), 3.86-3.74 (m, 1H), 3.65-3.56 (m, 2H), 2.68-2.58 (m, 2H), 2.03-1.93 (m, 2H), 1.61-1.42 (m, 2H).

Example 81: 6-(4-((4-((5-(Trifluoromethyl)pyridin-2-yl)amino)piperidin-1-yl)sulfonyl)phenyl)indolin-2-one

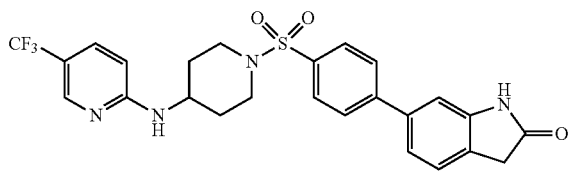 [SMILES: O=C1Cc2ccc(-c3ccc(S(=O)(=O)N4CCC(Nc5ccc(C(F)(F)F)cn5)CC4)cc3)cc2N1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K₂CO₃ (82 mg, 0.58 mmol), 6-bromoindolin-2-one (42 mg, 0.20 mmol), and Pd(dppf)Cl₂.DCM (16 mg, 0.020 mmol).

To this were added 1.6 mL dioxane and 0.4 mL of water. The mixture was sparged with nitrogen for 20 minutes. The vial was sealed, the mixture stirred at 100° C. for 1 hour, and cooled when the reaction had proceeded to completion. The mixture was purified via SiO₂ gel chromatography and reverse-phase HPLC to give 6-(4-((4-((5-(trifluoromethyl)pyridin-2-yl)amino)piperidin-1-yl)sulfonyl)phenyl)indolin-2-one. MS: (ES) m/z calculated for C₂₅H₂₃F₃N₄O₃S [M+H]⁺ 517.2, found 517. ¹H NMR (400 MHz, DMSO-d₆) δ 10.56 (s, 1H), 8.22 (s, 1H), 7.92-7.78 (m, 4H), 7.60 (d, J=9.1 Hz, 1H), 7.38-7.25 (m, 3H), 7.10 (s, 1H), 6.54 (d, J=9.0 Hz, 1H), 3.84-3.73 (m, 1H), 3.61-3.50 (m, 4H), 2.63-2.54 (m, 2H), 2.01-1.92 (m, 2H), 1.57-1.44 (m, 2H).

Example 82: 6-(4-((4-((5-(Trifluoromethyl)pyridin-2-yl)amino)piperidin-1-yl)sulfonyl)phenyl)imidazo[1,2-a]pyridine-3-carboxamide

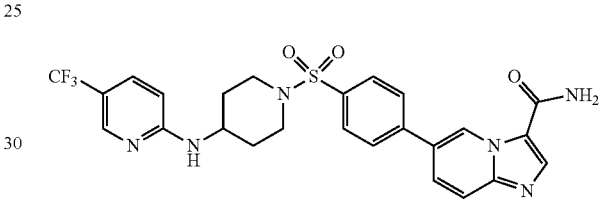

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K₂CO₃ (41 mg, 0.29 mmol), 6-bromoimidazo[1,2-a]pyridine-3-carbonitrile (22 mg, 0.10 mmol), and Pd(dppf)Cl₂.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 12 hours, and cooled when the reaction had proceeded to completion. The mixture was purified via SiO₂ gel chromatography and reverse-phase HPLC to give 6-(4-((4-((5-(trifluoromethyl)pyridin-2-yl)amino)piperidin-1-yl)sulfonyl)phenyl)imidazo[1,2-a]pyridine-3-carboxamide. MS: (ES) m/z calculated for C₂₅H₂₃F₃N₆O₃S [M+H]⁺ 545.2, found 545. ¹H NMR (400 MHz, DMSO-d₆) δ 9.91 (s, 1H), 8.51 (s, 1H), 8.27-8.13 (m, 2H), 8.07-7.87 (m, 6H), 7.72-7.56 (m, 2H), 7.46-7.33 (m, 1H), 6.57 (d, J=9.0 Hz, 1H), 3.85-3.73 (m, 1H), 3.63-3.52 (m, 2H), 2.68-2.56 (m, 2H), 2.03-1.92 (m, 2H), 1.59-1.44 (m, 2H).

Example 83: 6-(4-((4-((5-(Trifluoromethyl)pyridin-2-yl)amino)piperidin-1-yl)sulfonyl)phenyl)benzo-[d]oxazol-2-amine

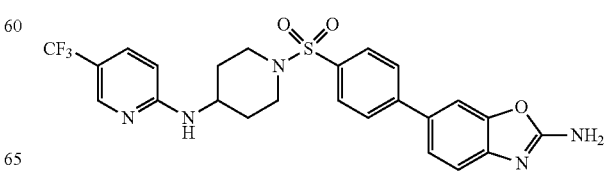

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 6-bromobenzo[d]oxazol-2-amine (21 mg, 0.10 mmol), and Pd(dppf)$Cl_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 12 hours, and cooled when the reaction had proceeded to completion. The mixture was purified via $SiO_2$ gel chromatography and reverse-phase HPLC to give 6-(4-((4-((5-(trifluoromethyl)pyridin-2-yl)amino)piperidin-1-yl)sulfonyl)phenyl)benzo[d]oxazol-2-amine. MS: (ES) m/z calculated for $C_{24}H_{22}F_3N_5O_3S$ [M+H]$^+$ 518.2, found 518. $^1$H NMR (400 MHz, DMSO-$d_6$) δ 8.26-8.19 (m, 1H), 7.99-7.90 (m, 2H), 7.83-7.74 (m, 3H), 7.67-7.49 (m, 4H), 7.36-7.25 (m, 2H), 6.58-6.50 (m, 1H), 3.84-3.70 (m, 1H), 3.62-3.52 (m, 2H), 2.63-2.54 (m, 2H), 2.02-1.91 (m, 2H), 1.61-1.43 (m, 2H).

Example 84: 5-(Trifluoromethyl)-N-(1-((4-(3-(trifluoromethyl)-1H-indazol-5-yl)phenyl]sulfonyl)piperidin-4-yl)pyridin-2-amine

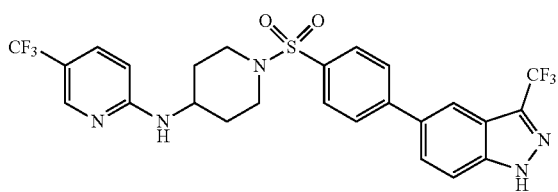 [SMILES: O=S(=O)(c1ccc(-c2ccc3[nH]nc(C(F)(F)F)c3c2)cc1)N1CCC(Nc2ccc(C(F)(F)F)cn2)CC1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5-bromo-3-(trifluoromethyl)-1H-indazole (26 mg, 0.10 mmol), and Pd(dppf)$Cl_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 12 hours, and cooled when the reaction had proceeded to completion. The mixture was purified via $SiO_2$ gel chromatography and reverse-phase HPLC to give 5-(trifluoromethyl)-N-(1-((4-(3-(trifluoromethyl)-1H-indazol-5-yl)phenyl)sulfonyl)piperidin-4-yl)pyridin-2-amine. MS: (ES) m/z calculated for $C_{25}H_{21}F_6N_5O_2S$ [M+H]$^+$ 570.1, found 570. $^1$H NMR (400 MHz, DMSO-$d_6$) δ 8.25-8.19 (m, 1H), 8.14-8.07 (m, 1H), 8.07-7.98 (m, 2H), 7.97-7.80 (m, 4H), 7.64-7.56 (m, 1H), 7.34-7.28 (m, 1H), 6.59-6.50 (m, 1H), 3.84-3.70 (m, 1H), 3.65-3.52 (m, 2H), 2.64-2.55 (m, 2H), 2.02-1.90 (m, 2H), 1.59-1.44 (m, 2H).

Example 85: 5-(4-((4-((5-(Trifluoromethyl)pyridin-2-yl)amino)piperidin-1-yl)sulfonyl)phenyl)-1H-pyrrolo[2,3-b]pyridine-3-carbonitrile

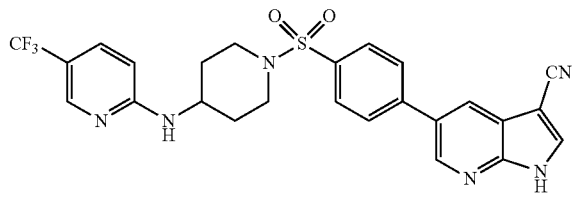 [SMILES: N#Cc1c[nH]c2ncc(-c3ccc(S(=O)(=O)N4CCC(Nc5ccc(C(F)(F)F)cn5)CC4)cc3)cc12]

A solution of 4:1 dioxane:dI $H_2O$ was prepared and degassed for 20 min under vacuum with vigorous stirring. While the solvent system is degassing, N-(1-((4-(4,4,5,5-tetramethyl-1,3,2-dioxaborolan-2-yl)phenyl)sulfonyl)piperidin-4-yl)-5-(trifluoromethyl)pyridin-2-amine (100 mg, 0.20 mmol, 1.0 equiv), 5-bromo-1H-pyrrolo[2,3-b]pyridine-3-carbonitrile (43 mg, 0.20 mmol, 1.0 equiv), $K_2CO_3$ (43 mg, 0.60 mmol, 3.0 equiv), and Pd(dppf)$Cl_2$.DCM (16 mg, 0.02 mmol, 0.1 equiv) were added to a separate vessel along with a stir bar. Once the solvent system was thoroughly degassed, nitrogen gas was bubbled through the 4:1 solvent system for 20 min with vigorous stirring. After the solvent system atmosphere was thoroughly replaced by nitrogen gas, 2 mL of the 4:1 dioxane:DI $H_2O$ solution was added to the reaction vessel containing the reagents. Nitrogen gas was then bubbled through the reaction vessel for ~ 2 min, then removed. The reaction was heated at 100° C. and stirred for 3 h and monitored by LC-MS. Once reaction was complete, the reaction contents were adhered to Celite® and a normal phase column (12 g column, gradient: 0%-100% EtOAc in DCM) was run. The product eluted at ~60% EtOAc. Pure fractions were combined and the solvent was removed under reduced pressure to yield the title compound as an off-white solid (48 mg, 46%). MS: (ES) m/z calculated for $C_{25}H_{21}F_3N_6O_2S$ [M+H]$^+$ 526.5, found 527. $^1$H NMR (400 MHz, DMSO-$d_6$) δ 13.02 (s, 1H), 8.82 (s, 1H), 8.61-8.46 (m, 2H), 8.22 (s, 1H), 8.12 (d, J=8.1 Hz, 2H), 7.85 (d, J=8.2 Hz, 2H), 7.60 (dd, J=9.0, 2.6 Hz, 1H), 7.31 (d, J=7.2 Hz, 1H), 6.55 (d, J=8.8 Hz, 1H), 3.84-3.71 (m, 1H), 3.64-3.52 (m, 2H), 2.65-2.54 (m, 2H), 2.03-1.91 (m, 2H), 1.59-1.43 (m, 2H).

Example 86: N-(1-((4-(1H-pyrrolo[2,3-b]pyridin-5-yl)phenyl)sulfonyl)piperidin-4-yl)-5-(trifluoromethyl)pyridin-2-amine

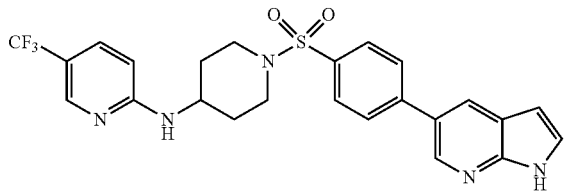 [SMILES: O=S(=O)(c1ccc(-c2cnc3[nH]ccc3c2)cc1)N1CCC(Nc2ccc(C(F)(F)F)cn2)CC1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5-bromo-1H-pyrrolo[2,3-b]pyridine (19 mg, 0.10 mmol), and Pd(dppf)$Cl_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 12 hours, and cooled when the reaction had proceeded to completion. The mixture was purified via $SiO_2$ gel chromatography and reverse-phase HPLC to give N-(1-((4-(1H-pyrrolo[2,3-b]pyridin-5-yl)phenyl)sulfonyl)piperidin-4-yl)-5-(trifluoromethyl)pyridin-2-amine. MS: (ES) m/z calculated for $C_{24}H_{22}F_3N_5O_2S$ [M+H]$^+$ 502.2, found 502. $^1$H NMR (400 MHz, DMSO-$d_6$) δ 11.84 (s, 1H), 8.62 (s, 1H), 8.39-8.32 (m, 1H), 8.23 (app s, 1H), 8.06-7.97 (m, 2H), 7.87-7.78 (m, 2H), 7.65-7.51 (m, 2H), 7.35-7.27 (m, 1H), 6.60-6.50 (m, 2H), 3.84-3.72 (m, 1H), 3.63-3.52 (m, 2H), 2.65-2.54 (m, 2H), 2.02-1.92 (m, 2H), 1.60-1.44 (m, 2H).

Example 87: 1-Methyl-5-(4-((4-((5-(trifluoromethyl) pyridin-2-yl)amino)piperidin-1-yl)sulfonyl)phenyl)-1H-indazole-3-carboxamide

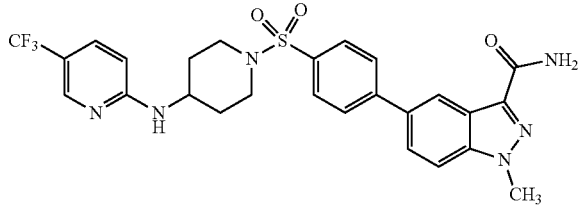 [SMILES: Cn1nc(C(N)=O)c2cc(-c3ccc(S(=O)(=O)N4CCC(Nc5ccc(C(F)(F)F)cn5)CC4)cc3)ccc21]

1-Methyl-5-(4-((4-((5-(trifluoromethyl)pyridin-2-yl) amino)piperidin-1-yl)sulfonyl)phenyl)-1H-indazole-3-carboxamide isolated as hydrolysis product from 1-methyl-5-[4-[[4-[[5-(trifluoromethyl)-2-pyridyl]amino]-1-piperidyl] sulfonyl]phenyl]indazole-3-carbonitrile. MS: (ES) m/z calculated for $C_{26}H_{25}F_3N_6O_3S$ [M+H]$^+$ 559.2, found 558.9.

Example 88: 1-Methyl-5-(4-((4-((5-(trifluoromethyl)pyridin-2-yl)amino)piperidin-1-yl)sulfonyl)phenyl)-1H-indazole-3-carbonitrile

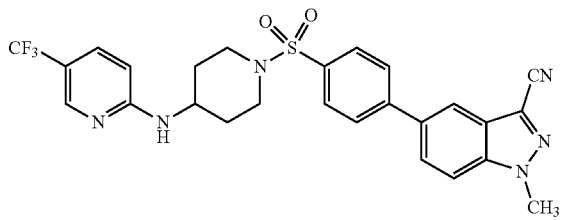 [SMILES: Cn1nc(C#N)c2cc(-c3ccc(S(=O)(=O)N4CCC(Nc5ccc(C(F)(F)F)cn5)CC4)cc3)ccc21]

To N-[1-[4-(4,4,5,5-tetramethyl-1,3,2-dioxaborolan-2-yl) phenyl]sulfonyl-4-piperidyl]-5-(trifluoromethyl)pyridin-2-amine (50.0 mg, 0.10 mmol) in 2.25 mL dioxane were added $K_2CO_3$ (45.0 mg, 0.32 mmol), 5-bromo-1-methyl-indazole-3-carbonitrile (50.0 mg, 0.21 mmol), Pd(dppf)Cl$_2$.DCM (10.0 mg, 0.01 mmol) and 0.75 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, to give 1-methyl-5-[4-[[4-[[5-(trifluoromethyl)-2-pyridyl]amino]-1-piperidyl]sulfonyl]phenyl]indazole-3-carbonitrile. MS: (ES) m/z calculated for $C_{26}H_{23}F_3N_6O_2S$ [M+H]$^+$ 541.2, found 540.9.

Example 89: N-(1-((4-(2-methyl-1H-benzo[d]imidazol-5-yl)phenyl)sulfonyl)piperidin-4-yl)-5-(trifluoromethyl)pyridin-2-amine

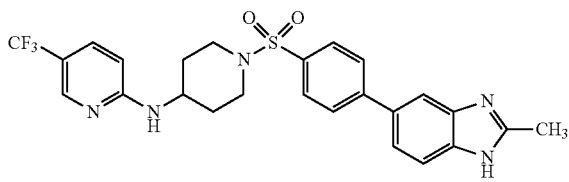 [SMILES: Cc1nc2cc(-c3ccc(S(=O)(=O)N4CCC(Nc5ccc(C(F)(F)F)cn5)CC4)cc3)ccc2[nH]1]

To N-(1-((4-bromophenyl)sulfonyl)piperidin-4-yl)-5-(trifluoromethyl)pyridin-2-amine in a septum-cap vial were added $K_2CO_3$ (45 mg, 0.32 mmol), (3-methyl-1H-indazol-5-yl)boronic acid (19 mg, 0.11 mmol), and Pd(dppf) Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16-24 hours, and cooled when the reaction had proceeded to completion. The mixture was purified via SiO$_2$ gel chromatography and preparative reverse-phase HPLC to give N-(1-((4-(2-methyl-1H-benzo [d]imidazol-5-yl)phenyl)sulfonyl)piperidin-4-yl)-5-(trifluoromethyl)pyridin-2-amine. MS: (ES) m/z calculated for $C_{25}H_{24}F_3N_5O_2S$ [M+H]$^+$ 516.2, found 516. $^1$H NMR (400 MHz, DMSO-d$_6$) δ 8.20 (s, 1H), 8.08 (s, 1H), 8.05-7.96 (m, 2H), 7.92-7.80 (m, 4H), 7.62-7.53 (m, 1H), 7.36-7.29 (m, 1H), 6.56-6.49 (m, 1H), 3.81-3.69 (m, 1H), 3.64-3.53 (m, 2H), 2.79 (s, 3H), 2.60-2.51 (m, 2H), 2.02-1.90 (m, 2H), 1.58-1.43 (m, 2H).

Example 90: 6-(4-((4-((5-(Trifluoromethyl)pyridin-2-yl)amino)piperidin-1-yl)sulfonyl)phenyl)isoindolin-1-one

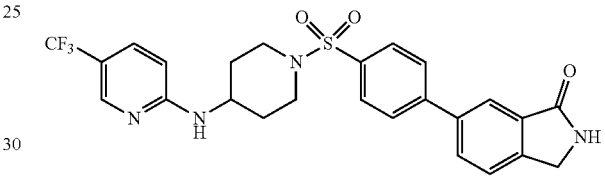

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 6-bromoisoindolin-1-one (21 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via SiO$_2$ gel chromatography and reverse-phase HPLC to give 6-(4-((4-((5-(trifluoromethyl) pyridin-2-yl)amino)piperidin-1-yl)sulfonyl)phenyl)isoindolin-1-one. MS: (ES) m/z calculated for $C_{25}H_{23}F_3N_4O_3S$ [M+H]$^+$ 517.2, found 517. $^1$H NMR (400 MHz, DMSO-d$_6$) δ 8.69 (s, 1H), 8.23 (s, 1H), 8.11-7.95 (m, 4H), 7.91-7.81 (m, 2H), 7.74 (dd, J=6.9, 3.3 Hz, 1H), 7.66-7.57 (m, 1H), 7.46-7.33 (m, 1H), 6.62-6.52 (m, 1H), 4.46 (s, 2H), 3.85-3.71 (m, 1H), 3.65-3.51 (m, 2H), 2.65-2.55 (m, 2H), 2.05-1.90 (m, 2H), 1.60-1.43 (m, 2H).

Example 91: N-(1-((4-(3-methyl-1H-indazol-5-yl) phenyl)sulfonyl)piperidin-4-yl)-5-(trifluoromethyl) pyridin-2-amine

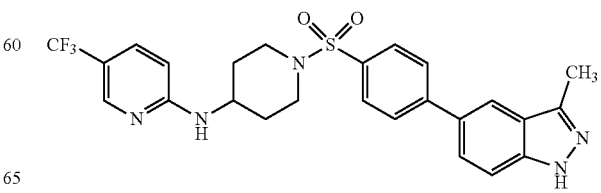

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), (3-methyl-1H-indazol-5-yl)boronic acid (19 mg, 0.11 mmol), and Pd(dppf)Cl$_2$·DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16-24 hours, and cooled when the reaction had proceeded to completion. The mixture was purified via SiO$_2$ gel chromatography and preparative reverse-phase HPLC to give N-(1-((4-(3-methyl-1H-indazol-5-yl)phenyl)sulfonyl)piperidin-4-yl)-5-(trifluoromethyl)pyridin-2-amine. MS: (ES) m/z calculated for C$_{25}$H$_{24}$F$_3$N$_5$O$_2$S [M+H]$^+$ 516.2, found 516. $^1$H NMR (400 MHz, DMSO-d$_6$) δ 8.23 (s, 1H), 8.13 (s, 1H), 8.01 (d, J=8.1 Hz, 2H), 7.82 (d, J=8.1 Hz, 2H), 7.74 (d, J=8.8 Hz, 1H), 7.66-7.55 (m, 2H), 7.46-7.37 (m, 1H), 6.57 (d, J=9.1 Hz, 1H), 3.85-3.70 (m, 1H), 3.63-3.53 (m, 2H), 2.64-2.53 (m, 5H), 2.04-1.92 (m, 2H), 1.61-1.44 (m, 2H).

Example 92: 5-(4-((4-((5-(Trifluoromethyl)pyridin-2-yl)amino)piperidin-1-yl)sulfonyl)phenyl)-1H-indazole-3-carboxamide

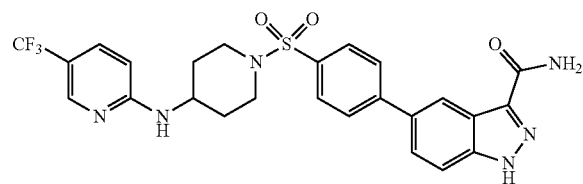 [SMILES: NC(=O)c1n[nH]c2ccc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-1H-indazole-3-carboxamide (23 mg, 0.10 mmol), and Pd(dppf)Cl$_2$·DCM (8 mg, 0.010 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography and reverse-phase HPLC to give 5-(4-((4-((5-(trifluoromethyl)pyridin-2-yl)amino)piperidin-1-yl)sulfonyl)phenyl)-1H-indazole-3-carboxamide. MS: (ES) m/z calculated for C$_{25}$H$_{23}$F$_3$N$_6$O$_3$S [M+H]$^+$ 545.2, found 545. $^1$H NMR (400 MHz, DMSO-d$_6$) δ 13.68 (s, 1H), 8.48 (s, 1H), 8.21 (s, 1H), 7.96 (d, J=8.1 Hz, 2H), 7.88-7.70 (m, 5H), 7.62-7.56 (m, 1H), 7.48-7.32 (m, 2H), 6.55 (d, J=8.8 Hz, 1H), 3.83-3.70 (m, 1H), 3.61-3.49 (m, 2H), 2.64-2.54 (m, 2H), 2.01-1.89 (m, 2H), 1.58-1.43 (m, 2H).

Example 93: N-(1-((4-(1H-indazol-5-yl)phenyl)sulfonyl)piperidin-4-yl)-5-(trifluoromethyl)pyridin-2-amine

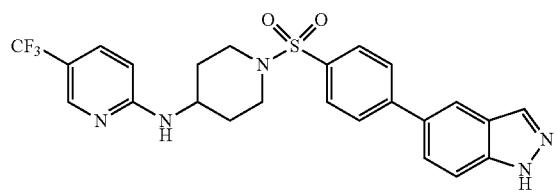

To N-(1-((4-(4,4,5,5-tetramethyl-1,3,2-dioxaborolan-2-yl)phenyl)sulfonyl)piperidin-4-yl)-5-(trifluoromethyl)pyridin-2-amine in a septum-cap vial were added K$_2$CO$_3$ (41 mg, 0.29 mmol), 5-bromo-1H-indazole (19 mg, 0.10 mmol), and Pd(dppf)Cl$_2$·DCM (8 mg, 0.010 mmol).

To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via SiO$_2$ gel chromatography and reverse-phase HPLC to give N-(1-((4-(1H-indazol-5-yl)phenyl)sulfonyl)piperidin-4-yl)-5-(trifluoromethyl)pyridin-2-amine. MS: (ES) m/z calculated for C$_{24}$H$_{22}$F$_3$N$_5$O$_2$S [M+H]$^+$ 502.2, found 502. $^1$H NMR (400 MHz, DMSO-d$_6$) δ 8.27-8.14 (m, 3H), 7.99 (d, J=8.3 Hz, 2H), 7.83 (d, J=8.1 Hz, 2H), 7.76 (dd, J=8.9, 1.7 Hz, 1H), 7.72-7.59 (m, 2H), 7.52-7.42 (m, 1H), 6.59 (d, J=9.1 Hz, 1H), 3.83-3.71 (m, 1H), 3.64-3.54 (m, 2H), 2.64-2.54 (m, 2H), 2.03-1.93 (m, 2H), 1.59-1.46 (m, 2H).

Example 94: 6-(4-((4-((5-(Trifluoromethyl)pyridin-2-yl)amino)piperidin-1-yl)sulfonyl)phenyl)benzo-[d]oxazol-2(3H)-one

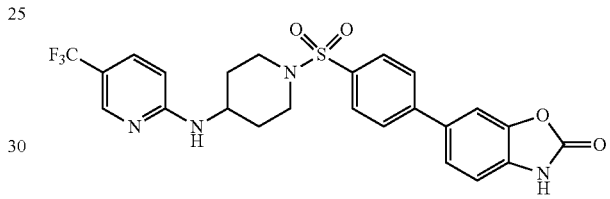

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 6-bromobenzo[d]oxazol-2(3H)-one (21 mg, 0.10 mmol), and Pd(dppf)Cl$_2$·DCM (8 mg, 0.010 mmol). To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via SiO$_2$ gel chromatography and reverse-phase HPLC to give 6-(4-((4-((5-(trifluoromethyl)pyridin-2-yl)amino)piperidin-1-yl)sulfonyl)phenyl)benzo-[d]oxazol-2(3H)-one. MS: (ES) m/z calculated for C$_{24}$H$_{21}$F$_3$N$_4$O$_4$S [M+H]$^+$ 519.1, found 519. $^1$H NMR (400 MHz, DMSO-d$_6$) δ 11.84 (s, 1H), 8.23 (app s, 1H), 7.95 (d, J=8.1 Hz, 2H), 7.86-7.73 (m, 3H), 7.65-7.54 (m, 2H), 7.44-7.36 (m, 1H), 7.23 (d, J=8.1 Hz, 1H), 6.57 (d, J=9.0 Hz, 1H), 3.83-3.71 (m, 1H), 3.62-3.52 (m, 2H), 2.62-2.53 (m, 2H), 2.02-1.91 (m, 2H), 1.58-1.44 (m, 2H).

Example 95: 5-(4-((4-((5-(Trifluoromethyl)pyridin-2-yl)amino)piperidin-1-yl)sulfonyl)phenyl)-1H-indole-2-carboxamide

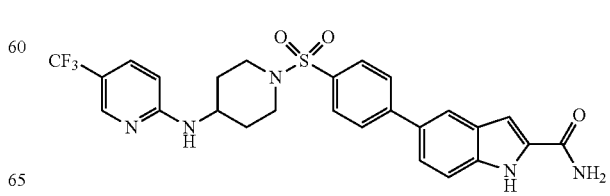

To N-(1-((4-(4,4,5,5-tetramethyl-1,3,2-dioxaborolan-2-yl)phenyl)sulfonyl)piperidin-4-yl)-5-(trifluoromethyl)pyridin-2-amine in a septum-cap vial were added $K_2CO_3$ (41 mg, 0.29 mmol), 5-bromo-1H-indole-2-carboxamide (23 mg, 0.10 mmol), and Pd(dppf)$Cl_2$·DCM (8 mg, 0.010 mmol). To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via $SiO_2$ gel chromatography and reverse-phase HPLC to give 5-(4-((4-((5-(trifluoromethyl)pyridin-2-yl)amino)piperidin-1-yl)sulfonyl)phenyl)-1H-indole-2-carboxamide. MS: (ES) m/z calculated for $C_{26}H_{24}F_3N_5O_3S$ [M+H]$^+$ 544.2, found 544. $^1$H NMR (300 MHz, DMSO-d$_6$) δ 11.71 (s, 1H), 8.23 (app s, 1H), 8.06-7.94 (m, 3H), 7.83-7.76 (m, 2H), 7.66-7.49 (m, 3H), 7.45-7.36 (m, 1H), 7.23 (s, 1H), 6.58 (dd, J=8.2, 4.2 Hz, 1H), 3.86-3.66 (m, 3H), 3.63-3.51 (m, 2H), 2.63-2.53 (m, 2H), 2.01-1.90 (m, 2H), 1.61-1.43 (m, 2H).

Example 96: 2-Amino-5-(4-((4-((5-(trifluoromethyl)pyridin-2-yl)amino)piperidin-1-yl)sulfonyl)phenyl)-1H-indole-3-carbonitrile

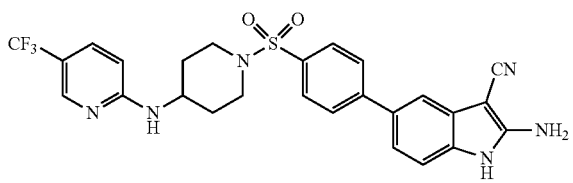 [SMILES: N#Cc1c(N)[nH]c2ccc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoromethyl)pyridin-2-amine in a septum-cap vial were added $K_2CO_3$ (41 mg, 0.29 mmol), 2-amino-5-bromo-1H-indole-3-carbonitrile (23 mg, 0.10 mmol), and Pd(dppf)$Cl_2$·DCM (8 mg, 0.010 mmol). To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via $SiO_2$ gel chromatography and reverse-phase HPLC to give 2-amino-5-(4-((4-((5-(trifluoromethyl)pyridin-2-yl)amino)piperidin-1-yl)sulfonyl)phenyl)-1H-indole-3-carbonitrile. MS: (ES) m/z calculated for $C_{26}H_{23}F_3N_6O_2S$ [M+H]$^+$ 541.2, found 541. $^1$H NMR (300 MHz, DMSO-d$_6$) δ 10.88 (s, 1H), 8.24 (app s, 1H), 7.93 (d, J=8.3 Hz, 2H), 7.78 (d, J=8.3 Hz, 2H), 7.62 (dd, J=9.0, 2.5 Hz, 1H), 7.52-7.38 (m, 2H), 7.35-7.23 (m, 2H), 6.58 (d, J=8.9 Hz, 1H), 3.75-3.58 (m, 3H, under residual H$_2$O peak), 2.64-2.54 (m, 2H), 2.04-1.89 (m, 2H), 1.59-1.44 (m, 2H).

Example 97: 5-(4-((4-((5-(Trifluoromethyl)pyridin-2-yl)amino)piperidin-1-yl)sulfonyl)phenyl)-1H-indazole-3-carbonitrile

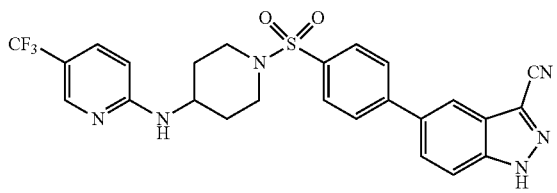 [SMILES: N#Cc1n[nH]c2ccc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 5-bromo-1H-indazole-3-carbonitrile (22 mg, 0.10 mmol), and Pd(dppf)$Cl_2$·DCM (8 mg, 0.010 mmol). To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via $SiO_2$ gel chromatography and reverse-phase HPLC to give 5-(4-((4-((5-(trifluoromethyl)pyridin-2-yl)amino)piperidin-1-yl)sulfonyl)phenyl)-1H-indazole-3-carbonitrile. MS: (ES) m/z calculated for $C_{25}H_{21}F_3N_6O_2S$ [M+H]$^+$ 527.2, found 527. $^1$H NMR (300 MHz, DMSO-d$_6$) δ 8.30-8.21 (m, 2H), 8.09 (d, J=8.3 Hz, 2H), 7.99-7.81 (m, 4H), 7.62 (dd, J=9.1, 2.6 Hz, 1H), 7.45-7.36 (m, 1H), 6.57 (d, J=8.9 Hz, 1H), 3.75-3.58 (m, 3H, under residual H$_2$O peak), 2.65-2.53 (m, 2H), 2.03-1.92 (m, 2H), 1.60-1.44 (m, 2H).

Example 98: 6-(4-((4-((5-(Trifluoromethyl)pyridin-2-yl)amino)piperidin-1-yl)sulfonyl)phenyl)-1H-indole-3-carbonitrile

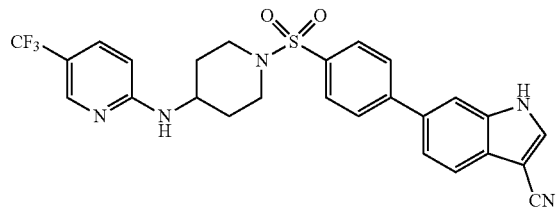 [SMILES: N#Cc1c[nH]c2cc(-c3ccc(S(=O)(=O)N4CCC(Nc5ccc(C(F)(F)F)cn5)CC4)cc3)ccc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (41 mg, 0.29 mmol), 6-bromo-1H-indole-3-carbonitrile (22 mg, 0.10 mmol), and Pd(dppf)$Cl_2$·DCM (8 mg, 0.010 mmol). To this were added 1.6 mL dioxane and 0.4 mL of water. The mixture was sparged with nitrogen for 20 minutes. The vial was sealed, the mixture stirred at 100° C. for 24 hours, and cooled when the reaction had proceeded to completion. The mixture was purified via $SiO_2$ gel chromatography and reverse-phase HPLC to give 6-(4-((4-((5-(trifluoromethyl)pyridin-2-yl)amino)piperidin-1-yl)sulfonyl)phenyl)-1H-indole-3-carbonitrile. MS: (ES) m/z calculated for $C_{26}H_{22}F_3N_5O_2S$ [M+H]$^+$ 526.2, found 526. $^1$H NMR (300 MHz, DMSO-d$_6$) δ 12.40 (d, J=3.1 Hz, 1H), 8.35 (d, J=2.9 Hz, 1H), 8.23 (app s, 1H), 7.99 (d, J=8.5 Hz, 2H), 7.91-7.81 (m, 3H), 7.78 (d, J=8.3 Hz, 1H), 7.69-7.57 (m, 2H), 7.40 (d, J=4.8 Hz, 1H), 6.58 (d, J=9.0 Hz, 1H), 3.75-3.58 (m, 3H, under residual H$_2$O peak), 2.66-2.55 (m, 2H), 2.03-1.91 (m, 2H), 1.60-1.42 (m, 2H).

Example 99: 2-(4-((4-((5-(Trifluoromethyl)pyridin-2-yl)amino)piperidin-1-yl)sulfonyl)phenyl)-6,7-dihydrothiazolo-[5,4-c]pyridine-5(4H)-carboxamide

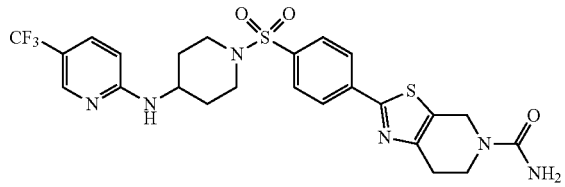 [SMILES: NC(=O)N1CCc2nc(-c3ccc(S(=O)(=O)N4CCC(Nc5ccc(C(F)(F)F)cn5)CC4)cc3)sc2C1]

To 2-(4-((4-((5-(trifluoromethyl)pyridin-2-yl)amino)piperidin-1-yl)sulfonyl)phenyl)-4,5,6,7-tetrahydro-thiazolo[5,4-c]pyridin-5-ium chloride in a septum-cap vial were added DCM (3 mL) and DIPEA (35 µL, 0.20 mmol) followed by (Trimethylsilyl)isocyanate (27 uL, 0.20 mmol). The mixture stirred at RT until the reaction had proceeded to completion. The mixture was purified via SiO$_2$ gel chromatography to give 2-(4-((4-((5-(trifluoromethyl)pyridin-2-yl)amino)piperidin-1-yl)sulfonyl)phenyl)-6,7-dihydrothiazolo-[5,4-c]pyridine-5(4H)-carboxamide. MS: (ES) m/z calculated for $C_{24}H_{25}F_3N_6O_3S_2$ [M+H]$^+$ 567.2, found 567. $^1$H NMR (300 MHz, DMSO-d$_6$) δ 8.22 (s, 1H), 8.13 (d, J=8.5 Hz, 2H), 7.85 (d, J=8.5 Hz, 2H), 7.59 (dd, J=8.9, 2.6 Hz, 1H), 7.28 (d, J=7.4 Hz, 1H), 6.54 (d, J=8.9 Hz, 1H), 6.23 (bs, 2H), 4.67 (s, 2H), 3.84-3.75 (m, 1H), 3.69 (t, J=5.7 Hz, 2H), 3.62-3.50 (m, 2H), 2.85 (t, J=5.8 Hz, 2H), 2.69-2.58 (m, 2H), 2.01-1.89 (m, 2H), 1.58-1.42 (m, 2H).

Example 100: 2-(4-((4-((5-(trifluoromethyl)pyridin-2-yl)amino)piperidin-1-yl)sulfonyl)phenyl)-4,5,6,7-tetrahydrothiazolo[5,4-c]pyridin-5-ium chloride

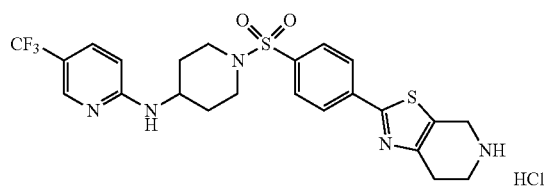 [SMILES: O=S(=O)(c1ccc(-c2nc3c(s2)CNCC3)cc1)N1CCC(Nc2ccc(C(F)(F)F)cn2)CC1 ; Cl]

To tert-butyl 4-oxo-2-(4-((4-((5-(trifluoromethyl)pyridin-2-yl)amino)piperidin-1-yl)sulfonyl)phenyl)-6,7-dihydrothiazolo[5,4-c]pyridine-5(4H)-carboxylate in a septum-cap vial were added 3 mL dioxane and 15 drops of conc. HCl. The mixture stirred at RT for 90 min and the solvent was removed when the reaction had proceeded to completion. The mixture was dissolved in minimal MeOH and acetone and solid precipitated and was filtered to give 2-(4-((4-((5-(trifluoromethyl)pyridin-2-yl)amino)piperidin-1-yl)sulfonyl)phenyl)-4,5,6,7-tetrahydrothiazolo[5,4-c]pyridin-5-ium chloride. MS: (ES) m/z calculated for $C_{23}H_{24}F_3N_5O_2S_2$ (Free base) [M+H]$^+$ 524.1, found 524. $^1$H NMR (400 MHz, DMSO-d$_6$) $^1$H NMR (400 MHz, DMSO-d$_6$) δ 9.69-9.60 (m, 2H), 8.22 (s, 1H), 8.17 (d, J=8.3 Hz, 2H), 7.88 (d, J=8.5 Hz, 2H), 7.67 (d, J=8.4 Hz, 1H), 6.64 (d, J=9.1 Hz, 1H), 4.53-4.46 (m, 2H), 3.84-3.74 (m, 1H), 3.64-3.55 (m, 2H), 3.56-3.46 (m, 2H), 3.11 (t, J=6.2 Hz, 2H), 2.64-2.54 (m, 2H), 2.02-1.91 (m, 2H), 1.57-1.44 (m, 2H).

Example 101: 5-(4-((4-((5-(Trifluoromethyl)pyridin-2-yl)amino)piperidin-1-yl)sulfonyl)phenyl)-1H-benzo[d]imidazol-2-amine

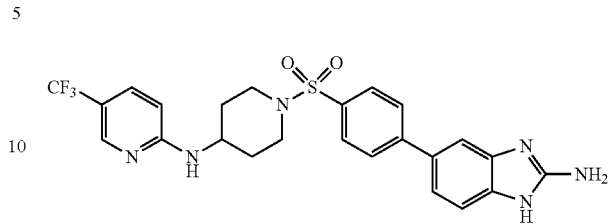

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (41 mg, 0.29 mmol), 5-bromo-1H-benzo[d]imidazol-2-amine (21 mg, 0.10 mmol), and Pd(dppf)Cl$_2$.DCM (8 mg, 0.010 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via reverse-phase HPLC to give 5-(4-((4-((5-(trifluoromethyl)pyridin-2-yl)amino)piperidin-1-yl)sulfonyl)phenyl)-1H-benzo[d]imidazol-2-amine. MS: (ES) m/z calculated for $C_{24}H_{23}F_3N_6O_2S$ [M+H]$^+$ 517.2, found 517. $^1$H NMR (400 MHz, DMSO-d$_6$) δ 10.85 (bs, 1H), 8.22 (s, 1H), 7.94-7.85 (m, 2H), 7.76 (d, J=8.1 Hz, 2H), 7.62-7.56 (m, 1H), 7.48 (s, 1H), 7.35-7.17 (m, 3H), 6.54 (d, J=9.0 Hz, 1H), 6.37-6.24 (m, 2H), 3.83-3.69 (m, 1H), 3.60-3.50 (m, 2H), 2.63-2.53 (m, 2H), 2.01-1.91 (m, 2H), 1.59-1.44 (m, 2H).

Example 102: 5-(4-((4-((5-(Trifluoromethyl)pyridin-2-yl)amino)piperidin-1-yl)sulfonyl)phenyl)indolin-2-one

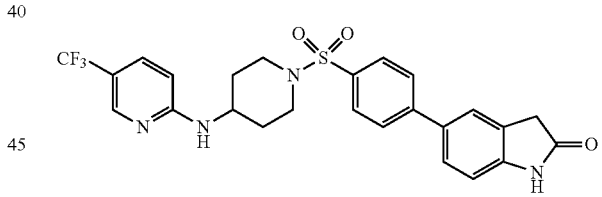

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 5-(4,4,5,5-tetramethyl-1,3,2-dioxaborolan-2-yl)indolin-2-one (28 mg, 0.11 mmol), and Pd(dppf)Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography and preparative reverse-phase HPLC to give 5-(4-((4-((5-(trifluoromethyl)pyridin-2-yl)amino)piperidin-1-yl)sulfonyl)phenyl)indolin-2-one. MS: (ES) m/z calculated for $C_{25}H_{23}F_3N_4O_3S$ [M+H]$^+$ 517.2, found 517. $^1$H NMR (400 MHz, DMSO-d$_6$) δ 10.56 (s, 1H), 8.22 (s, 1H), 7.88 (d, J=8.2 Hz, 2H), 7.78 (d, J=8.2 Hz, 2H), 7.65-7.56 (m, 3H), 7.31 (d, J=7.1 Hz, 1H), 6.95 (d, J=8.1 Hz, 1H), 6.54 (d, J=8.9 Hz, 1H), 3.82-3.70 (m, 1H), 3.61-3.51 (m, 2H), 2.62-2.52 (m, 2H), 2.01-1.92 (m, 2H), 1.57-1.44 (m, 2H).

Example 103: N-(1-((4-(1H-benzo[d][1,2,3]triazol-5-yl)phenyl)sulfonyl)piperidin-4-yl)-5-(trifluoromethyl)pyridin-2-amine

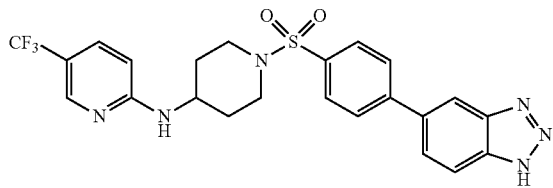 [SMILES: O=S(=O)(c1ccc(-c2ccc3[nH]nnc3c2)cc1)N1CCC(Nc2ccc(C(F)(F)F)cn2)CC1]

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), (1H-benzo[d][1,2,3]triazol-5-yl)boronic acid (18 mg, 0.11 mmol), and Pd(dppf)Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via reverse-phase HPLC to give N-(1-((4-(1H-benzo[d][1,2,3]triazol-5-yl)phenyl)sulfonyl)piperidin-4-yl)-5-(trifluoromethyl)pyridin-2-amine. MS: (ES) m/z calculated for C$_{23}$H$_{21}$F$_3$N$_6$O$_2$S [M+H]$^+$ 503.2, found 503. $^1$H NMR (400 MHz, DMSO-d$_6$) δ 8.30 (bs, 1H), 8.23 (s, 1H), 8.11-8.01 (m, 3H), 7.90-7.81 (m, 3H), 7.61 (d, J=8.8 Hz, 1H), 7.37 (bs, 1H), 6.56 (d, J=9.2 Hz, 1H), 3.84-3.74 (m, 1H), 3.64-3.55 (m, 2H), 2.64-2.55 (m, 2H), 2.02-1.92 (m, 2H), 1.58-1.46 (m, 2H).

Example 104: N-(1-((4-(1H-benzo[d]imidazol-5-yl)phenyl)sulfonyl)piperidin-4-yl)-5-(trifluoromethyl)pyridin-2-amine

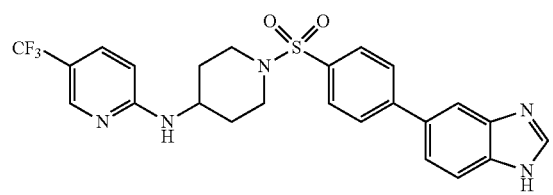 [SMILES: O=S(=O)(c1ccc(-c2ccc3[nH]cnc3c2)cc1)N1CCC(Nc2ccc(C(F)(F)F)cn2)CC1]

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 5-(4,4,5,5-tetramethyl-1,3,2-dioxaborolan-2-yl)-1H-benzo[d]imidazole (26 mg, 0.11 mmol), and Pd(dppf)Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via reverse-phase HPLC to give N-(1-((4-(1H-benzo[d]imidazol-5-yl)phenyl)sulfonyl)piperidin-4-yl)-5-(trifluoromethyl)pyridin-2-amine. MS: (ES) m/z calculated for C$_{24}$H$_{22}$F$_3$N$_5$O$_2$S [M+H]$^+$ 502.2, found 502. $^1$H NMR (400 MHz, DMSO-d$_6$) δ 12.63 (bs, 1H), 8.31 (s, 1H), 8.22 (s, 1H), 7.99 (d, J=7.9 Hz, 2H), 7.82 (d, J=8.1 Hz, 2H), 7.64-7.55 (m, 2H), 7.31 (d, J=7.1 Hz, 1H), 6.55 (d, J=8.9 Hz, 1H), 3.84-3.73 (m, 1H), 3.62-3.52 (m, 2H), 2.65-2.54 (m, 2H), 2.01-1.93 (m, 2H), 1.58-1.44 (m, 2H).

Example 105: tert-Butyl 4-oxo-2-(4-((4-((5-(trifluoromethyl)pyridin-2-yl)amino)piperidin-1-yl)sulfonyl)phenyl)-6,7-dihydrothiazolo[5,4-c]pyridine-5(4H)-carboxylate

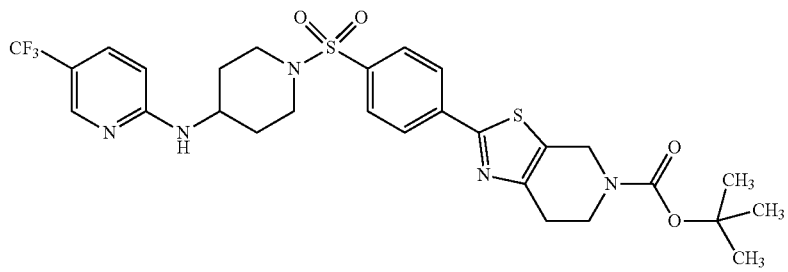 [SMILES: CC(C)(C)OC(=O)N1CCc2nc(-c3ccc(S(=O)(=O)N4CCC(Nc5ccc(C(F)(F)F)cn5)CC4)cc3)sc2C1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added K$_2$CO$_3$ (82 mg, 0.59 mmol), tert-butyl 7-bromo-3,4-dihydroisoquinoline-2(1H)-carboxylate (62 mg, 0.20 mmol), and Pd(dppf)Cl$_2$.DCM (16 mg, 0.020 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography to give Tert-butyl 4-oxo-2-(4-((4-((5-(trifluoromethyl)pyridin-2-yl)amino)piperidin-1-yl)sulfonyl)phenyl)-6,7-dihydrothiazolo[5,4-c]pyridine-5(4H)-carboxylate. MS: (ES) m/z calculated for C$_{28}$H$_{32}$F$_3$N$_5$O$_4$S$_2$ [M+H]$^+$ 624.2, found 624. $^1$H NMR (400 MHz, DMSO-d$_6$) δ 8.22 (s, 1H), 8.13 (d, J=8.2 Hz, 2H), 7.85 (d, J=8.3 Hz, 2H), 7.59 (dd, J=8.8, 2.1 Hz, 1H), 7.29 (d, J=7.2 Hz, 1H), 6.54 (d, J=8.9 Hz, 1H), 4.69 (s, 2H), 3.81-3.75 (m, 1H), 3.71 (t, J=5.8 Hz, 2H), 3.60-3.52 (m, 2H), 2.91-2.82 (m, 2H), 2.68-2.56 (m, 2H), 2.02-1.88 (m, 2H), 1.56-1.38 (m, 11H).

Example 106: 5-(4-((4-((5-(Trifluoromethyl)pyridin-2-yl)amino)piperidin-1-yl)sulfonyl)phenyl)-1H-indazol-3-amine

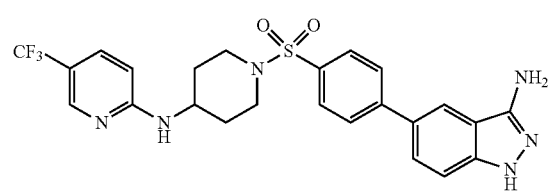 [SMILES: Nc1n[nH]c2ccc(-c3ccc(S(=O)(=O)N4CCC(Nc5ccc(C(F)(F)F)cn5)CC4)cc3)cc12]

To N-(1-((4-bromophenyl)sulfonyl)piperidin-4-yl)-5-(trifluoromethyl)pyridin-2-amine in a septum-cap vial were added $K_2CO_3$ (45 mg, 0.32 mmol), 5-(4,4,5,5-tetramethyl-1,3,2-dioxaborolan-2-yl)-1H-indazol-3-amine (28 mg, 0.11 mmol), and $Pd(dppf)Cl_2 \cdot DCM$ (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via reverse-phase HPLC to give 5-(4-((4-((5-(trifluoromethyl)pyridin-2-yl)amino)piperidin-1-yl)sulfonyl)phenyl)-1H-indazol-3-amine. MS: (ES) m/z calculated for $C_{24}H_{23}F_3N_6O_2S$ [M+H]$^+$ 517.2, found 518. $^1$H NMR (400 MHz, DMSO-$d_6$) δ 11.58 (bs, 1H), 8.22 (s, 1H), 8.18 (s, 1H), 7.92 (d, J=8.4 Hz, 2H), 7.82 (d, J=8.3 Hz, 2H), 7.66 (dd, J=8.7, 1.8 Hz, 1H), 7.59 (dd, J=8.9, 2.6 Hz, 1H), 7.36 (d, J=8.7 Hz, 1H), 7.31 (d, J=7.3 Hz, 1H), 6.54 (d, J=8.9 Hz, 1H), 5.64 (bs, 2H), 3.83-3.72 (m, 1H), 3.61-3.51 (m, 2H), 2.64-2.51 (m, 2H), 2.02-1.91 (m, 2H), 1.58-1.44 (m, 2H).

Example 107: 5-(4-((4-((5-(Trifluoromethyl)pyridin-2-yl)amino)piperidin-1-yl)sulfonyl)phenyl)-1H-indole-2-carbonitrile

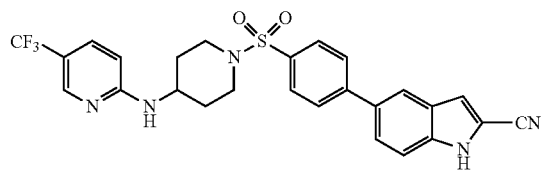 [SMILES: N#Cc1cc2cc(-c3ccc(S(=O)(=O)N4CCC(Nc5ccc(C(F)(F)F)cn5)CC4)cc3)ccc2[nH]1]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (81 mg, 0.59 mmol), 5-bromo-1H-indole-2-carbonitrile (43 mg, 0.20 mmol), and $Pd(dppf)Cl_2 \cdot DCM$ (16 mg, 0.020 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via $SiO_2$ gel chromatography and preparative reverse-phase HPLC to give 5-(4-((4-((5-(trifluoromethyl) pyridin-2-yl)amino)piperidin-1-yl)sulfonyl)phenyl)-1H-indole-2-carbonitrile. MS: (ES) m/z calculated for $C_{26}H_{22}F_3N_5O_2S$ [M+H]$^+$ 526.2, found 526. $^1$H NMR (400 MHz, DMSO-$d_6$) δ 12.58 (s, 1H), 8.23 (s, 1H), 8.10 (s, 1H), 7.98 (d, J=8.5 Hz, 2H), 7.82 (d, J=8.5 Hz, 2H), 7.76 (dd, J=8.7, 1.8 Hz, 1H), 7.65-7.59 (m, 2H), 7.50-7.40 (m, 2H), 6.58 (d, J=9.1 Hz, 1H), 3.83-3.71 (m, 1H), 3.62-3.53 (m, 2H), 2.63-2.52 (m, 2H), 2.02-1.92 (m, 2H), 1.57-1.44 (m, 2H).

Example 108: 5-(4-((4-((5-(Trifluoromethyl)pyridin-2-yl)amino)piperidin-1-yl)sulfonyl)phenyl)-1H-indole-3-carbonitrile

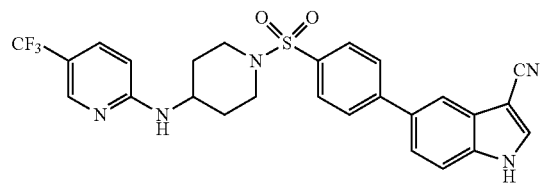 [SMILES: N#Cc1c[nH]c2ccc(-c3ccc(S(=O)(=O)N4CCC(Nc5ccc(C(F)(F)F)cn5)CC4)cc3)cc12]

To N-(1-((4-(4,4,5,5-tetramethyl-1,3,2-dioxaborolan-2-yl)phenyl)sulfonyl)piperidin-4-yl)-5-(trifluoro-methyl)pyridin-2-amine in a septum-cap vial were added $K_2CO_3$ (81 mg, 0.59 mmol), 5-bromo-1H-indole-3-carbonitrile (43 mg, 0.20 mmol), and $Pd(dppf)Cl_2 \cdot DCM$ (16 mg, 0.020 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via $SiO_2$ gel chromatography and preparative reverse-phase HPLC to give 5-(4-((4-((5-(trifluoromethyl) pyridin-2-yl)amino)piperidin-1-yl)sulfonyl)phenyl)-1H-indole-3-carbonitrile. MS: (ES) m/z calculated for $C_{26}H_{22}F_3N_5O_2S$ [M+H]$^+$ 526.2, found 526. $^1$H NMR (400 MHz, DMSO-$d_6$) δ 12.37 (s, 1H), 8.35 (s, 1H), 8.23 (s, 1H), 8.03 (d, J=8.4 Hz, 2H), 7.99 (s, 1H), 7.82 (d, J=8.3 Hz, 2H), 7.70 (s, 2H), 7.62 (d, J=9.0 Hz, 1H), 7.43 (bs, 1H), 6.58 (d, J=9.1 Hz, 1H), 3.83-3.73 (m, 1H), 3.63-3.53 (m, 2H), 2.64-2.53 (m, 2H), 2.02-1.92 (m, 2H), 1.59-1.45 (m, 2H).

Example 109: 5-(4-((4-((5-(Trifluoromethyl)pyridin-2-yl)amino)piperidin-1-yl)sulfonyl)phenyl)-1,3-dihydro-2H-benzo[d]-imidazol-2-one

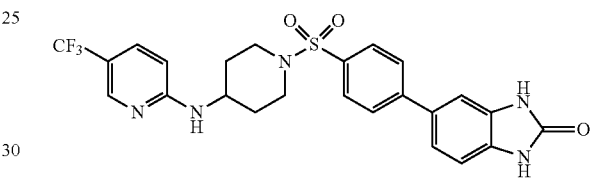

To N-(1-((4-bromophenyl)sulfonyl)piperidin-4-yl)-5-(trifluoromethyl)pyridin-2-amine in a septum-cap vial were added $K_2CO_3$ (45 mg, 0.32 mmol), (2-oxo-2,3-dihydro-1H-benzo[d]imidazol-5-yl)boronic acid (28 mg, 0.11 mmol), and $Pd(dppf)Cl_2 \cdot DCM$ (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via $SiO_2$ gel chromatography and preparative reverse-phase HPLC to give 5-(4-((4-((5-(trifluoromethyl) pyridin-2-yl)amino)piperidin-1-yl)sulfonyl)phenyl)-1,3-dihydro-2H-benzo[d]-imidazol-2-one. MS: (ES) m/z calculated for $C_{24}H_{22}F_3N_5O_3S$ [M+H]$^+$ 518.2, found 518. $^1$H NMR (400 MHz, DMSO-$d_6$) δ 10.81 (d, J=7.1 Hz, 2H), 8.23 (s, 1H), 7.88 (d, J=8.3 Hz, 2H), 7.78 (d, J=8.3 Hz, 2H), 7.63-7.59 (m, 1H), 7.40-7.33 (m, 2H), 7.26 (s, 1H), 7.05 (d, J=8.1 Hz, 1H), 6.56 (d, J=9.1 Hz, 1H), 3.81-3.72 (m, 1H), 3.60-3.52 (m, 2H), 2.62-2.51 (m, 2H), 2.01-1.91 (m, 2H), 1.58-1.43 (m, 2H).

Example 110: 5-(4-((4-((5-(Trifluoromethyl)pyridin-2-yl)amino)piperidin-1-yl)sulfonyl)phenyl)isoindolin-1-one

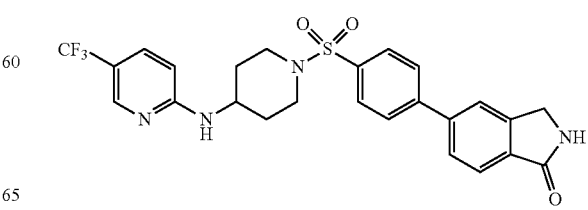

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 5-(4,4,5,5-tetramethyl-1,3,2-dioxaborolan-2-yl)isoindolin-1-one (28 mg, 0.11 mmol), and Pd(dppf)Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography and preparative reverse-phase HPLC to give 5-(4-((4-((5-(trifluoromethyl)pyridin-2-yl)amino)piperidin-1-yl)sulfonyl)phenyl)isoindolin-1-one. MS: (ES) m/z calculated for C$_{25}$H$_{23}$F$_3$N$_4$O$_3$S [M+H]$^+$ 517.2, found 517. $^1$H NMR (400 MHz, DMSO-d$_6$) δ 8.67 (s, 1H), 8.24-8.22 (m, 1H), 8.01 (d, J=8.4 Hz, 2H), 7.96 (s, 1H), 7.89-7.84 (m, 3H), 7.80 (d, J=7.9 Hz, 1H), 7.61 (dd, J=9.1, 2.5 Hz, 1H), 7.41-7.34 (m, 1H), 6.56 (d, J=8.9 Hz, 1H), 4.46 (s, 2H), 3.82-3.73 (m, 1H), 3.63-3.53 (m, 2H), 2.65-2.54 (m, 2H), 2.02-1.92 (m, 2H), 1.57-1.44 (m, 2H).

Example 111: 5-(4-((4-((5-(Trifluoromethyl)pyridin-2-yl)amino)piperidin-1-yl)sulfonyl)phenyl)benzo[d]-oxazol-2-amine

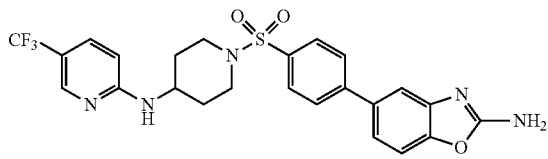 [SMILES: Nc1nc2cc(-c3ccc(S(=O)(=O)N4CCC(Nc5ccc(C(F)(F)F)cn5)CC4)cc3)ccc2o1]

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 5-(4,4,5,5-tetramethyl-1,3,2-dioxaborolan-2-yl)benzo[d]oxazol-2-amine (28 mg, 0.11 mmol), and Pd(dppf)Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography and preparative reverse-phase HPLC to give 5-(4-((4-((5-(trifluoromethyl)pyridin-2-yl)amino)piperidin-1-yl)sulfonyl)phenyl)benzo[d]-oxazol-2-amine. MS: (ES) m/z calculated for C$_{24}$H$_{22}$F$_3$N$_5$O$_3$S [M+H]$^+$ 518.2, found 518. $^1$H NMR (400 MHz, DMSO-d$_6$) δ 8.24 (app s, 1H), 7.94 (d, J=8.5 Hz, 2H), 7.89 (bs, 2H), 7.80 (d, J=8.4 Hz, 2H), 7.64 (dd, J=8.9, 2.5 Hz, 1H), 7.59 (d, J=1.8 Hz, 1H), 7.52-7.46 (m, 2H), 7.40 (dd, J=8.3, 1.9 Hz, 1H), 6.59 (d, J=8.9 Hz, 1H), 3.83-3.72 (m, 1H), 3.62-3.54 (m, 2H), 2.62-2.51 (m, 2H), 2.01-1.92 (m, 2H), 1.59-1.45 (m, 2H).

Example 112: N-(1-((4-(1H-Indol-5-yl)phenyl)sulfonyl)piperidin-4-yl)-5-(trifluoromethyl)pyridin-2-amine

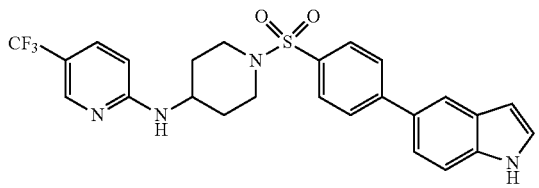 [SMILES: O=S(=O)(c1ccc(-c2ccc3[nH]ccc3c2)cc1)N1CCC(Nc2ccc(C(F)(F)F)cn2)CC1]

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 5-(4,4,5,5-tetramethyl-1,3,2-dioxaborolan-2-yl)-1H-indole (26 mg, 0.11 mmol), and Pd(dppf)Cl$_2$.DCM (9.0 mg, 0.011 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography and preparative reverse-phase HPLC to give N-(1-((4-(1H-indol-5-yl)phenyl)sulfonyl)piperidin-4-yl)-5-(trifluoromethyl)pyridin-2-amine. MS: (ES) m/z calculated for C$_{25}$H$_{23}$F$_3$N$_4$O$_2$S [M+H]$^+$ 501.2, found 501. $^1$H NMR (400 MHz, DMSO-d$_6$) δ 11.27 (s, 1H), 8.23 (app s, 1H), 7.95 (d, J=8.2 Hz, 2H), 7.79 (d, J=8.4 Hz, 2H), 7.63 (d, J=8.8 Hz, 1H), 7.55-7.40 (m, 4H), 6.58 (d, J=9.0 Hz, 1H), 6.53 (t, J=2.5 Hz, 1H), 3.82-3.70 (m, 1H), 3.61-3.52 (m, 2H), 2.63-2.52 (m, 2H), 2.03-1.91 (m, 2H), 1.59-1.45 (m, 2H).

Example 113: N-(1-((4-(2,3-Dihydro-1H-inden-5-yl)phenyl)sulfonyl)piperidin-4-yl)-5-(trifluoromethyl)pyridin-2-amine

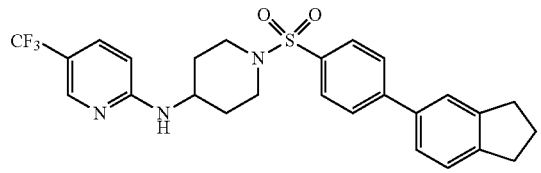 [SMILES: O=S(=O)(c1ccc(-c2ccc3c(c2)CCC3)cc1)N1CCC(Nc2ccc(C(F)(F)F)cn2)CC1]

To N-(1-((4-bromophenyl)sulfonyl)piperidin-4-yl)-5-(trifluoromethyl)pyridin-2-amine in a septum-cap vial were added K$_2$CO$_3$ (45 mg, 0.32 mmol), 2-(2,3-dihydro-1H-inden-5-yl)-4,4,5,5-tetramethyl-1,3,2-dioxaborolane (26 mg, 0.11 mmol), and Pd(dppf)Cl$_2$.DCM (9 mg, 0.01 mmol). To this were added 1.6 mL dioxane and 0.4 mL of water. The mixture was sparged with nitrogen for 20 minutes. The vial was sealed, the mixture stirred at 100° C. for 16 hours, and cooled when the reaction had proceeded to completion. The mixture was purified via SiO$_2$ gel chromatography and preparative reverse-phase HPLC to give N-(1-((4-(2,3-dihydro-1H-inden-5-yl)phenyl)sulfonyl)piperidin-4-yl)-5-(trifluoromethyl)pyridin-2-amine. MS: (ES) m/z calculated for C$_{26}$H$_{26}$F$_3$N$_3$O$_2$S [M+H]$^+$ 502.2, found 502. $^1$H NMR (400 MHz, DMSO-d$_6$) δ 8.23 (app s, 1H), 7.91 (d, J=8.4 Hz, 2H), 7.80 (d, J=8.4 Hz, 2H), 7.64-7.59 (m, 2H), 7.53-7.49 (m, 1H), 7.43-7.34 (d, J=8.2 Hz, 2H), 6.57 (d, J=8.9 Hz, 1H), 3.82-3.72 (m, 1H), 3.61-3.51 (m, 2H), 2.93 (dt, J=11.5, 7.4 Hz, 4H), 2.62-2.52 (m, 2H), 2.06 (p, J=7.4 Hz, 2H), 2.01-1.91 (m, 2H), 1.58-1.44 (m, 2H).

Example 114: N-(1-((4-(piperidin-1-yl)phenyl)sulfonyl)piperidin-4-yl)-5-(trifluoromethyl)pyridin-2-amine

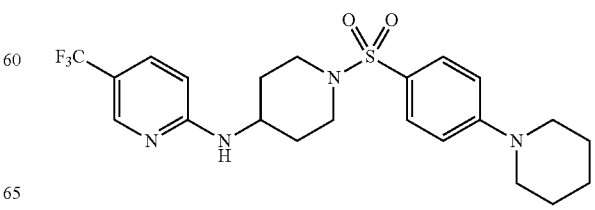

To a septum-cap vial were added piperidine (13 mg, 0.15 mmol), N-(1-((4-bromophenyl)sulfonyl)piperidin-4-yl)-5-(trifluoromethyl)pyridin-2-amine (46 mg, 0.10 mmol), (+/−)-BINAP (12 mg, 0.020 mmol), NaOtBu (19 mg, 0.20 mmol), and dioxane (2 mL). The mixture was sparged with $N_2$ for 20 minutes. $Pd_2(dba)_3$ (9 mg, 0.010 mmol) was added, and the reaction mixture was sparged with $N_2$ for 5 minutes and stirred at 90° C. for 3 hours. The reaction mixture was cooled to room temperature, diluted with ethyl acetate (10 mL), filtered through Celite, and concentrated. Purification by $SiO_2$ gel chromatography (hexanes/ethyl acetate), followed by preparative reverse-phase HPLC gave N-(1-((4-(piperidin-1-yl)phenyl)sulfonyl)piperidin-4-yl)-5-(trifluoromethyl)pyridin-2-amine. MS: (ES) m/z calculated for $C_{22}H_{28}F_3N_4O_2S$ [M+H]$^+$ 469.2, found 469.2. $^1$H NMR (400 MHz, DMSO-d$_6$) δ 8.22 (d, J=2.5 Hz, 1H), 7.60 (dd, J=9.0, 2.6 Hz, 1H), 7.49 (d, J=9.0 Hz, 2H), 7.29 (d, J=7.3 Hz, 1H), 7.05 (d, J=9.1 Hz, 2H), 6.55 (d, J=8.9 Hz, 1H), 3.71 (s, 1H), 3.52-3.41 (m, 2H), 3.38-3.30 (m, 4H), 2.42 (dd, J=12.0, 9.4 Hz, 2H), 1.98-1.87 (m, 2H), 1.59 (d, J=3.9 Hz, 6H), 1.53-1.41 (m, 2H).

Example 115: N-(1-((4-(4-(phenylamino)piperidin-1-yl)phenyl)sulfonyl)piperidin-4-yl)-5-(trifluoromethyl)pyridin-2-amine

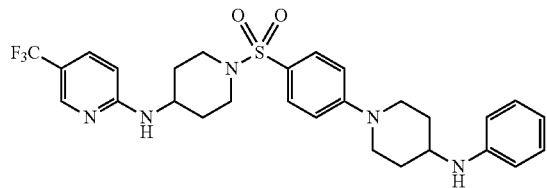 [SMILES: O=S(=O)(c1ccc(N2CCC(Nc3ccccc3)CC2)cc1)N1CCC(Nc2ccc(C(F)(F)F)cn2)CC1]

A mixture of N-(1-((4-fluorophenyl)sulfonyl)piperidin-4-yl)-5-(trifluoromethyl)pyridin-2-amine (48 mg 0.12 mmol), N-phenylpiperidin-4-amine (42 mg, 0.24 mmol), and potassium carbonate (66 mg, 0.48 mmol) in NMP (1 mL) was stirred at 120° C. for 12 hours. The reaction mixture was cooled to room temperature and diluted with water (10 mL). The resulting solid was filtered, washed with water, and purified by $SiO_2$ gel chromatography (hexanes/ethyl acetate), followed by preparative reverse-phase HPLC to give N-(1-((4-(4-(phenylamino)piperidin-1-yl)phenyl)sulfonyl)piperidin-4-yl)-5-(trifluoromethyl)pyridin-2-amine. MS: (ES) m/z calculated for $C_{28}H_{33}F_3N_5O_2S$ [M+H]$^+$ 560.2, found 560.4. $^1$H NMR (400 MHz, DMSO-d$_6$) δ 8.23 (d, J=1.7 Hz, 1H), 7.60 (dd, J=9.0, 2.6 Hz, 1H), 7.51 (d, J=8.9 Hz, 2H), 7.30 (d, J=7.3 Hz, 1H), 7.12-7.02 (m, 4H), 6.61 (d, J=8.0 Hz, 2H), 6.55 (d, J=8.9 Hz, 1H), 6.51 (t, J=7.3 Hz, 1H), 5.50 (d, J=8.2 Hz, 1H), 3.94-3.84 (m, 2H), 3.71 (s, 1H), 3.48 (d, J=12.0 Hz, 3H), 3.12-3.00 (m, 2H), 2.43 (t, J=11.1 Hz, 2H), 1.97 (t, J=15.3 Hz, 4H), 1.56-1.34 (m, 4H).

Example 116: 4-(4-((4-((5-(trifluoromethyl)pyridin-2-yl)amino)piperidin-1-yl)sulfonyl)phenyl)piperazin-2-one

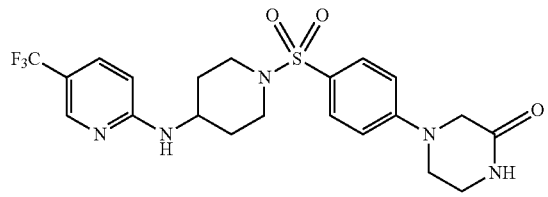 [SMILES: O=C1CN(c2ccc(S(=O)(=O)N3CCC(Nc4ccc(C(F)(F)F)cn4)CC3)cc2)CCN1]

To a septum-cap vial were added 2-oxopiperazine (15 mg, 0.15 mmol), N-(1-((4-bromophenyl)sulfonyl)piperidin-4-yl)-5-(trifluoromethyl)pyridin-2-amine (46 mg, 0.10 mmol), RuPhos (19 mg, 0.040 mmol), NaOtBu (19 mg, 0.20 mmol), and dioxane (2 mL). The mixture was sparged with $N_2$ for 20 minutes. $Pd_2(dba)_3$ (9 mg, 0.010 mmol) was added, and the reaction mixture was sparged with $N_2$ for 5 minutes and stirred at 90° C. for 16 hours. The reaction mixture was cooled to room temperature, diluted with ethyl acetate (10 mL), filtered through Celite, and concentrated. Purification by $SiO_2$ gel chromatography (hexanes/ethyl acetate, then ethyl acetate/methanol) gave 4-(4-((4-((5-(trifluoromethyl)pyridin-2-yl)amino)piperidin-1-yl)sulfonyl)phenyl)piperazin-2-one. MS: (ES) m/z calculated for $C_{21}H_{25}F_3N_5O_3S$ [M+H]$^+$ 484.2, found 484.2. $^1$H NMR (300 MHz, DMSO-d$_6$) δ 8.24-8.17 (m, 2H), 7.62-7.56 (m, 1H), 7.55 (d, J=9.0 Hz, 2H), 7.30-7.25 (m, 1H), 7.04 (d, J=9.0 Hz, 2H), 6.55 (d, J=9.0 Hz, 1H), 3.88 (s, 2H), 3.71 (s, 1H), 3.78-3.62 (m, 1H), 3.59-3.53 (m, 2H), 3.51-3.42 (m, 3H), 2.45-2.38 (m, 2H), 2.00-1.89 (m, 2H), 1.56-1.40 (m, 2H).

Biological Example 1: Migration Assay

A chemotaxis assay can be used to determine the efficacy of potential receptor antagonists at blocking the migration mediated through chemokine receptors, such as CCR6. This assay is routinely performed using the ChemoTX® microchamber system with a 5-μm pore-sized polycarbonate membrane. Chemokine receptor-expressing cells are required for such an assay. In this case, Ba/F3 cells (Palacios et al., Nature, 309:126, 1984) transfected with the gene for human CCR6 under control of the CMV promotor were used. To begin such an assay, hCCR6-transfected Ba/F$_3$ cells are first grown for 24 hr in medium supplemented with sodium butyrate, which increases CCR6 transcription via the CMV promotor. The prepared Ba/F3 cells, are collected by centrifugation at 400×g at room temperature, then suspended at 4 million/ml in human serum. The compound being tested is serially diluted from a maximum final concentration of 10 μM (or an equivalent volume of its solvent (DMSO)) and is then added to the cell/serum mixture. Separately, recombinant human CCL20 (MIP-3α/LARC) at its EC$_{50}$ concentration (10 nM) is placed in the lower wells of the ChemoTX® plate. The 5-μm (pore size) polycarbonate membrane is placed onto the plate, and 20 μL of the cell/compound mixture is transferred onto each well of the membrane. The plates are incubated at 37° C. for 45 minutes, after which the polycarbonate membranes are removed and 5 μl of the DNA-intercalating dye CyQUANT (Invitrogen, Carlsbad, CA) is added to the lower wells. The amount of fluorescence, corresponding to the number of migrated cells, is measured using a Spectrafluor Plus plate reader (TECAN, San Jose, CA).

Compounds in Table 1 having an $IC_{50}$ value in the migration assay of less than 5 nM are labeled (+++); from 5-100 nM are labeled (++); and less than or equal to 10 μM but above 100 nM are labeled (+).

TABLE 1

| Compound | Structure | Potency |
|---|---|---|
| 1.001 | 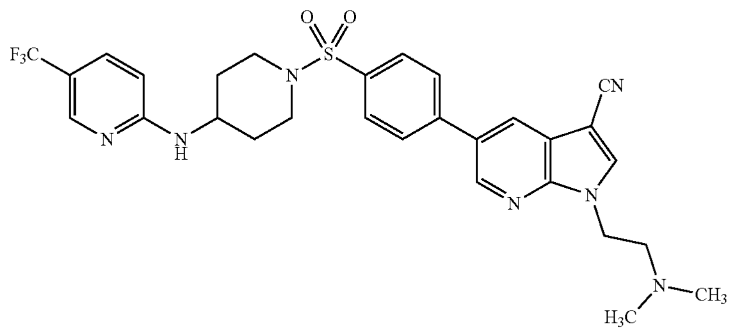 [SMILES: CN(C)CCn1cc(C#N)c2cc(-c3ccc(S(=O)(=O)N4CCC(Nc5ccc(C(F)(F)F)cn5)CC4)cc3)cnc21] | ++ |
| 1.002 | 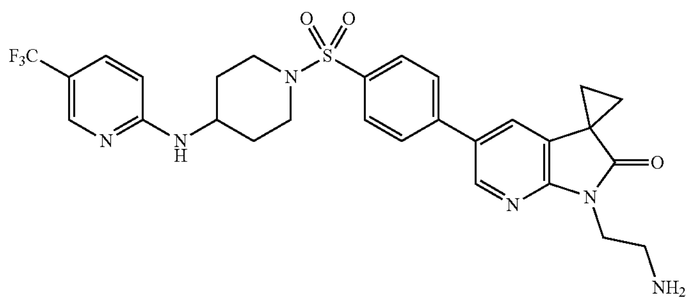 [SMILES: NCCN1C(=O)C2(CC2)c2cc(-c3ccc(S(=O)(=O)N4CCC(Nc5ccc(C(F)(F)F)cn5)CC4)cc3)cnc21] | ++ |
| 1.003 | 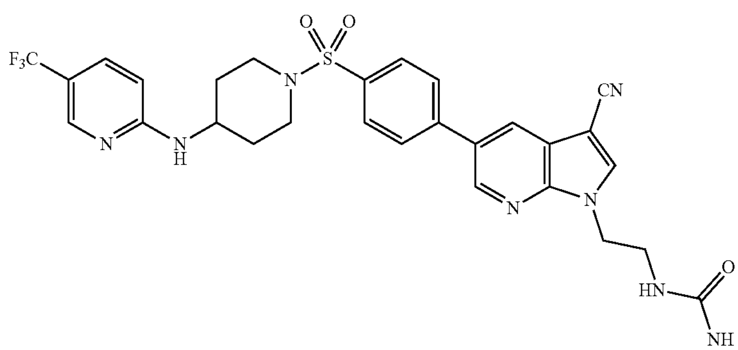 [SMILES: N#Cc1cn(CCNC(N)=O)c2ncc(-c3ccc(S(=O)(=O)N4CCC(Nc5ccc(C(F)(F)F)cn5)CC4)cc3)cc12] | +++ |
| 1.004 | 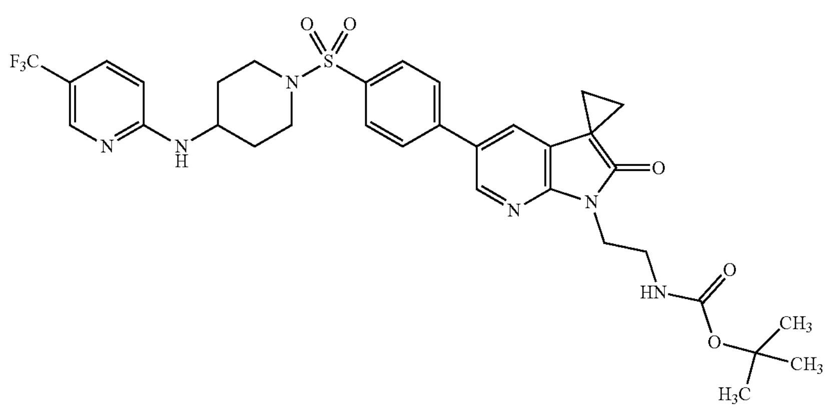 | ++ |

TABLE 1-continued

| Compound | Structure | Potency |
|---|---|---|
| 1.005 | 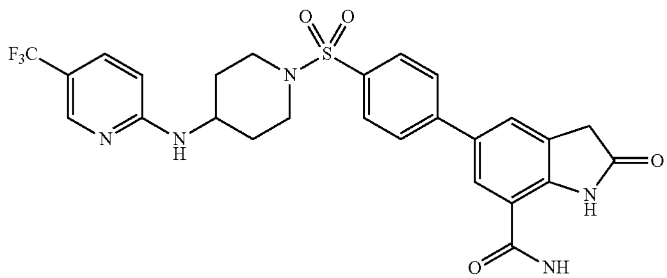 [SMILES: NC(=O)c1cc(-c2ccc(S(=O)(=O)N3CCC(Nc4ccc(C(F)(F)F)cn4)CC3)cc2)cc2c1NC(=O)C2] | +++ |
| 1.006 | 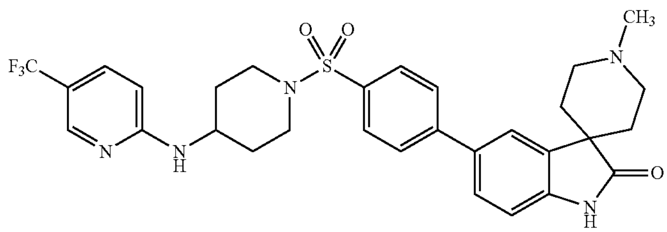 [SMILES: CN1CCC2(CC1)C(=O)Nc1ccc(-c3ccc(S(=O)(=O)N4CCC(Nc5ccc(C(F)(F)F)cn5)CC4)cc3)cc12] | + |
| 1.007 | 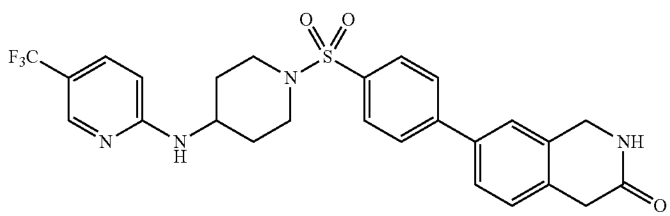 [SMILES: O=C1Cc2ccc(-c3ccc(S(=O)(=O)N4CCC(Nc5ccc(C(F)(F)F)cn5)CC4)cc3)cc2CN1] | ++ |
| 1.008 | 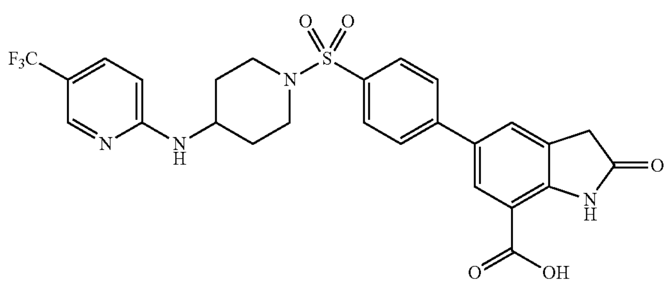 [SMILES: O=C1Cc2cc(-c3ccc(S(=O)(=O)N4CCC(Nc5ccc(C(F)(F)F)cn5)CC4)cc3)cc(C(=O)O)c2N1] | + |
| 1.009 | 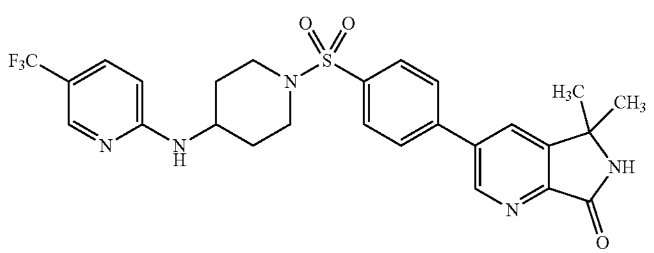 [SMILES: CC1(C)NC(=O)c2ncc(-c3ccc(S(=O)(=O)N4CCC(Nc5ccc(C(F)(F)F)cn5)CC4)cc3)cc21] | +++ |
| 1.010 | 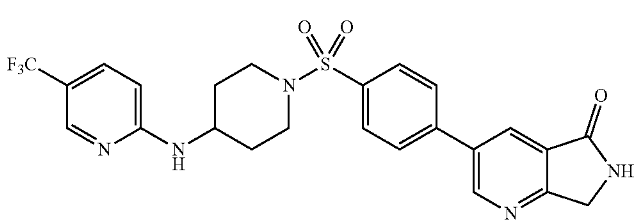 [SMILES: O=C1NCc2ncc(-c3ccc(S(=O)(=O)N4CCC(Nc5ccc(C(F)(F)F)cn5)CC4)cc3)cc21] | ++ |

TABLE 1-continued

| Compound | Structure | Potency |
|---|---|---|
| 1.011 | 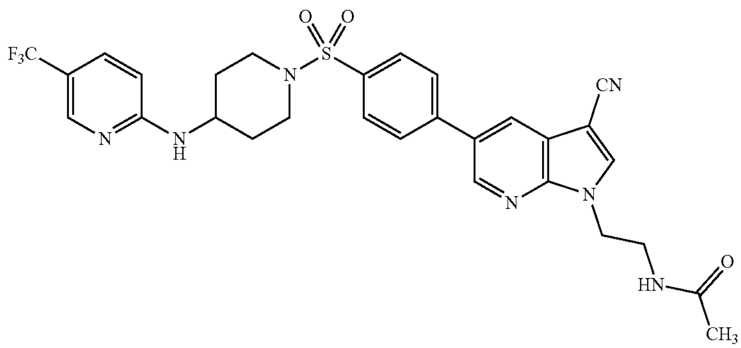 [SMILES: CC(=O)NCCn1cc(C#N)c2cc(-c3ccc(S(=O)(=O)N4CCC(Nc5ccc(C(F)(F)F)cn5)CC4)cc3)cnc21] | +++ |
| 1.012 | 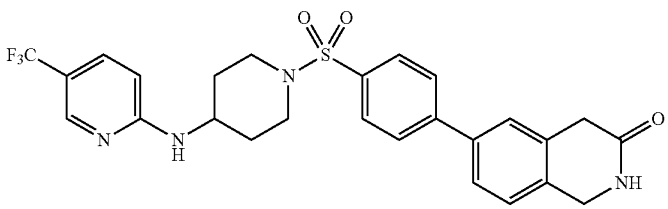 [SMILES: O=C1Cc2cc(-c3ccc(S(=O)(=O)N4CCC(Nc5ccc(C(F)(F)F)cn5)CC4)cc3)ccc2CN1] | +++ |
| 1.013 | 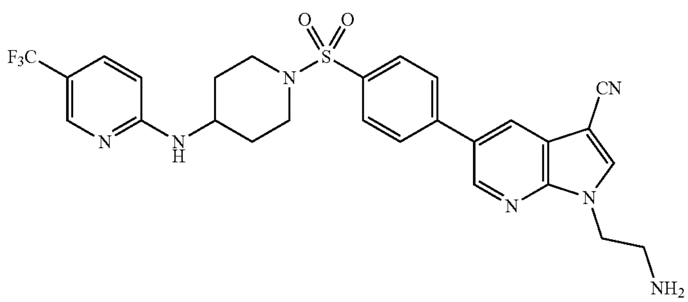 [SMILES: N#Cc1cn(CCN)c2ncc(-c3ccc(S(=O)(=O)N4CCC(Nc5ccc(C(F)(F)F)cn5)CC4)cc3)cc12] | ++ |
| 1.014 | 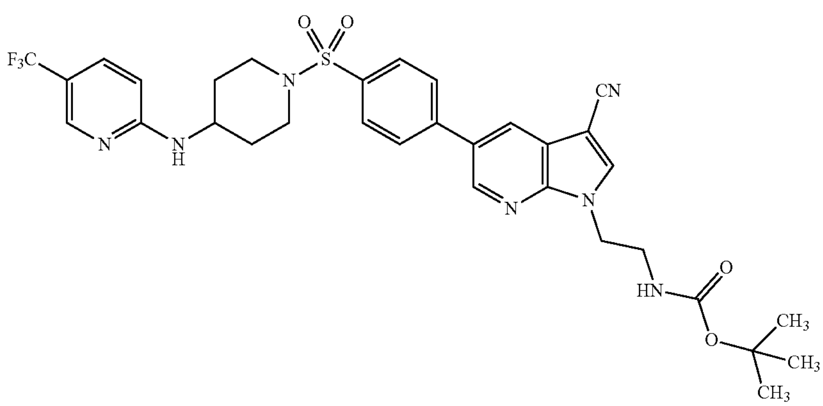 [SMILES: CC(C)(C)OC(=O)NCCn1cc(C#N)c2cc(-c3ccc(S(=O)(=O)N4CCC(Nc5ccc(C(F)(F)F)cn5)CC4)cc3)cnc21] | +++ |
| 1.015 | 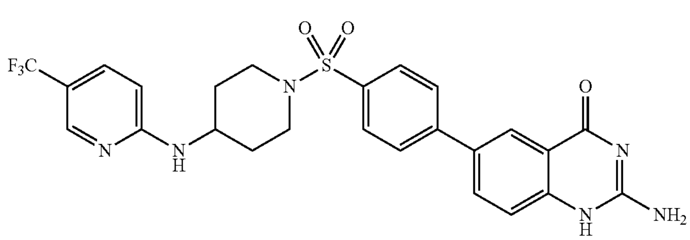 [SMILES: Nc1nc(=O)c2cc(-c3ccc(S(=O)(=O)N4CCC(Nc5ccc(C(F)(F)F)cn5)CC4)cc3)ccc2[nH]1] | +++ |

TABLE 1-continued

| Compound | Structure | Potency |
|---|---|---|
| 1.016 | 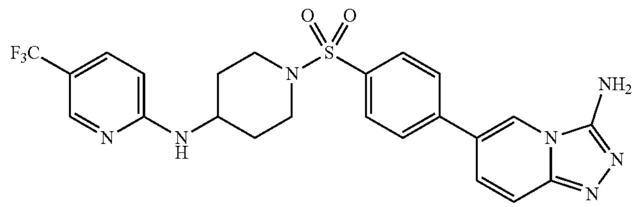 [SMILES: Nc1nnc2ccc(-c3ccc(S(=O)(=O)N4CCC(Nc5ccc(C(F)(F)F)cn5)CC4)cc3)cn12] | +++ |
| 1.017 | 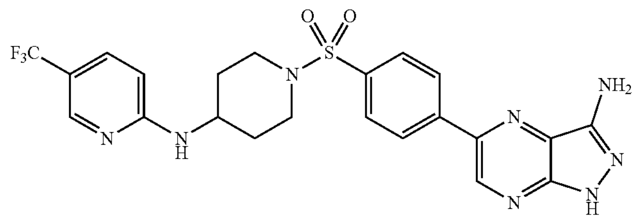 [SMILES: Nc1n[nH]c2ncc(-c3ccc(S(=O)(=O)N4CCC(Nc5ccc(C(F)(F)F)cn5)CC4)cc3)nc12] | ++ |
| 1.018 | 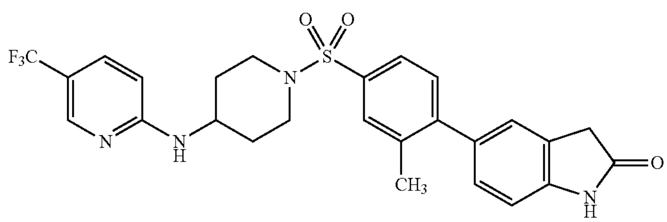 [SMILES: Cc1cc(S(=O)(=O)N2CCC(Nc3ccc(C(F)(F)F)cn3)CC2)ccc1-c1ccc2c(c1)CC(=O)N2] | + |
| 1.019 | 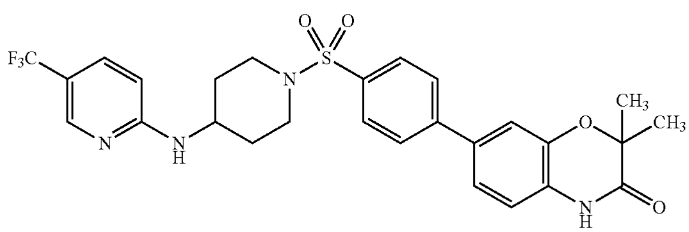 [SMILES: CC1(C)Oc2cc(-c3ccc(S(=O)(=O)N4CCC(Nc5ccc(C(F)(F)F)cn5)CC4)cc3)ccc2NC1=O] | ++ |
| 1.020 | 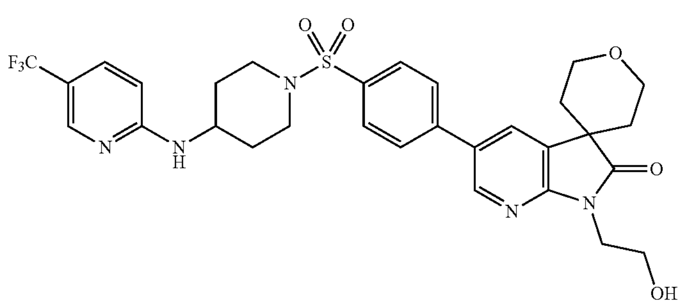 [SMILES: O=C1N(CCO)c2ncc(-c3ccc(S(=O)(=O)N4CCC(Nc5ccc(C(F)(F)F)cn5)CC4)cc3)cc2C12CCOCC2] | ++ |
| 1.021 | 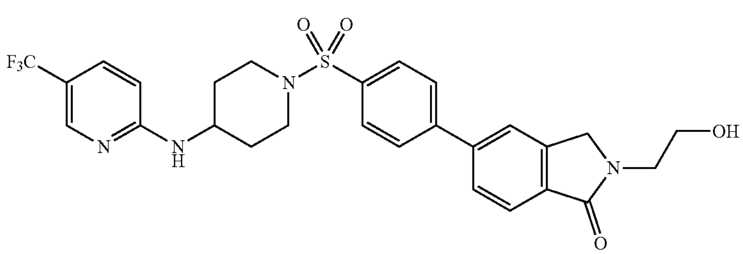 [SMILES: O=C1c2ccc(-c3ccc(S(=O)(=O)N4CCC(Nc5ccc(C(F)(F)F)cn5)CC4)cc3)cc2CN1CCO] | ++ |

TABLE 1-continued

| Compound | Structure | Potency |
|---|---|---|
| 1.022 | 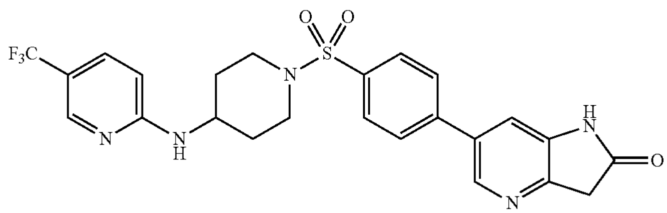 [SMILES: O=C1Cc2ncc(-c3ccc(S(=O)(=O)N4CCC(Nc5ccc(C(F)(F)F)cn5)CC4)cc3)cc2N1] | ++ |
| 1.023 | 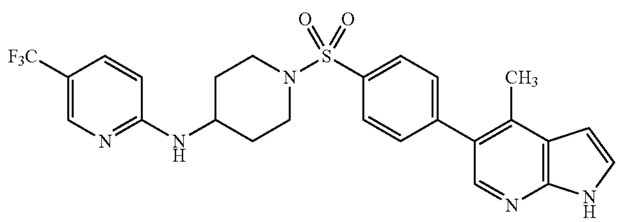 [SMILES: Cc1c(-c2ccc(S(=O)(=O)N3CCC(Nc4ccc(C(F)(F)F)cn4)CC3)cc2)cnc2[nH]ccc12] | +++ |
| 1.024 | 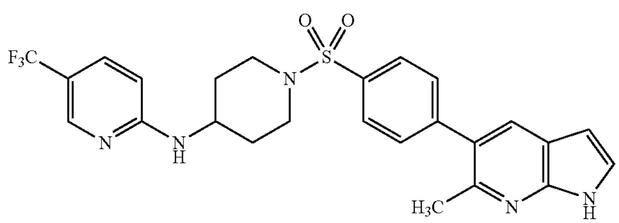 [SMILES: Cc1nc2[nH]ccc2cc1-c1ccc(S(=O)(=O)N2CCC(Nc3ccc(C(F)(F)F)cn3)CC2)cc1] | +++ |
| 1.025 | 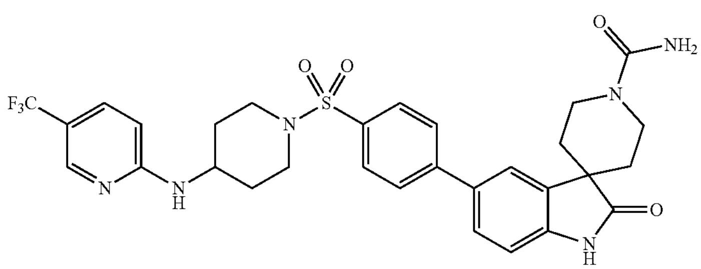 | ++ |
| 1.026 | 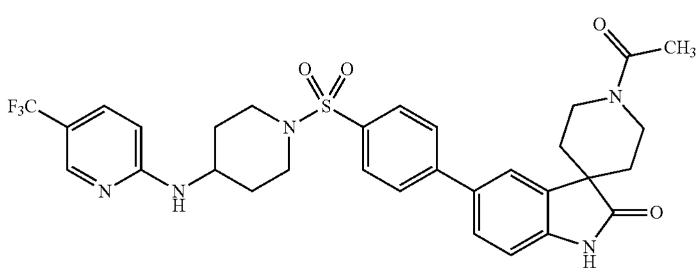 [SMILES: NC(=O)N1CCC2(CC1)C(=O)Nc1ccc(-c3ccc(S(=O)(=O)N4CCC(Nc5ccc(C(F)(F)F)cn5)CC4)cc3)cc12] | ++ |
| 1.027 | 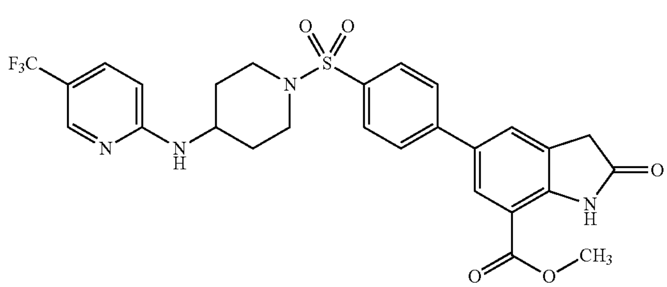 [SMILES: COC(=O)c1cc(-c2ccc(S(=O)(=O)N3CCC(Nc4ccc(C(F)(F)F)cn4)CC3)cc2)cc2c1NC(=O)C2] | +++ |

TABLE 1-continued
| Compound | Structure | Potency |
|---|---|---|
| 1.028 | 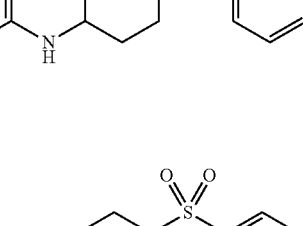 | ++ |
| 1.029 | 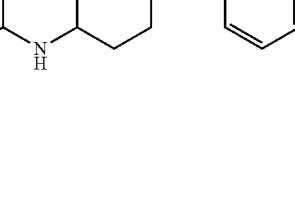 | +++ |
| 1.030 | 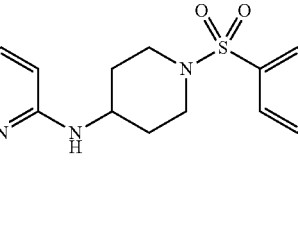 | +++ |
| 1.031 | 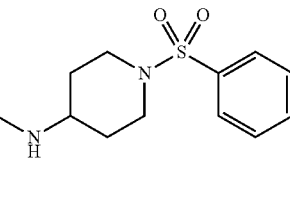 | ++ |
| 1.032 | 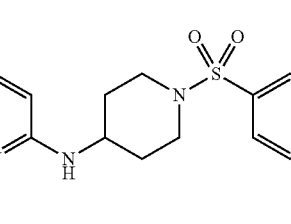 | + |
| 1.033 | 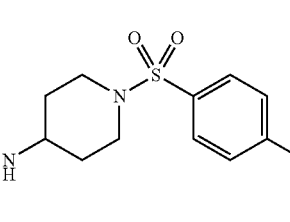 | +++ |

TABLE 1-continued

| Compound | Structure | Potency |
|---|---|---|
| 1.034 | 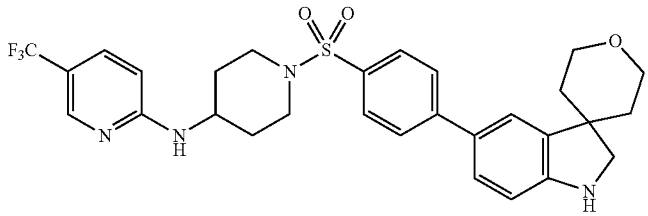 [SMILES: O=S(=O)(c1ccc(-c2ccc3c(c2)C2(CCOCC2)CN3)cc1)N1CCC(Nc2ccc(C(F)(F)F)cn2)CC1] | ++ |
| 1.035 | 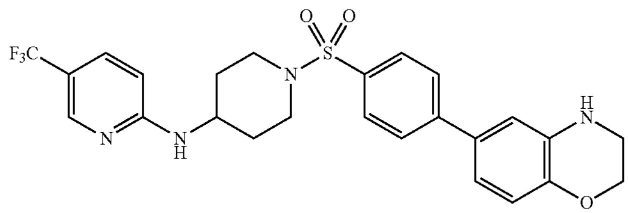 [SMILES: O=S(=O)(c1ccc(-c2ccc3c(c2)NCCO3)cc1)N1CCC(Nc2ccc(C(F)(F)F)cn2)CC1] | ++ |
| 1.036 | 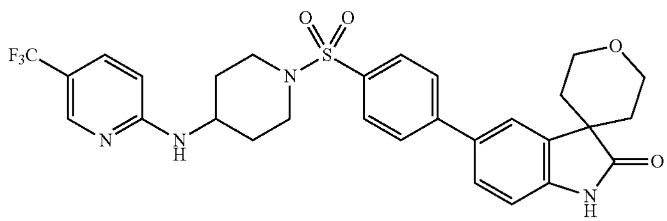 [SMILES: O=C1Nc2ccc(-c3ccc(S(=O)(=O)N4CCC(Nc5ccc(C(F)(F)F)cn5)CC4)cc3)cc2C12CCOCC2] | +++ |
| 1.037 | 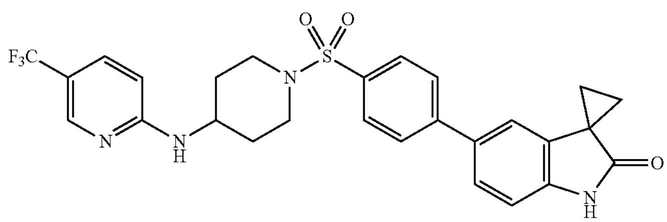 [SMILES: O=C1Nc2ccc(-c3ccc(S(=O)(=O)N4CCC(Nc5ccc(C(F)(F)F)cn5)CC4)cc3)cc2C12CC2] | +++ |
| 1.038 | 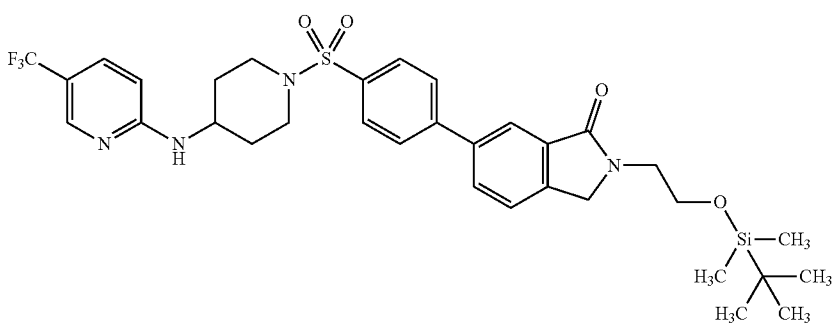 [SMILES: CC(C)(C)[Si](C)(C)OCCN1Cc2ccc(-c3ccc(S(=O)(=O)N4CCC(Nc5ccc(C(F)(F)F)cn5)CC4)cc3)cc2C1=O] | ++ |
| 1.039 | 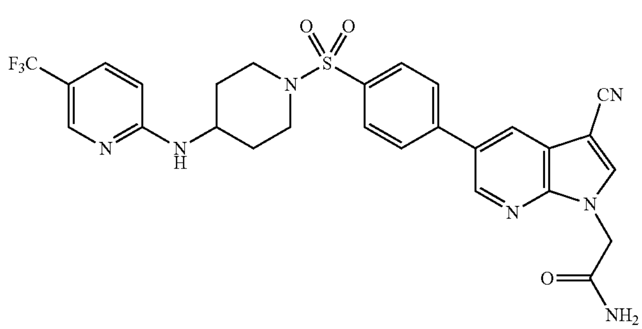 [SMILES: N#Cc1cn(CC(N)=O)c2ncc(-c3ccc(S(=O)(=O)N4CCC(Nc5ccc(C(F)(F)F)cn5)CC4)cc3)cc12] | +++ |

TABLE 1-continued

| Compound | Structure | Potency |
|---|---|---|
| 1.040 | 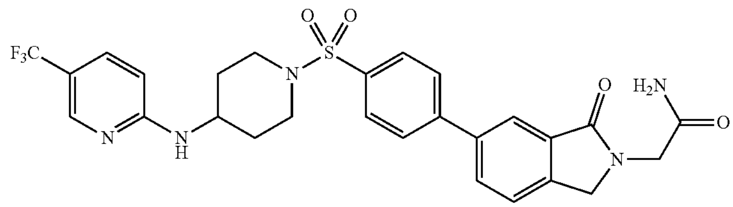 [SMILES: NC(=O)CN1Cc2ccc(-c3ccc(S(=O)(=O)N4CCC(Nc5ccc(C(F)(F)F)cn5)CC4)cc3)cc2C1=O] | ++ |
| 1.041 | 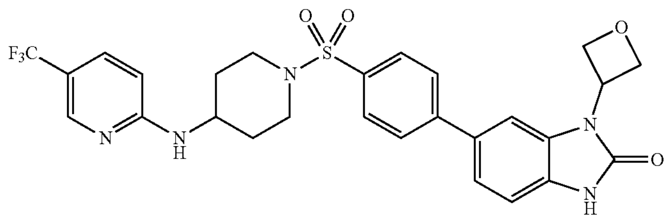 [SMILES: O=c1[nH]c2ccc(-c3ccc(S(=O)(=O)N4CCC(Nc5ccc(C(F)(F)F)cn5)CC4)cc3)cc2n1C1COC1] | ++ |
| 1.042 | 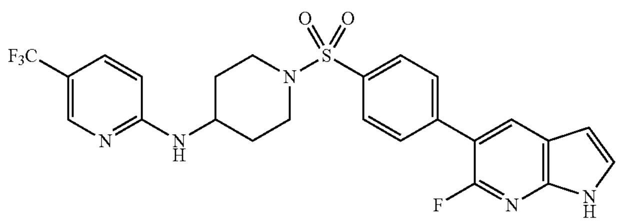 [SMILES: O=S(=O)(c1ccc(-c2cc3cc[nH]c3nc2F)cc1)N1CCC(Nc2ccc(C(F)(F)F)cn2)CC1] | ++ |
| 1.043 | 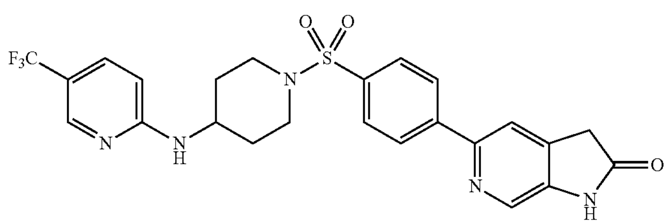 [SMILES: O=C1Cc2cc(-c3ccc(S(=O)(=O)N4CCC(Nc5ccc(C(F)(F)F)cn5)CC4)cc3)ncc2N1] | + |
| 1.044 | 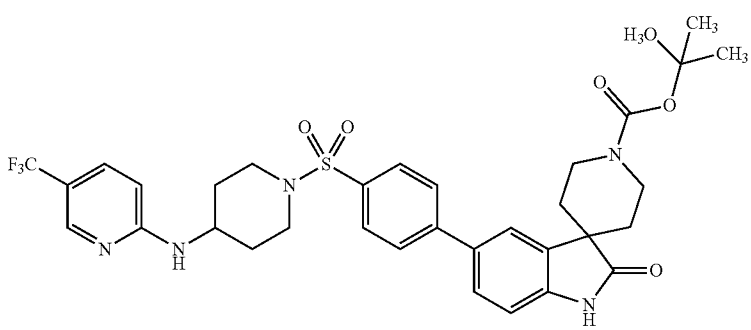 [SMILES: CC(C)(O)OC(=O)N1CCC2(CC1)C(=O)Nc1ccc(-c3ccc(S(=O)(=O)N4CCC(Nc5ccc(C(F)(F)F)cn5)CC4)cc3)cc12] | ++ |
| 1.045 | 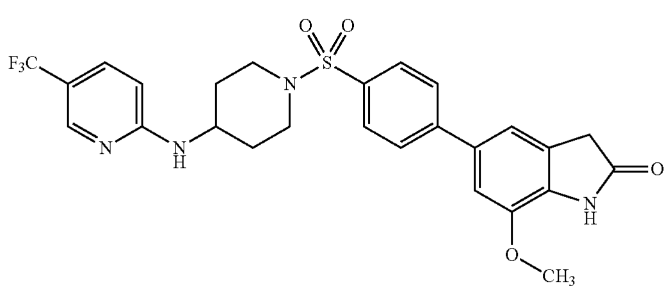 [SMILES: COc1cc(-c2ccc(S(=O)(=O)N3CCC(Nc4ccc(C(F)(F)F)cn4)CC3)cc2)cc2c1NC(=O)C2] | ++ |

TABLE 1-continued

| Compound | Structure | Potency |
|---|---|---|
| 1.046 | 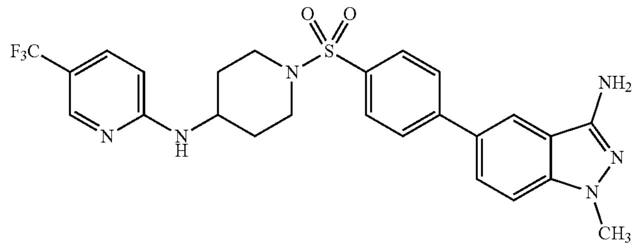 [SMILES: Cn1nc(N)c2cc(-c3ccc(S(=O)(=O)N4CCC(Nc5ccc(C(F)(F)F)cn5)CC4)cc3)ccc21] | +++ |
| 1.047 | 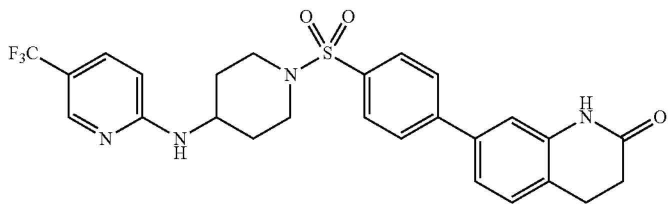 [SMILES: O=C1CCc2ccc(-c3ccc(S(=O)(=O)N4CCC(Nc5ccc(C(F)(F)F)cn5)CC4)cc3)cc2N1] | ++ |
| 1.048 | 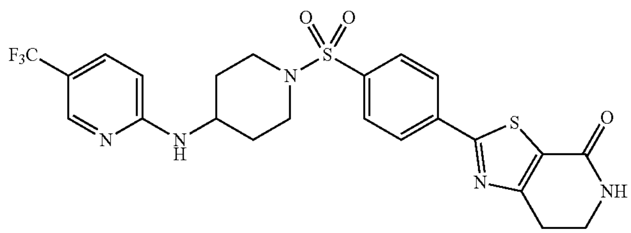 [SMILES: O=C1NCCc2nc(-c3ccc(S(=O)(=O)N4CCC(Nc5ccc(C(F)(F)F)cn5)CC4)cc3)sc21] | ++ |
| 1.049 | 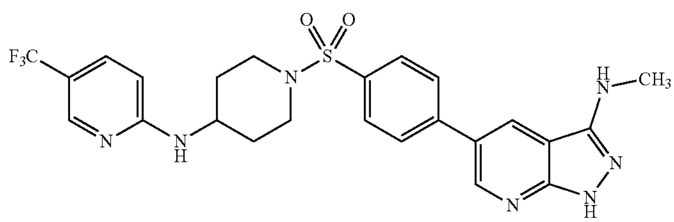 [SMILES: CNc1n[nH]c2ncc(-c3ccc(S(=O)(=O)N4CCC(Nc5ccc(C(F)(F)F)cn5)CC4)cc3)cc12] | +++ |
| 1.050 | 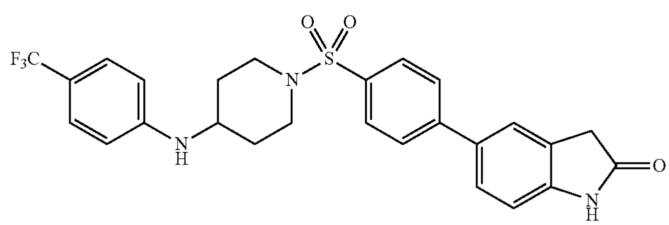 [SMILES: O=C1Cc2cc(-c3ccc(S(=O)(=O)N4CCC(Nc5ccc(C(F)(F)F)cc5)CC4)cc3)ccc2N1] | ++ |
| 1.051 | 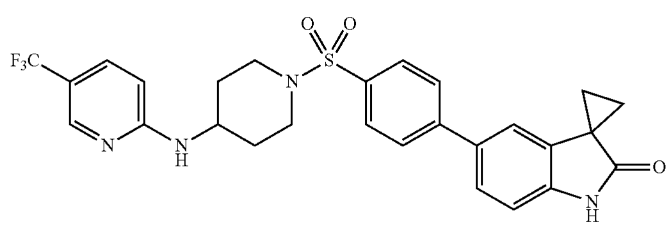 [SMILES: O=C1Nc2ccc(-c3ccc(S(=O)(=O)N4CCC(Nc5ccc(C(F)(F)F)cn5)CC4)cc3)cc2C12CC2] | +++ |
| 1.052 | 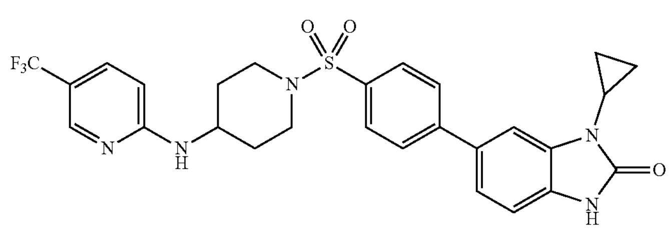 [SMILES: O=c1[nH]c2ccc(-c3ccc(S(=O)(=O)N4CCC(Nc5ccc(C(F)(F)F)cn5)CC4)cc3)cc2n1C1CC1] | ++ |

TABLE 1-continued

| Compound | Structure | Potency |
|---|---|---|
| 1.053 | 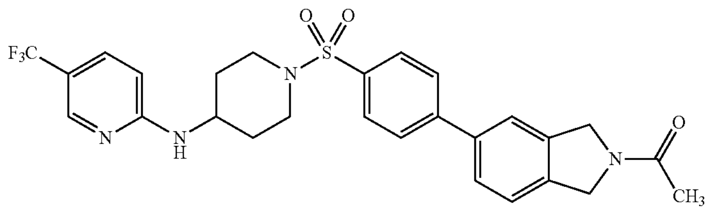 [SMILES: CC(=O)N1Cc2ccc(-c3ccc(S(=O)(=O)N4CCC(Nc5ccc(C(F)(F)F)cn5)CC4)cc3)cc2C1] | +++ |
| 1.054 | 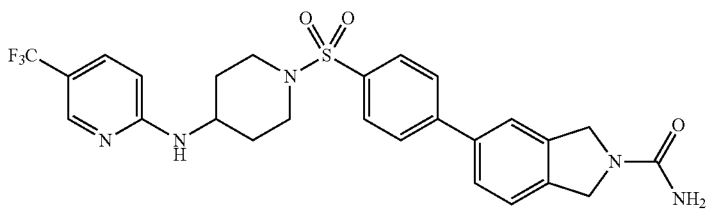 [SMILES: NC(=O)N1Cc2ccc(-c3ccc(S(=O)(=O)N4CCC(Nc5ccc(C(F)(F)F)cn5)CC4)cc3)cc2C1] | +++ |
| 1.055 | 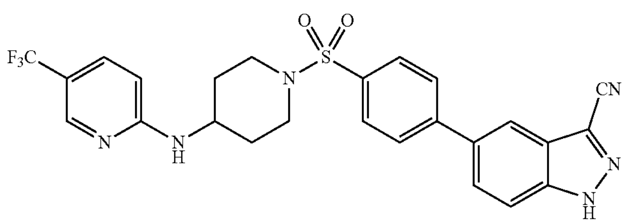 [SMILES: N#Cc1n[nH]c2ccc(-c3ccc(S(=O)(=O)N4CCC(Nc5ccc(C(F)(F)F)cn5)CC4)cc3)cc12] | +++ |
| 1.056 | 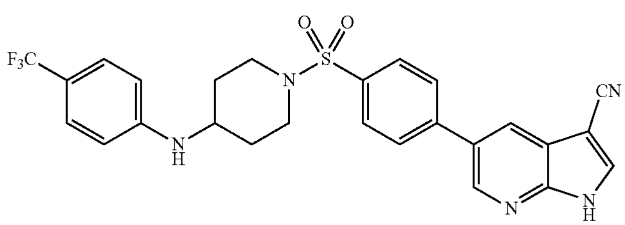 [SMILES: N#Cc1c[nH]c2ncc(-c3ccc(S(=O)(=O)N4CCC(Nc5ccc(C(F)(F)F)cc5)CC4)cc3)cc12] | +++ |
| 1.057 | 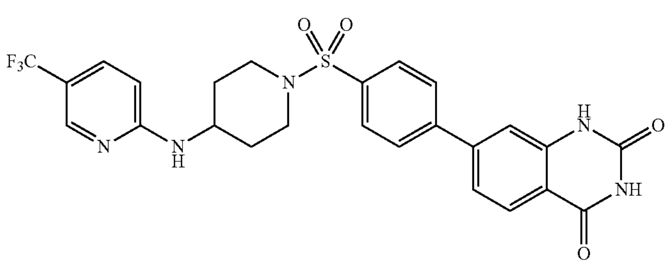 [SMILES: O=c1[nH]c(=O)c2ccc(-c3ccc(S(=O)(=O)N4CCC(Nc5ccc(C(F)(F)F)cn5)CC4)cc3)cc2[nH]1] | ++ |
| 1.058 | 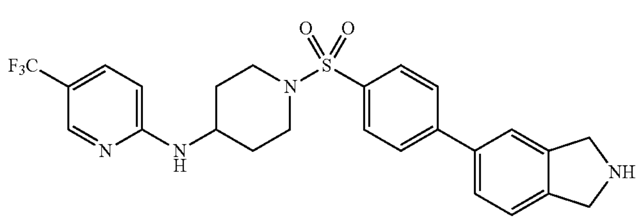 [SMILES: O=S(=O)(c1ccc(-c2ccc3c(c2)CNC3)cc1)N1CCC(Nc2ccc(C(F)(F)F)cn2)CC1] | + |

TABLE 1-continued

| Compound | Structure | Potency |
|---|---|---|
| 1.059 | 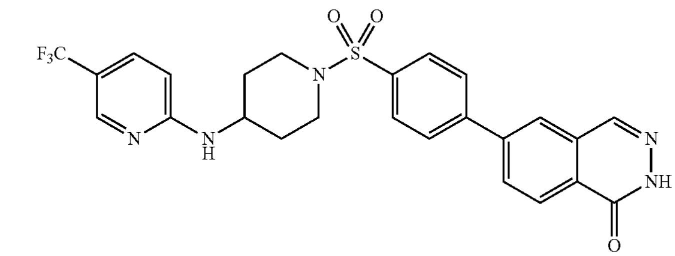 [SMILES: O=c1[nH]ncc2cc(-c3ccc(S(=O)(=O)N4CCC(Nc5ccc(C(F)(F)F)cn5)CC4)cc3)ccc12] | +++ |
| 1.060 | 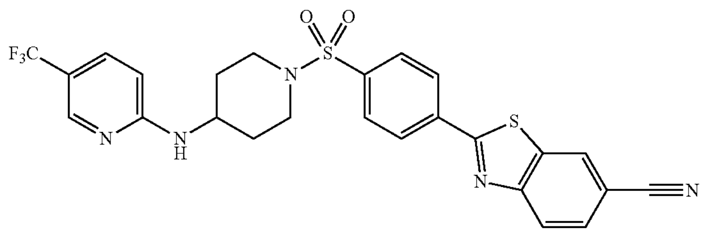 [SMILES: N#Cc1ccc2nc(-c3ccc(S(=O)(=O)N4CCC(Nc5ccc(C(F)(F)F)cn5)CC4)cc3)sc2c1] | ++ |
| 1.061 | 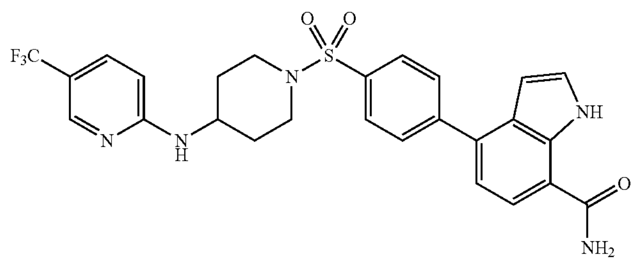 [SMILES: NC(=O)c1ccc(-c2ccc(S(=O)(=O)N3CCC(Nc4ccc(C(F)(F)F)cn4)CC3)cc2)c2cc[nH]c12] | ++ |
| 1.062 | 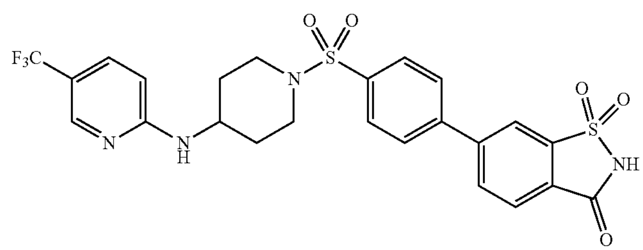 [SMILES: O=C1NS(=O)(=O)c2cc(-c3ccc(S(=O)(=O)N4CCC(Nc5ccc(C(F)(F)F)cn5)CC4)cc3)ccc21] | ++ |
| 1.063 | 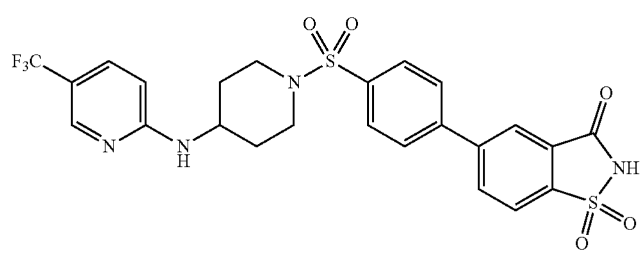 [SMILES: O=C1NS(=O)(=O)c2ccc(-c3ccc(S(=O)(=O)N4CCC(Nc5ccc(C(F)(F)F)cn5)CC4)cc3)cc21] | ++ |
| 1.064 | 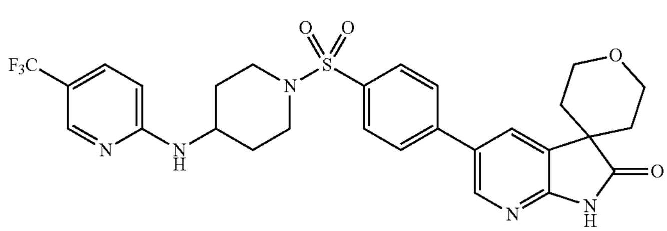 [SMILES: O=C1Nc2ncc(-c3ccc(S(=O)(=O)N4CCC(Nc5ccc(C(F)(F)F)cn5)CC4)cc3)cc2C12CCOCC2] | +++ |

TABLE 1-continued

| Compound | Structure | Potency |
|---|---|---|
| 1.065 | 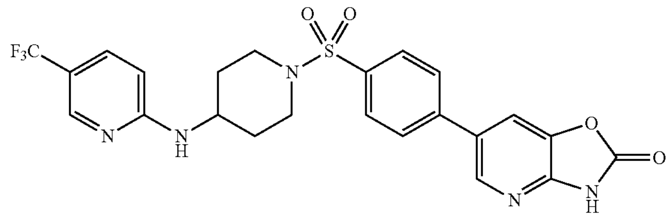 [SMILES: O=c1[nH]c2ncc(-c3ccc(S(=O)(=O)N4CCC(Nc5ccc(C(F)(F)F)cn5)CC4)cc3)cc2o1] | ++ |
| 1.066 | 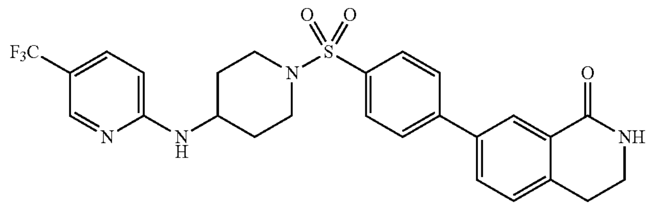 [SMILES: O=C1NCCc2ccc(-c3ccc(S(=O)(=O)N4CCC(Nc5ccc(C(F)(F)F)cn5)CC4)cc3)cc21] | +++ |
| 1.067 | 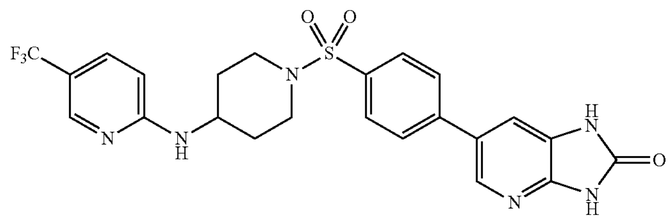 [SMILES: O=c1[nH]c2cc(-c3ccc(S(=O)(=O)N4CCC(Nc5ccc(C(F)(F)F)cn5)CC4)cc3)cnc2[nH]1] | +++ |
| 1.068 | 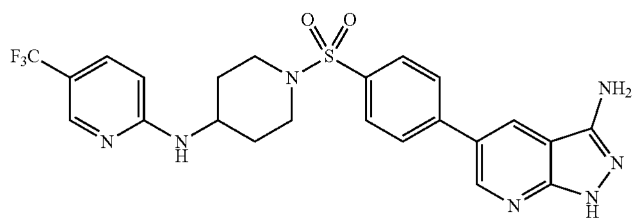 [SMILES: Nc1n[nH]c2ncc(-c3ccc(S(=O)(=O)N4CCC(Nc5ccc(C(F)(F)F)cn5)CC4)cc3)cc12] | +++ |
| 1.069 | 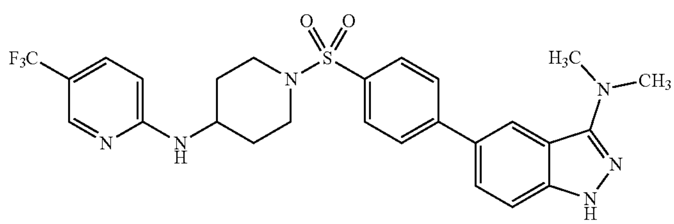 [SMILES: CN(C)c1n[nH]c2ccc(-c3ccc(S(=O)(=O)N4CCC(Nc5ccc(C(F)(F)F)cn5)CC4)cc3)cc12] | ++ |
| 1.070 | 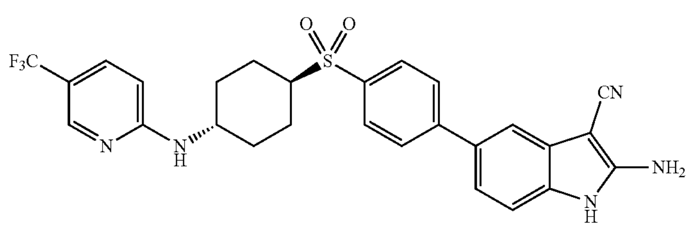 [SMILES: N#Cc1c(N)[nH]c2ccc(-c3ccc(S(=O)(=O)[C@H]4CC[C@H](Nc5ccc(C(F)(F)F)cn5)CC4)cc3)cc12] | +++ |
| 1.071 | 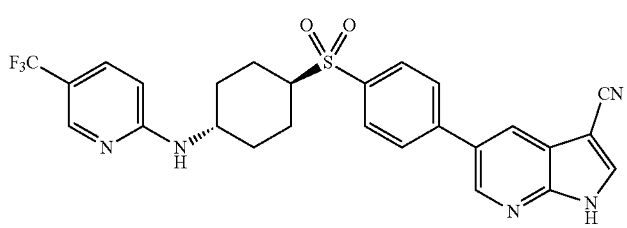 [SMILES: N#Cc1c[nH]c2ncc(-c3ccc(S(=O)(=O)[C@H]4CC[C@H](Nc5ccc(C(F)(F)F)cn5)CC4)cc3)cc12] | +++ |

TABLE 1-continued

| Compound | Structure | Potency |
|---|---|---|
| 1.072 | 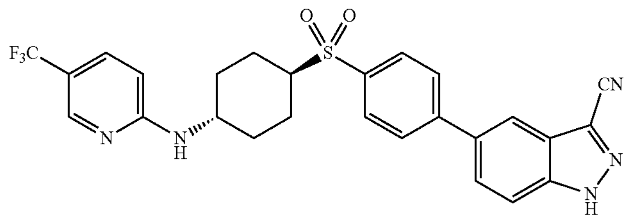 [SMILES: N#Cc1n[nH]c2ccc(-c3ccc(S(=O)(=O)[C@H]4CC[C@H](Nc5ccc(C(F)(F)F)cn5)CC4)cc3)cc12] | +++ |
| 1.073 | 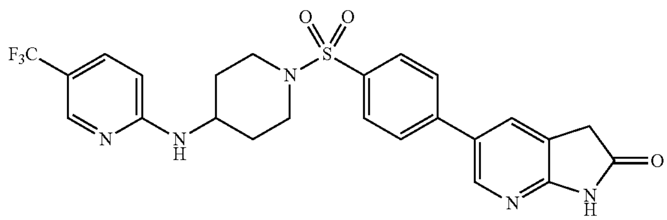 [SMILES: O=C1Cc2cc(-c3ccc(S(=O)(=O)N4CCC(Nc5ccc(C(F)(F)F)cn5)CC4)cc3)cnc2N1] | +++ |
| 1.074 | 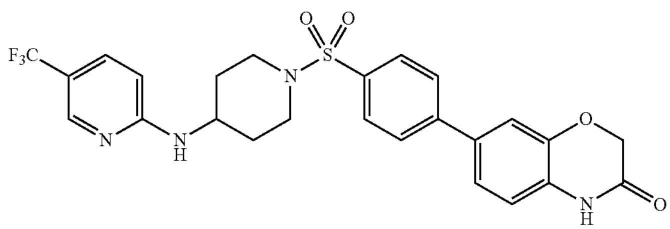 [SMILES: O=C1COc2cc(-c3ccc(S(=O)(=O)N4CCC(Nc5ccc(C(F)(F)F)cn5)CC4)cc3)ccc2N1] | ++ |
| 1.075 | 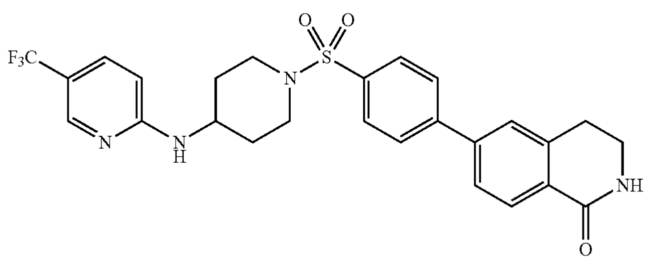 [SMILES: O=C1NCCc2cc(-c3ccc(S(=O)(=O)N4CCC(Nc5ccc(C(F)(F)F)cn5)CC4)cc3)ccc21] | +++ |
| 1.076 | 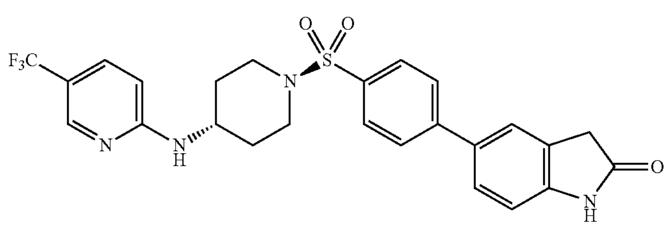 | +++ |
| 1.077 | 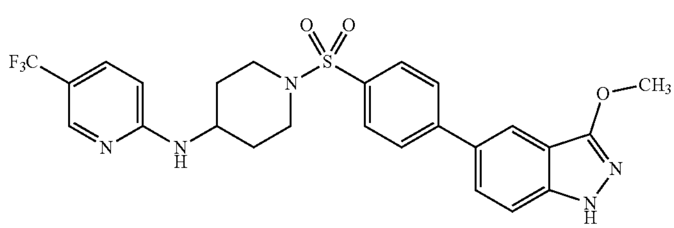 [SMILES: COc1n[nH]c2ccc(-c3ccc(S(=O)(=O)N4CCC(Nc5ccc(C(F)(F)F)cn5)CC4)cc3)cc12] | ++ |

TABLE 1-continued

| Compound | Structure | Potency |
|---|---|---|
| 1.078 | 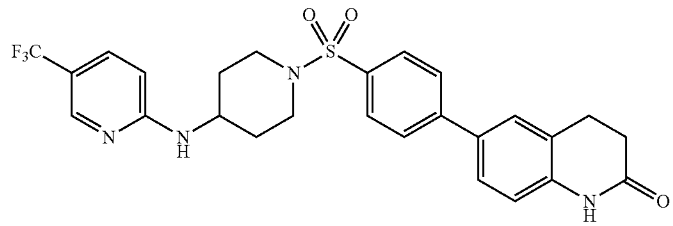 [SMILES: O=C1CCc2cc(-c3ccc(S(=O)(=O)N4CCC(Nc5ccc(C(F)(F)F)cn5)CC4)cc3)ccc2N1] | ++ |
| 1.079 | 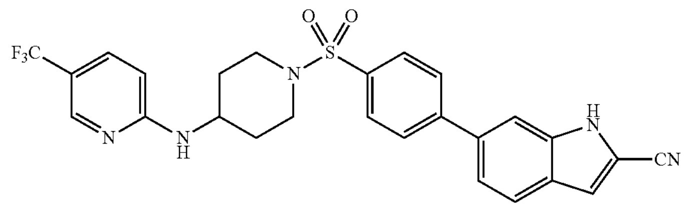 [SMILES: N#Cc1cc2ccc(-c3ccc(S(=O)(=O)N4CCC(Nc5ccc(C(F)(F)F)cn5)CC4)cc3)cc2[nH]1] | ++ |
| 1.080 | 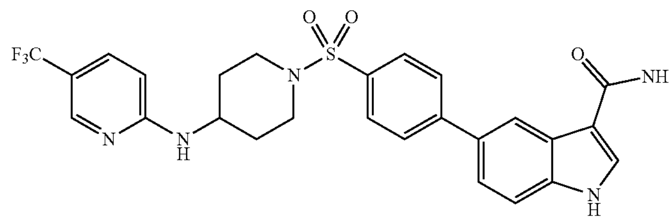 [SMILES: NC(=O)c1c[nH]c2ccc(-c3ccc(S(=O)(=O)N4CCC(Nc5ccc(C(F)(F)F)cn5)CC4)cc3)cc12] | ++ |
| 1.081 | 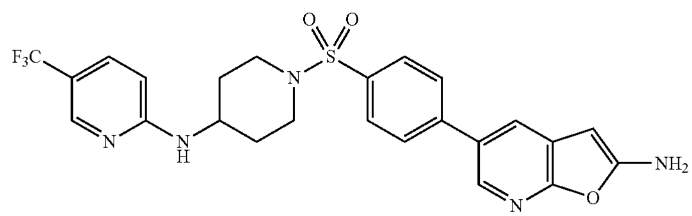 [SMILES: Nc1cc2cc(-c3ccc(S(=O)(=O)N4CCC(Nc5ccc(C(F)(F)F)cn5)CC4)cc3)cnc2o1] | +++ |
| 1.082 | 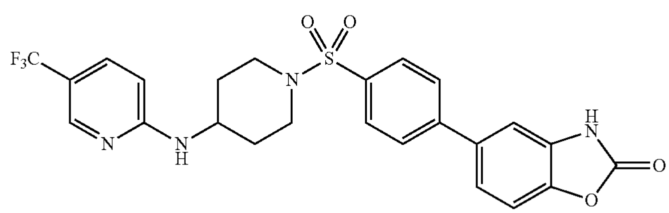 [SMILES: O=c1[nH]c2cc(-c3ccc(S(=O)(=O)N4CCC(Nc5ccc(C(F)(F)F)cn5)CC4)cc3)ccc2o1] | ++ |
| 1.083 | 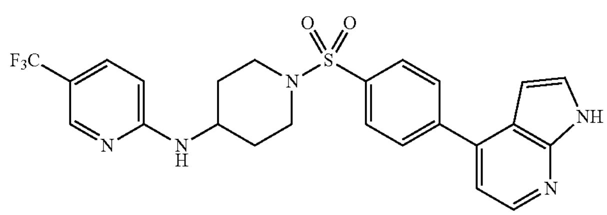 [SMILES: O=S(=O)(c1ccc(-c2ccnc3[nH]ccc23)cc1)N1CCC(Nc2ccc(C(F)(F)F)cn2)CC1] | ++ |
| 1.084 | 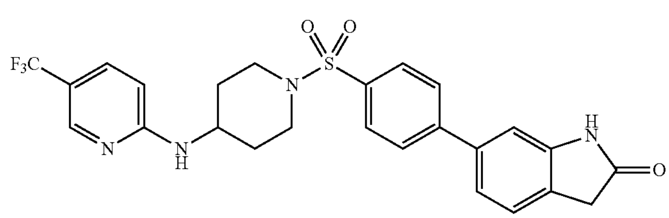 [SMILES: O=C1Cc2ccc(-c3ccc(S(=O)(=O)N4CCC(Nc5ccc(C(F)(F)F)cn5)CC4)cc3)cc2N1] | ++ |

TABLE 1-continued

| Compound | Structure | Potency |
|---|---|---|
| 1.085 | 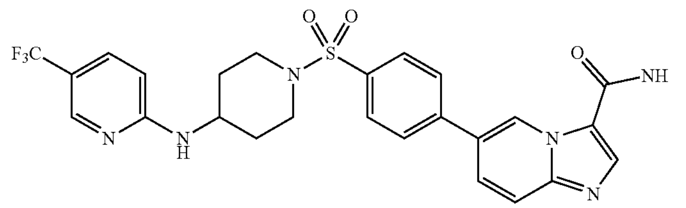 [SMILES: NC(=O)c1cnc2ccc(-c3ccc(S(=O)(=O)N4CCC(Nc5ccc(C(F)(F)F)cn5)CC4)cc3)cn12] | +++ |
| 1.086 | 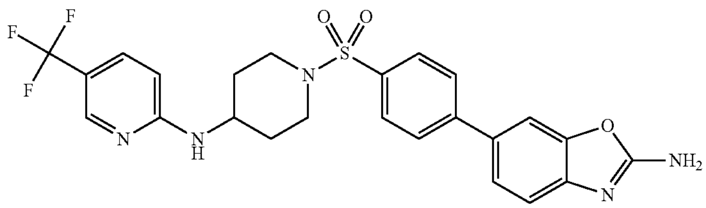 [SMILES: Nc1nc2ccc(-c3ccc(S(=O)(=O)N4CCC(Nc5ccc(C(F)(F)F)cn5)CC4)cc3)cc2o1] | +++ |
| 1.087 | 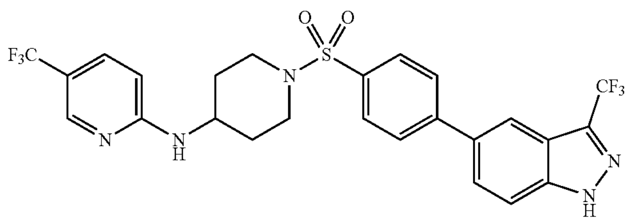 [SMILES: O=S(=O)(c1ccc(-c2ccc3[nH]nc(C(F)(F)F)c3c2)cc1)N1CCC(Nc2ccc(C(F)(F)F)cn2)CC1] | ++ |
| 1.088 | 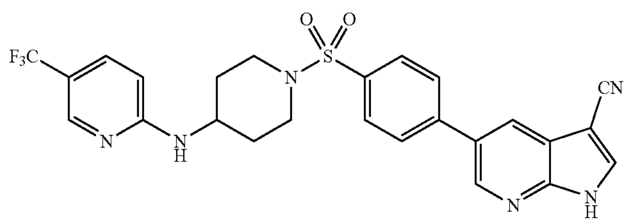 [SMILES: N#Cc1c[nH]c2ncc(-c3ccc(S(=O)(=O)N4CCC(Nc5ccc(C(F)(F)F)cn5)CC4)cc3)cc12] | +++ |
| 1.089 | 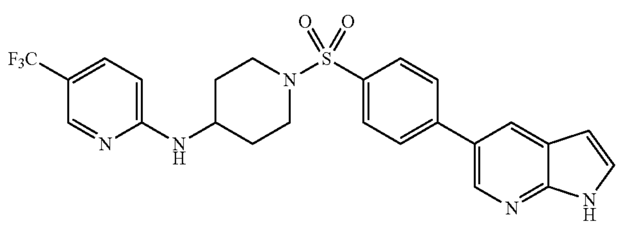 [SMILES: O=S(=O)(c1ccc(-c2cnc3[nH]ccc3c2)cc1)N1CCC(Nc2ccc(C(F)(F)F)cn2)CC1] | +++ |
| 1.090 | 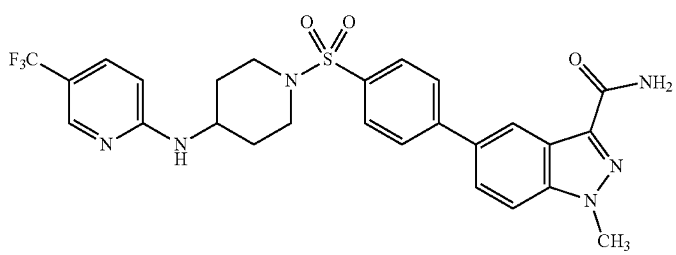 [SMILES: Cn1nc(C(N)=O)c2cc(-c3ccc(S(=O)(=O)N4CCC(Nc5ccc(C(F)(F)F)cn5)CC4)cc3)ccc21] | +++ |
| 1.091 | 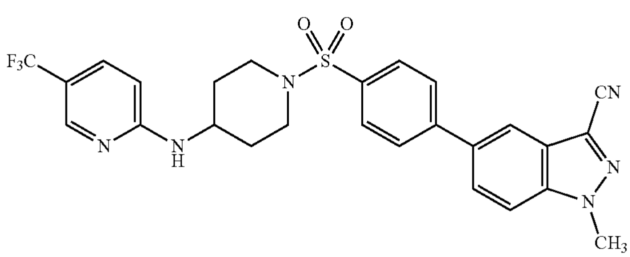 [SMILES: Cn1nc(C#N)c2cc(-c3ccc(S(=O)(=O)N4CCC(Nc5ccc(C(F)(F)F)cn5)CC4)cc3)ccc21] | +++ |

TABLE 1-continued
| Compound | Structure | Potency |
|---|---|---|
| 1.092 | 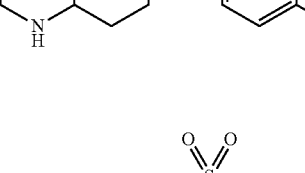 | ++ |
| 1.093 | 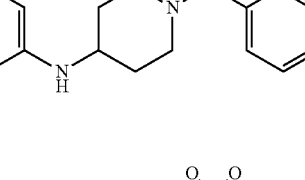 | +++ |
| 1.094 | 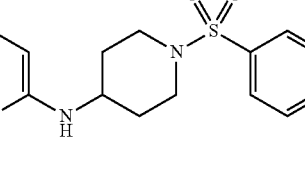 | ++ |
| 1.095 | 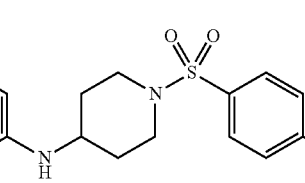 | +++ |
| 1.096 | 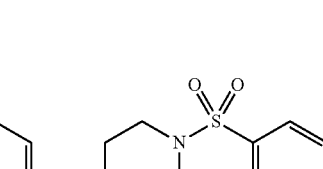 | ++ |
| 1.097 | 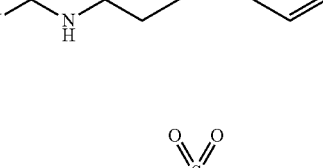 | +++ |
| 1.098 | 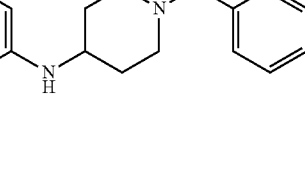 | ++ |

TABLE 1-continued

| Compound | Structure | Potency |
|---|---|---|
| 1.099 | 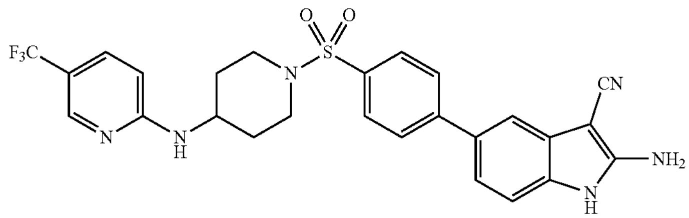 [SMILES: N#Cc1c(N)[nH]c2ccc(-c3ccc(S(=O)(=O)N4CCC(Nc5ccc(C(F)(F)F)cn5)CC4)cc3)cc12] | +++ |
| 1.100 | 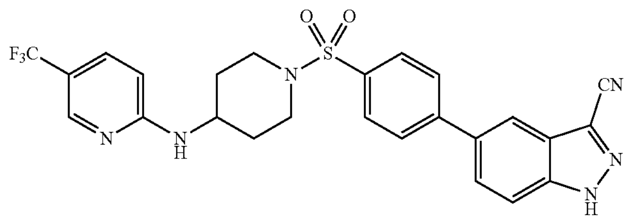 [SMILES: N#Cc1n[nH]c2ccc(-c3ccc(S(=O)(=O)N4CCC(Nc5ccc(C(F)(F)F)cn5)CC4)cc3)cc12] | +++ |
| 1.101 | 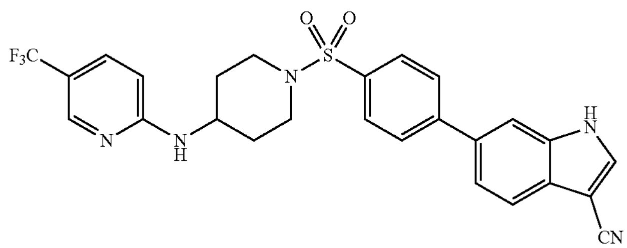 [SMILES: N#Cc1c[nH]c2cc(-c3ccc(S(=O)(=O)N4CCC(Nc5ccc(C(F)(F)F)cn5)CC4)cc3)ccc12] | ++ |
| 1.102 | 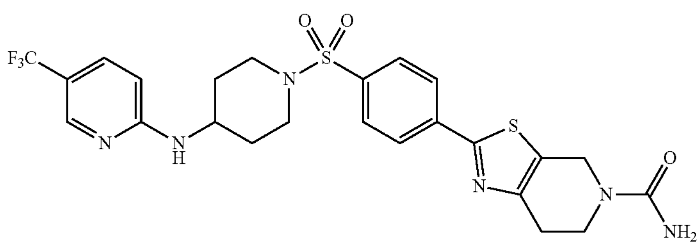 [SMILES: NC(=O)N1CCc2nc(-c3ccc(S(=O)(=O)N4CCC(Nc5ccc(C(F)(F)F)cn5)CC4)cc3)sc2C1] | + |
| 1.103 | 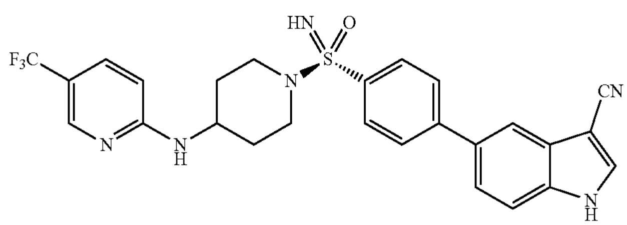 [SMILES: N#Cc1c[nH]c2ccc(-c3ccc([S@](=N)(=O)N4CCC(Nc5ccc(C(F)(F)F)cn5)CC4)cc3)cc12] | ++ |
| 1.104 | 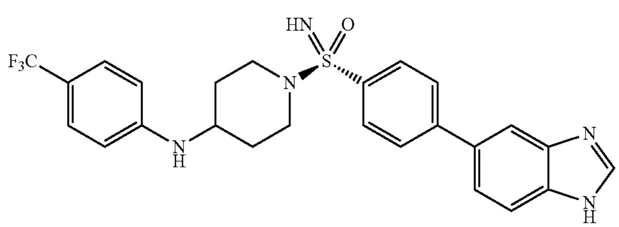 [SMILES: N=[S@](=O)(c1ccc(-c2ccc3[nH]cnc3c2)cc1)N1CCC(Nc2ccc(C(F)(F)F)cc2)CC1] | ++ |
| 1.105 | 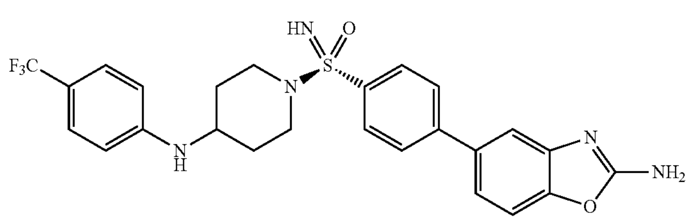 [SMILES: N=[S@](=O)(c1ccc(-c2ccc3oc(N)nc3c2)cc1)N1CCC(Nc2ccc(C(F)(F)F)cc2)CC1] | ++ |

TABLE 1-continued

| Compound | Structure | Potency |
|---|---|---|
| 1.106 | 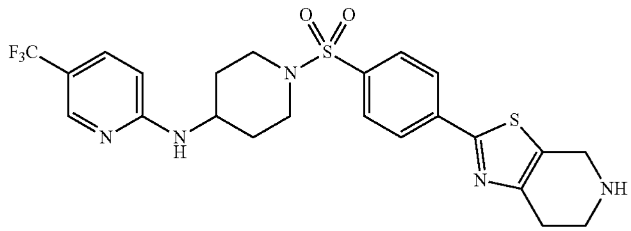 [SMILES: O=S(=O)(c1ccc(-c2nc3c(s2)CNCC3)cc1)N1CCC(Nc2ccc(C(F)(F)F)cn2)CC1] | + |
| 1.107 | 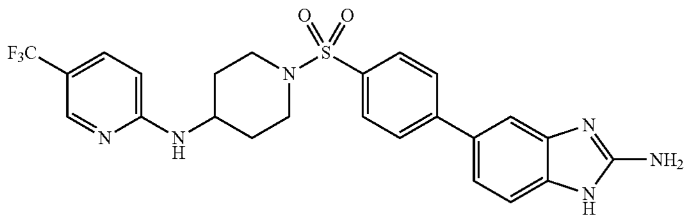 [SMILES: Nc1nc2cc(-c3ccc(S(=O)(=O)N4CCC(Nc5ccc(C(F)(F)F)cn5)CC4)cc3)ccc2[nH]1] | ++ |
| 1.108 | 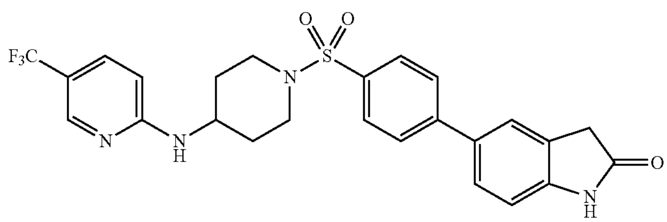 | +++ |
| 1.109 | 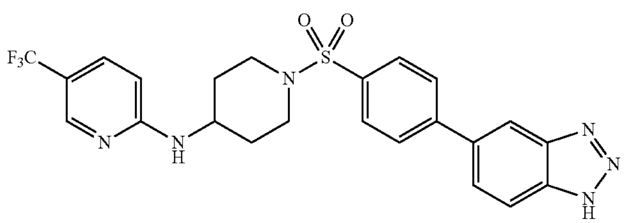 [SMILES: O=S(=O)(c1ccc(-c2ccc3[nH]nnc3c2)cc1)N1CCC(Nc2ccc(C(F)(F)F)cn2)CC1] | + |
| 1.110 | 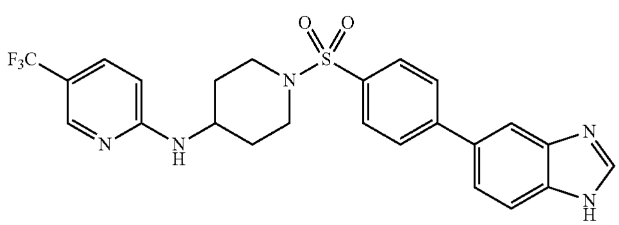 [SMILES: O=S(=O)(c1ccc(-c2ccc3[nH]cnc3c2)cc1)N1CCC(Nc2ccc(C(F)(F)F)cn2)CC1] | +++ |
| 1.111 | 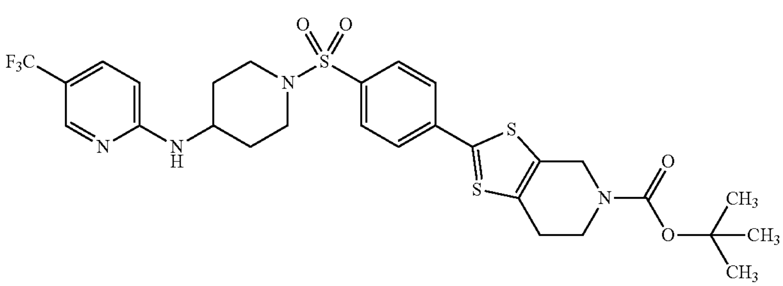 | + |

TABLE 1-continued

| Compound | Structure | Potency |
| --- | --- | --- |
| 1.112 | 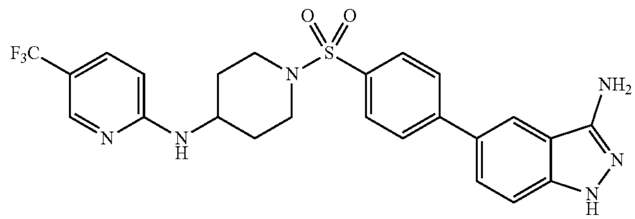 [SMILES: Nc1n[nH]c2ccc(-c3ccc(S(=O)(=O)N4CCC(Nc5ccc(C(F)(F)F)cn5)CC4)cc3)cc12] | +++ |
| 1.113 | 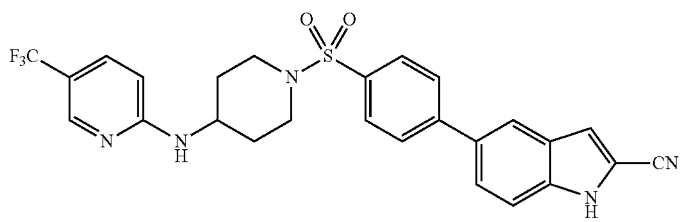 [SMILES: N#Cc1cc2cc(-c3ccc(S(=O)(=O)N4CCC(Nc5ccc(C(F)(F)F)cn5)CC4)cc3)ccc2[nH]1] | ++ |
| 1.114 | 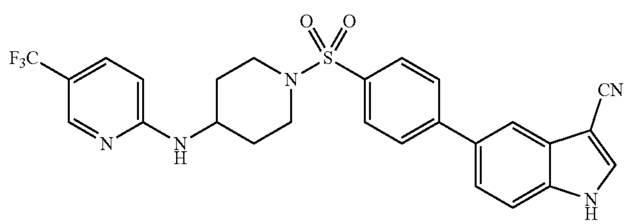 [SMILES: N#Cc1c[nH]c2ccc(-c3ccc(S(=O)(=O)N4CCC(Nc5ccc(C(F)(F)F)cn5)CC4)cc3)cc12] | +++ |
| 1.115 | 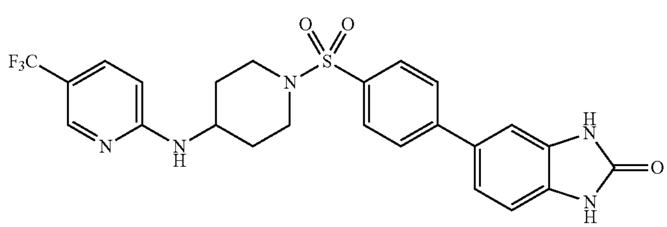 | ++ |
| 1.116 | 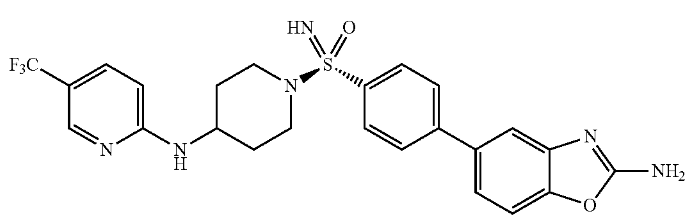 [SMILES: N=[S@](=O)(c1ccc(-c2ccc3oc(N)nc3c2)cc1)N1CCC(Nc2ccc(C(F)(F)F)cn2)CC1] | ++ |

TABLE 1-continued

| Compound | Structure | Potency |
|---|---|---|
| 1.117 | 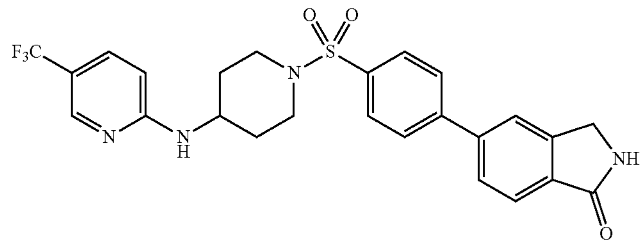 [SMILES: O=C1NCc2cc(-c3ccc(S(=O)(=O)N4CCC(Nc5ccc(C(F)(F)F)cn5)CC4)cc3)ccc21] | +++ |
| 1.118 | 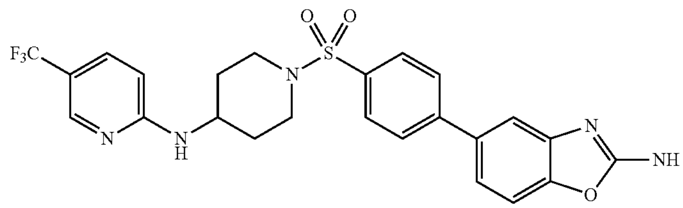 [SMILES: Nc1nc2cc(-c3ccc(S(=O)(=O)N4CCC(Nc5ccc(C(F)(F)F)cn5)CC4)cc3)ccc2o1] | +++ |
| 1.119 | 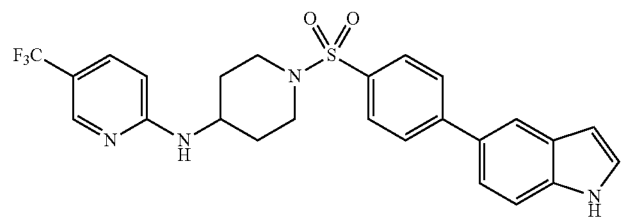 [SMILES: O=S(=O)(c1ccc(-c2ccc3[nH]ccc3c2)cc1)N1CCC(Nc2ccc(C(F)(F)F)cn2)CC1] | + |
| 1.120 | 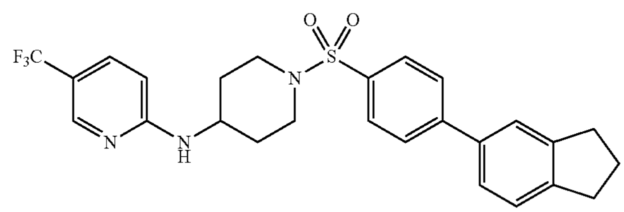 [SMILES: O=S(=O)(c1ccc(-c2ccc3c(c2)CCC3)cc1)N1CCC(Nc2ccc(C(F)(F)F)cn2)CC1] | + |
| 1.121 | 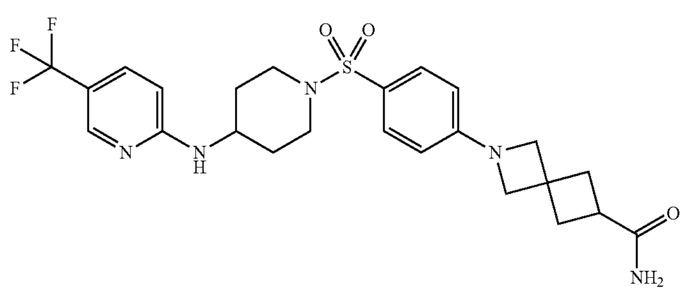 [SMILES: NC(=O)C1CC2(C1)CN(c1ccc(S(=O)(=O)N3CCC(Nc4ccc(C(F)(F)F)cn4)CC3)cc1)C2] | ++ |
| 1.122 | 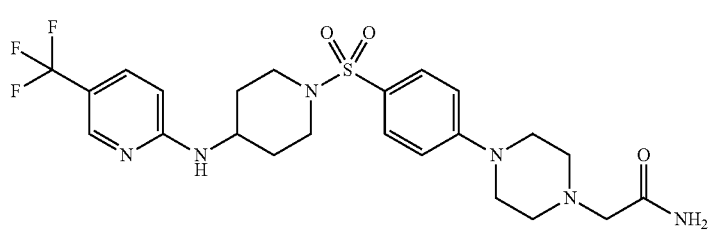 [SMILES: NC(=O)CN1CCN(c2ccc(S(=O)(=O)N3CCC(Nc4ccc(C(F)(F)F)cn4)CC3)cc2)CC1] | ++ |

TABLE 1-continued

| Compound | Structure | Potency |
|---|---|---|
| 1.123 | 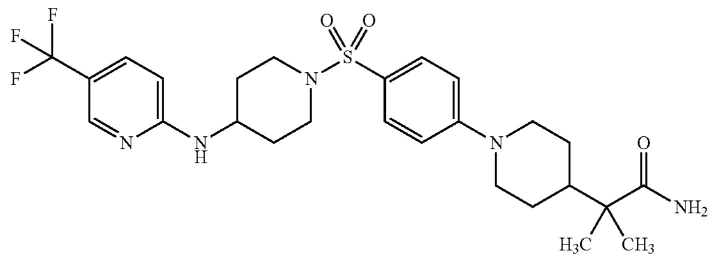 [SMILES: CC(C)(C(N)=O)C1CCN(c2ccc(S(=O)(=O)N3CCC(Nc4ccc(C(F)(F)F)cn4)CC3)cc2)CC1] | ++ |
| 1.124 | 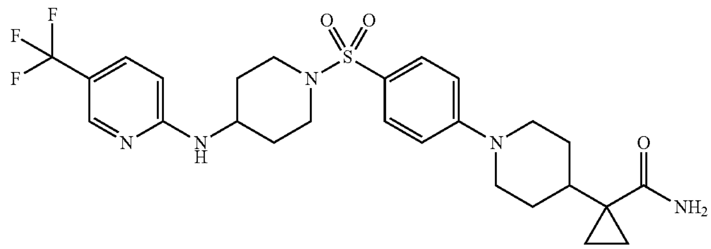 [SMILES: NC(=O)C1(C2CCN(c3ccc(S(=O)(=O)N4CCC(Nc5ccc(C(F)(F)F)cn5)CC4)cc3)CC2)CC1] | ++ |
| 1.125 | 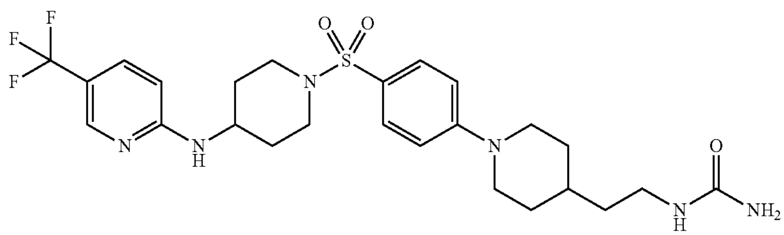 [SMILES: NC(=O)NCCC1CCN(c2ccc(S(=O)(=O)N3CCC(Nc4ccc(C(F)(F)F)cn4)CC3)cc2)CC1] | ++ |
| 1.126 | 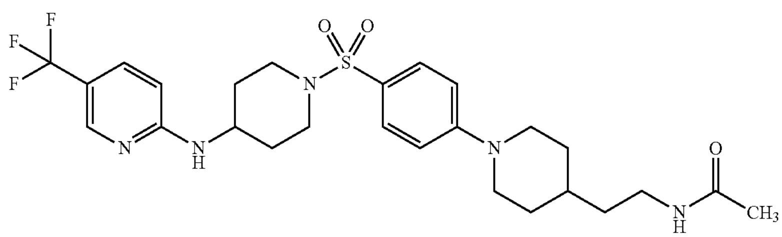 [SMILES: CC(=O)NCCC1CCN(c2ccc(S(=O)(=O)N3CCC(Nc4ccc(C(F)(F)F)cn4)CC3)cc2)CC1] | ++ |
| 1.127 | 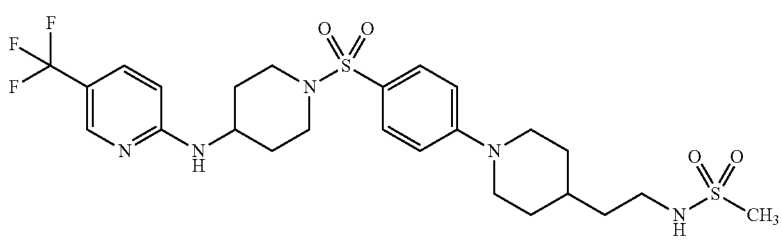 [SMILES: CS(=O)(=O)NCCC1CCN(c2ccc(S(=O)(=O)N3CCC(Nc4ccc(C(F)(F)F)cn4)CC3)cc2)CC1] | ++ |
| 1.128 | 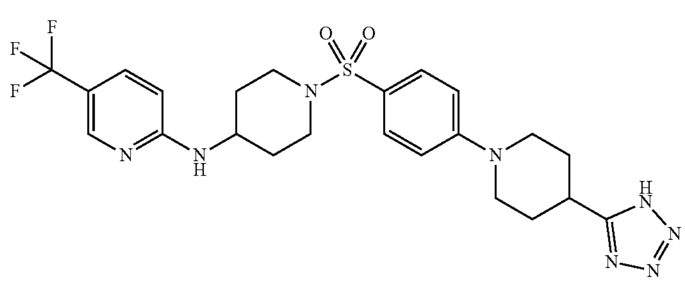 [SMILES: O=S(=O)(c1ccc(N2CCC(c3nnn[nH]3)CC2)cc1)N1CCC(Nc2ccc(C(F)(F)F)cn2)CC1] | + |

TABLE 1-continued

| Compound | Structure | Potency |
|---|---|---|
| 1.129 | 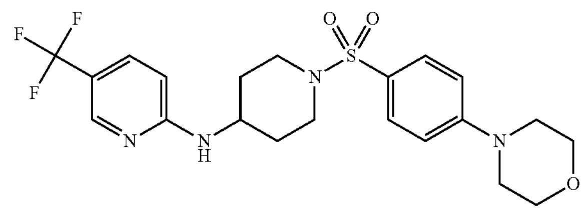 [SMILES: O=S(=O)(c1ccc(N2CCOCC2)cc1)N1CCC(Nc2ccc(C(F)(F)F)cn2)CC1] | ++ |
| 1.130 | 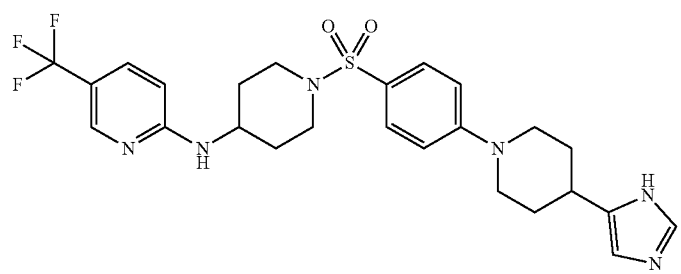 [SMILES: O=S(=O)(c1ccc(N2CCC(c3cnc[nH]3)CC2)cc1)N1CCC(Nc2ccc(C(F)(F)F)cn2)CC1] | + |
| 1.131 | 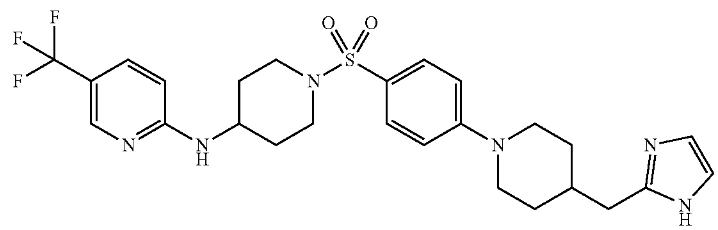 [SMILES: O=S(=O)(c1ccc(N2CCC(Cc3ncc[nH]3)CC2)cc1)N1CCC(Nc2ccc(C(F)(F)F)cn2)CC1] | + |
| 1.132 | 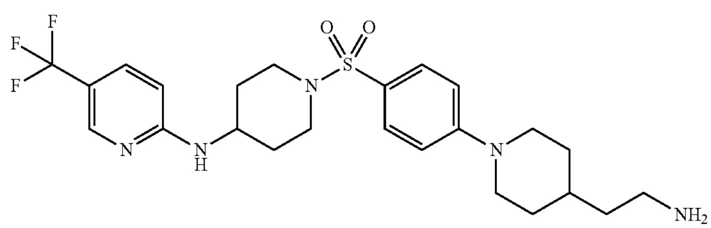 [SMILES: NCCC1CCN(c2ccc(S(=O)(=O)N3CCC(Nc4ccc(C(F)(F)F)cn4)CC3)cc2)CC1] | + |
| 1.133 | 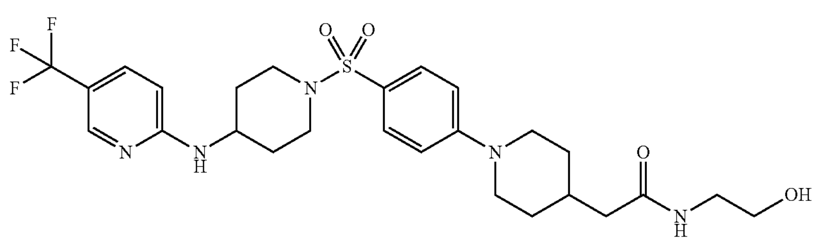 [SMILES: O=C(CC1CCN(c2ccc(S(=O)(=O)N3CCC(Nc4ccc(C(F)(F)F)cn4)CC3)cc2)CC1)NCCO] | + |
| 1.134 | 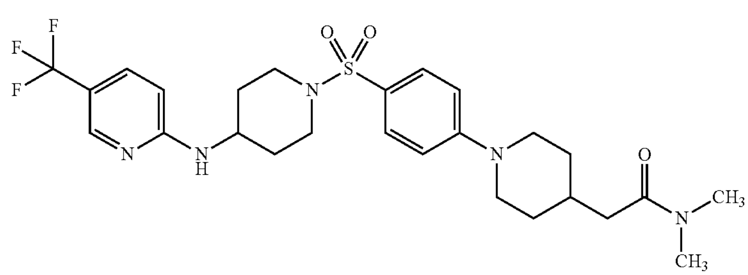 [SMILES: CN(C)C(=O)CC1CCN(c2ccc(S(=O)(=O)N3CCC(Nc4ccc(C(F)(F)F)cn4)CC3)cc2)CC1] | + |

TABLE 1-continued

| Compound | Structure | Potency |
|---|---|---|
| 1.135 | 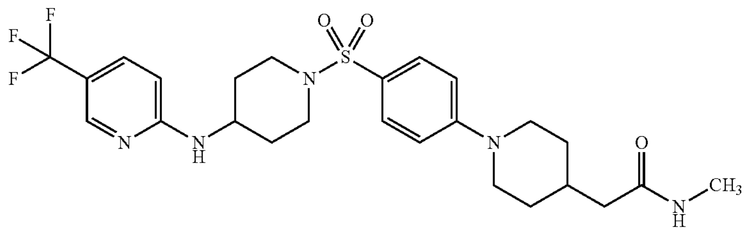 [SMILES: CNC(=O)CC1CCN(c2ccc(S(=O)(=O)N3CCC(Nc4ccc(C(F)(F)F)cn4)CC3)cc2)CC1] | ++ |
| 1.136 | 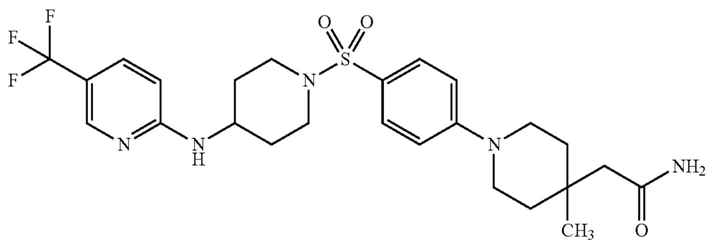 [SMILES: CC1(CC(N)=O)CCN(c2ccc(S(=O)(=O)N3CCC(Nc4ccc(C(F)(F)F)cn4)CC3)cc2)CC1] | ++ |
| 1.137 | 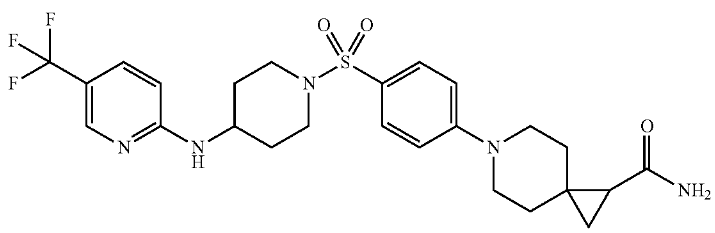 [SMILES: NC(=O)C1CC12CCN(c1ccc(S(=O)(=O)N3CCC(Nc4ccc(C(F)(F)F)cn4)CC3)cc1)CC2] | + |
| 1.138 | 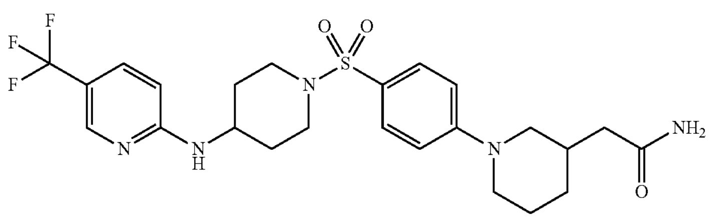 [SMILES: NC(=O)CC1CCCN(c2ccc(S(=O)(=O)N3CCC(Nc4ccc(C(F)(F)F)cn4)CC3)cc2)C1] | + |
| 1.139 | 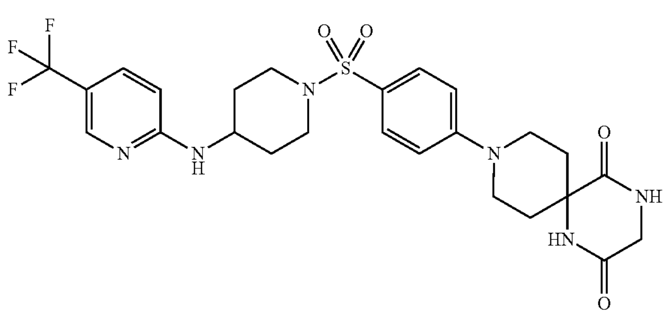 [SMILES: O=C1CNC(=O)C2(CCN(c3ccc(S(=O)(=O)N4CCC(Nc5ccc(C(F)(F)F)cn5)CC4)cc3)CC2)N1] | + |
| 1.140 | 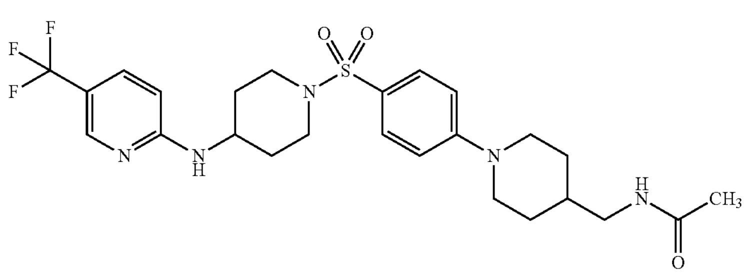 | ++ |

TABLE 1-continued

| Compound | Structure | Potency |
|---|---|---|
| 1.141 | 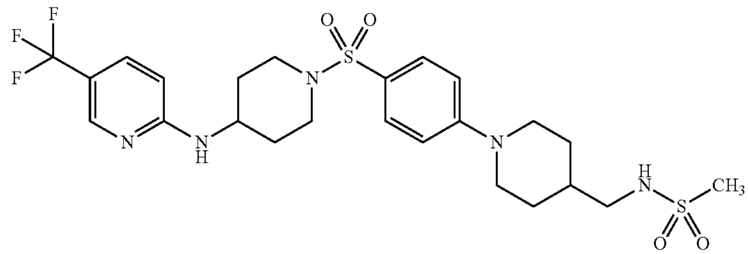 [SMILES: CS(=O)(=O)NCC1CCN(c2ccc(S(=O)(=O)N3CCC(Nc4ccc(C(F)(F)F)cn4)CC3)cc2)CC1] | ++ |
| 1.142 | 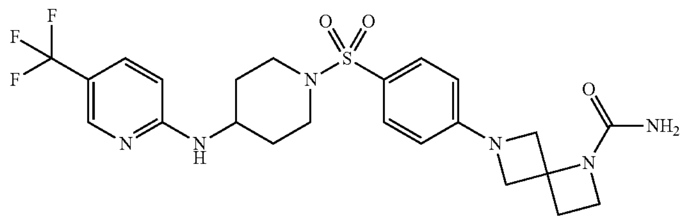 [SMILES: NC(=O)N1CCC12CN(c1ccc(S(=O)(=O)N3CCC(Nc4ccc(C(F)(F)F)cn4)CC3)cc1)C2] | ++ |
| 1.143 | 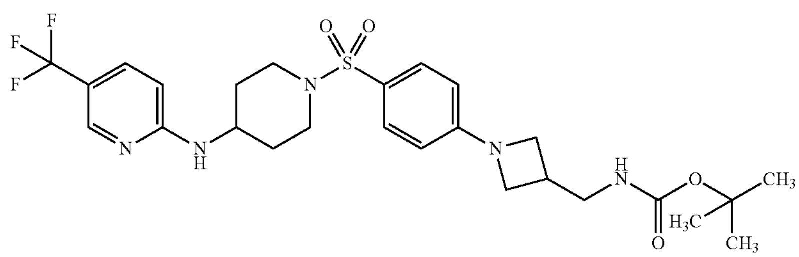 [SMILES: CC(C)(C)OC(=O)NCC1CN(c2ccc(S(=O)(=O)N3CCC(Nc4ccc(C(F)(F)F)cn4)CC3)cc2)C1] | ++ |
| 1.144 | 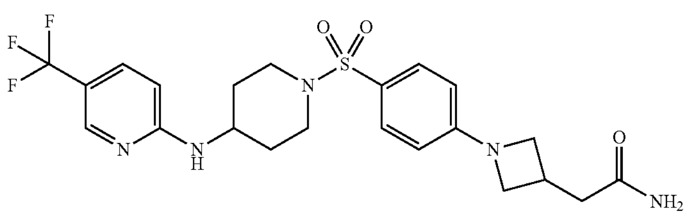 [SMILES: NC(=O)CC1CN(c2ccc(S(=O)(=O)N3CCC(Nc4ccc(C(F)(F)F)cn4)CC3)cc2)C1] | + |
| 1.145 | 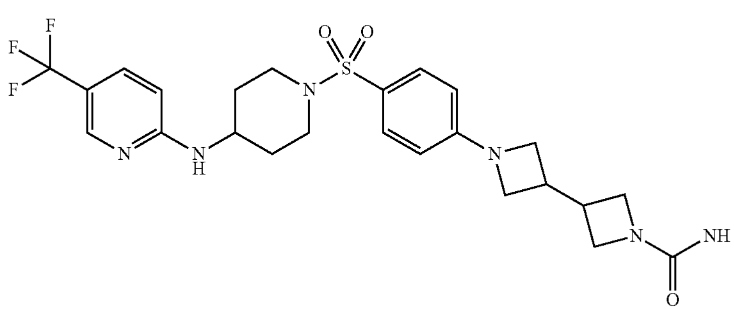 [SMILES: NC(=O)N1CC(C2CN(c3ccc(S(=O)(=O)N4CCC(Nc5ccc(C(F)(F)F)cn5)CC4)cc3)C2)C1] | ++ |
| 1.146 | 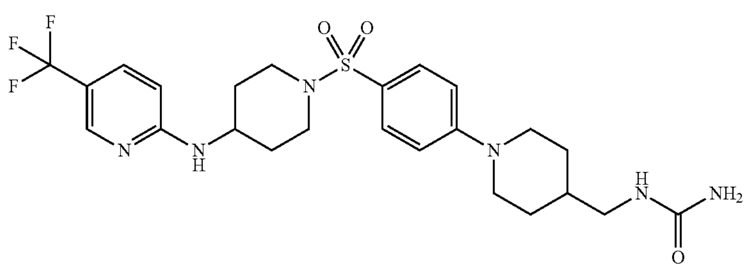 [SMILES: NC(=O)NCC1CCN(c2ccc(S(=O)(=O)N3CCC(Nc4ccc(C(F)(F)F)cn4)CC3)cc2)CC1] | +++ |

TABLE 1-continued

| Compound | Structure | Potency |
|---|---|---|
| 1.147 | 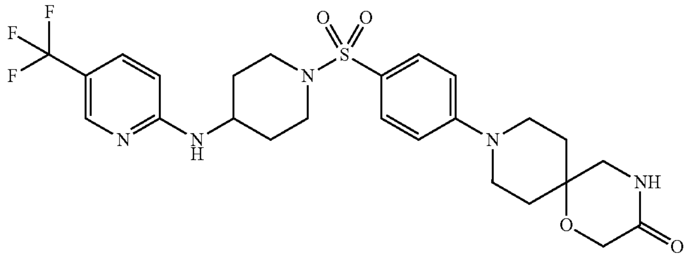 [SMILES: O=C1COC2(CCN(c3ccc(S(=O)(=O)N4CCC(Nc5ccc(C(F)(F)F)cn5)CC4)cc3)CC2)CN1] | ++ |
| 1.148 | 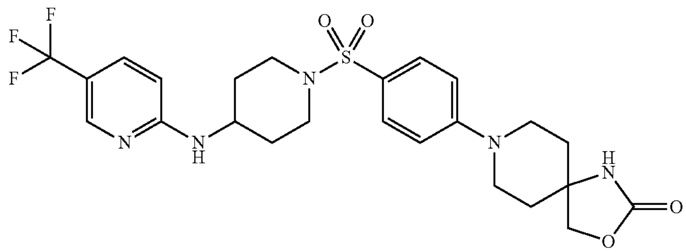 [SMILES: O=C1NC2(CCN(c3ccc(S(=O)(=O)N4CCC(Nc5ccc(C(F)(F)F)cn5)CC4)cc3)CC2)CO1] | +++ |
| 1.149 | 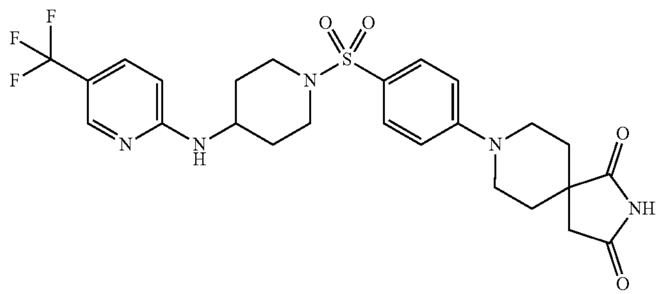 [SMILES: O=C1CC2(CCN(c3ccc(S(=O)(=O)N4CCC(Nc5ccc(C(F)(F)F)cn5)CC4)cc3)CC2)C(=O)N1] | ++ |
| 1.150 | 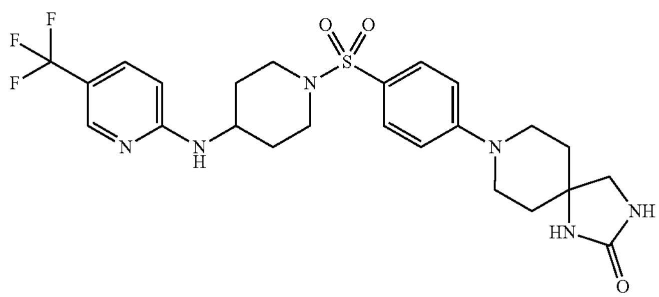 [SMILES: O=C1NCC2(CCN(c3ccc(S(=O)(=O)N4CCC(Nc5ccc(C(F)(F)F)cn5)CC4)cc3)CC2)N1] | ++ |
| 1.151 | 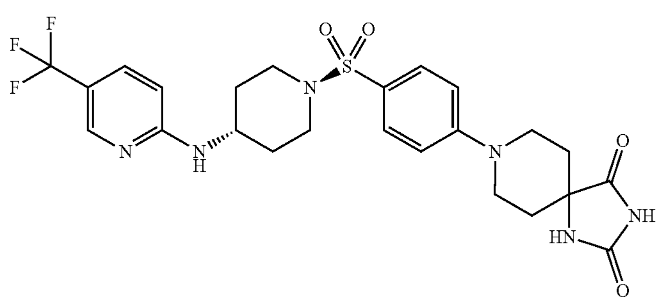 | +++ |

TABLE 1-continued

| Compound | Structure | Potency |
|---|---|---|
| 1.152 | 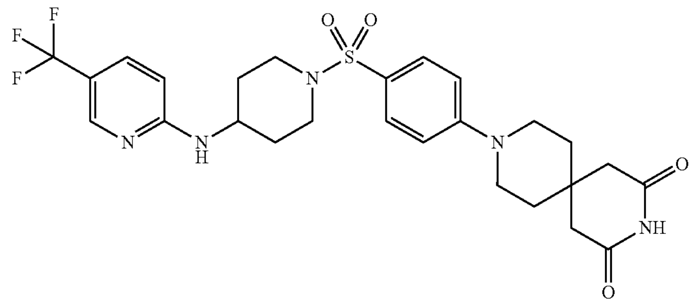 [SMILES: O=C1CC2(CCN(c3ccc(S(=O)(=O)N4CCC(Nc5ccc(C(F)(F)F)cn5)CC4)cc3)CC2)CC(=O)N1] | +++ |
| 1.153 | 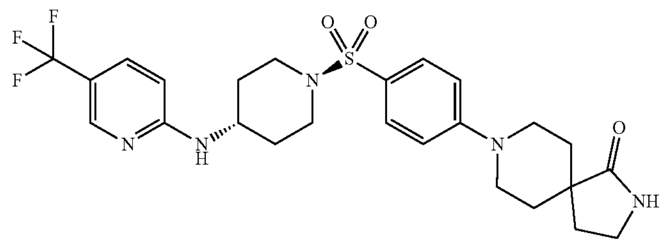 | ++ |
| 1.154 | 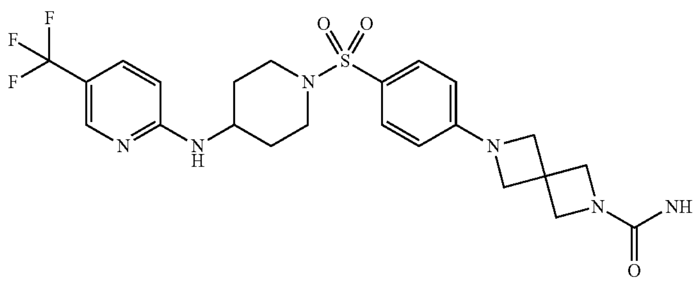 [SMILES: NC(=O)N1CC2(C1)CN(c1ccc(S(=O)(=O)N3CCC(Nc4ccc(C(F)(F)F)cn4)CC3)cc1)C2] | +++ |
| 1.155 | 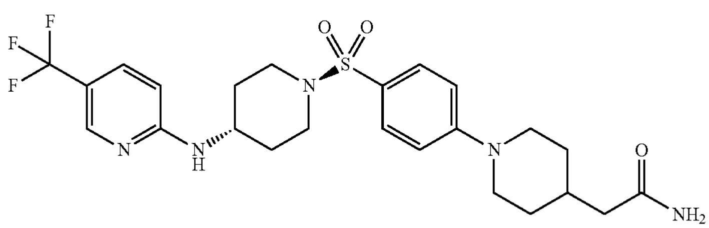 | +++ |
| 1.156 | 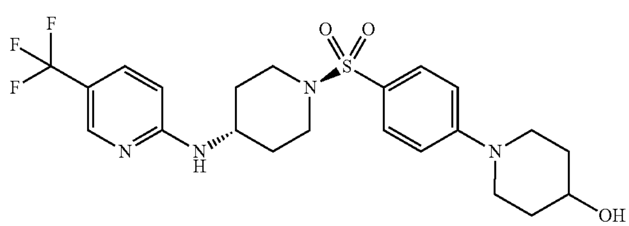 | ++ |
| 1.157 | 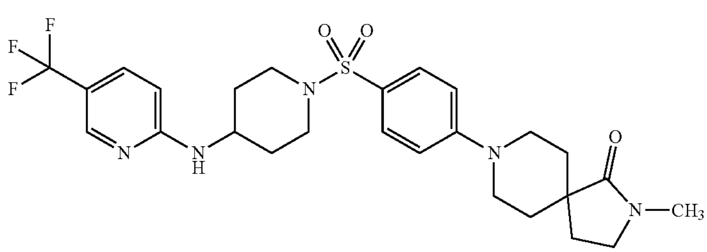 [SMILES: CN1CCC2(CCN(c3ccc(S(=O)(=O)N4CCC(Nc5ccc(C(F)(F)F)cn5)CC4)cc3)CC2)C1=O] | ++ |

TABLE 1-continued

| Compound | Structure | Potency |
|---|---|---|
| 1.158 | 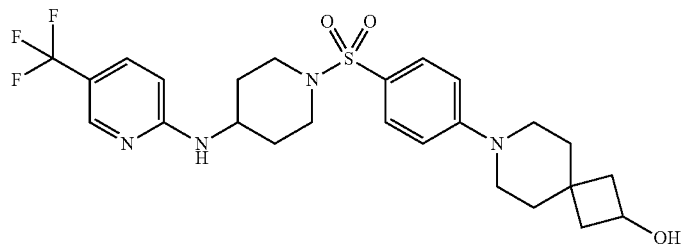 [SMILES: O=S(=O)(c1ccc(N2CCC3(CC2)CC(O)C3)cc1)N1CCC(Nc2ccc(C(F)(F)F)cn2)CC1] | ++ |
| 1.159 | 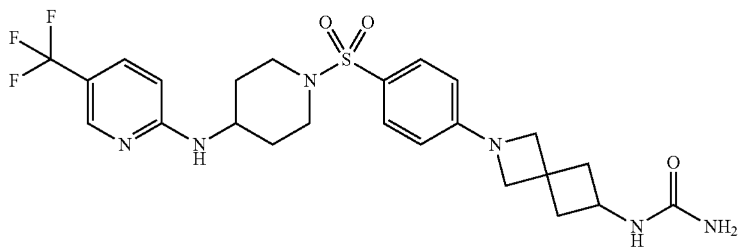 [SMILES: NC(=O)NC1CC2(C1)CN(c1ccc(S(=O)(=O)N3CCC(Nc4ccc(C(F)(F)F)cn4)CC3)cc1)C2] | + |
| 1.160 | 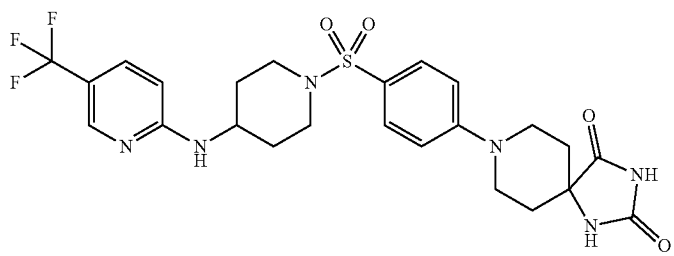 [SMILES: O=C1NC(=O)C2(CCN(c3ccc(S(=O)(=O)N4CCC(Nc5ccc(C(F)(F)F)cn5)CC4)cc3)CC2)N1] | +++ |
| 1.161 | 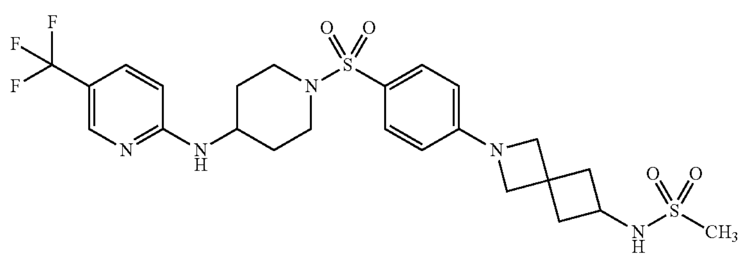 [SMILES: CS(=O)(=O)NC1CC2(C1)CN(c1ccc(S(=O)(=O)N3CCC(Nc4ccc(C(F)(F)F)cn4)CC3)cc1)C2] | ++ |
| 1.162 | 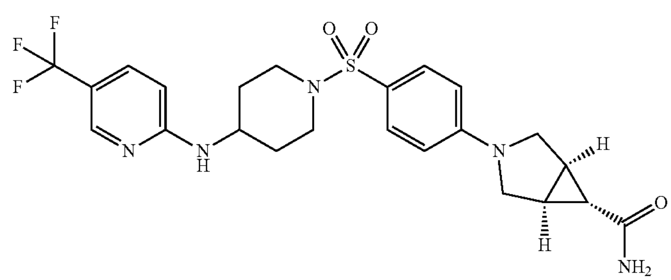 [SMILES: NC(=O)[C@H]1[C@@H]2CN(c3ccc(S(=O)(=O)N4CCC(Nc5ccc(C(F)(F)F)cn5)CC4)cc3)C[C@@H]21] | + |
| 1.163 | 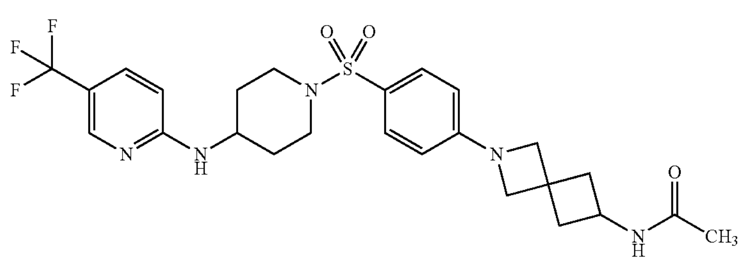 [SMILES: CC(=O)NC1CC2(C1)CN(c1ccc(S(=O)(=O)N3CCC(Nc4ccc(C(F)(F)F)cn4)CC3)cc1)C2] | ++ |

TABLE 1-continued

| Compound | Structure | Potency |
|---|---|---|
| 1.164 | 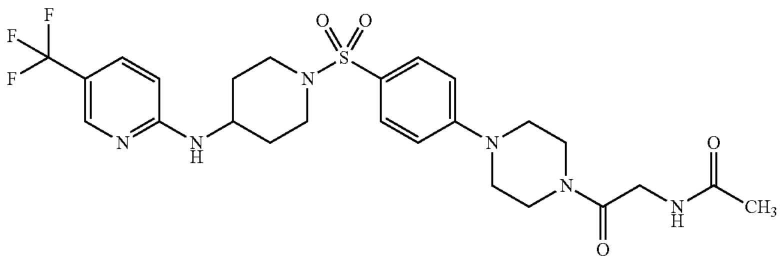 [SMILES: CC(=O)NCC(=O)N1CCN(c2ccc(S(=O)(=O)N3CCC(Nc4ccc(C(F)(F)F)cn4)CC3)cc2)CC1] | + |
| 1.165 | 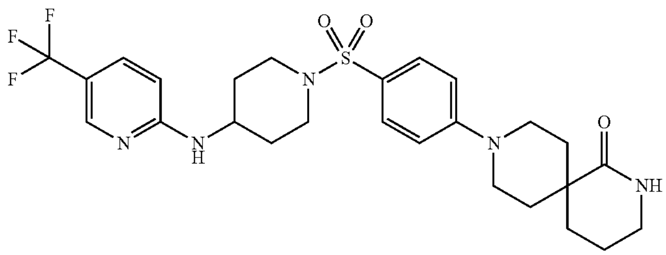 [SMILES: O=C1NCCCC12CCN(c1ccc(S(=O)(=O)N3CCC(Nc4ccc(C(F)(F)F)cn4)CC3)cc1)CC2] | +++ |
| 1.166 | 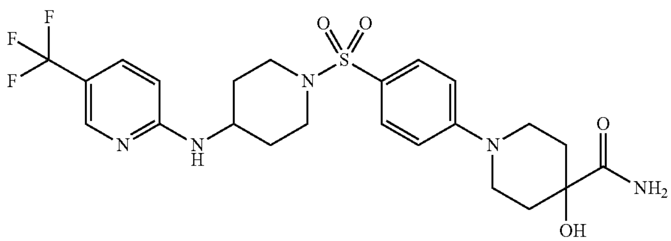 [SMILES: NC(=O)C1(O)CCN(c2ccc(S(=O)(=O)N3CCC(Nc4ccc(C(F)(F)F)cn4)CC3)cc2)CC1] | ++ |
| 1.167 | 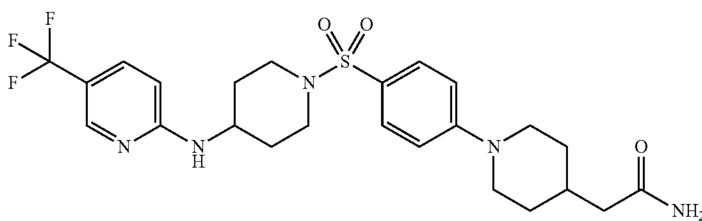 [SMILES: NC(=O)CC1CCN(c2ccc(S(=O)(=O)N3CCC(Nc4ccc(C(F)(F)F)cn4)CC3)cc2)CC1] | ++ |
| 1.168 | 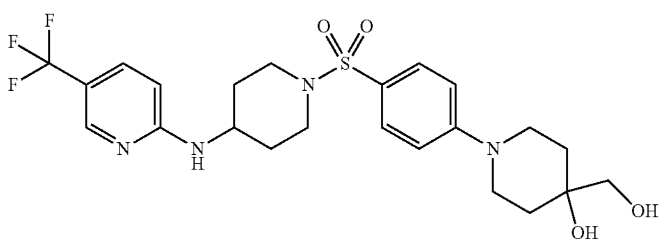 [SMILES: O=S(=O)(c1ccc(N2CCC(O)(CO)CC2)cc1)N1CCC(Nc2ccc(C(F)(F)F)cn2)CC1] | ++ |
| 1.169 | AND Enantiomer | + |

TABLE 1-continued

| Compound | Structure | Potency |
|---|---|---|
| 1.170 | 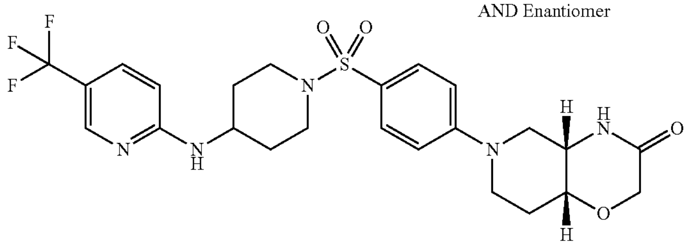 [SMILES: O=C1CO[C@@H]2CCN(c3ccc(S(=O)(=O)N4CCC(Nc5ccc(C(F)(F)F)cn5)CC4)cc3)C[C@@H]2N1] | + |
| | AND Enantiomer | |
| 1.171 | 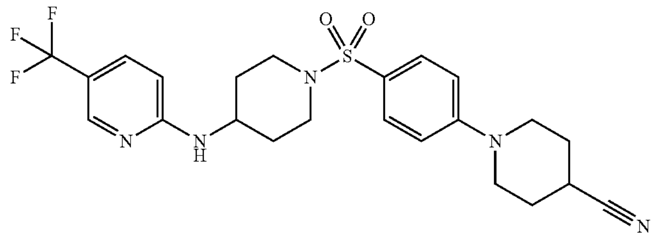 [SMILES: N#CC1CCN(c2ccc(S(=O)(=O)N3CCC(Nc4ccc(C(F)(F)F)cn4)CC3)cc2)CC1] | + |
| 1.172 | 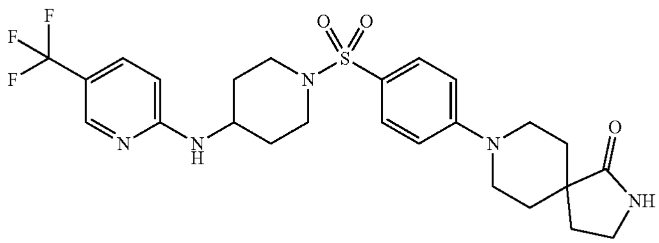 [SMILES: O=C1NCCC12CCN(c1ccc(S(=O)(=O)N3CCC(Nc4ccc(C(F)(F)F)cn4)CC3)cc1)CC2] | +++ |
| 1.173 | 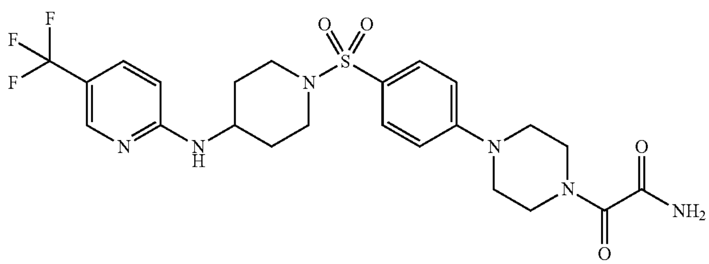 [SMILES: NC(=O)C(=O)N1CCN(c2ccc(S(=O)(=O)N3CCC(Nc4ccc(C(F)(F)F)cn4)CC3)cc2)CC1] | ++ |
| 1.174 | 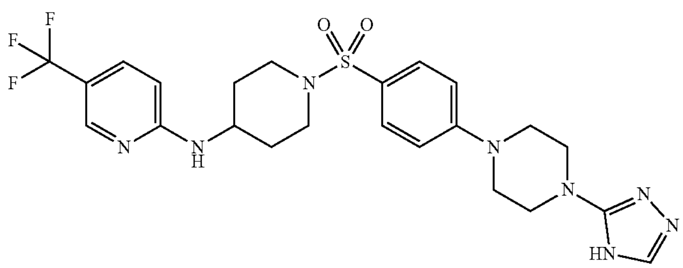 [SMILES: O=S(=O)(c1ccc(N2CCN(c3nnc[nH]3)CC2)cc1)N1CCC(Nc2ccc(C(F)(F)F)cn2)CC1] | + |
| 1.175 | 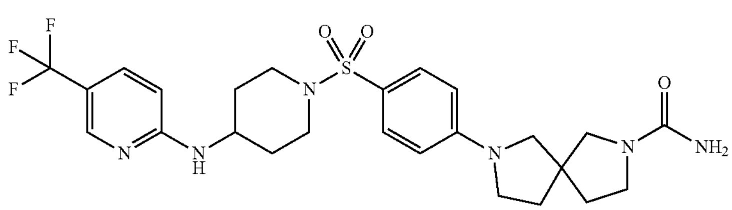 [SMILES: NC(=O)N1CCC2(CCN(c3ccc(S(=O)(=O)N4CCC(Nc5ccc(C(F)(F)F)cn5)CC4)cc3)C2)C1] | ++ |

TABLE 1-continued

| Compound | Structure | Potency |
|---|---|---|
| 1.176 | 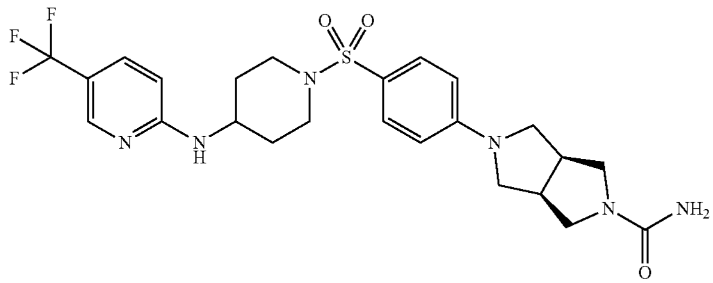 [SMILES: NC(=O)N1C[C@@H]2CN(c3ccc(S(=O)(=O)N4CCC(Nc5ccc(C(F)(F)F)cn5)CC4)cc3)C[C@@H]2C1] | ++ |
| 1.177 | 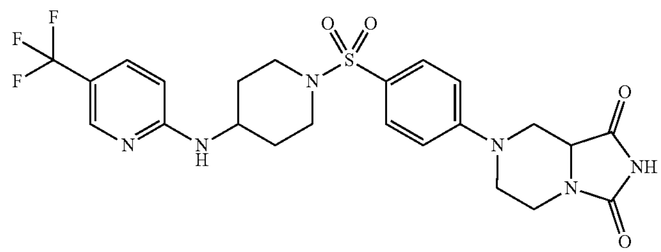 [SMILES: O=C1NC(=O)N2CCN(c3ccc(S(=O)(=O)N4CCC(Nc5ccc(C(F)(F)F)cn5)CC4)cc3)CC12] | ++ |
| 1.178 | AND Enantiomer | + |
| 1.179 | 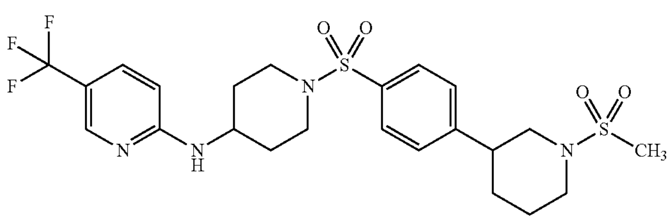 [SMILES: CS(=O)(=O)N1CCCC(c2ccc(S(=O)(=O)N3CCC(Nc4ccc(C(F)(F)F)cn4)CC3)cc2)C1] | ++ |
| 1.180 | 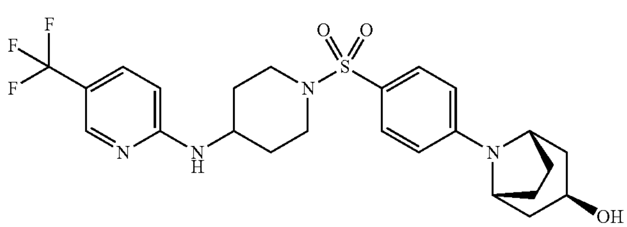 [SMILES: O=S(=O)(c1ccc(N2[C@@H]3CC[C@H]2C[C@@H](O)C3)cc1)N1CCC(Nc2ccc(C(F)(F)F)cn2)CC1] | ++ |
| 1.181 | 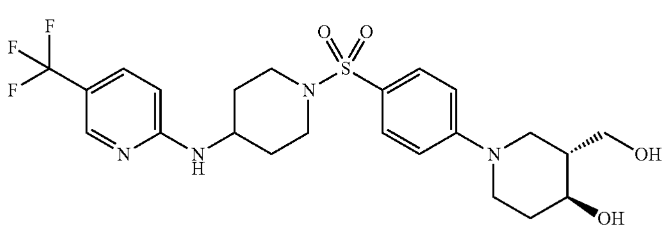 [SMILES: O=S(=O)(c1ccc(N2CC[C@H](O)[C@@H](CO)C2)cc1)N1CCC(Nc2ccc(C(F)(F)F)cn2)CC1] | ++ |

TABLE 1-continued

| Compound | Structure | Potency |
|---|---|---|
| 1.182 | 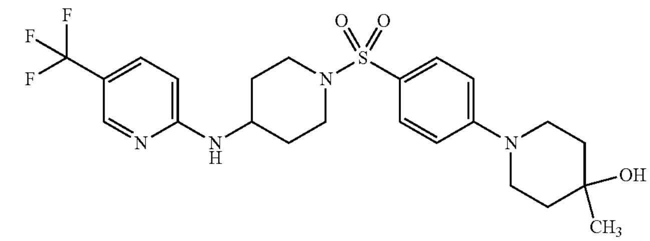 [SMILES: CC1(O)CCN(c2ccc(S(=O)(=O)N3CCC(Nc4ccc(C(F)(F)F)cn4)CC3)cc2)CC1] | ++ |
| 1.183 | 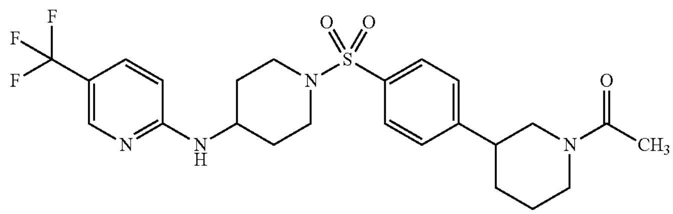 [SMILES: CC(=O)N1CCCC(c2ccc(S(=O)(=O)N3CCC(Nc4ccc(C(F)(F)F)cn4)CC3)cc2)C1] | ++ |
| 1.184 | 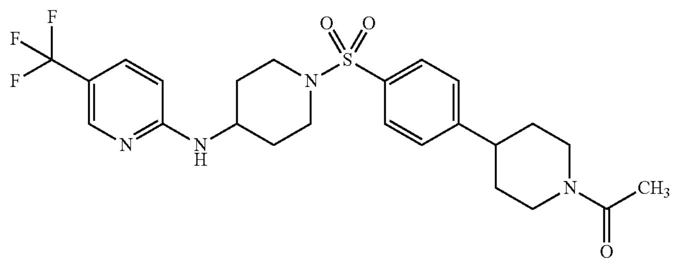 | ++ |
| 1.185 | 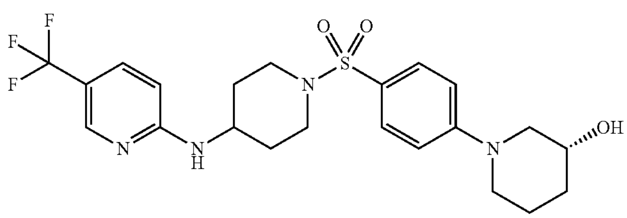 [SMILES: O=S(=O)(c1ccc(N2CCC[C@@H](O)C2)cc1)N1CCC(Nc2ccc(C(F)(F)F)cn2)CC1] | ++ |
| 1.186 | 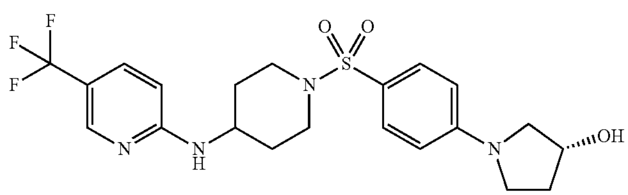 [SMILES: O=S(=O)(c1ccc(N2CC[C@@H](O)C2)cc1)N1CCC(Nc2ccc(C(F)(F)F)cn2)CC1] | + |
| 1.187 | 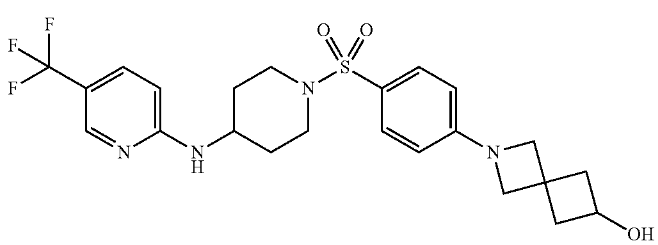 [SMILES: O=S(=O)(c1ccc(N2CC3(CC(O)C3)C2)cc1)N1CCC(Nc2ccc(C(F)(F)F)cn2)CC1] | ++ |
| 1.188 | 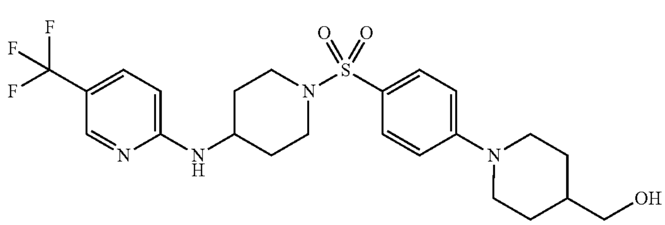 [SMILES: O=S(=O)(c1ccc(N2CCC(CO)CC2)cc1)N1CCC(Nc2ccc(C(F)(F)F)cn2)CC1] | ++ |

TABLE 1-continued

| Compound | Structure | Potency |
|---|---|---|
| 1.189 | 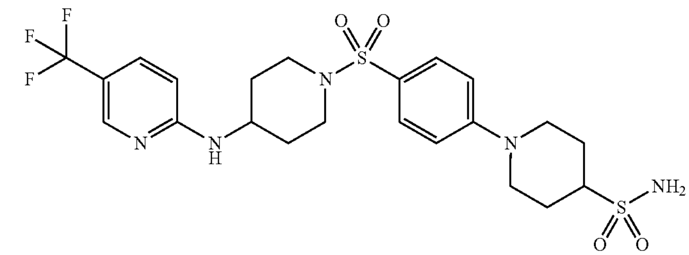 [SMILES: NS(=O)(=O)C1CCN(c2ccc(S(=O)(=O)N3CCC(Nc4ccc(C(F)(F)F)cn4)CC3)cc2)CC1] | + |
| 1.190 | 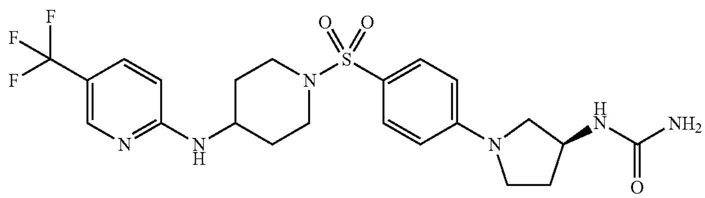 [SMILES: NC(=O)N[C@H]1CCN(c2ccc(S(=O)(=O)N3CCC(Nc4ccc(C(F)(F)F)cn4)CC3)cc2)C1] | + |
| 1.191 | 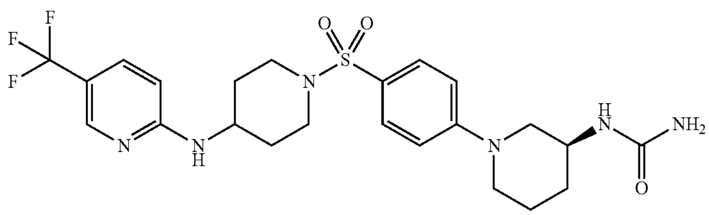 [SMILES: NC(=O)N[C@H]1CCCN(c2ccc(S(=O)(=O)N3CCC(Nc4ccc(C(F)(F)F)cn4)CC3)cc2)C1] | + |
| 1.192 | 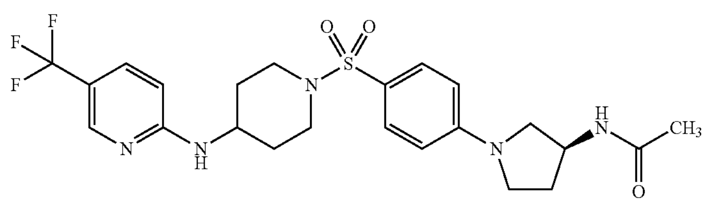 [SMILES: CC(=O)N[C@H]1CCN(c2ccc(S(=O)(=O)N3CCC(Nc4ccc(C(F)(F)F)cn4)CC3)cc2)C1] | + |
| 1.193 | 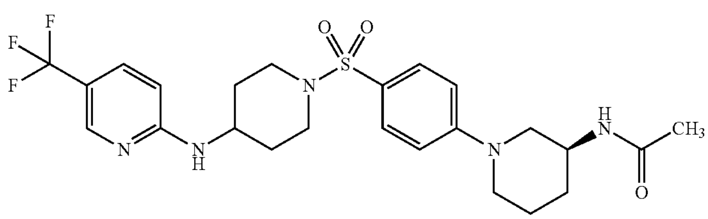 [SMILES: CC(=O)N[C@H]1CCCN(c2ccc(S(=O)(=O)N3CCC(Nc4ccc(C(F)(F)F)cn4)CC3)cc2)C1] | + |
| 1.194 | 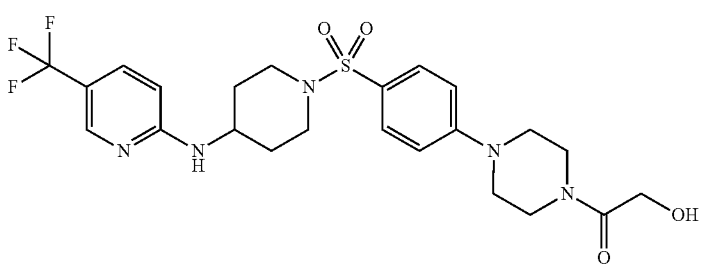 [SMILES: O=C(CO)N1CCN(c2ccc(S(=O)(=O)N3CCC(Nc4ccc(C(F)(F)F)cn4)CC3)cc2)CC1] | ++ |
| 1.195 | 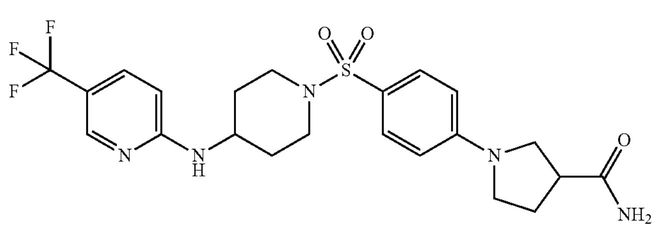 [SMILES: NC(=O)C1CCN(c2ccc(S(=O)(=O)N3CCC(Nc4ccc(C(F)(F)F)cn4)CC3)cc2)C1] | + |

TABLE 1-continued

| Compound | Structure | Potency |
|---|---|---|
| 1.196 | 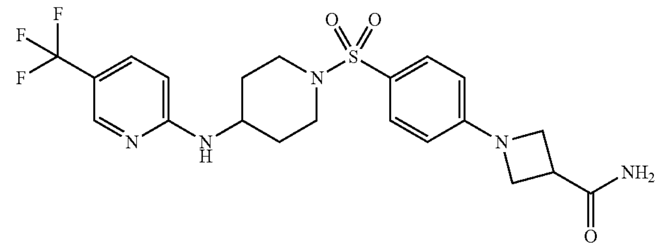 [SMILES: NC(=O)C1CN(c2ccc(S(=O)(=O)N3CCC(Nc4ccc(C(F)(F)F)cn4)CC3)cc2)C1] | + |
| 1.197 | 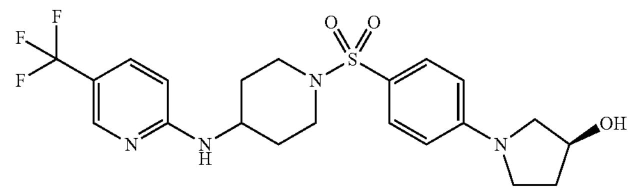 [SMILES: O=S(=O)(c1ccc(N2CC[C@H](O)C2)cc1)N1CCC(Nc2ccc(C(F)(F)F)cn2)CC1] | + |
| 1.198 | 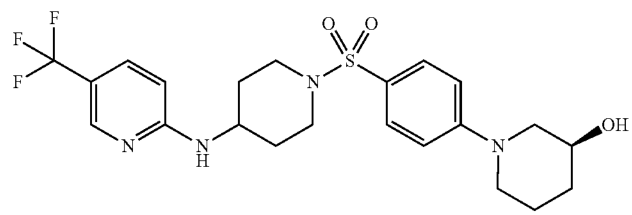 [SMILES: O=S(=O)(c1ccc(N2CCC[C@H](O)C2)cc1)N1CCC(Nc2ccc(C(F)(F)F)cn2)CC1] | ++ |
| 1.199 | 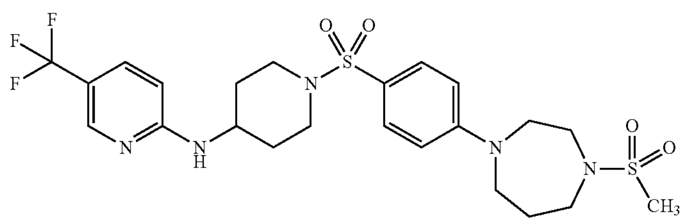 [SMILES: CS(=O)(=O)N1CCCN(c2ccc(S(=O)(=O)N3CCC(Nc4ccc(C(F)(F)F)cn4)CC3)cc2)CC1] | + |
| 1.200 | 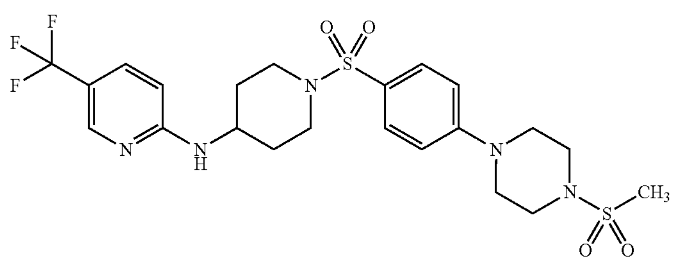 [SMILES: CS(=O)(=O)N1CCN(c2ccc(S(=O)(=O)N3CCC(Nc4ccc(C(F)(F)F)cn4)CC3)cc2)CC1] | ++ |
| 1.201 | 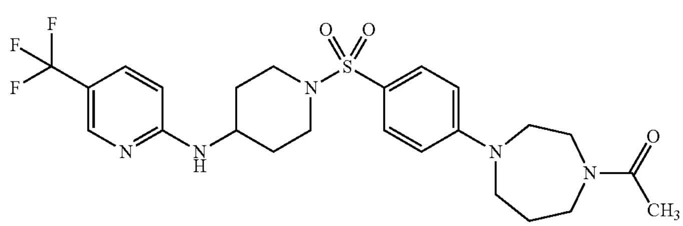 [SMILES: CC(=O)N1CCCN(c2ccc(S(=O)(=O)N3CCC(Nc4ccc(C(F)(F)F)cn4)CC3)cc2)CC1] | + |
| 1.202 | 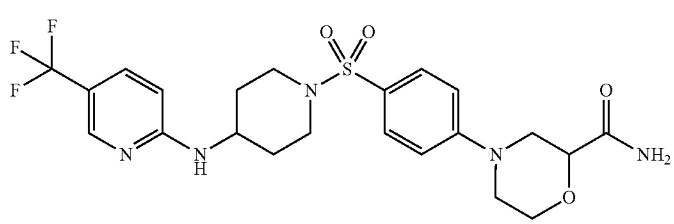 [SMILES: NC(=O)C1CN(c2ccc(S(=O)(=O)N3CCC(Nc4ccc(C(F)(F)F)cn4)CC3)cc2)CCO1] | ++ |

TABLE 1-continued

| Compound | Structure | Potency |
|---|---|---|
| 1.203 | 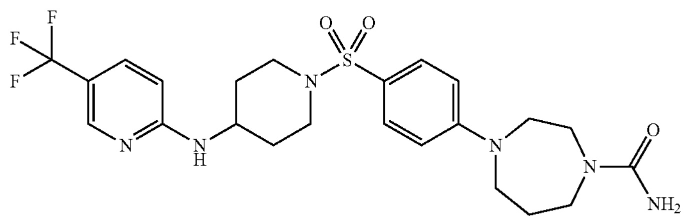 [SMILES: NC(=O)N1CCCN(c2ccc(S(=O)(=O)N3CCC(Nc4ccc(C(F)(F)F)cn4)CC3)cc2)CC1] | ++ |
| 1.204 | 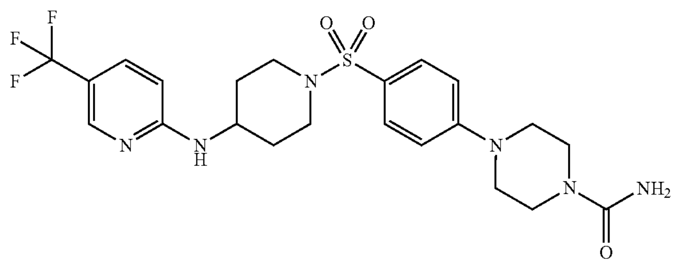 [SMILES: NC(=O)N1CCN(c2ccc(S(=O)(=O)N3CCC(Nc4ccc(C(F)(F)F)cn4)CC3)cc2)CC1] | ++ |
| 1.205 | 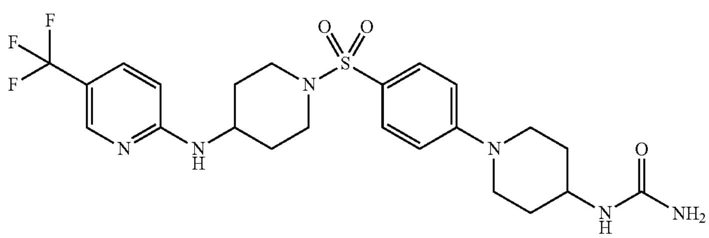 [SMILES: NC(=O)NC1CCN(c2ccc(S(=O)(=O)N3CCC(Nc4ccc(C(F)(F)F)cn4)CC3)cc2)CC1] | ++ |
| 1.206 | 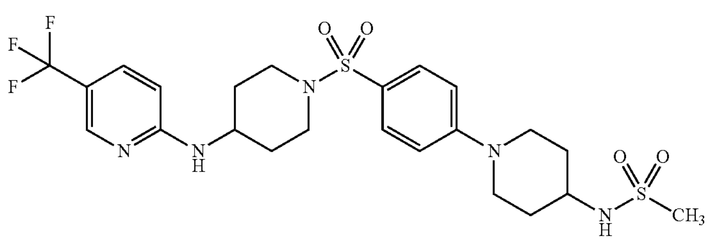 [SMILES: CS(=O)(=O)NC1CCN(c2ccc(S(=O)(=O)N3CCC(Nc4ccc(C(F)(F)F)cn4)CC3)cc2)CC1] | ++ |
| 1.207 | 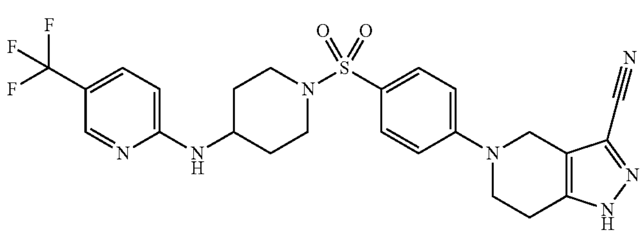 [SMILES: N#Cc1n[nH]c2c1CN(c1ccc(S(=O)(=O)N3CCC(Nc4ccc(C(F)(F)F)cn4)CC3)cc1)CC2] | + |
| 1.208 | 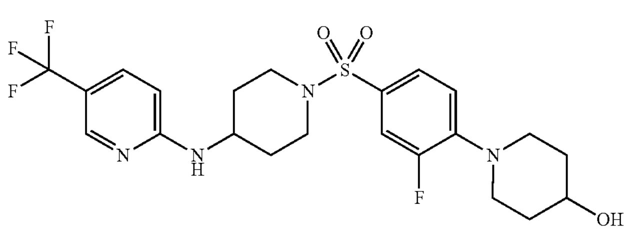 [SMILES: O=S(=O)(c1ccc(N2CCC(O)CC2)c(F)c1)N1CCC(Nc2ccc(C(F)(F)F)cn2)CC1] | + |

TABLE 1-continued

| Compound | Structure | Potency |
|---|---|---|
| 1.209 | 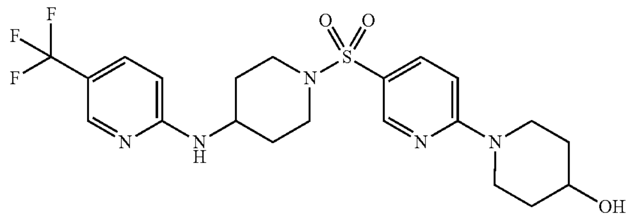 [SMILES: O=S(=O)(c1ccc(N2CCC(O)CC2)nc1)N1CCC(Nc2ccc(C(F)(F)F)cn2)CC1] | + |
| 1.210 | 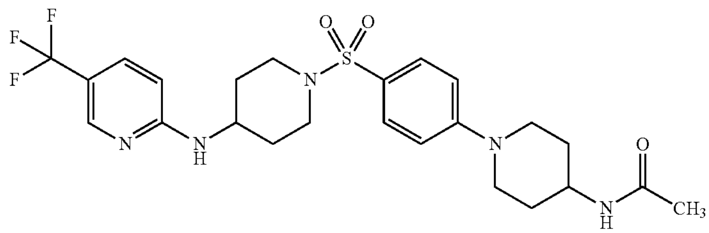 [SMILES: CC(=O)NC1CCN(c2ccc(S(=O)(=O)N3CCC(Nc4ccc(C(F)(F)F)cn4)CC3)cc2)CC1] | ++ |
| 1.211 | 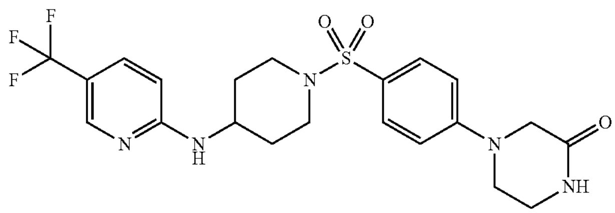 [SMILES: O=C1CN(c2ccc(S(=O)(=O)N3CCC(Nc4ccc(C(F)(F)F)cn4)CC3)cc2)CCN1] | + |
| 1.212 | 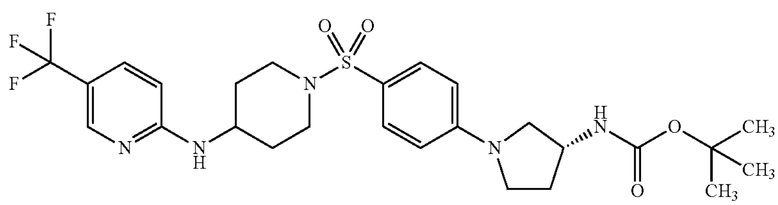 [SMILES: CC(C)(C)OC(=O)N[C@@H]1CCN(c2ccc(S(=O)(=O)N3CCC(Nc4ccc(C(F)(F)F)cn4)CC3)cc2)C1] | + |
| 1.213 | 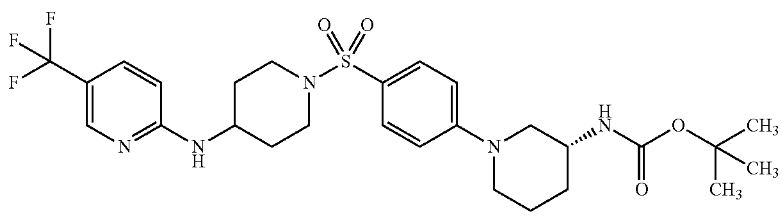 [SMILES: CC(C)(C)OC(=O)N[C@@H]1CCCN(c2ccc(S(=O)(=O)N3CCC(Nc4ccc(C(F)(F)F)cn4)CC3)cc2)C1] | + |
| 1.214 | 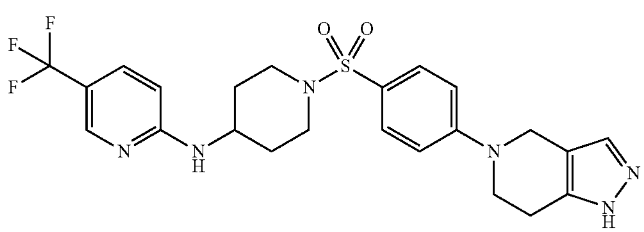 [SMILES: O=S(=O)(c1ccc(N2CCc3[nH]ncc3C2)cc1)N1CCC(Nc2ccc(C(F)(F)F)cn2)CC1] | ++ |
| 1.215 | 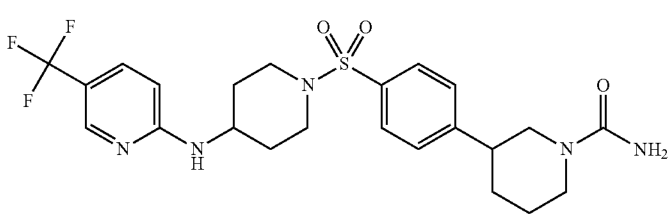 [SMILES: NC(=O)N1CCCC(c2ccc(S(=O)(=O)N3CCC(Nc4ccc(C(F)(F)F)cn4)CC3)cc2)C1] | ++ |

TABLE 1-continued

| Compound | Structure | Potency |
|---|---|---|
| 1.216 | 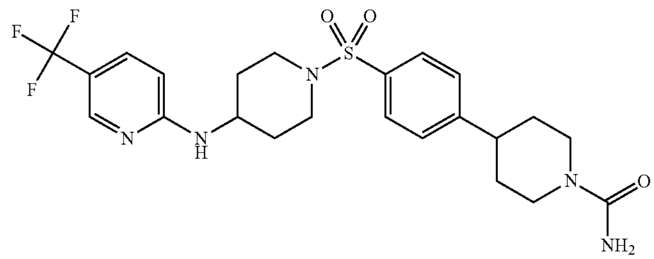 [SMILES: NC(=O)N1CCC(c2ccc(S(=O)(=O)N3CCC(Nc4ccc(C(F)(F)F)cn4)CC3)cc2)CC1] | ++ |
| 1.217 | 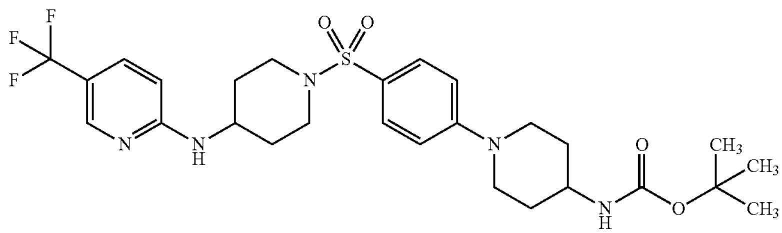 [SMILES: CC(C)(C)OC(=O)NC1CCN(c2ccc(S(=O)(=O)N3CCC(Nc4ccc(C(F)(F)F)cn4)CC3)cc2)CC1] | ++ |
| 1.218 | 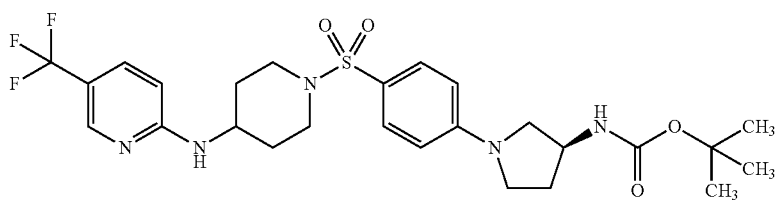 [SMILES: CC(C)(C)OC(=O)N[C@H]1CCN(c2ccc(S(=O)(=O)N3CCC(Nc4ccc(C(F)(F)F)cn4)CC3)cc2)C1] | + |
| 1.219 | 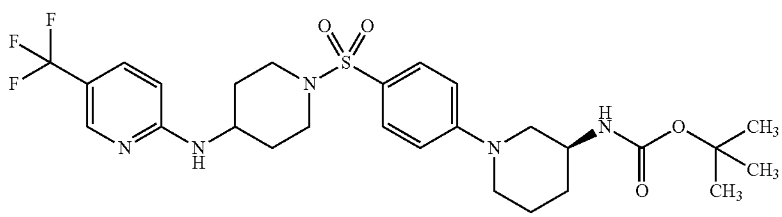 [SMILES: CC(C)(C)OC(=O)N[C@H]1CCCN(c2ccc(S(=O)(=O)N3CCC(Nc4ccc(C(F)(F)F)cn4)CC3)cc2)C1] | + |
| 1.220 | 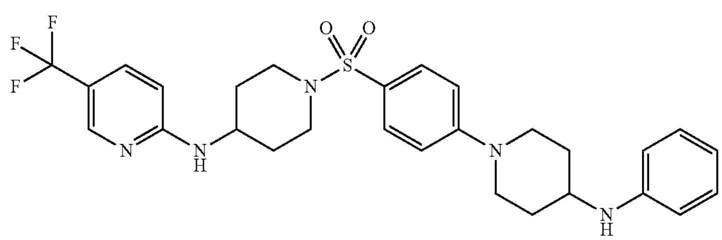 [SMILES: O=S(=O)(c1ccc(N2CCC(Nc3ccccc3)CC2)cc1)N1CCC(Nc2ccc(C(F)(F)F)cn2)CC1] | ++ |
| 1.221 | 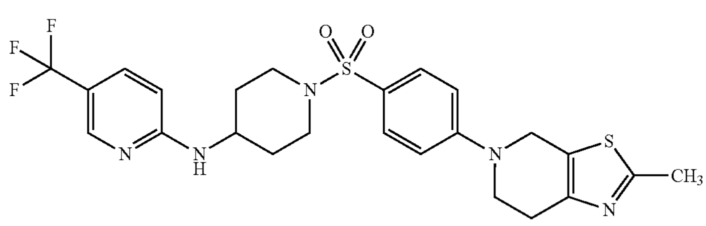 [SMILES: Cc1nc2c(s1)CN(c1ccc(S(=O)(=O)N3CCC(Nc4ccc(C(F)(F)F)cn4)CC3)cc1)CC2] | ++ |

TABLE 1-continued

| Compound | Structure | Potency |
|---|---|---|
| 1.222 | 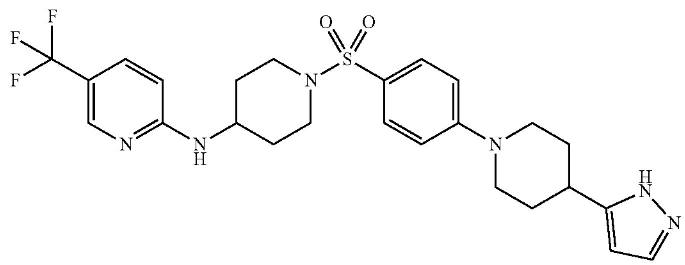 [SMILES: O=S(=O)(c1ccc(N2CCC(c3ccn[nH]3)CC2)cc1)N1CCC(Nc2ccc(C(F)(F)F)cn2)CC1] | ++ |
| 1.223 | 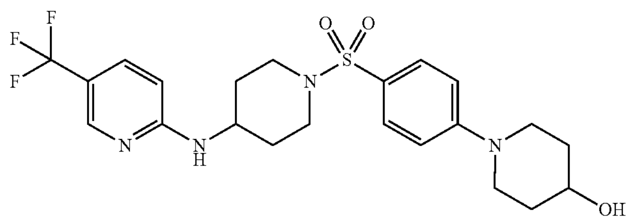 [SMILES: O=S(=O)(c1ccc(N2CCC(O)CC2)cc1)N1CCC(Nc2ccc(C(F)(F)F)cn2)CC1] | ++ |
| 1.224 | 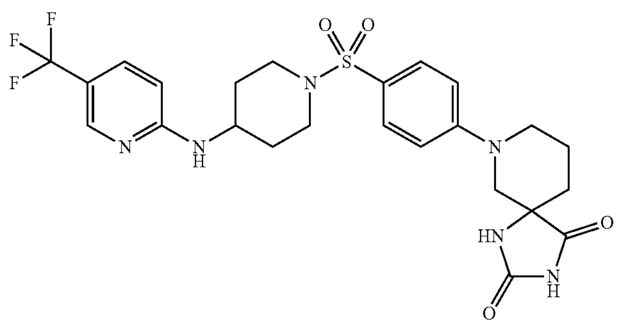 [SMILES: O=C1NC(=O)C2(CCCN(c3ccc(S(=O)(=O)N4CCC(Nc5ccc(C(F)(F)F)cn5)CC4)cc3)C2)N1] | + |
| 1.225 | 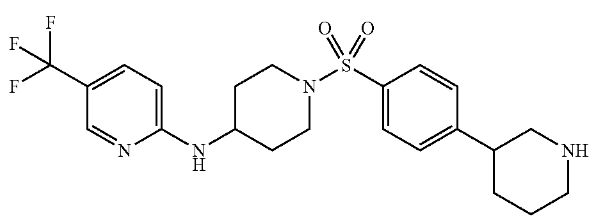 [SMILES: O=S(=O)(c1ccc(C2CCCNC2)cc1)N1CCC(Nc2ccc(C(F)(F)F)cn2)CC1] | + |
| 1.226 | 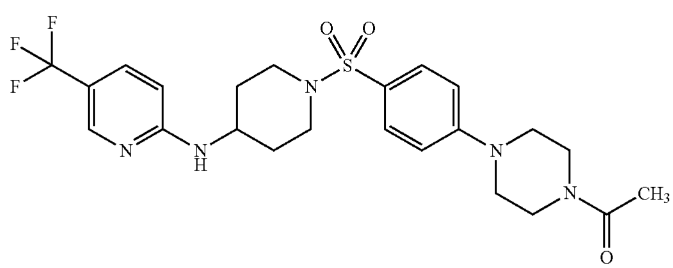 | ++ |
| 1.227 | 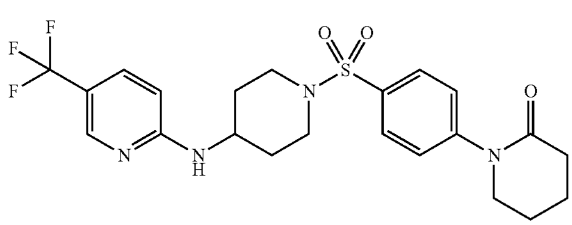 [SMILES: O=C1CCCCN1c1ccc(S(=O)(=O)N2CCC(Nc3ccc(C(F)(F)F)cn3)CC2)cc1] | + |

TABLE 1-continued
| Compound | Structure | Potency |
|---|---|---|
| 1.228 | 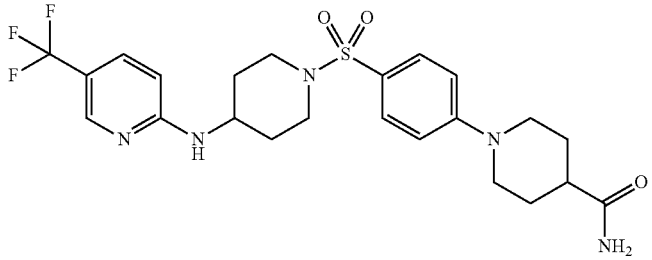 [SMILES: NC(=O)C1CCN(c2ccc(S(=O)(=O)N3CCC(Nc4ccc(C(F)(F)F)cn4)CC3)cc2)CC1] | ++ |
| 1.229 | 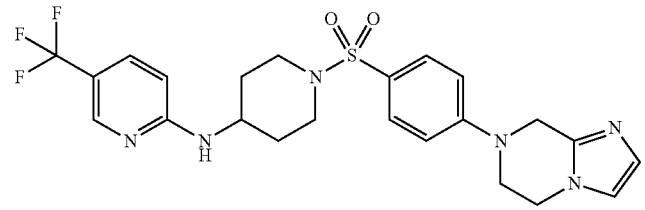 [SMILES: O=S(=O)(c1ccc(N2CCn3ccnc3C2)cc1)N1CCC(Nc2ccc(C(F)(F)F)cn2)CC1] | + |
| 1.230 | 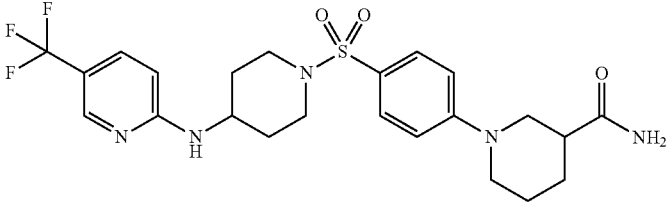 [SMILES: NC(=O)C1CCCN(c2ccc(S(=O)(=O)N3CCC(Nc4ccc(C(F)(F)F)cn4)CC3)cc2)C1] | ++ |
| 1.231 | 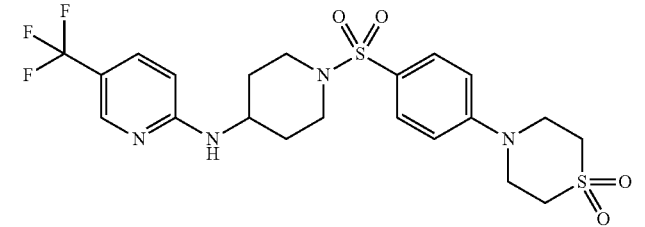 [SMILES: O=S1(=O)CCN(c2ccc(S(=O)(=O)N3CCC(Nc4ccc(C(F)(F)F)cn4)CC3)cc2)CC1] | + |
| 1.232 | 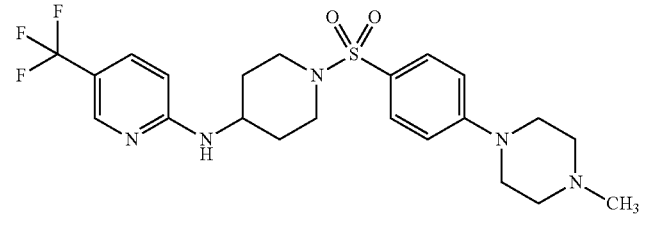 [SMILES: CN1CCN(c2ccc(S(=O)(=O)N3CCC(Nc4ccc(C(F)(F)F)cn4)CC3)cc2)CC1] | + |
| 1.233 | 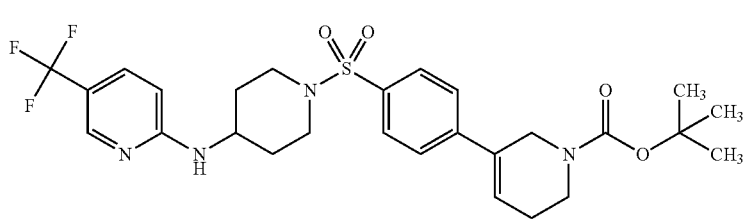 [SMILES: CC(C)(C)OC(=O)N1CCC=C(c2ccc(S(=O)(=O)N3CCC(Nc4ccc(C(F)(F)F)cn4)CC3)cc2)C1] | ++ |

TABLE 1-continued

| Compound | Structure | Potency |
|---|---|---|
| 1.234 | 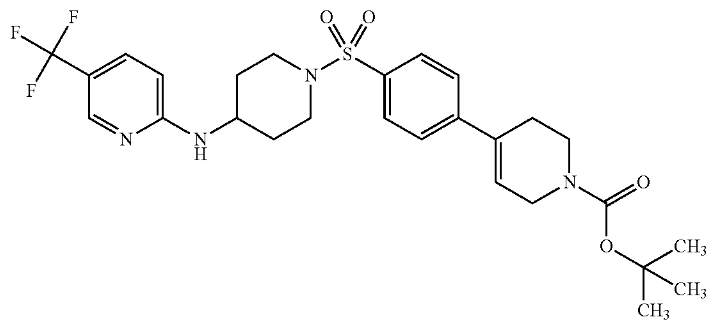 [SMILES: CC(C)(C)OC(=O)N1CC=C(c2ccc(S(=O)(=O)N3CCC(Nc4ccc(C(F)(F)F)cn4)CC3)cc2)CC1] | ++ |
| 1.235 | 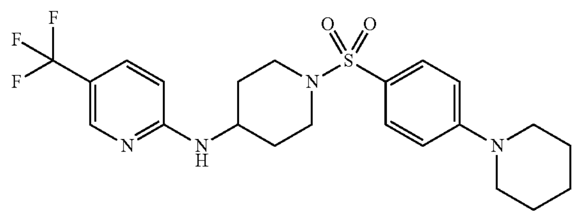 [SMILES: O=S(=O)(c1ccc(N2CCCCC2)cc1)N1CCC(Nc2ccc(C(F)(F)F)cn2)CC1] | ++ |
| 1.236 | 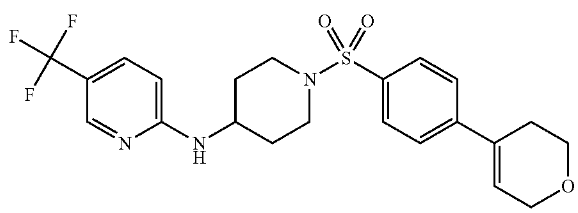 [SMILES: O=S(=O)(c1ccc(C2=CCOCC2)cc1)N1CCC(Nc2ccc(C(F)(F)F)cn2)CC1] | ++ |
| 1.237 | 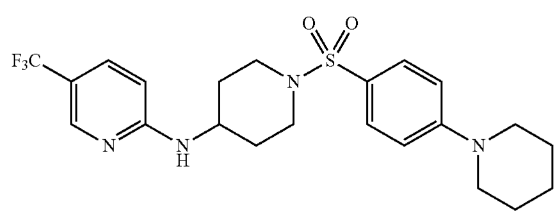 [SMILES: O=S(=O)(c1ccc(N2CCCCC2)cc1)N1CCC(Nc2ccc(C(F)(F)F)cn2)CC1] | |
| 1.238 | 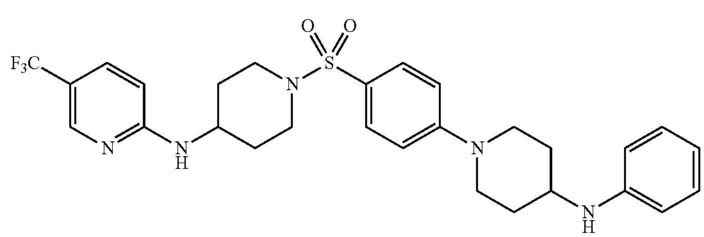 [SMILES: O=S(=O)(c1ccc(N2CCC(Nc3ccccc3)CC2)cc1)N1CCC(Nc2ccc(C(F)(F)F)cn2)CC1] | |
| 1.239 | 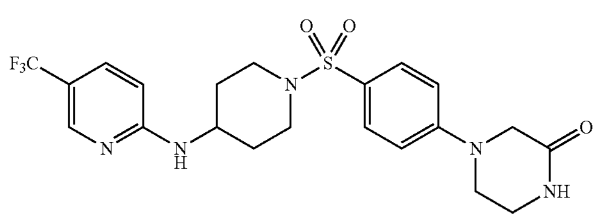 [SMILES: O=C1CN(c2ccc(S(=O)(=O)N3CCC(Nc4ccc(C(F)(F)F)cn4)CC3)cc2)CCN1] | |

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A compound having formula (I):

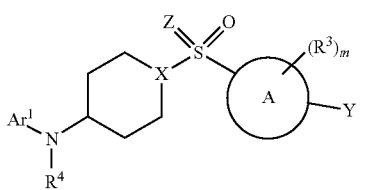

or a pharmaceutically acceptable salt, hydrate, solvate, N-oxide, optically enriched form, or rotamer thereof, wherein X is N or CH;

Z is O or —N($R^f$)—, wherein $R^f$ is selected from the group consisting of hydrogen, $C_{1-4}$ alkyl, $C_{1-4}$ haloalkyl, $C_{1-4}$ hydroxyalkyl, and $C_{3-6}$ cycloalkyl;

Ring A is a benzene or pyridine ring;

$Ar^1$ is a monocyclic 5- or 6-membered aromatic or heteroaromatic ring having 0 to 3 heteroatoms as ring vertices selected from N, O, and S, substituted with from 1 to 5 $R^1$ substituents independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, and —$NR^aR^b$;

each $R^a$ and $R^b$ is independently selected from the group consisting of hydrogen, hydroxyl, $C_{1-4}$ alkyl, $C_{1-4}$ haloalkyl, $C_{1-4}$ hydroxyalkyl, and $C_{3-6}$ cycloalkyl;

Y is selected from the group consisting of:
  i) bicyclic 9- or 10-membered fused aromatic or heteroaromatic ring having 0 to 4 heteroatoms as ring vertices selected from N, O, S and S(O)$_2$, and which is substituted with 0 to 5 $R^2$;
  ii) 4- to 7-membered monocyclic heterocyclic ring having 1 or 2 heteroatoms as ring vertices selected from N, O, S and S(O)$_2$, and which is substituted with 0 to 5 $R^2$;
  iii) 6- to 12-membered fused or bridged heterocyclic ring having 1 to 4 heteroatoms as ring vertices selected from N, O, S and S(O)$_2$, and which is substituted with 0 to 6 $R^2$; and
  iv) 7- to 12-membered spiroheterocyclic ring having 0 to 4 heteroatoms as ring vertices selected from N, O and S, and which is substituted with 0 to 6 $R^2$;

each $R^2$ is independently selected from the group consisting of halogen, CN, $C_{1-8}$ alkyl, $C_{3-8}$ cycloalkyl, $C_{2-8}$ alkenyl, $C_{2-8}$ alkynyl, haloalkyl, hydroxyalkyl, —$OR^c$, —$SR^c$, —$OSi(R^c)_3$, —$COR^c$, —$CO_2R^c$, —$NR^cR^d$, —$NR^cR^d$, —$CONR^cR^d$, —$(CO)_2NR^cR^d$, —$NR^cCO_2R^d$, —$NR^cCOR^d$, —$NR^cCONR^cR^d$, —$NR^cSO_2R^d$, —$SO_2R^d$, —$CO$—$C_{1-4}$ hydroxyalkyl, —$SO_2NR^cR^d$, —$X^2$—$NR^cR^d$, —$X^2$—$CONR^cR^d$, —$X^2$—$NR^cCONR^cR^d$, —$X^2$—$NR^cCO_2R^d$, —$X^2$—$NR^cCOR^d$, —$X^2$—$NR^cSO_2R^d$, —$CO$—$X^2$—$NR^c$—$COR^d$, oxo, 4- to 7-membered heterocyclic ring having 1 or 2 heteroatoms as ring vertices selected from N, O, S and S(O)$_2$, 5- or 6-membered heteroaryl, and —$X^2$-5- or 6-membered heteroaryl; and wherein the 5- or 6-membered heteroaryl ring and the 4- to 7-membered heterocyclic ring of $R^2$ have from 1 to 3 heteroatoms selected from N, O, and S, and are each unsubstituted or substituted with one or two members independently selected from the group consisting of halogen, hydroxyl, amino, $C_{1-4}$ alkyl, $C_{1-4}$ alkoxy, $C_{1-4}$ haloalkyl, —$COR^c$, —$CO_2R^c$, and —$CONR^cR^d$; and wherein two $R^2$ groups attached to the same carbon atom are optionally combined to form a 3- to 6-membered spirocyclic ring or a 3- to 6-membered spiroheterocyclic ring having 1 to 3 heteroatoms as ring vertices selected from N, O and S, and which is unsubstituted or substituted with 1 or 2 members independently selected from $C_{1-4}$ alkyl, —$COR^c$, —$CO_2R^c$, and —$CONR^cR^d$;

each $R^c$ and $R^d$ is independently selected from the group consisting of hydrogen, hydroxyl, $C_{1-6}$ alkyl, $C_{1-6}$ haloalkyl, $C_{1-6}$ hydroxyalkyl, and $C_{3-6}$ cycloalkyl; or $R^c$ and $R^d$, when attached to the same nitrogen atom are joined to form a 4- to 7-membered heterocyclic ring having from 0 to 2 additional heteroatoms as ring vertices selected from O, S, S(O), S(O)$_2$, NH and N($C_{1-4}$ alkyl);

each $R^e$ is selected from the group consisting of phenyl;

$X^2$ is $C_{1-4}$ alkylene or cyclopropyl;

the subscript m is 0, 1 or 2;

each $R^3$ is a member independently selected from the group consisting of halogen, CN, $C_{1-4}$ alkyl, $C_{1-4}$ alkoxy, $C_{3-8}$ cycloalkyl, $C_{1-4}$ haloalkyl, $C_{1-4}$ haloalkoxy, and $C_{2-4}$ hydroxyalkyl; and $R^4$ is a member selected from the group consisting of H, $C_{1-4}$ alkyl, $C_{3-8}$ cycloalkyl, and $C_{1-4}$ haloalkyl.

2. A compound having formula (I):

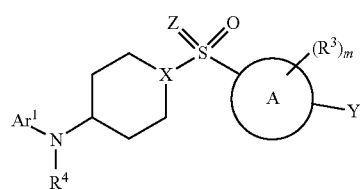

or a pharmaceutically acceptable salt, hydrate, solvate, N-oxide, optically enriched form, or rotamer thereof, wherein X is N or CH;

Z is O or —NH;

Ring A is a benzene or pyridine ring;

$Ar^1$ is a 5- or 6-membered aromatic or heteroaromatic ring, substituted with from 1 to 5 $R^1$ substituents independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, and —$NR^aR^b$;

each $R^a$ and $R^b$ is independently selected from the group consisting of hydrogen, hydroxyl, halogen, cyano, $C_{1-4}$ alkyl, $C_{1-4}$ haloalkyl, $C_{1-4}$ hydroxyalkyl, and $C_{3-6}$ cycloalkyl;

Y is selected from the group consisting of:
  i) bicyclic 9- or 10-membered fused aromatic or heteroaromatic ring having 0 to 4 heteroatoms as ring vertices selected from N, O, S and S(O)$_2$, and which is substituted with 0 to 5 R$^2$;
ii) 4- to 7-membered monocyclic heterocyclic ring having 1 or 2 heteroatoms as ring vertices selected from N, O, S and S(O)$_2$, and which is substituted with 0 to 5 R$^2$;
iii) 6- to 12-membered fused or bridged heterocyclic ring having 1 to 4 heteroatoms as ring vertices selected from N, O, S and S(O)$_2$, and which is substituted with 0 to 6 R$^2$; and
iv) 7- to 12-membered spiroheterocyclic ring having 0 to 4 heteroatoms as ring vertices selected from N, O and S, and which is substituted with 0 to 6 R$^2$;
each R$^2$ is independently selected from the group consisting of halogen, CN, C$_{1-8}$ alkyl, C$_{3-8}$ cycloalkyl, C$_{2-8}$ alkenyl, C$_{2-8}$ alkynyl, haloalkyl, hydroxyalkyl, —OR$^c$, —SR$^c$, —OSi(R$^c$)$_3$, —COR$^c$, —CO$_2$R$^c$, —NR$^c$R$^d$, —NR$^c$R$^d$, —CONR$^c$R$^d$, —(CO)$_2$NR$^c$R$^d$, —NR$^c$CO$_2$R$^d$, —NR$^c$COR$^d$, —NR$^c$CONR$^c$R$^d$, —NR$^c$SO$_2$R$^d$, —SO$_2$R$^d$, —CO—C$_{1-4}$ hydroxyalkyl, —SO$_2$NR$^c$R$^d$, —X$^2$—NR$^c$R$^d$, —X$^2$—CONR$^c$R$^d$, —X$^2$—NR$^c$CONR$^c$R$^d$, —X$^2$—NR$^c$CO$_2$R$^d$, —X$^2$—NR$^c$COR$^d$, —X$^2$—NR$^c$SO$_2$R$^d$, —CO—X$^2$—NR$^c$-COR$^d$, oxo, 4- to 7-membered heterocyclic ring having 1 or 2 heteroatoms as ring vertices selected from N, O, S and S(O)$_2$, 5- or 6-membered heteroaryl, and —X$^2$-5- or 6-membered heteroaryl; and wherein the 5- or 6-membered heteroaryl ring and the 4- to 7-membered heterocyclic ring of R$^2$ are each unsubstituted or substituted with one or two members independently selected from the group consisting of halogen, hydroxyl, amino, C$_{1-4}$ alkyl, C$_{1-4}$ alkoxy, C$_{1-4}$ haloalkyl, —COR$^c$, —CO$_2$R$^c$, and —CONR$^c$R$^d$; and wherein two R$^2$ groups attached to the same carbon atom are optionally combined to form a 3- to 6-membered spirocyclic or spiroheterocyclic ring having 0 to 3 heteroatoms as ring vertices selected from N, O and S, and which is unsubstituted or substituted with 1 or 2 members independently selected from C$_{1-4}$ alkyl, —COR$^c$, —CO$_2$R$^c$, and —CONR$^c$R$^d$;
each R$^c$ and R$^d$ is independently selected from the group consisting of hydrogen, hydroxyl, halogen, cyano, C$_{1-6}$ alkyl, C$_{1-6}$ haloalkyl, C$_{1-6}$ hydroxyalkyl, and C$_{3-6}$ cycloalkyl; or R$^c$ and R$^d$, when attached to the same nitrogen atom are joined to form a 4- to 7-membered heterocyclic ring having from 0 to 2 additional heteroatoms as ring vertices selected from O, S, S(O), S(O)$_2$, NH and N(C$_{1-4}$ alkyl);
each R$^e$ is selected from the group consisting of phenyl;
X$^2$ is C$_{1-4}$ alkylene or cyclopropyl;
the subscript m is 0, 1 or 2;
each R$^3$ is a member independently selected from the group consisting of halogen, CN, C$_{1-4}$ alkyl, C$_{1-4}$ alkoxy, C$_{3-8}$ cycloalkyl, C$_{1-4}$ haloalkyl, C$_{1-4}$ haloalkoxy, and C$_{2-4}$ hydroxyalkyl; and
R$^4$ is a member selected from the group consisting of H, C$_{1-4}$ alkyl, C$_{3-8}$ cycloalkyl, and C$_{1-4}$ haloalkyl.

3. A compound of claim 1, or a pharmaceutically acceptable salt, hydrate, solvate, N-oxide or rotamer thereof, wherein Y is a bicyclic 9- or 10-membered fused aromatic or heteroaromatic ring having 0 to 4 heteroatoms as ring vertices selected from N, O and S, and which is substituted with 0 to 5 R$^2$.

4. A compound of claim 3, or a pharmaceutically acceptable salt, hydrate, solvate, N-oxide or rotamer thereof, wherein Y is a bicyclic 9- or 10-membered fused aromatic or heteroaromatic ring selected from the group consisting of

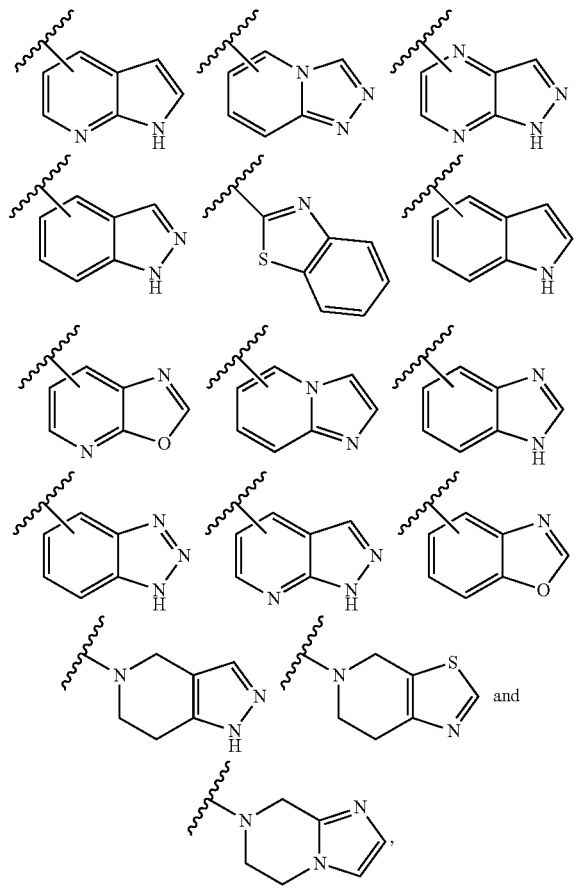

each of which is substituted with 0 to 5 R$^2$.

5. A compound of claim 3, or a pharmaceutically acceptable salt, hydrate, solvate, N-oxide or rotamer thereof, wherein Y is a bicyclic 9- or 10-membered fused aromatic or heteroaromatic ring selected from the group consisting of

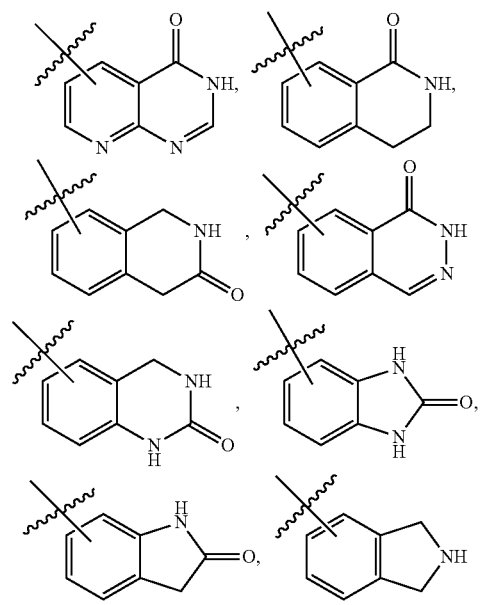

-continued

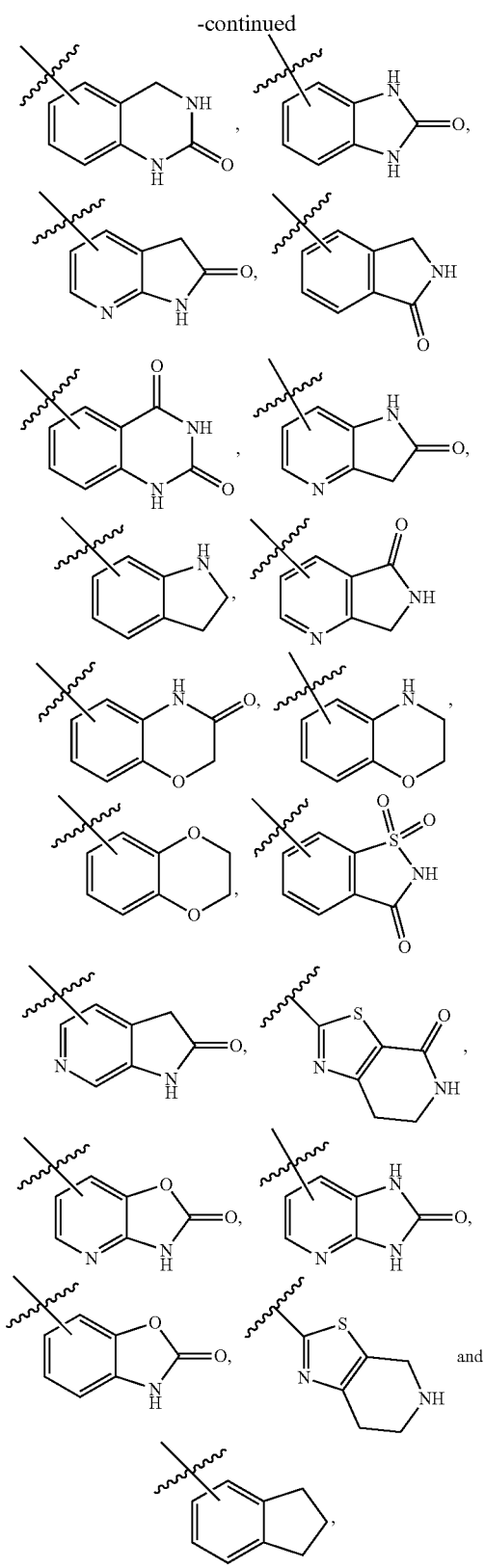

each of which is substituted with 0 to 3 $R^2$.

6. A compound of claim 1, or a pharmaceutically acceptable salt, hydrate, solvate, N-oxide or rotamer thereof, wherein Y is a 4- to 7-membered monocyclic heterocyclic ring having 1 or 2 heteroatoms as ring vertices selected from N, O and S, and which is substituted with 0 to 5 $R^2$.

7. A compound of claim 6, or a pharmaceutically acceptable salt, hydrate, solvate, N-oxide or rotamer thereof, wherein Y is a 4- to 7-membered monocyclic heterocyclic ring selected from the group consisting of

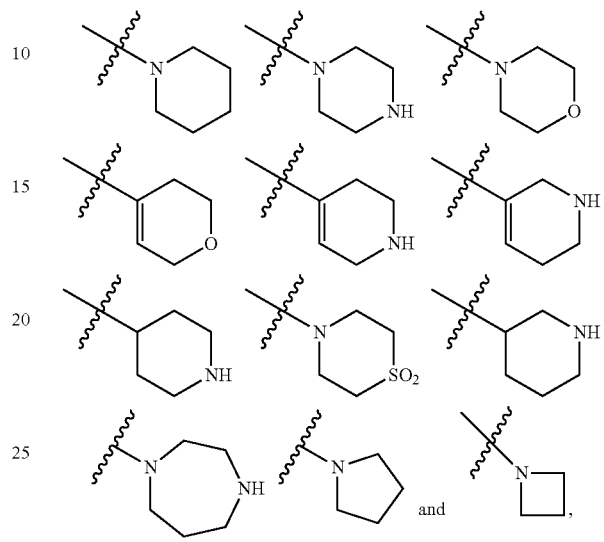

each of which is substituted with 0 to 5 $R^2$.

8. A compound of claim 1, or a pharmaceutically acceptable salt, hydrate, solvate, N-oxide or rotamer thereof, wherein Y is a 6- to 12-membered fused or bridged heterocyclic ring having 1 to 4 heteroatoms as ring vertices selected from N, O and S, and which is substituted with 0 to 6 $R^2$.

9. A compound of claim 8, or a pharmaceutically acceptable salt, hydrate, solvate, N-oxide or rotamer thereof, wherein Y is a 6- to 12-membered fused or bridged heterocyclic ring selected from the group consisting of

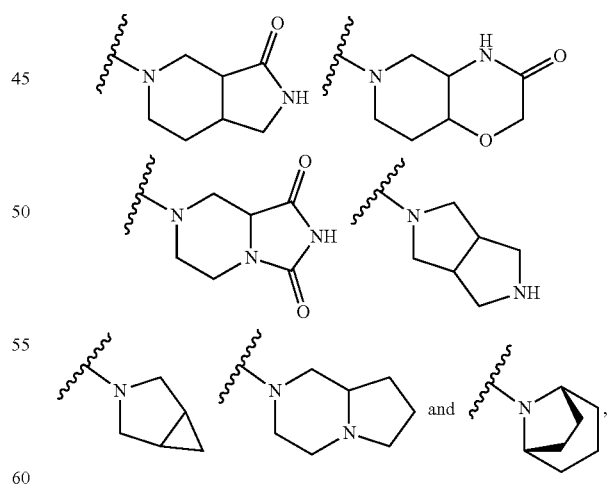

each of which is substituted with 0 to 4 $R^2$.

10. A compound of claim 1, or a pharmaceutically acceptable salt, hydrate, solvate, N-oxide or rotamer thereof, wherein Y is a 7- to 12-membered spiroheterocyclic ring having 0 to 4 heteroatoms as ring vertices selected from N, O and S, and which is substituted with 0 to 6 $R^2$.

11. A compound of claim 10, or a pharmaceutically acceptable salt, hydrate, solvate, N-oxide or rotamer thereof, wherein Y is a 7- to 12-membered spiroheterocyclic ring selected from the group consisting of

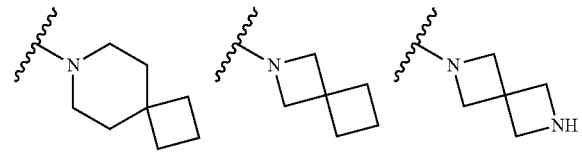

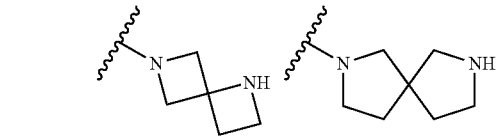

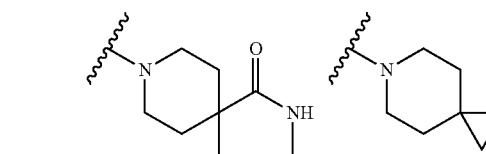

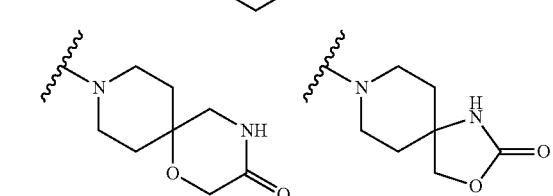

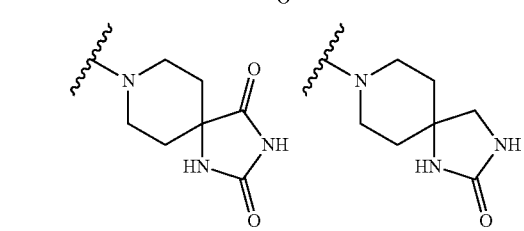

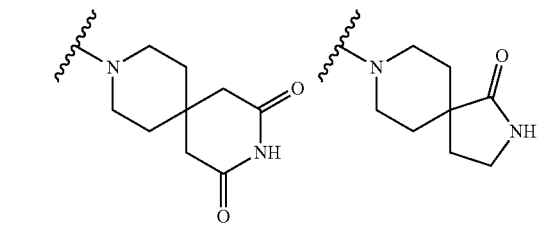

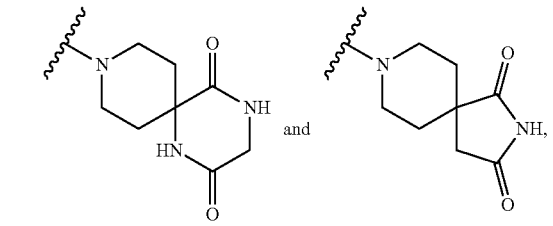

and each of which is substituted with 0 to 4 $R^2$.

12. A compound of claim 1, wherein $Ar^1$ is pyridyl, substituted with from 1 to 3 $R^1$ substituents.

13. A compound of claim 1, or a pharmaceutically acceptable salt, hydrate, solvate, N-oxide or rotamer thereof, wherein Z is O, and X is N.

14. A compound of claim 1, having the formula (Ia1):

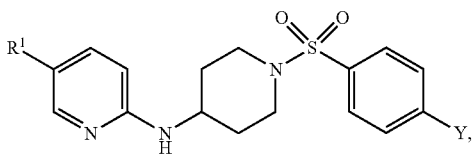

(Ia1)

wherein $R^1$ is —CN or —$CF_3$.

15. A compound of claim 14, wherein Y is selected from the group consisting of

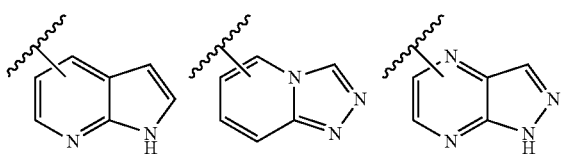

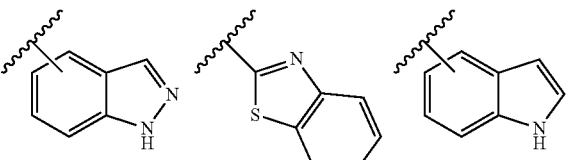

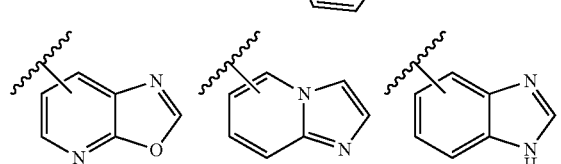

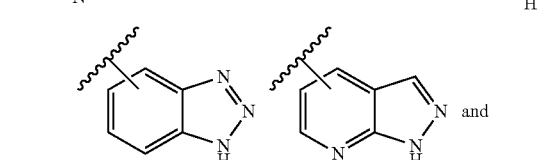

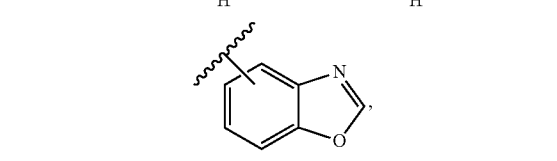

and each of which is substituted with 0 to 5 $R^2$.

16. A compound of claim 14, wherein Y is selected from the group consisting of

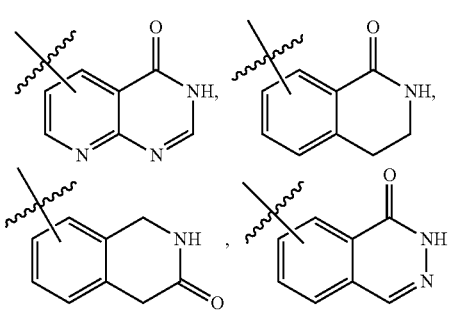

-continued
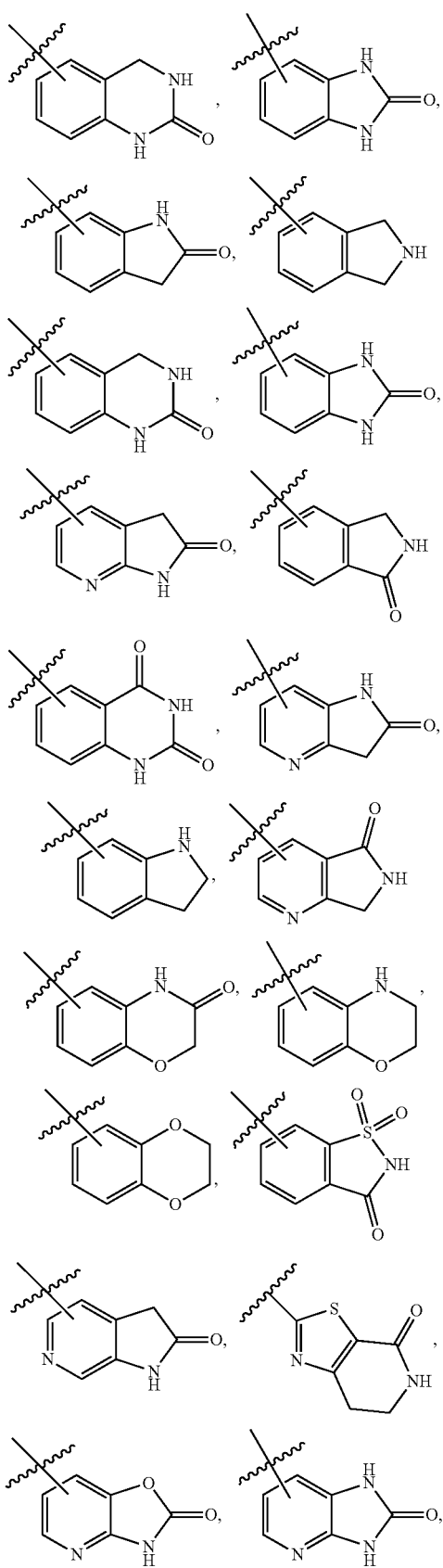
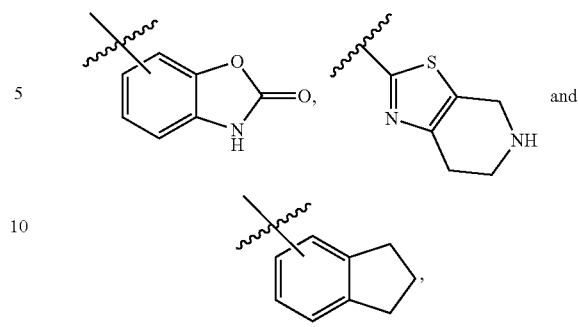
each of which is substituted with from 0 to 3 R².
17. A compound of claim 14, wherein Y is selected from the group consisting of
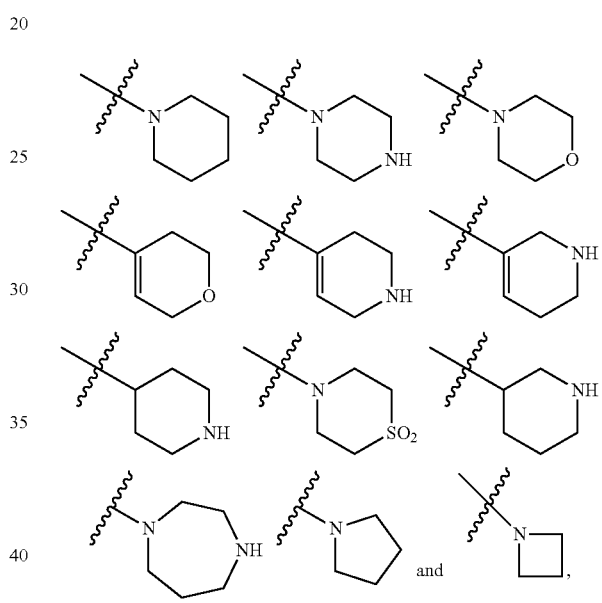
each of which is substituted with 0 to 5 R².
18. A compound of claim 14, wherein Y is selected from the group consisting of
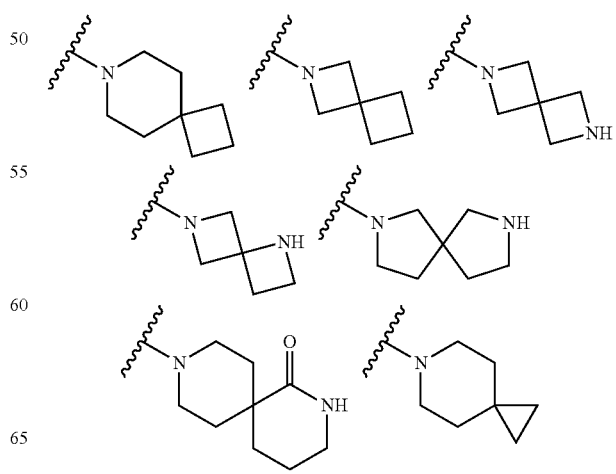

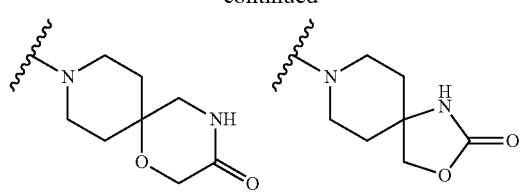
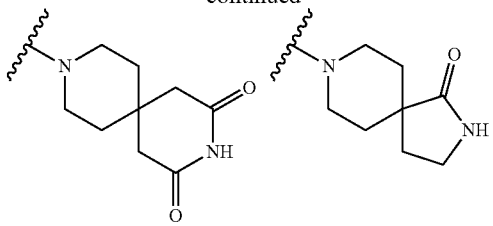
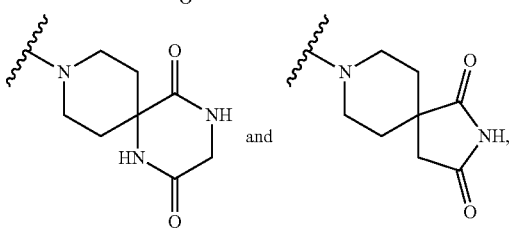
each of which is substituted with 0 to 4 $R^2$.
19. A compound of claim 1, selected from the group consisting of
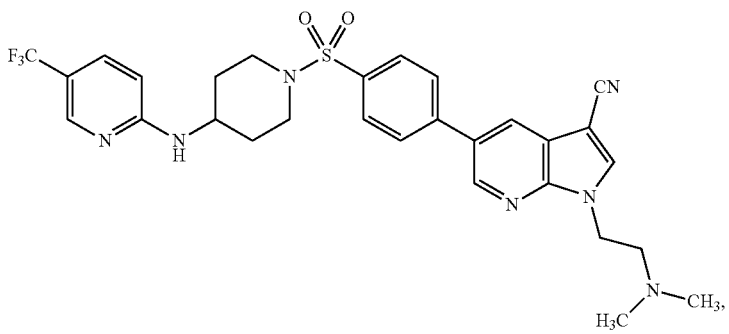
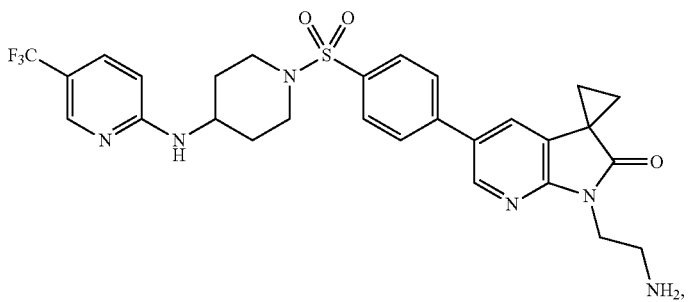
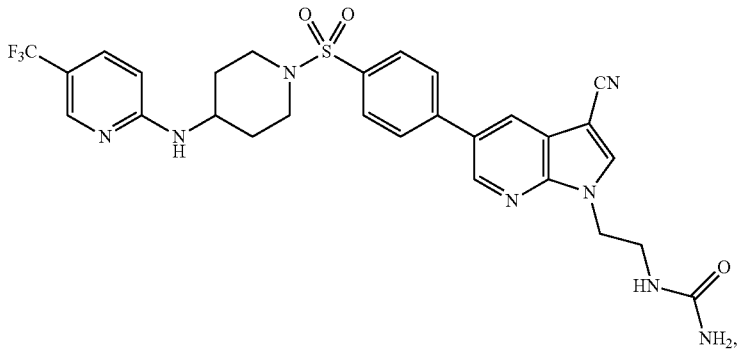

-continued
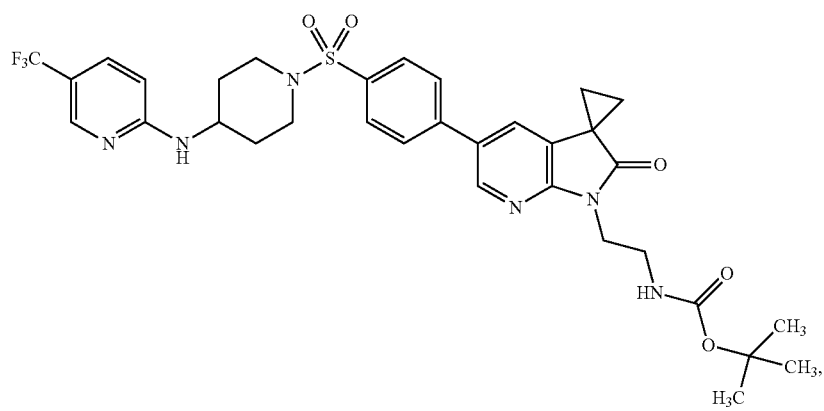
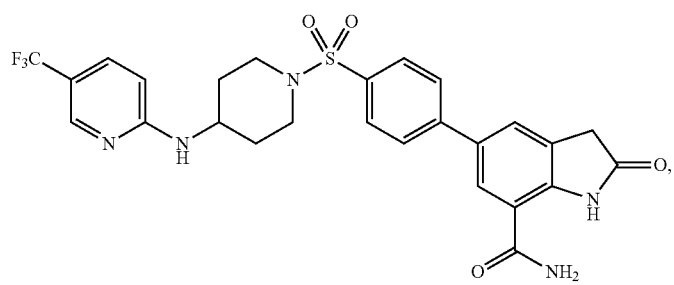
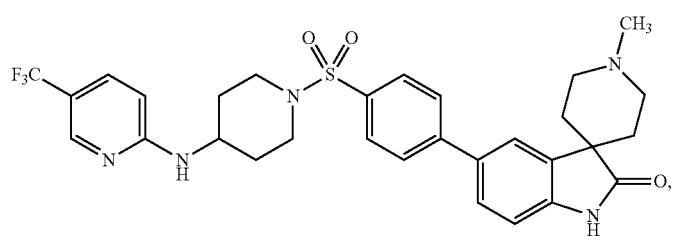
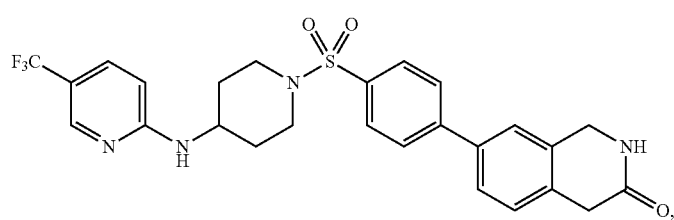
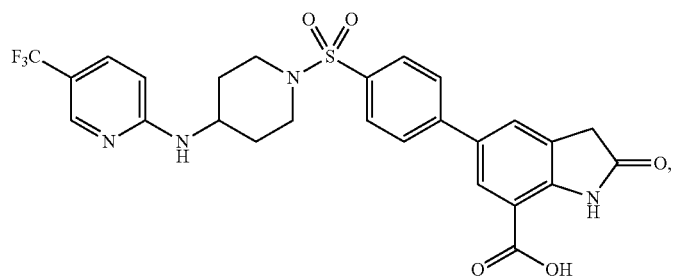
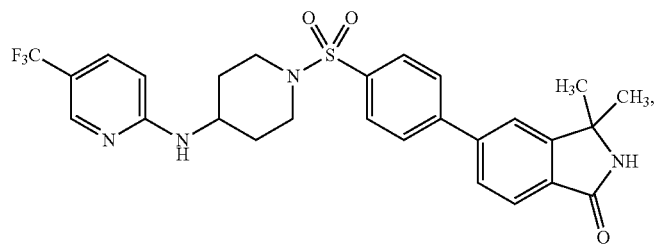

-continued
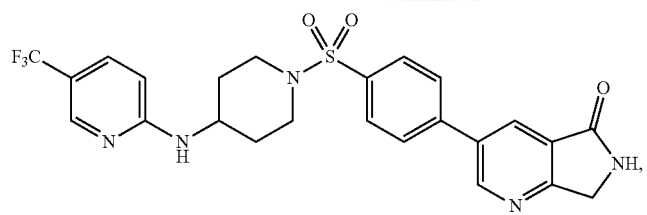
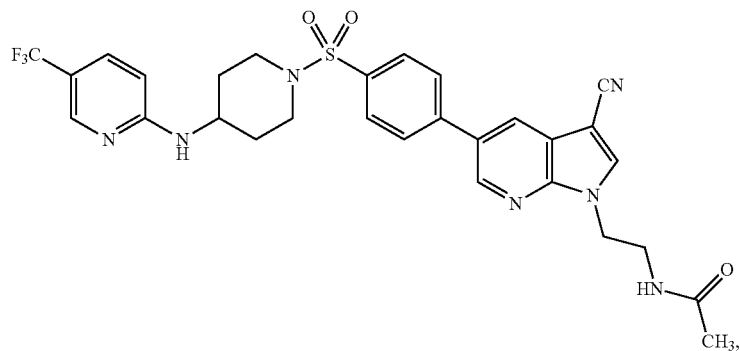
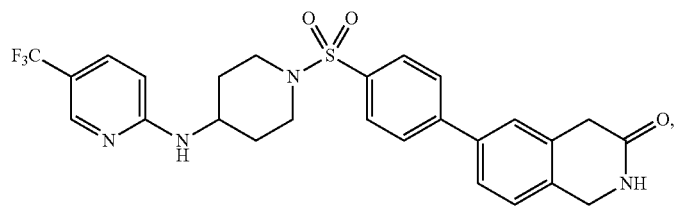
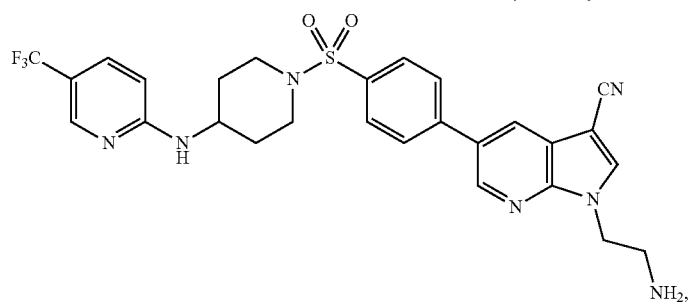
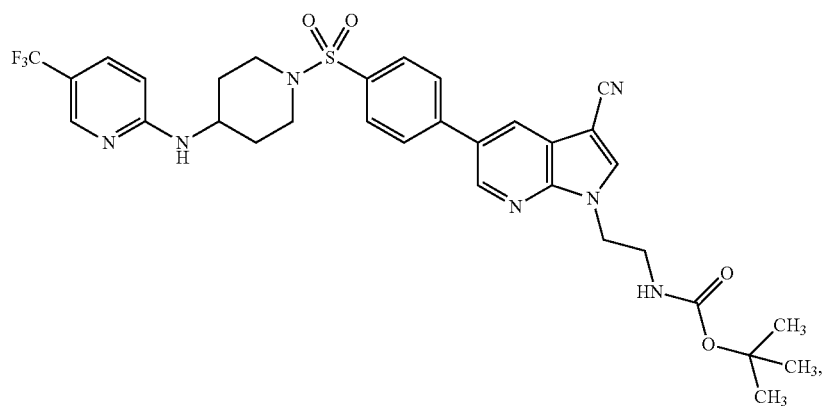
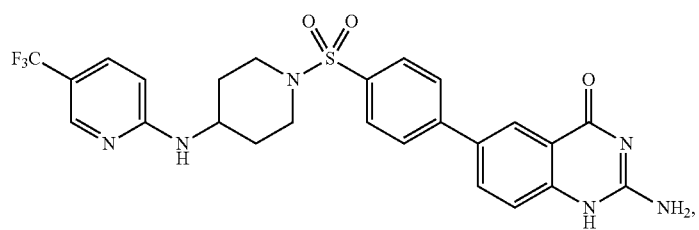

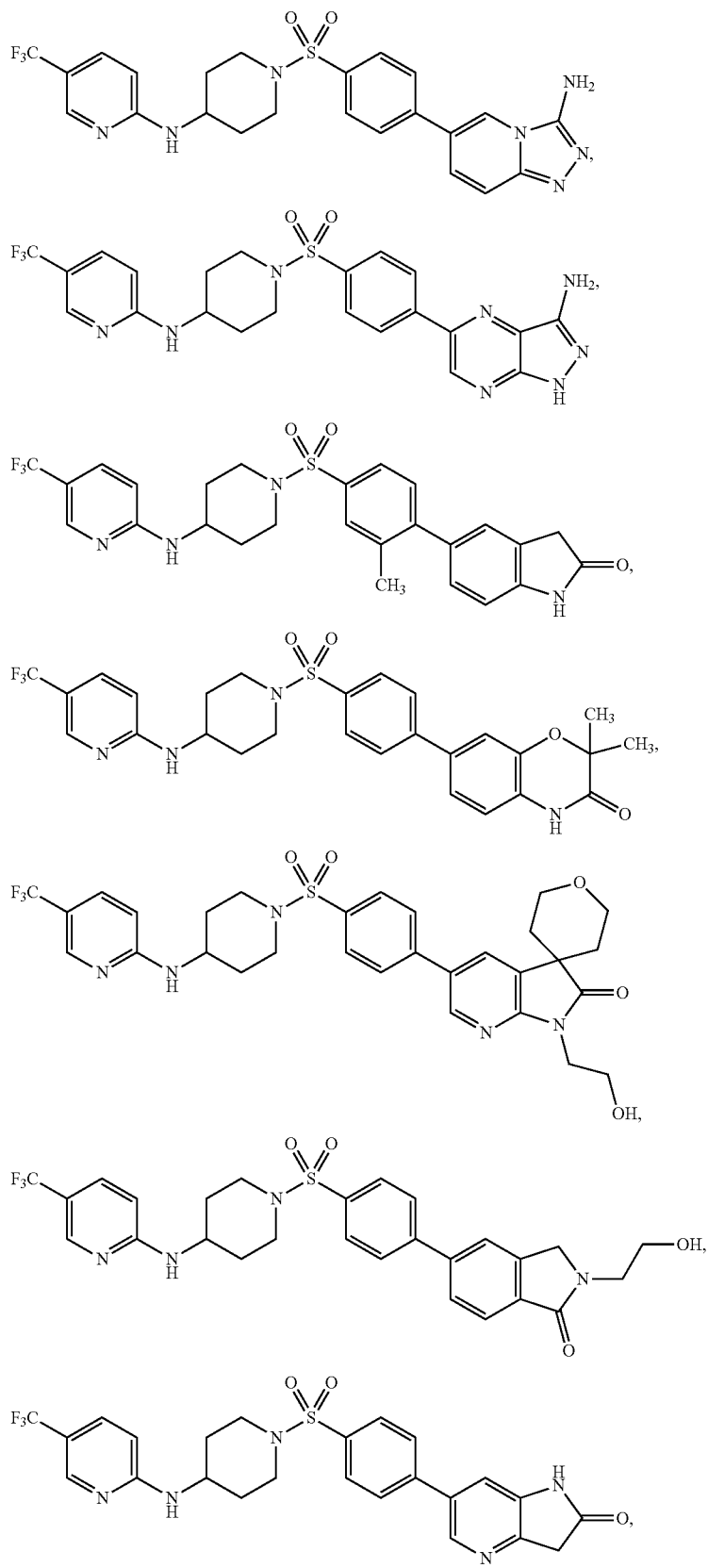

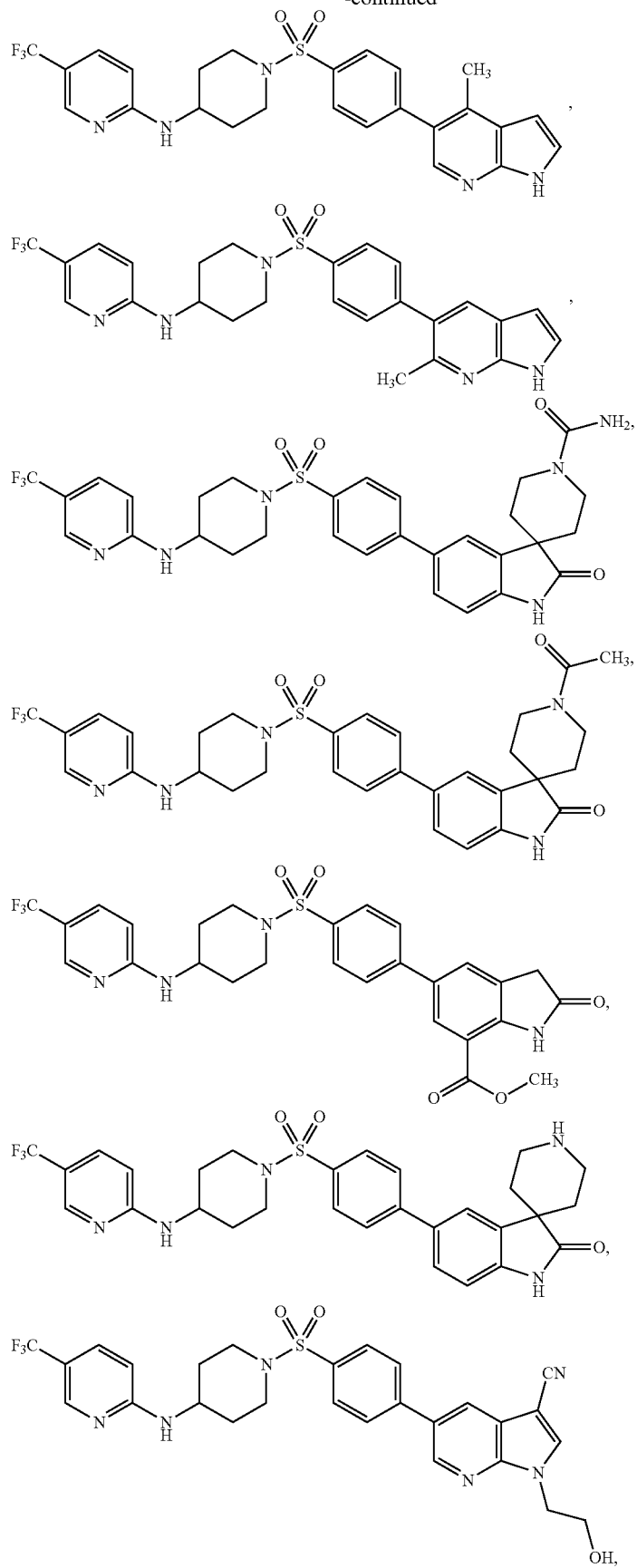

-continued
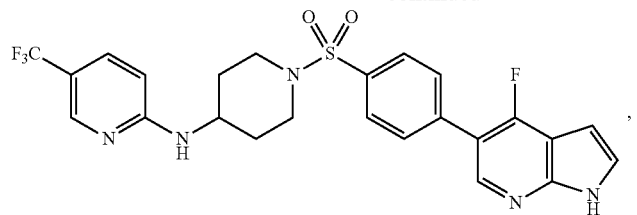
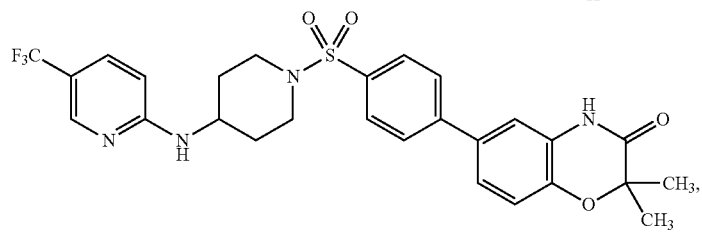
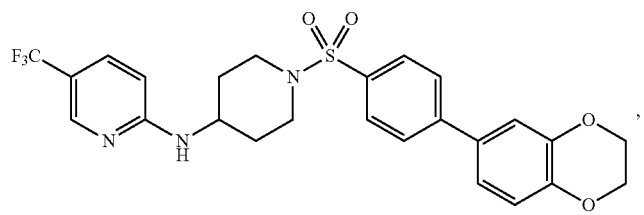
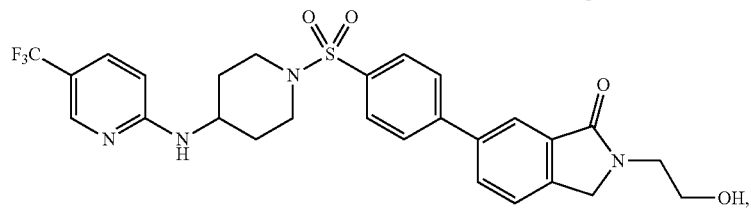
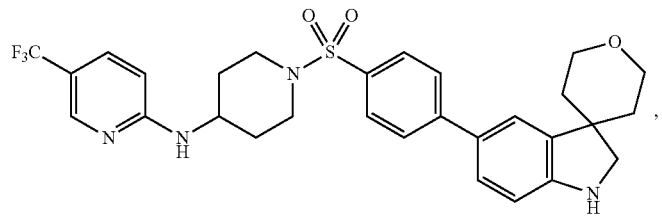
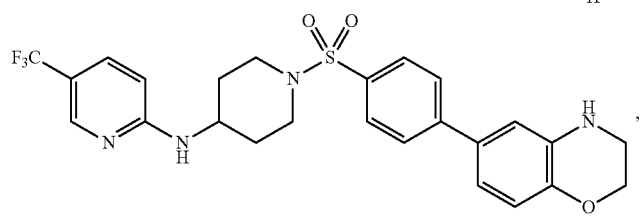
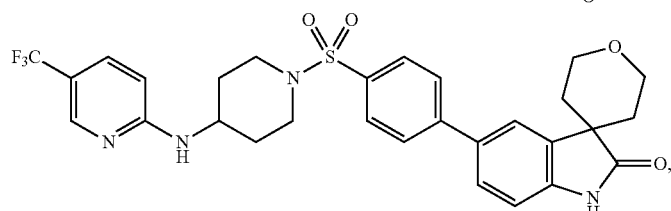
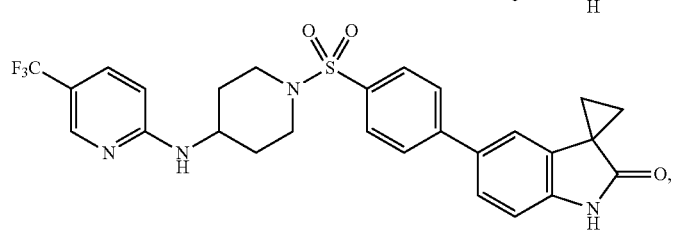

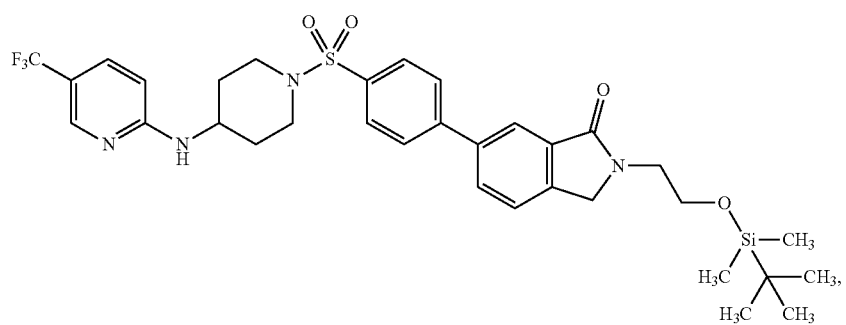
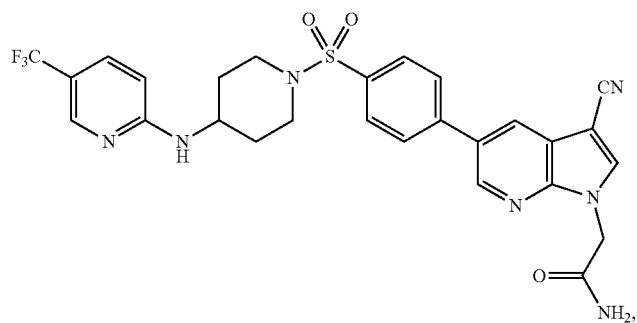
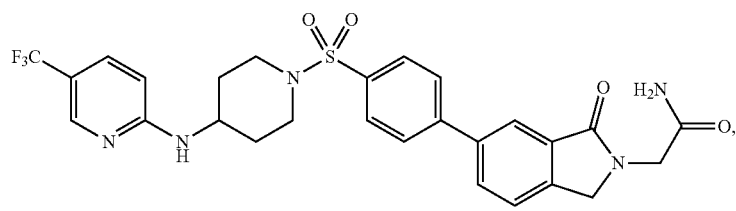
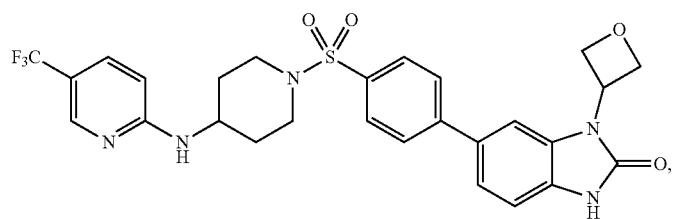
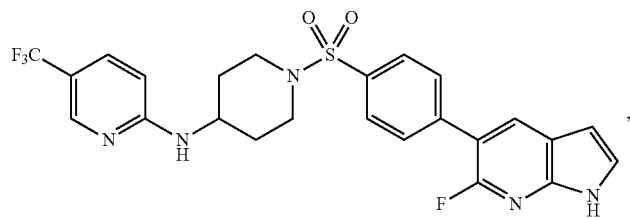
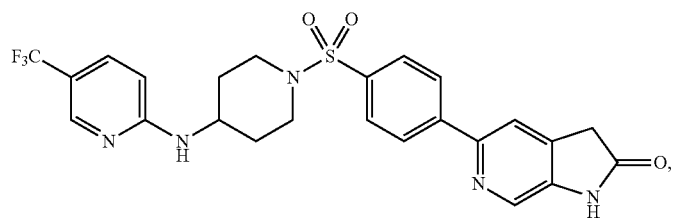

-continued
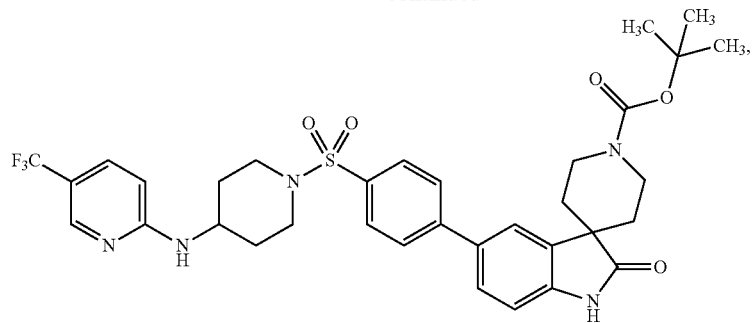
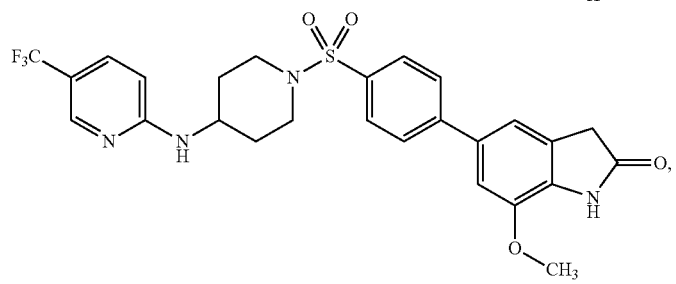
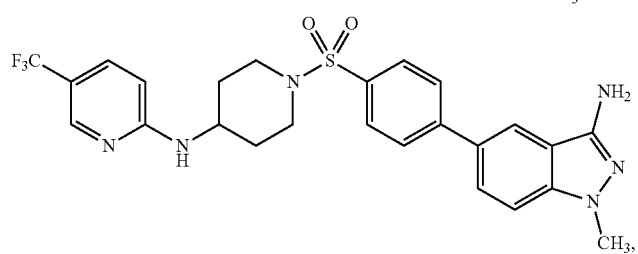
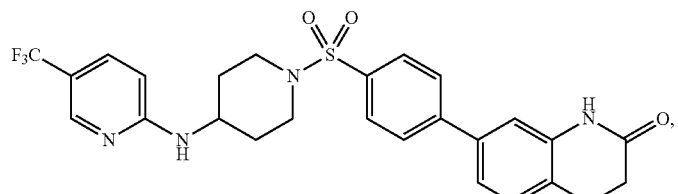
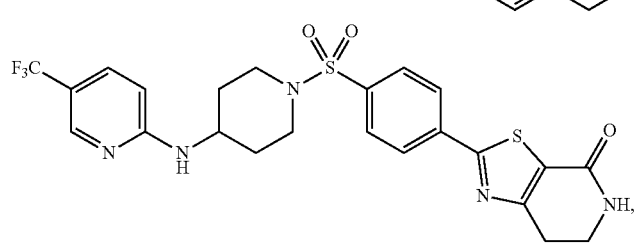
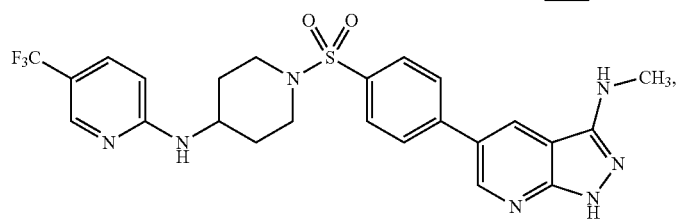
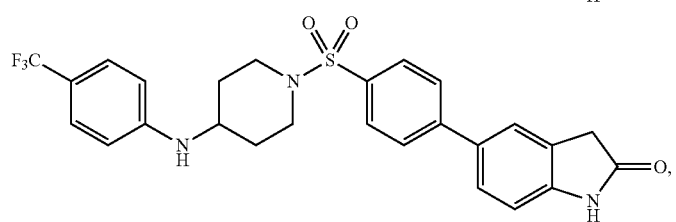

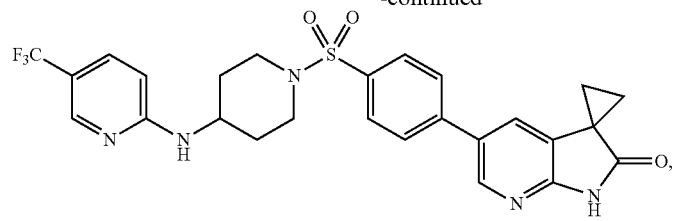
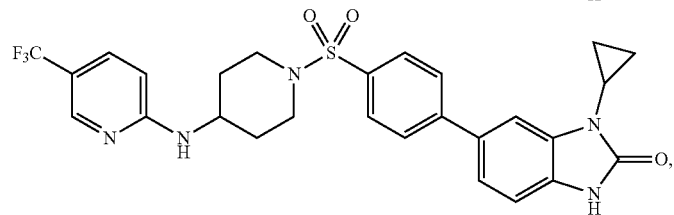
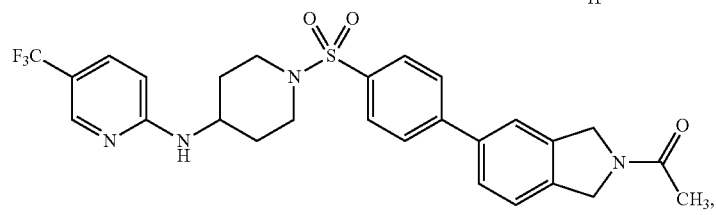
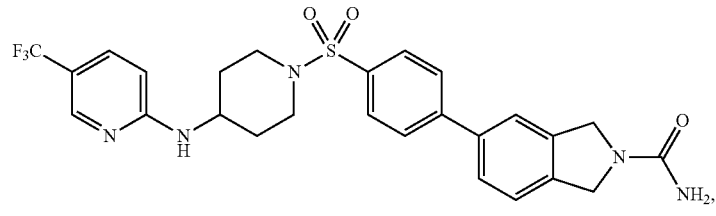
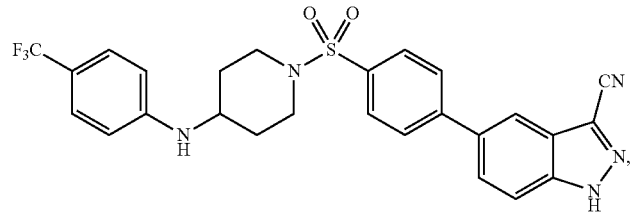
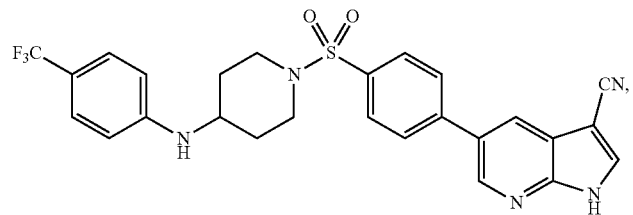
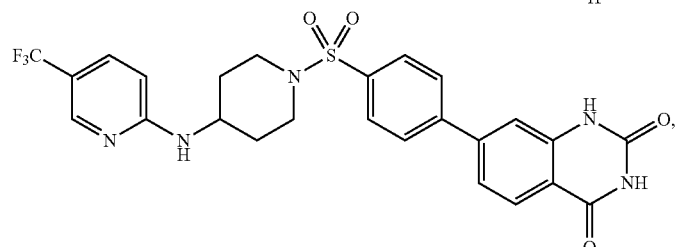
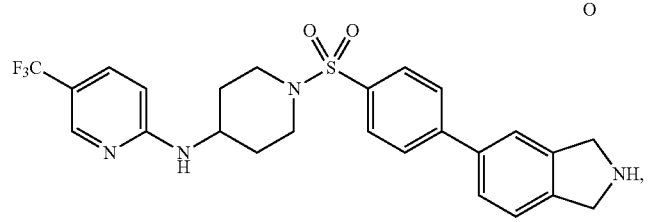

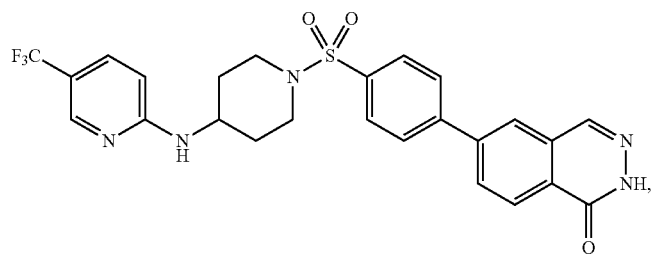
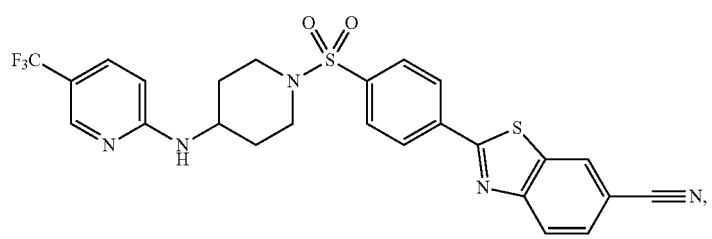
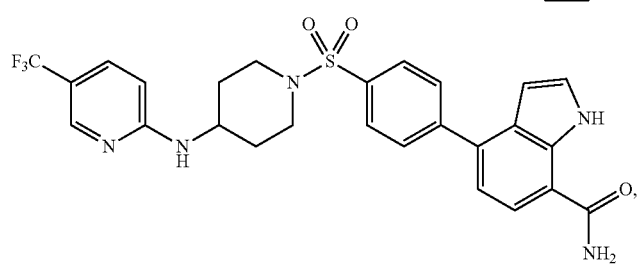
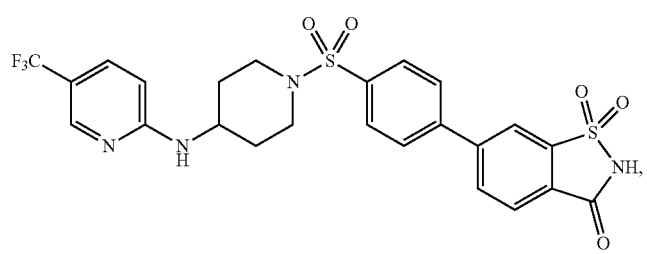
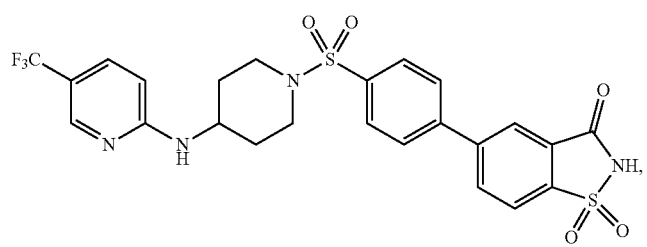
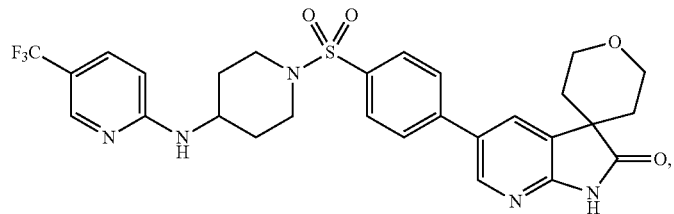
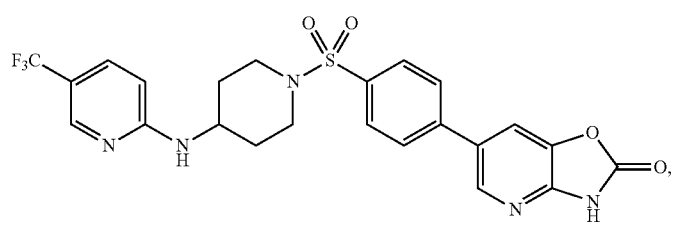

-continued
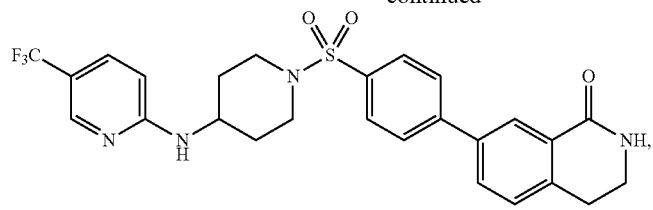
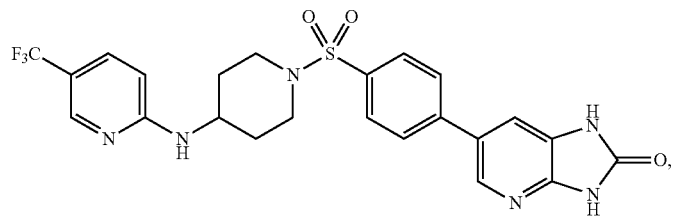
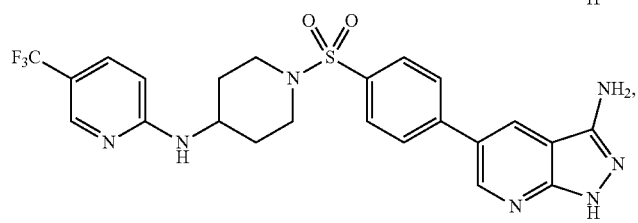
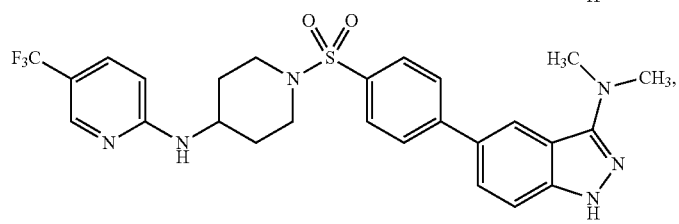
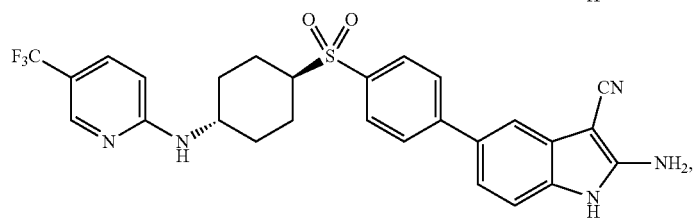
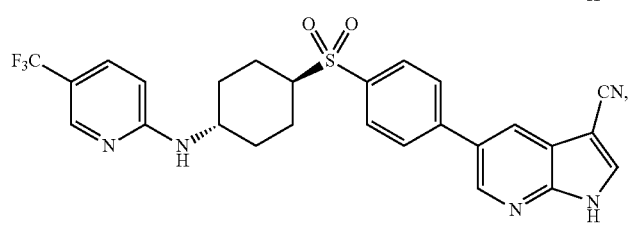
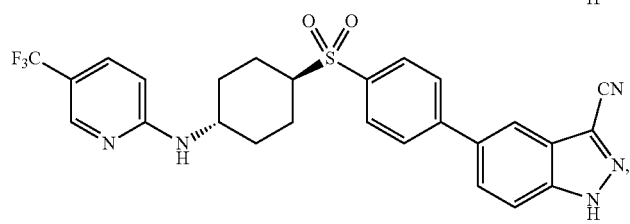
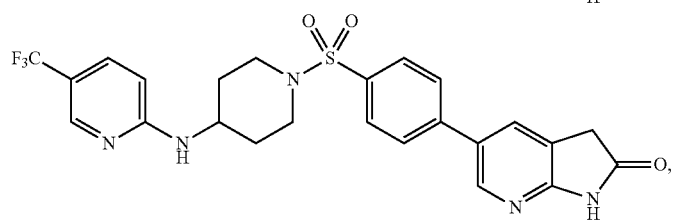

-continued
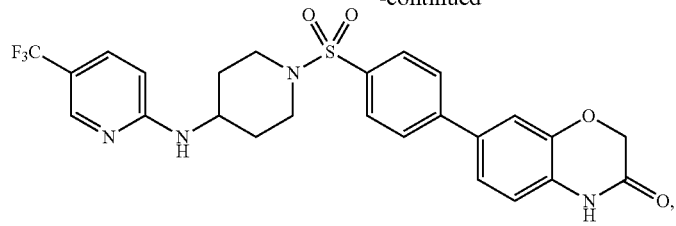
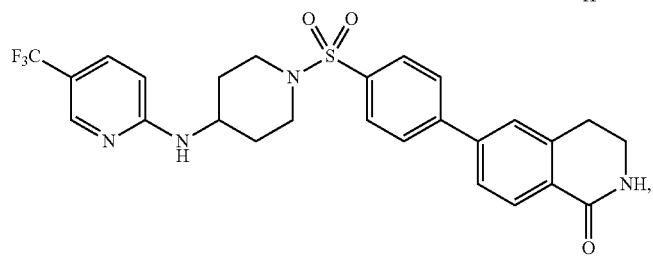
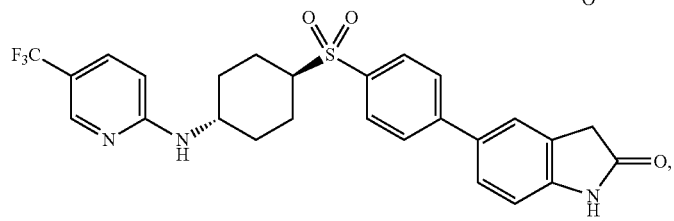
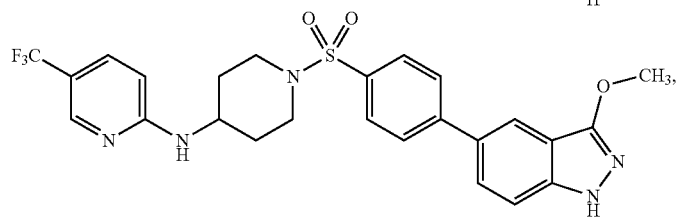
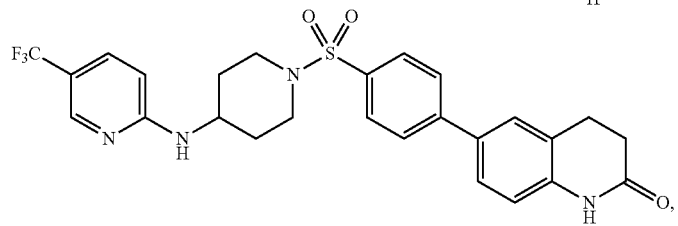
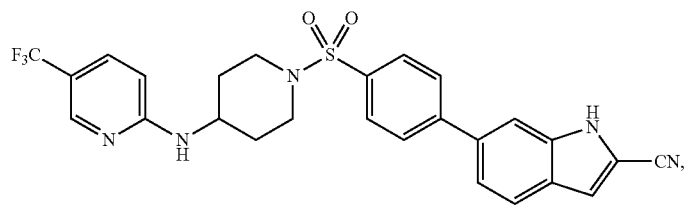
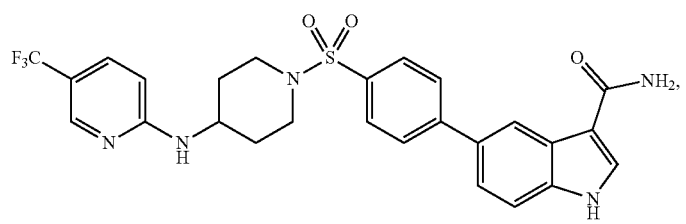

-continued
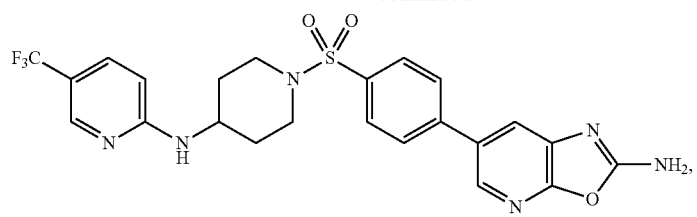
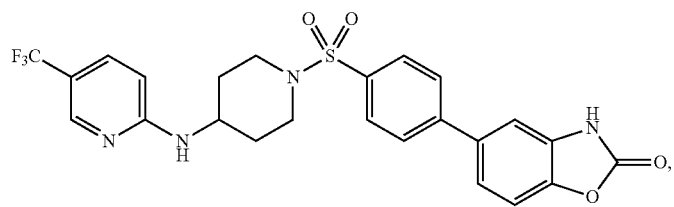
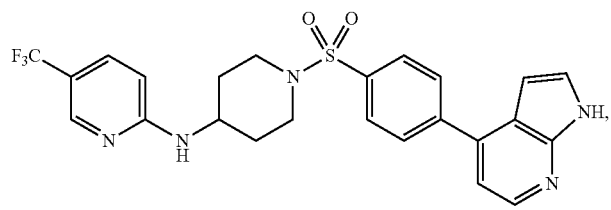
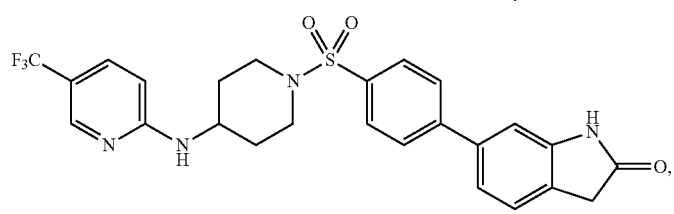
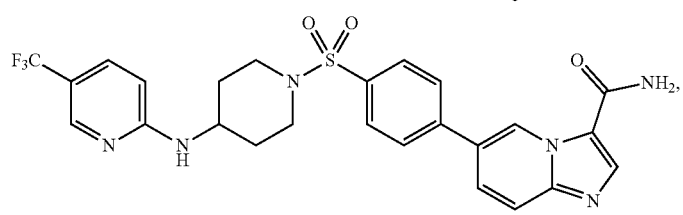
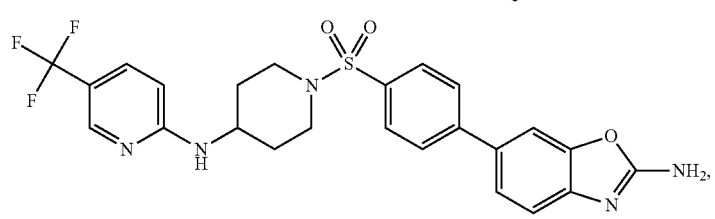
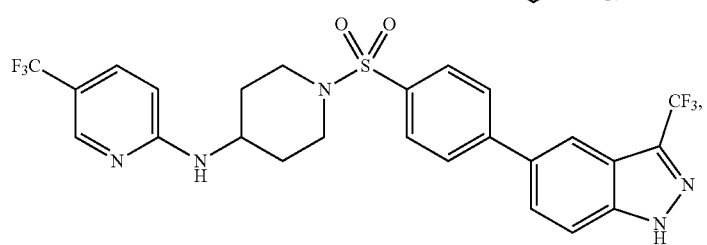
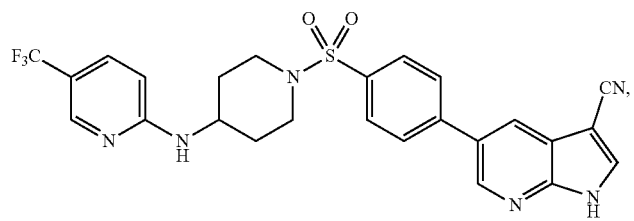

-continued
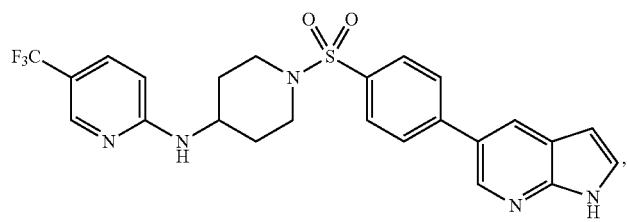
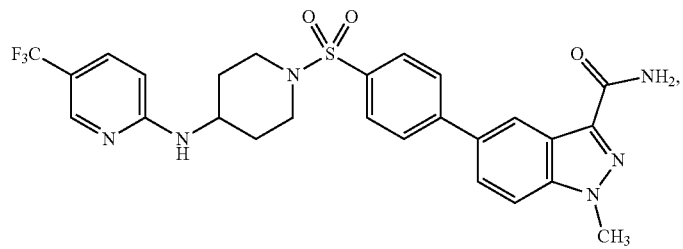
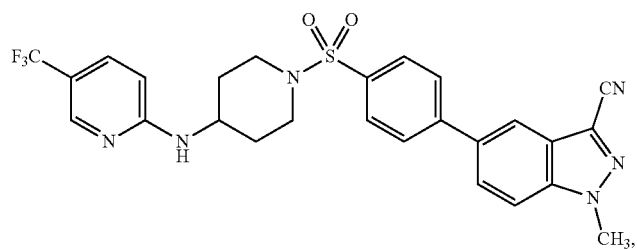
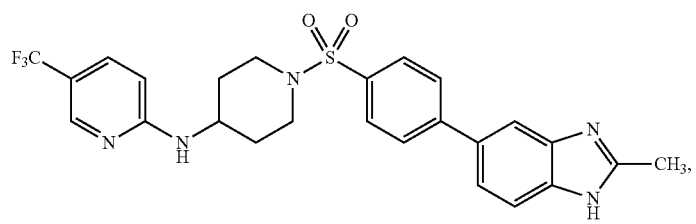
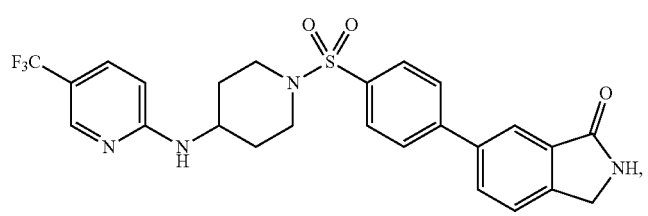
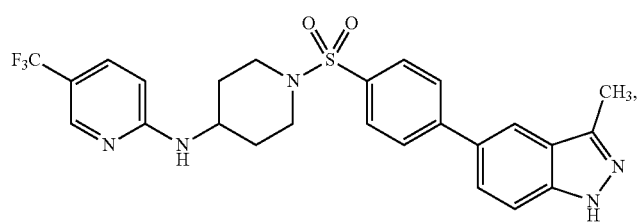
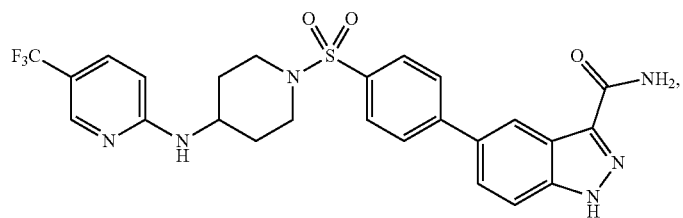

-continued
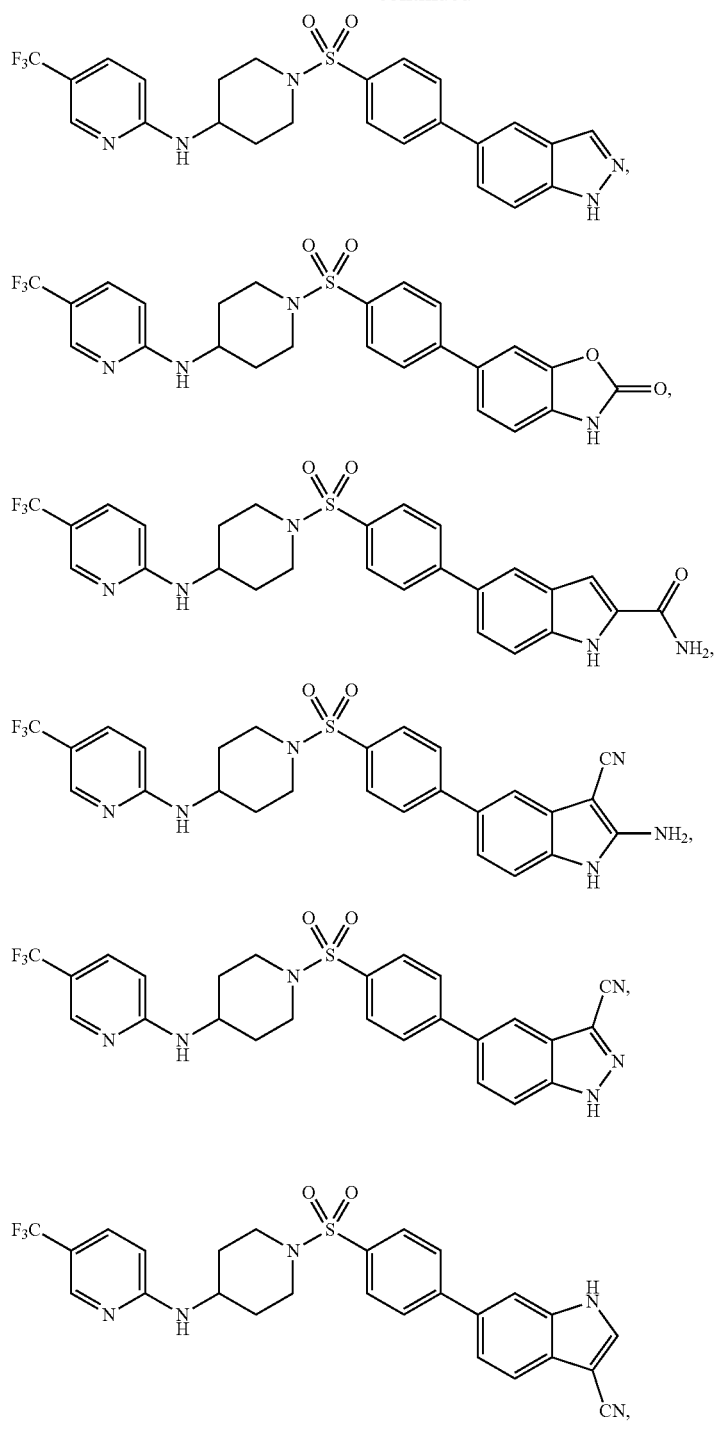
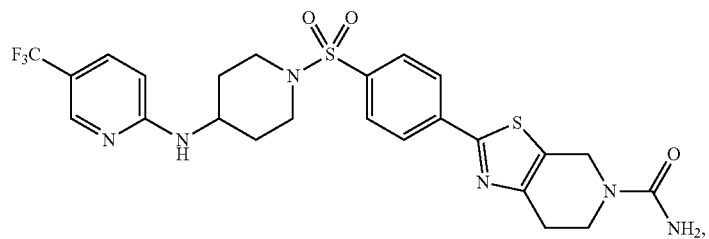

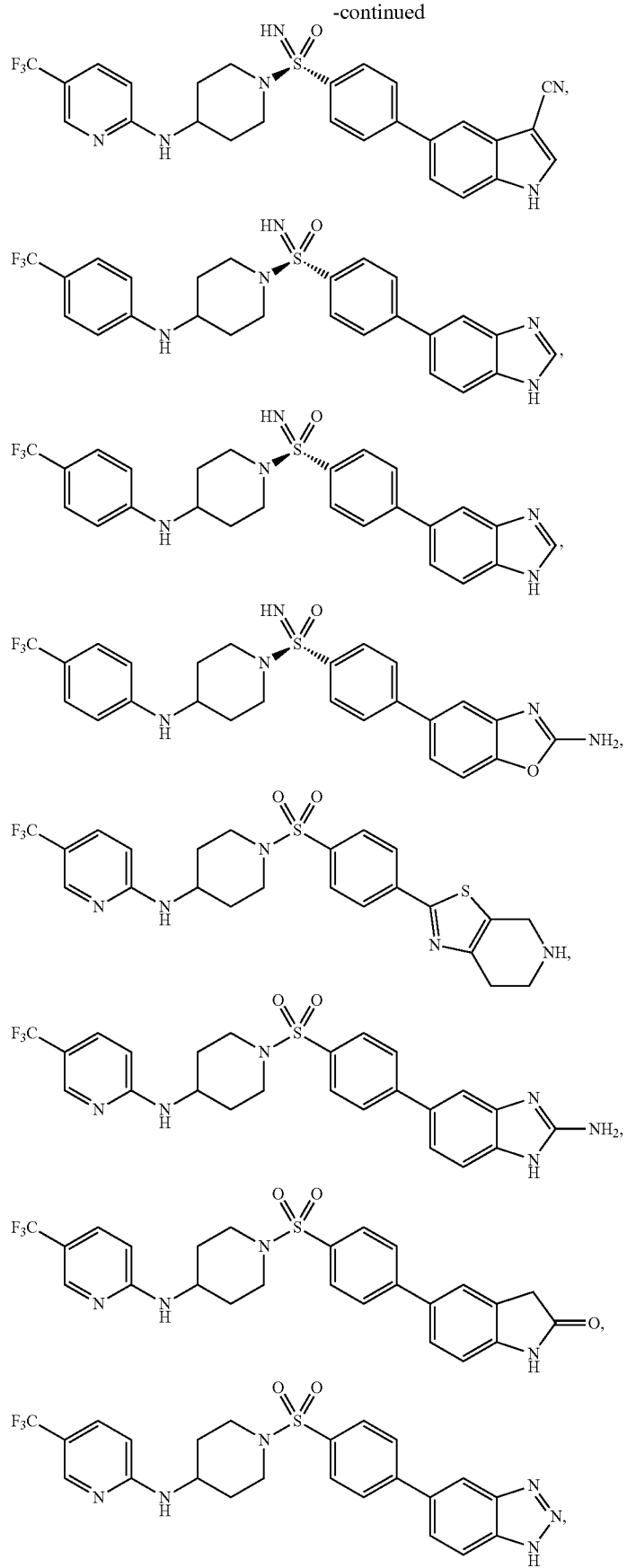

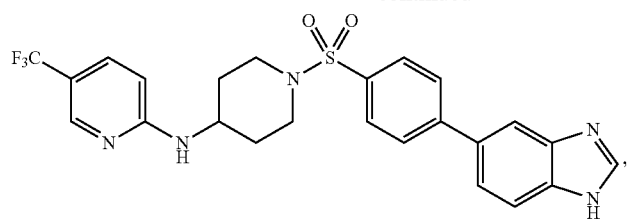
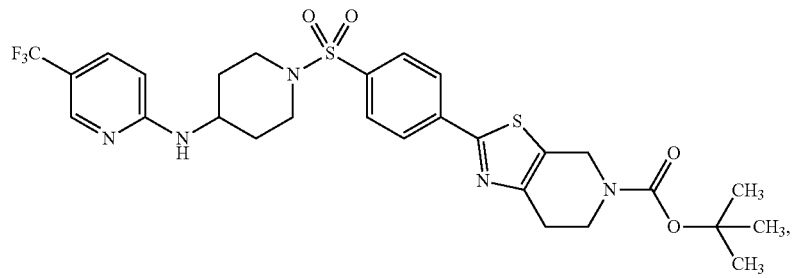
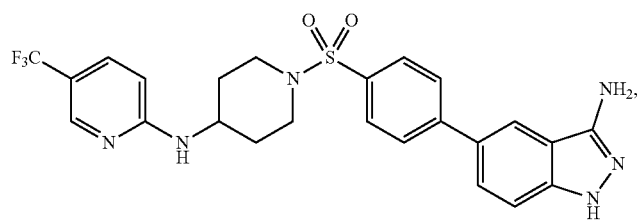
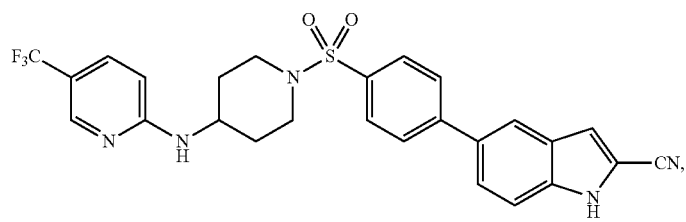
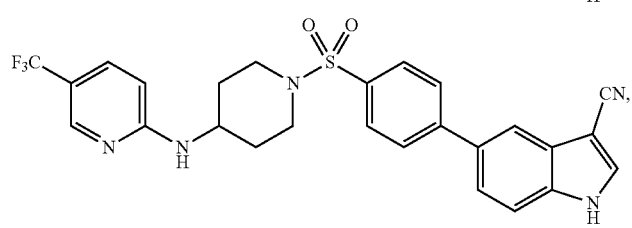
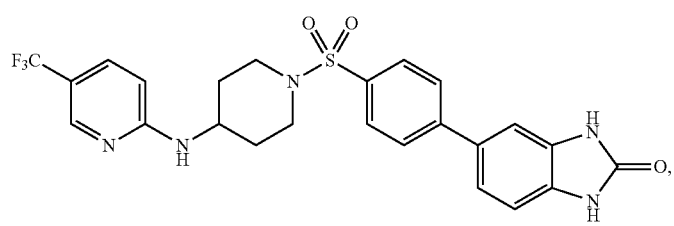
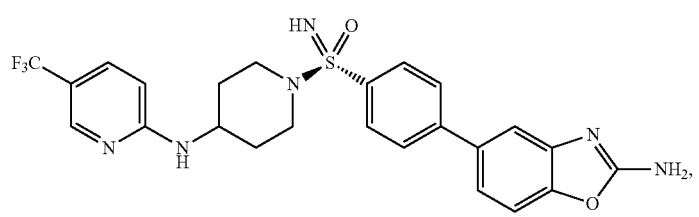

-continued
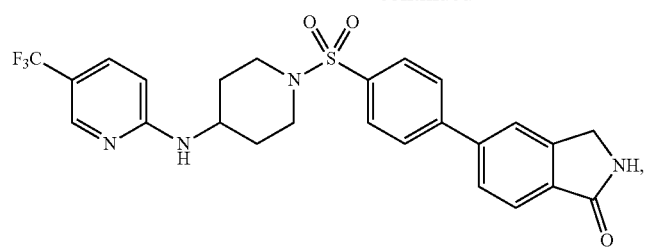
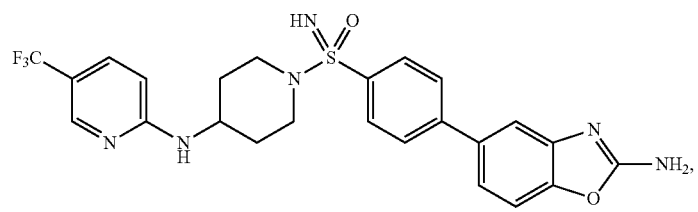
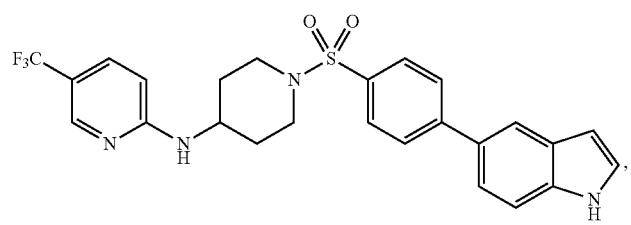
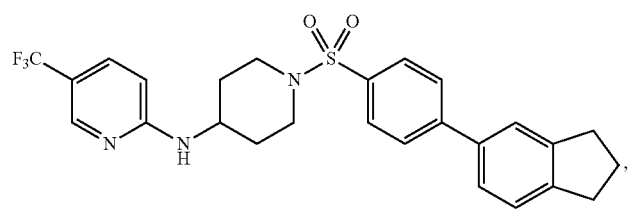
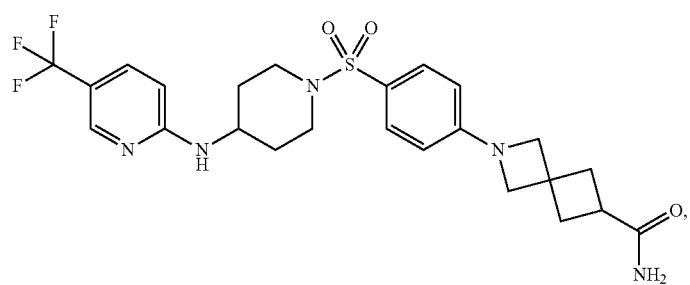
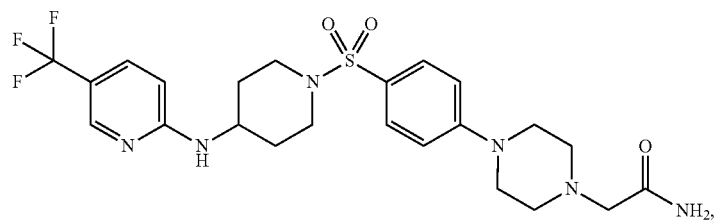
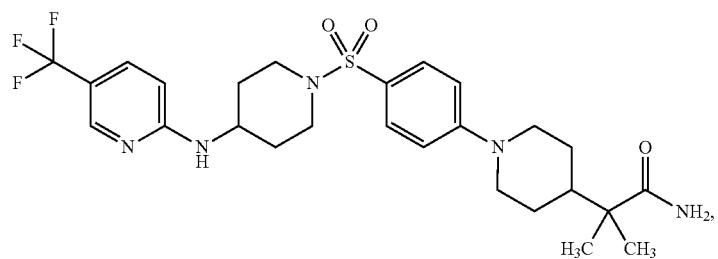

-continued
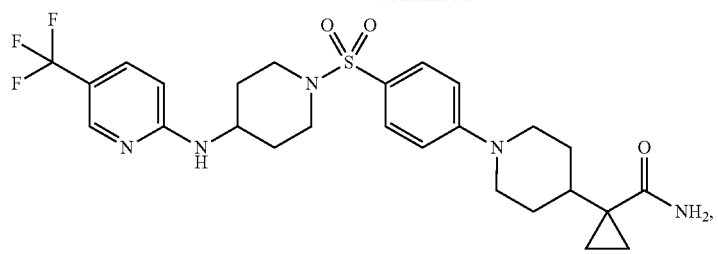
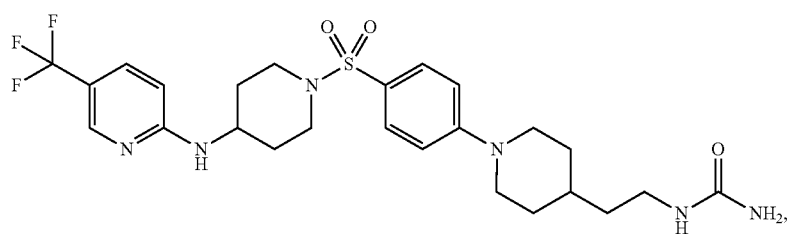
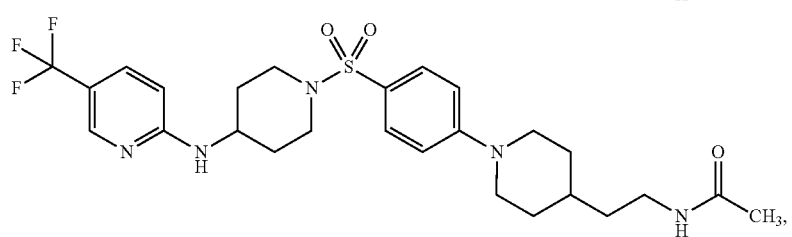
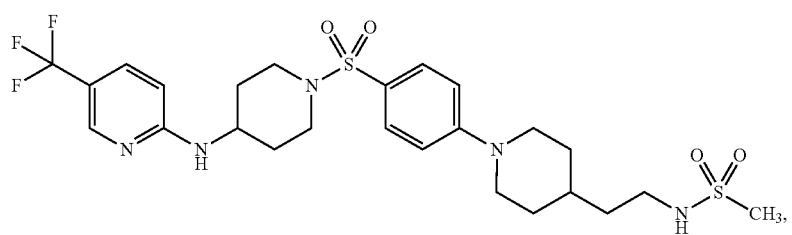
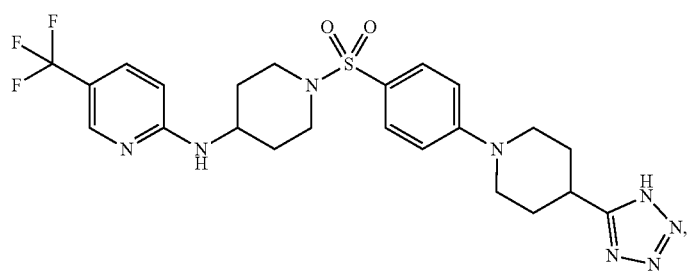
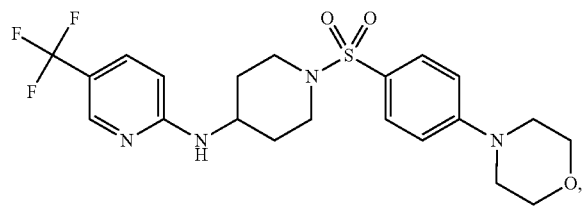
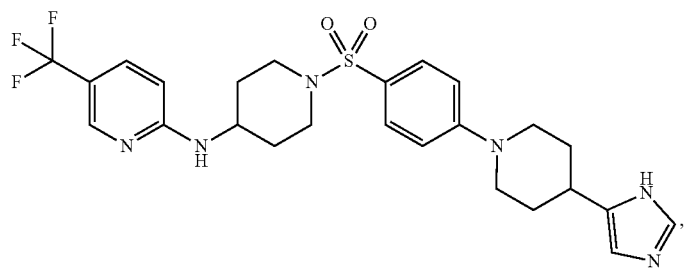

-continued
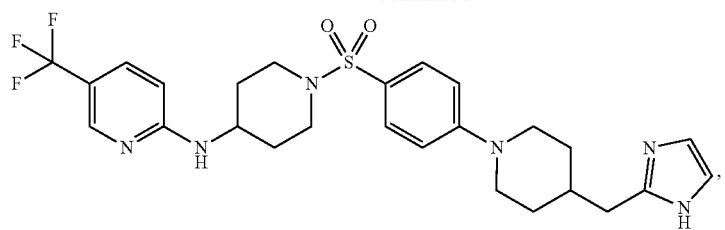
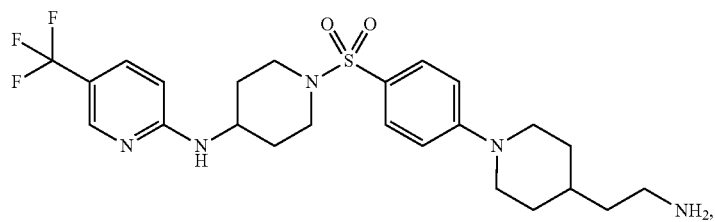
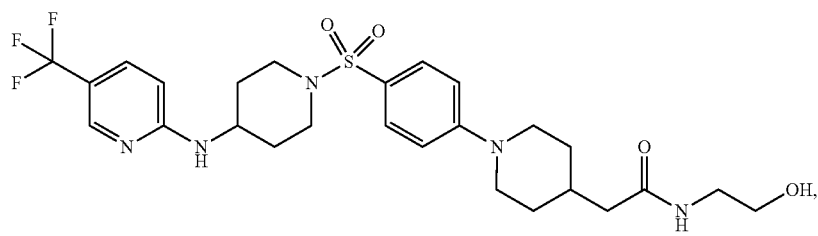
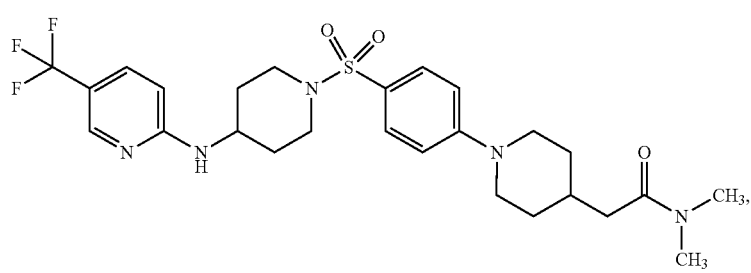
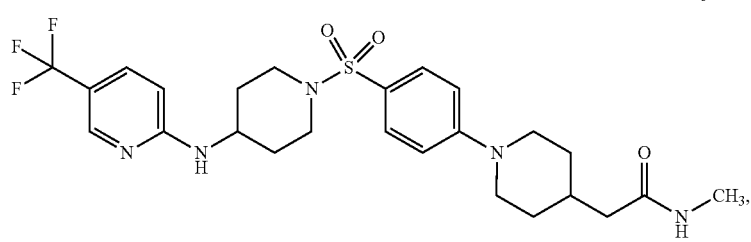
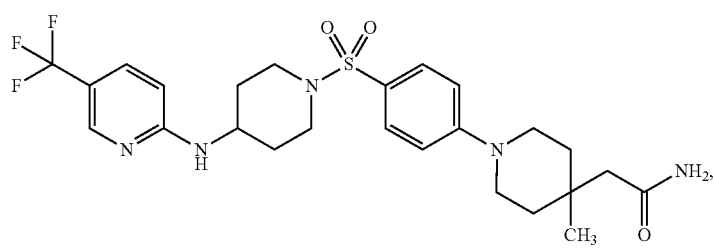
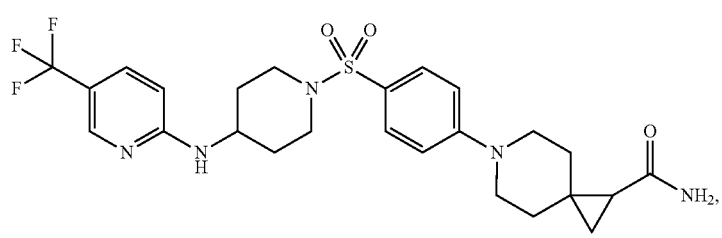

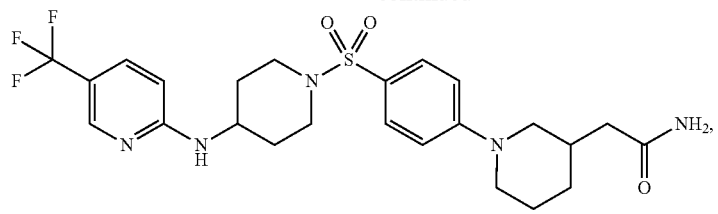
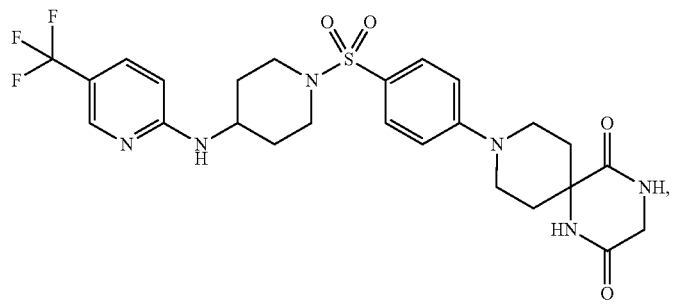
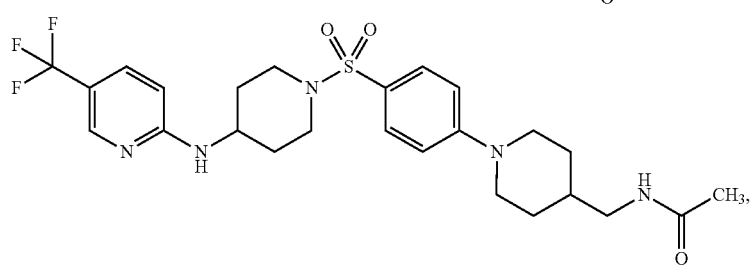
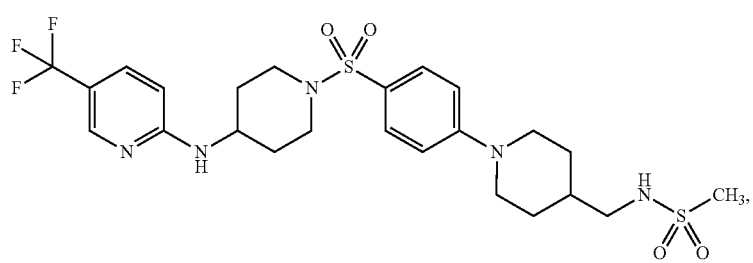
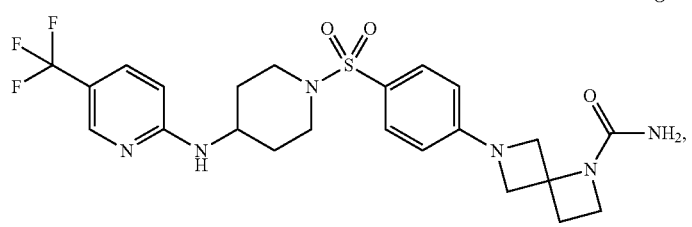
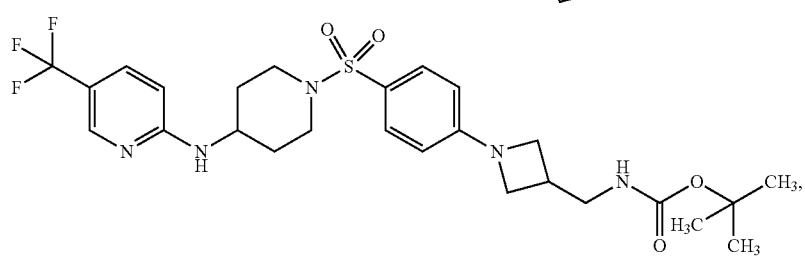
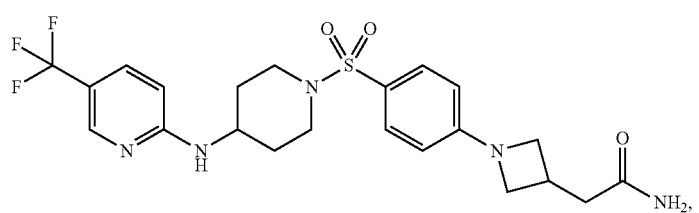

-continued
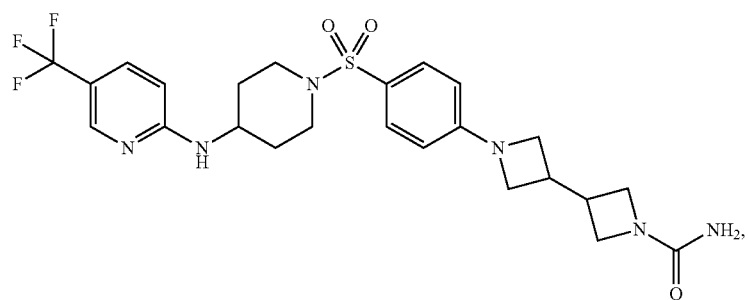
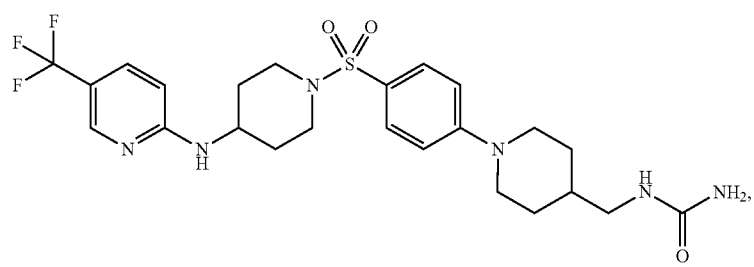
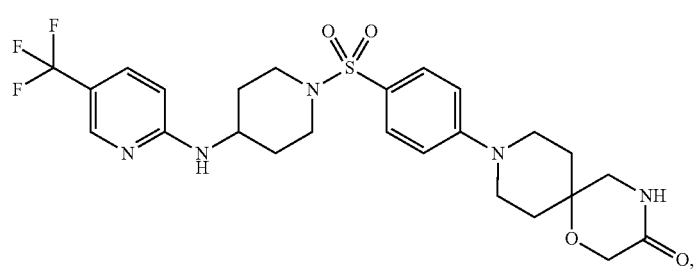
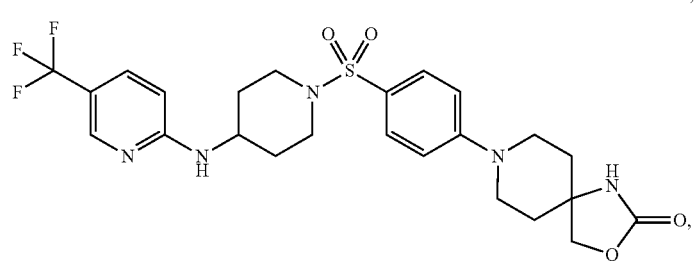
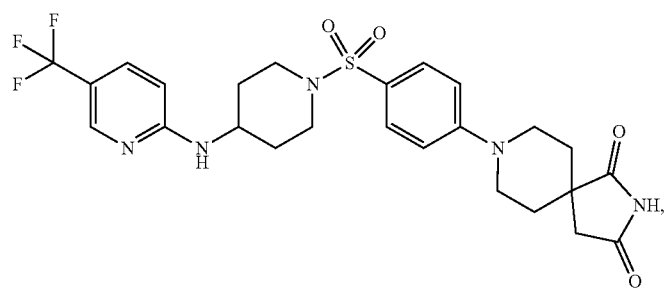
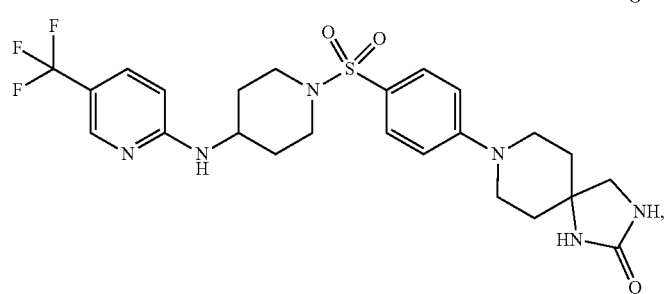

-continued
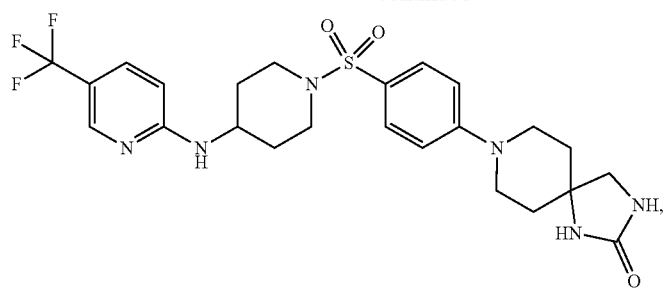
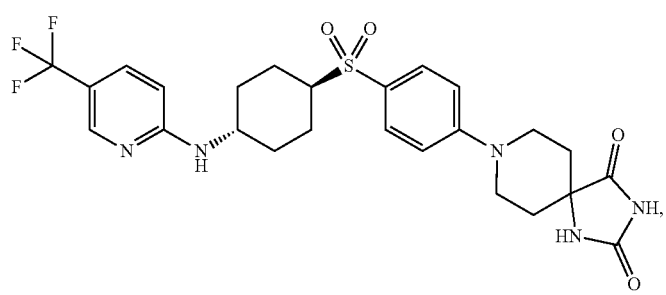
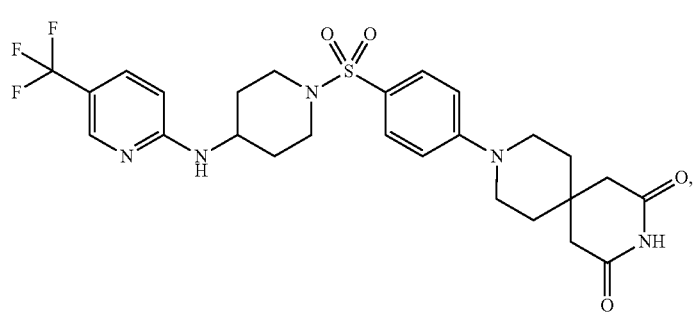
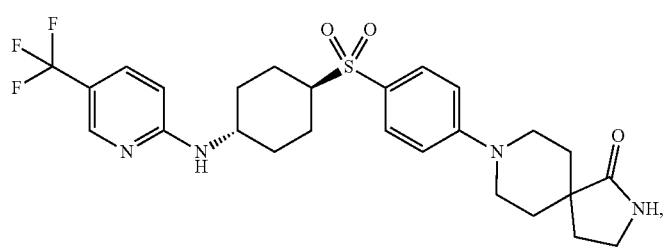
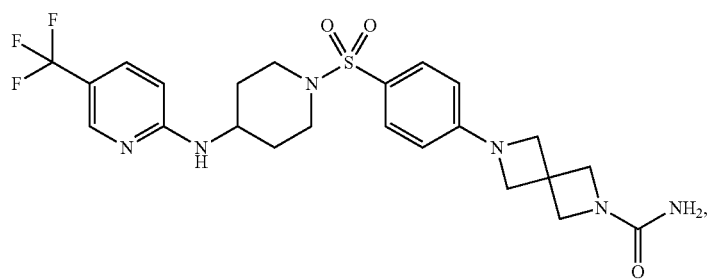
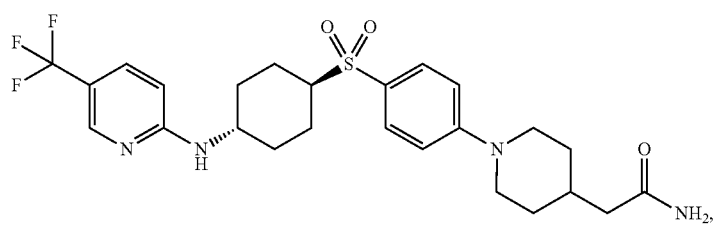

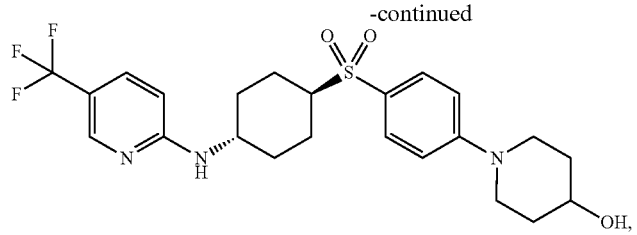
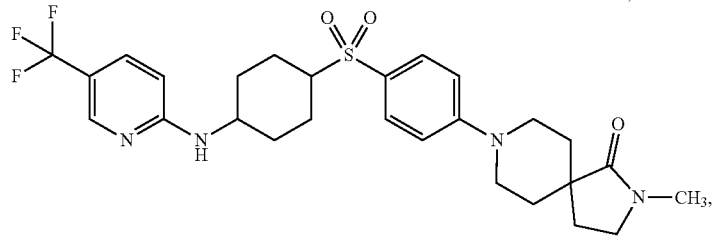
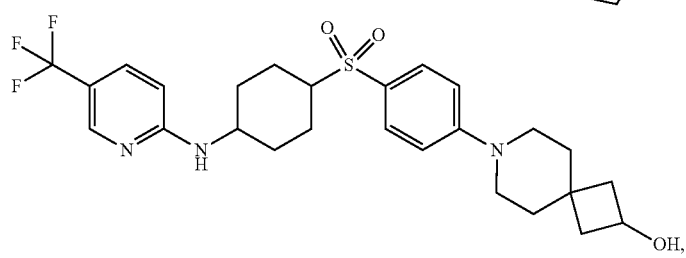
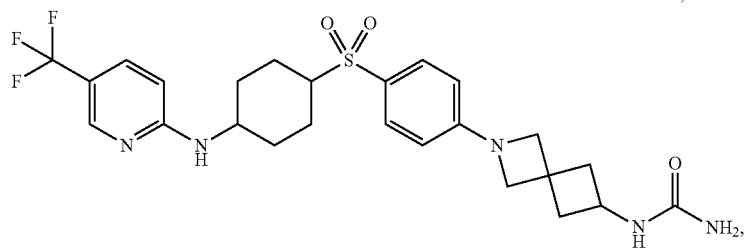
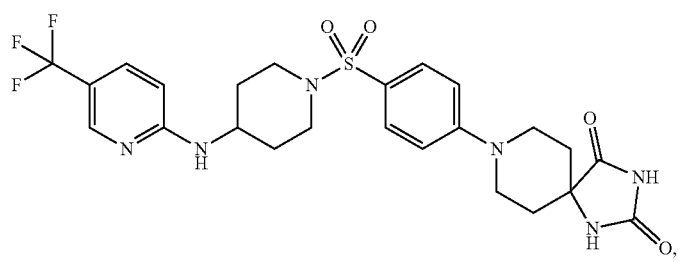
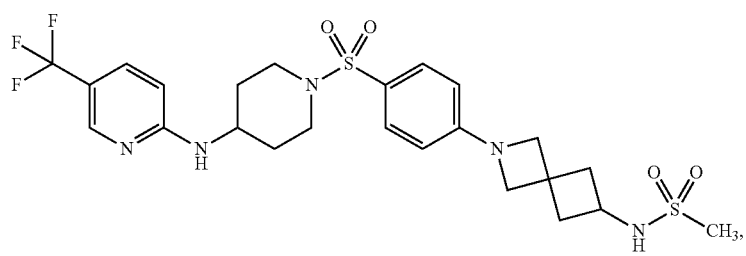

-continued
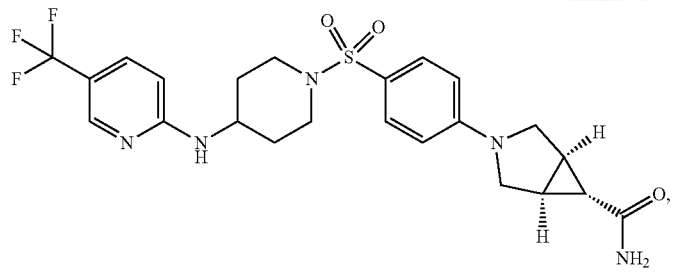
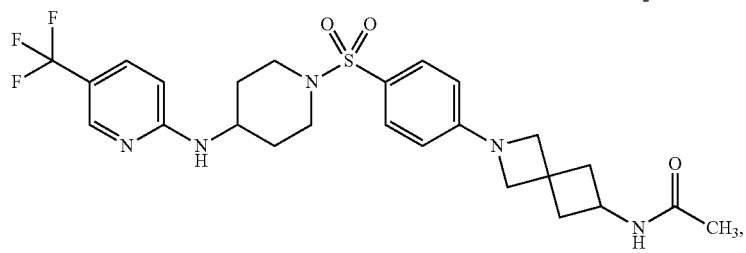
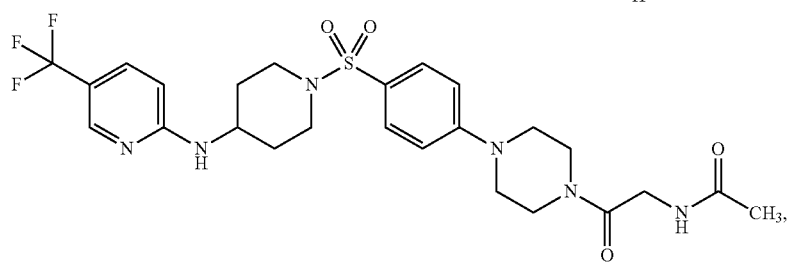
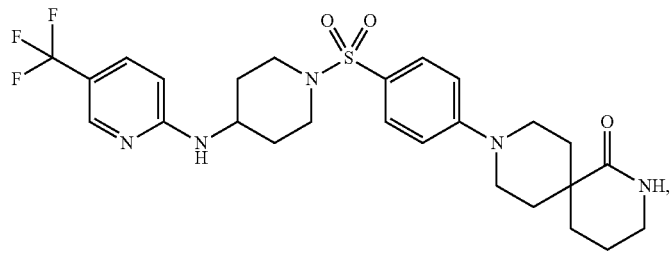
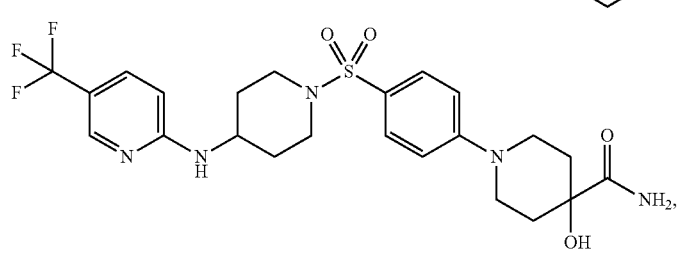
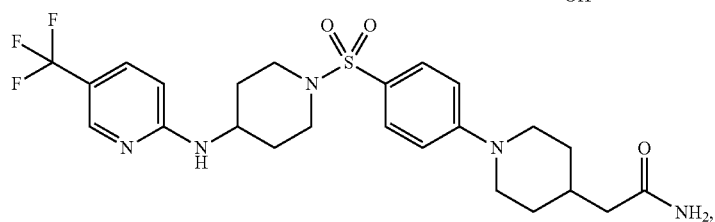
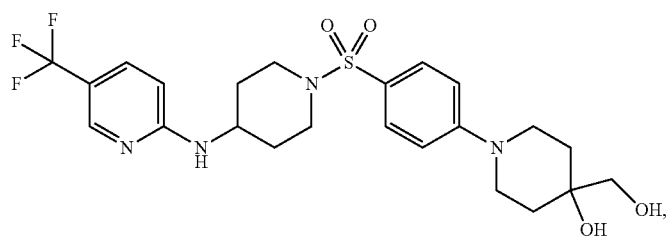

-continued
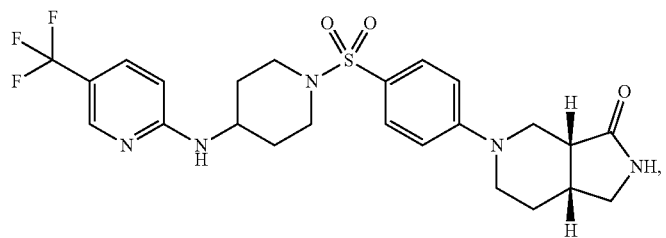
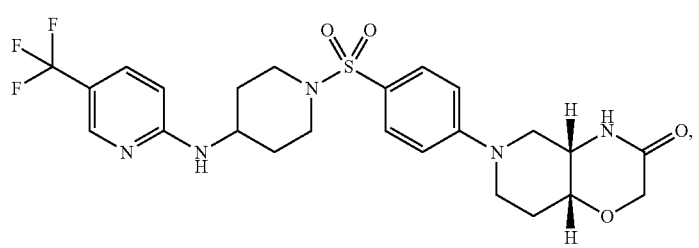
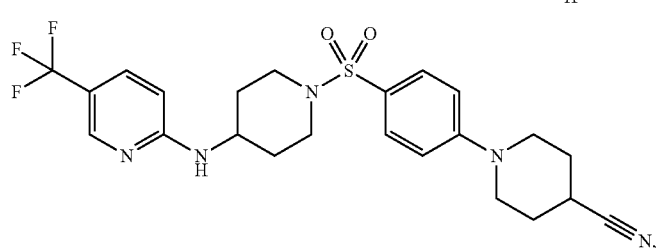
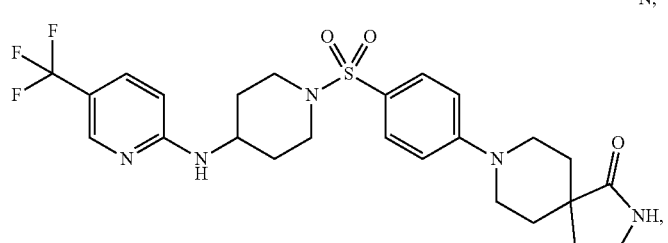
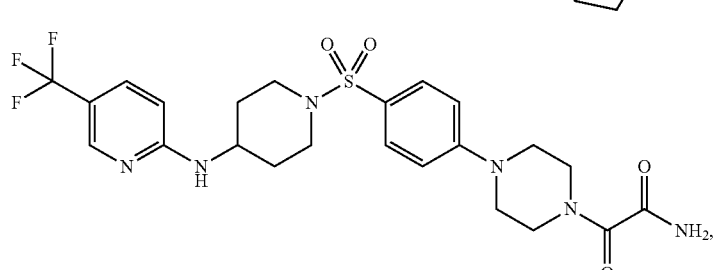
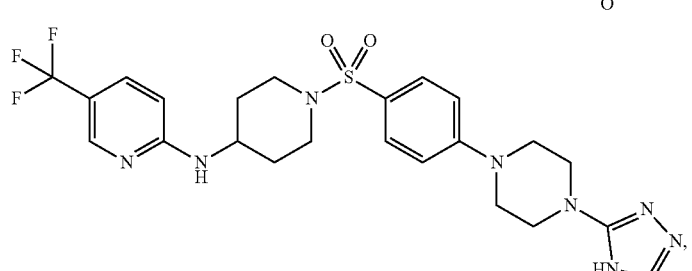
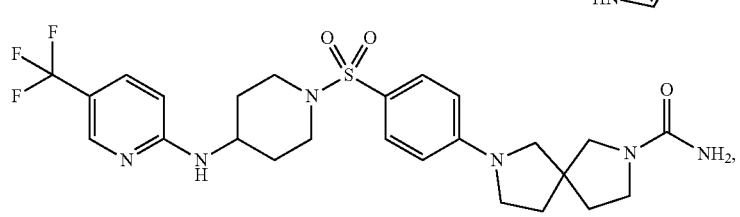

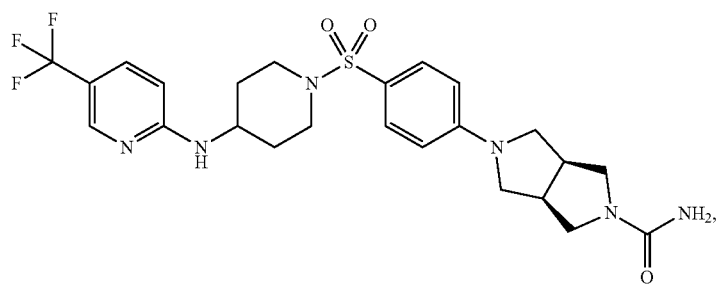
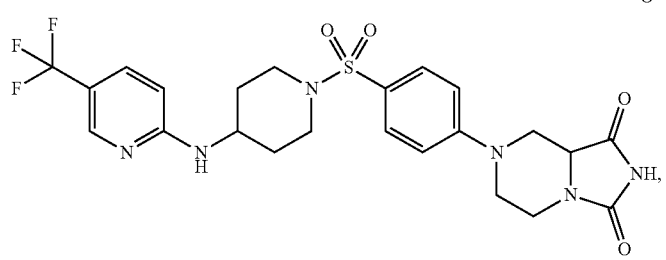
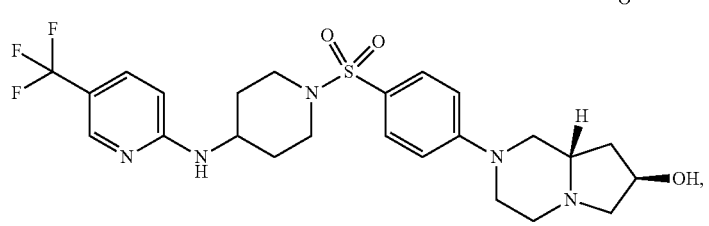
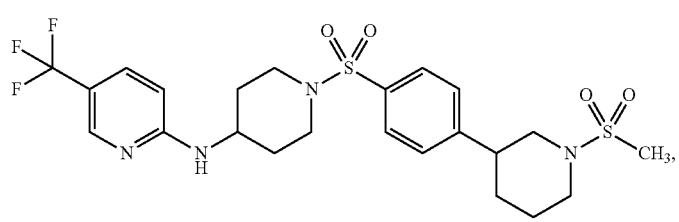
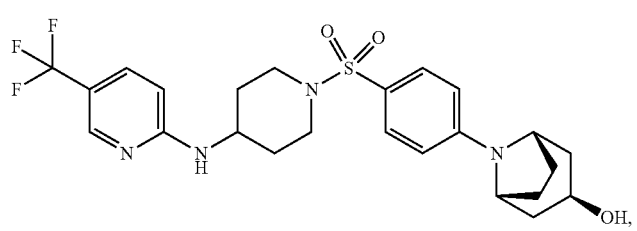
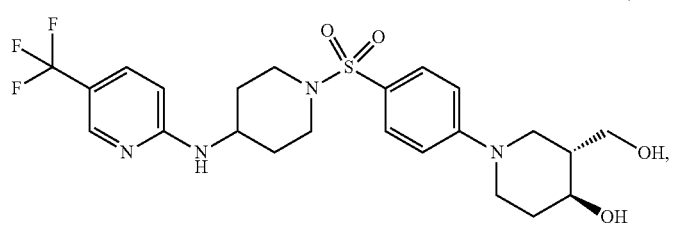
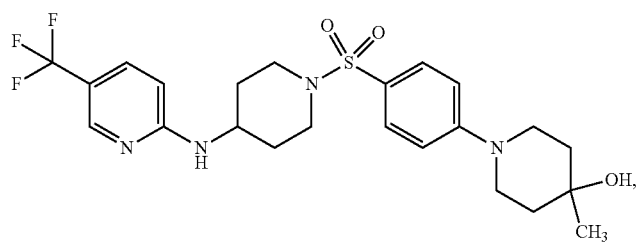

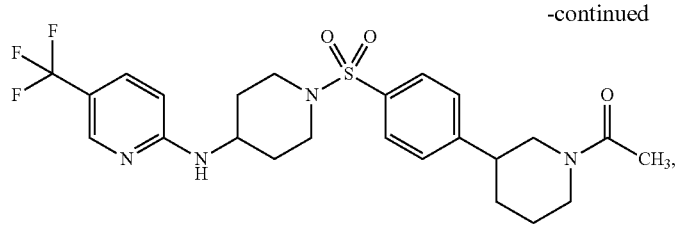
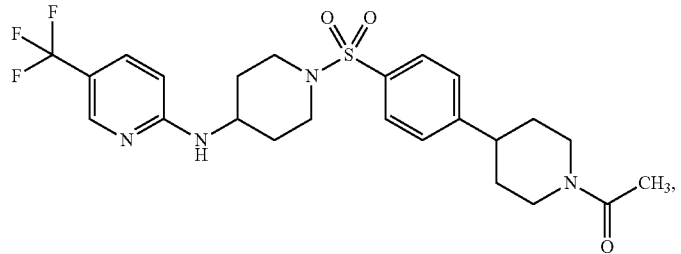
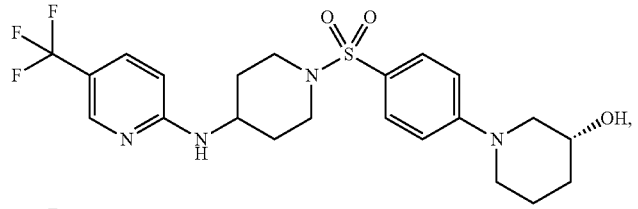
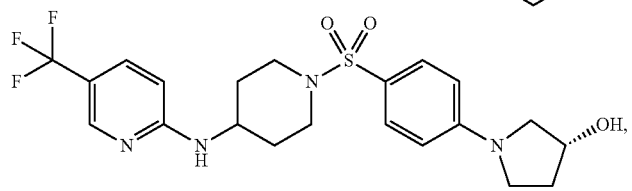
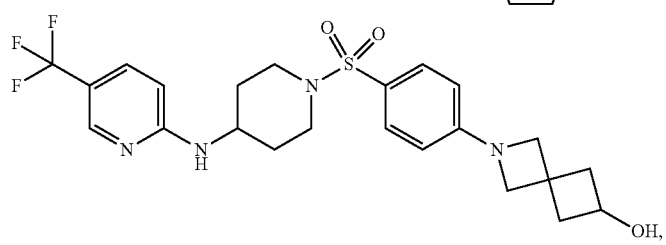
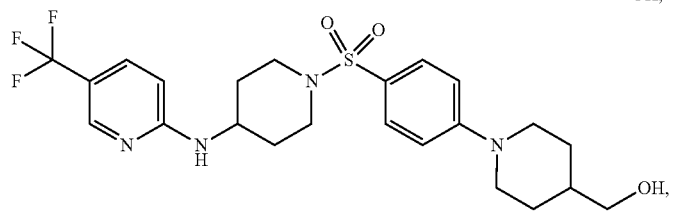
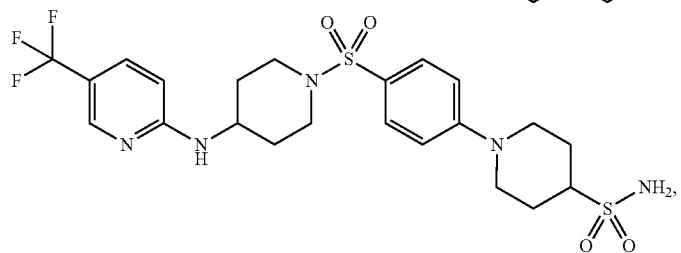
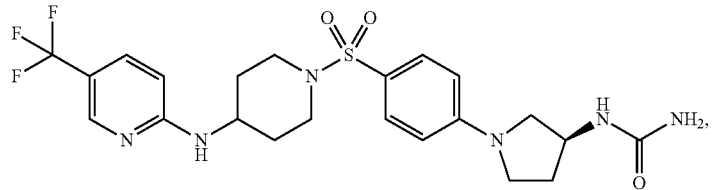

-continued
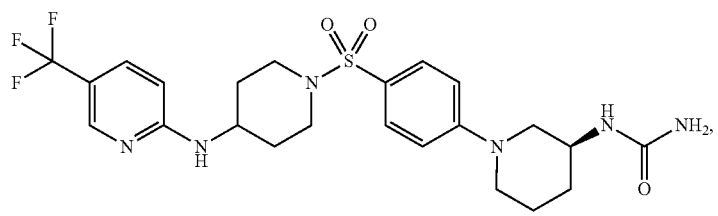
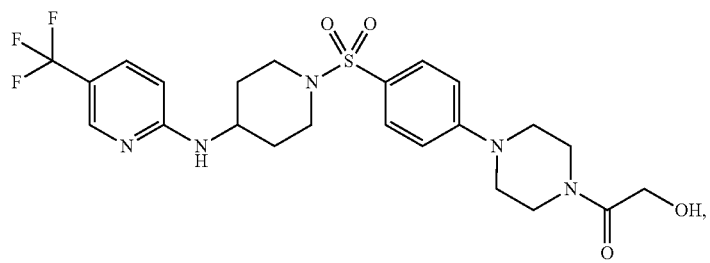
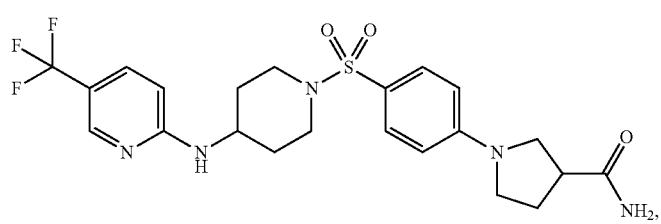
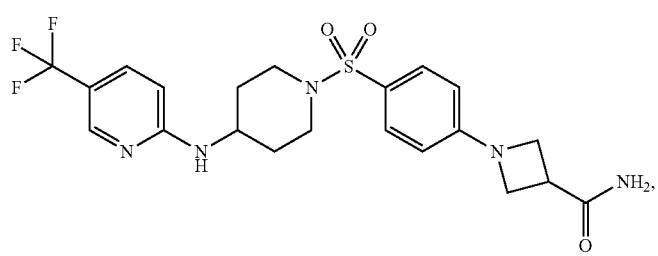
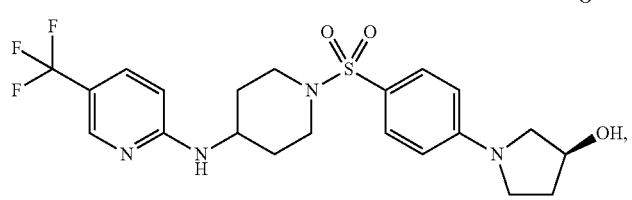
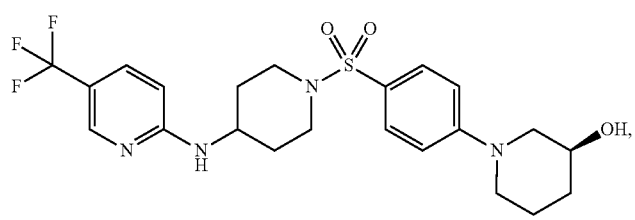
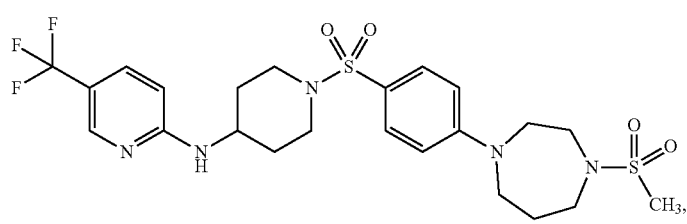

-continued
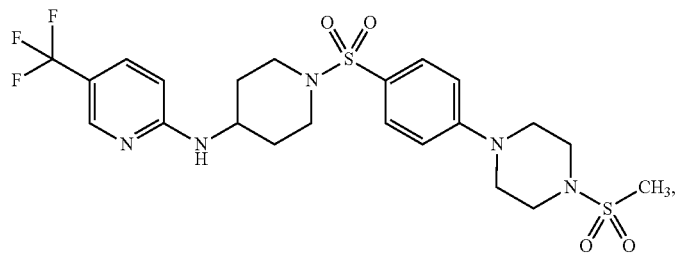
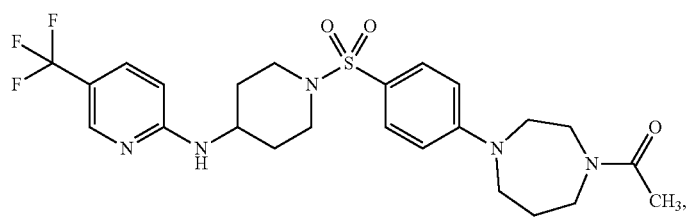
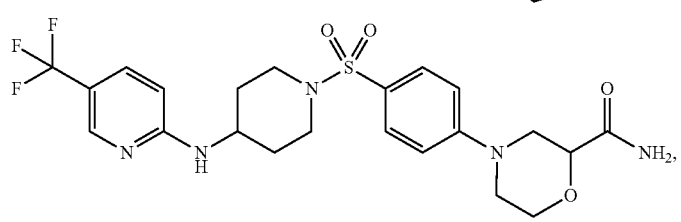
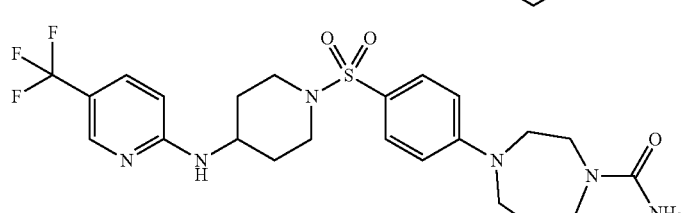
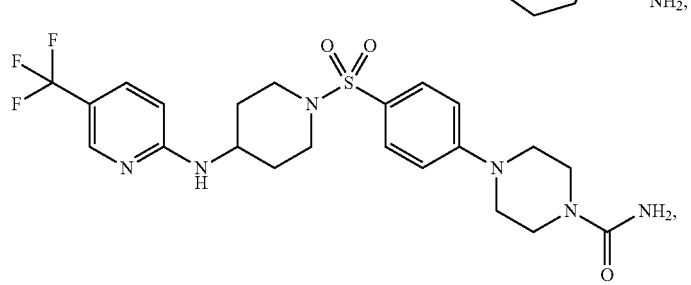
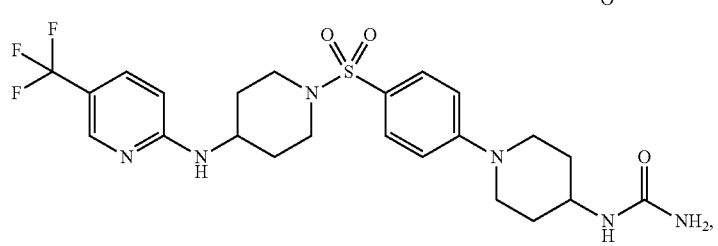
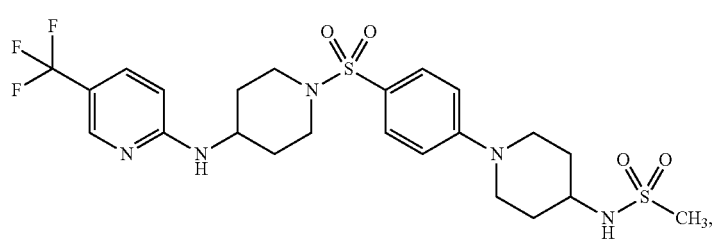

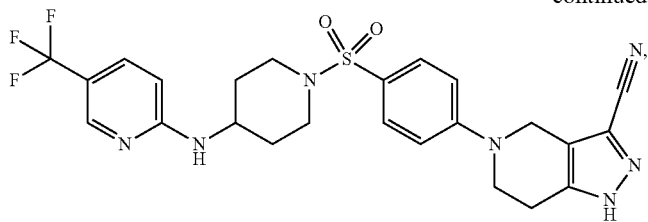
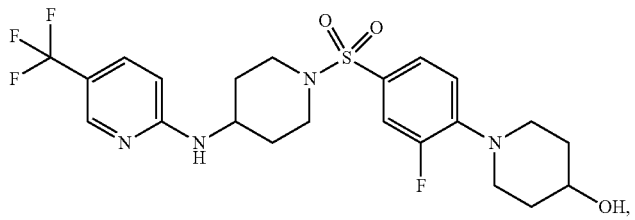
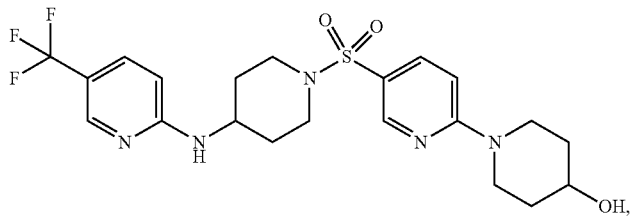
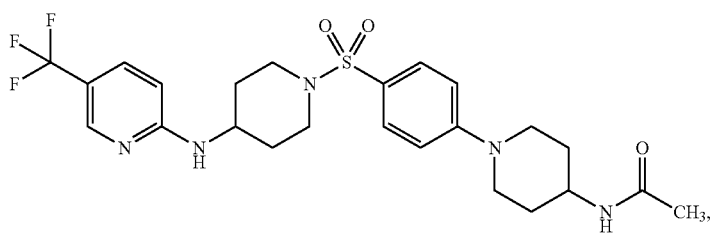
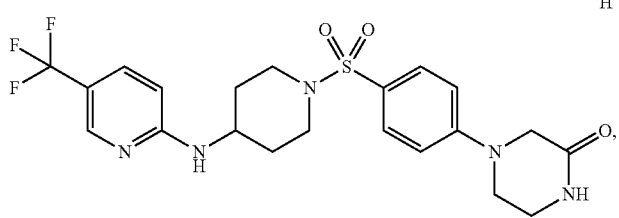
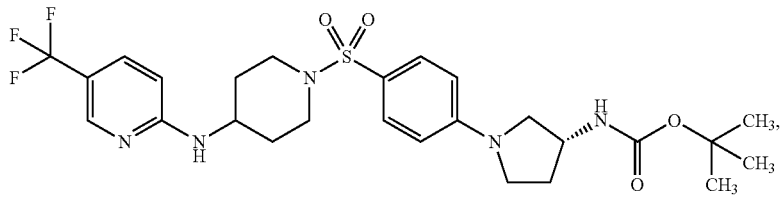
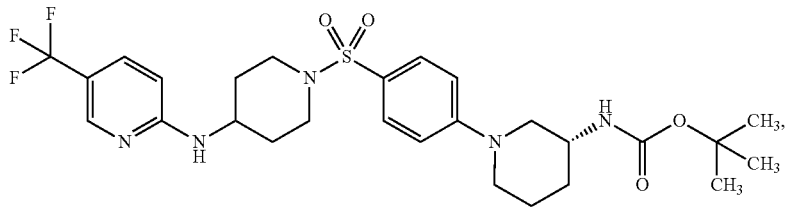
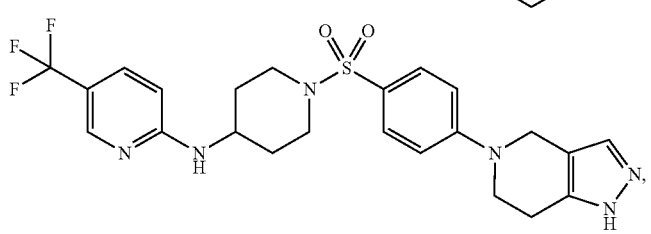

-continued
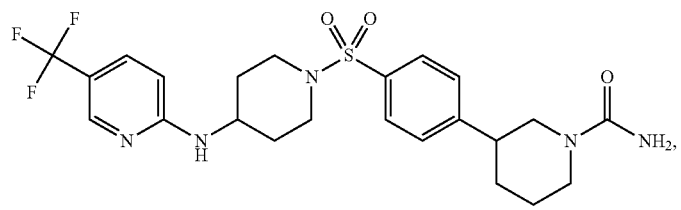
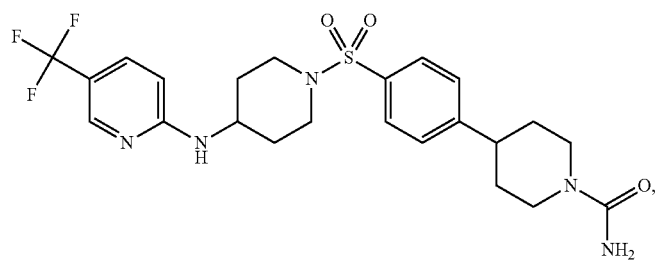
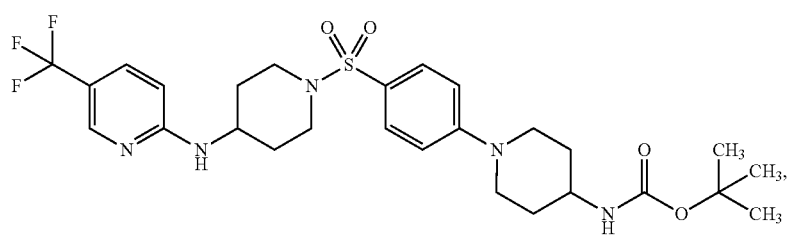
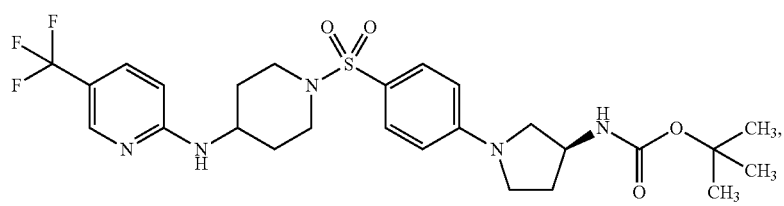
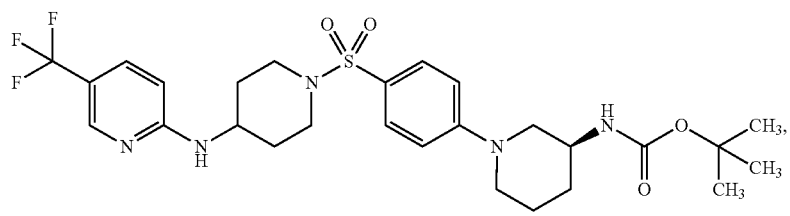
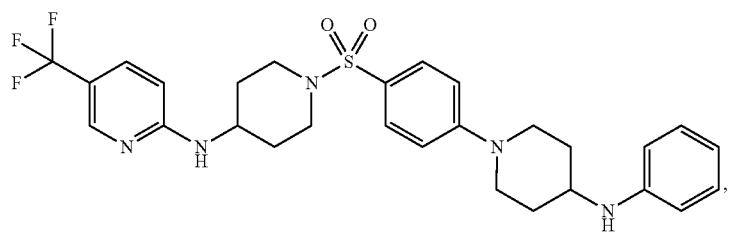
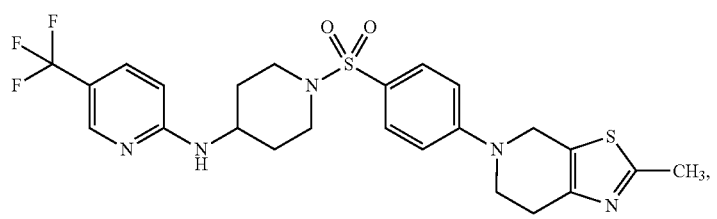

-continued
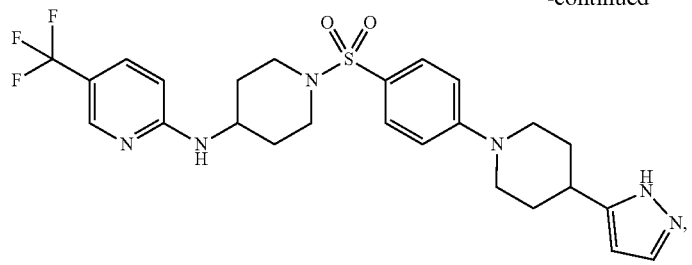
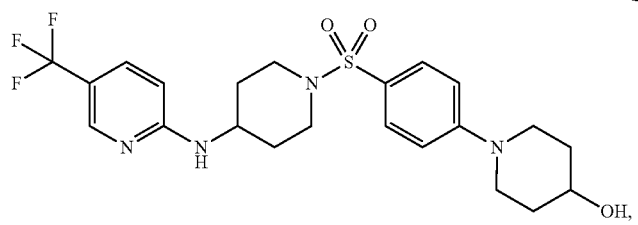
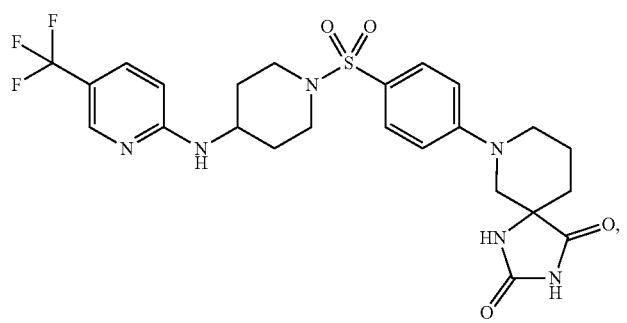
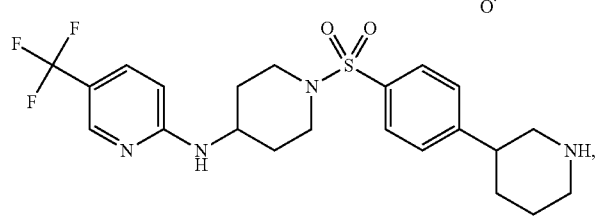
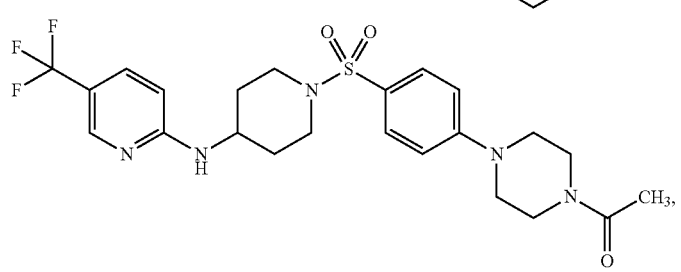
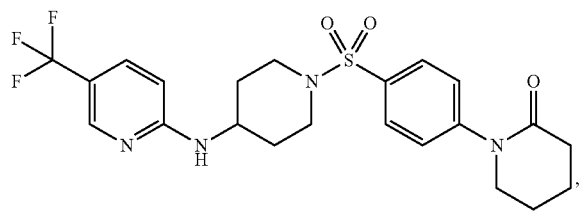
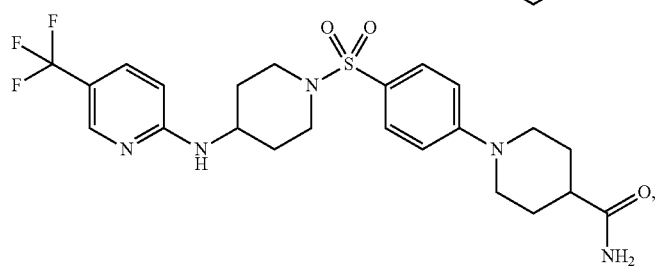

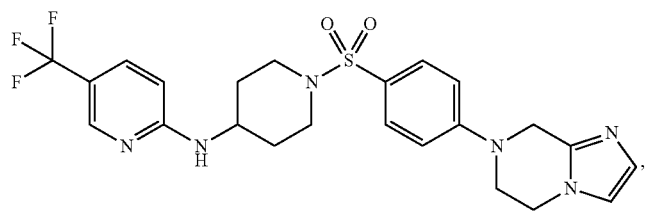
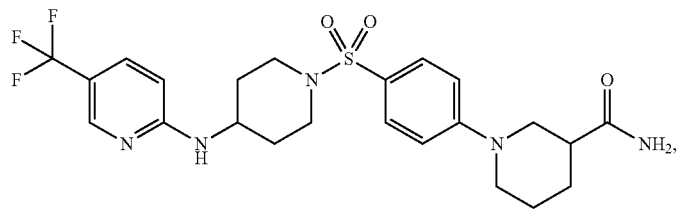
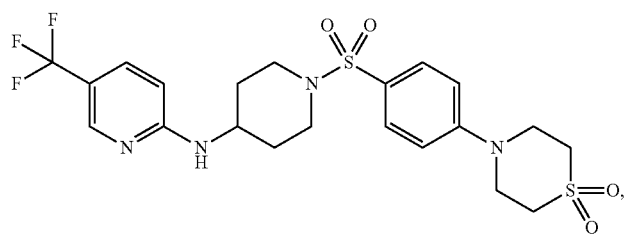
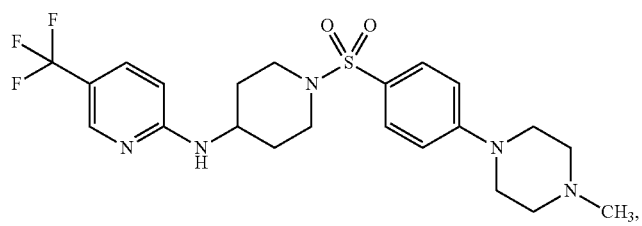
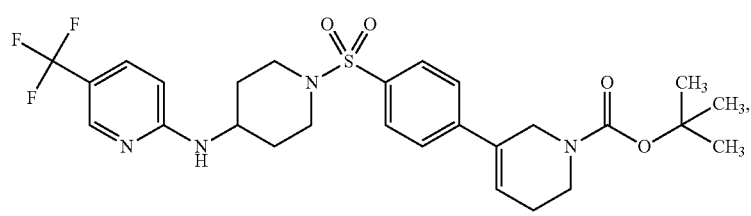
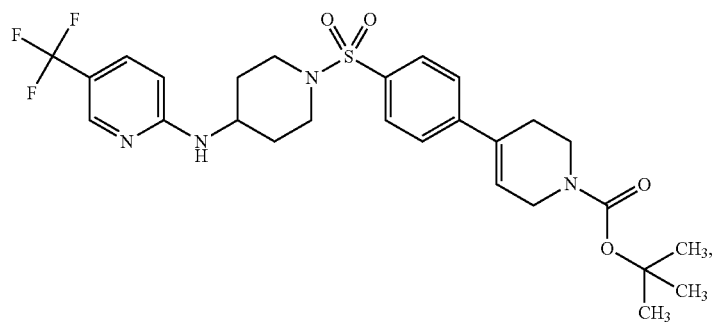
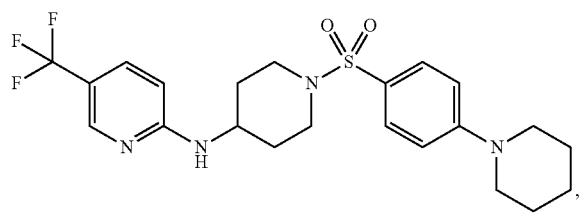
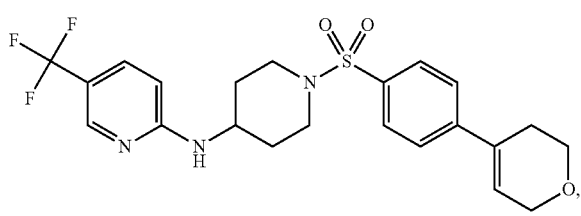

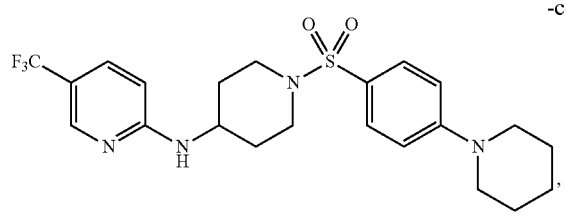

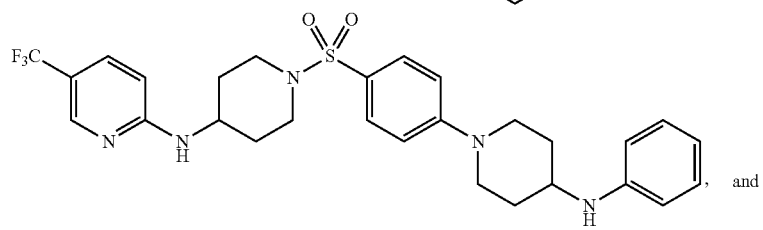, and

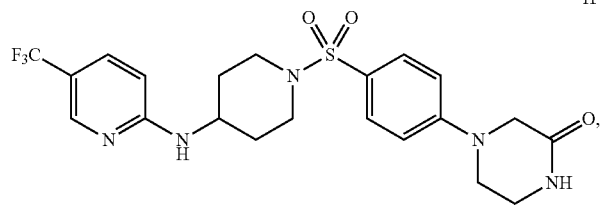

or a pharmaceutically acceptable salt thereof.

20. A pharmaceutical composition comprising a compound of claim 1, or a pharmaceutically acceptable salt, hydrate, solvate, N-oxide or rotamer thereof, with a pharmaceutically acceptable excipient.

21. A method of treating a disease or condition modulated at least in part by CCR6, comprising administering to a subject in need thereof, a compound of claim 1, or a pharmaceutically acceptable salt, hydrate, solvate, N-oxide or rotamer thereof.

* * * * *